(12) United States Patent
Felts et al.

(10) Patent No.: US 10,189,603 B2
(45) Date of Patent: Jan. 29, 2019

(54) PASSIVATION, PH PROTECTIVE OR LUBRICITY COATING FOR PHARMACEUTICAL PACKAGE, COATING PROCESS AND APPARATUS

(71) Applicant: SiO2 Medical Products, Inc., Auburn, AL (US)

(72) Inventors: John T. Felts, Alameda, CA (US); Thomas E. Fisk, Green Valley, AZ (US); Robert S. Abrams, Albany, NY (US); John Ferguson, Auburn, AL (US); Jonathan R. Freedman, Auburn, AL (US); Robert J. Pangborn, Harbor Springs, MI (US); Peter J. Sagona, Pottstown, PA (US); Christopher Weikart, Auburn, AL (US)

(73) Assignee: SIO2 MEDICAL PRODUCTS, INC., Auburn, AL (US)

( * ) Notice: Subject to any disclaimer, the term of this patent is extended or adjusted under 35 U.S.C. 154(b) by 1255 days.

(21) Appl. No.: 14/357,418

(22) PCT Filed: Nov. 9, 2012

(86) PCT No.: PCT/US2012/064489
§ 371 (c)(1),
(2) Date: May 9, 2014

(87) PCT Pub. No.: WO2013/071138
PCT Pub. Date: May 16, 2013

(65) Prior Publication Data
US 2015/0021339 A1    Jan. 22, 2015

Related U.S. Application Data

(60) Provisional application No. 61/645,003, filed on May 9, 2012, provisional application No. 61/636,377, filed
(Continued)

(51) Int. Cl.
*B65D 25/14* (2006.01)
*C23C 16/30* (2006.01)
(Continued)

(52) U.S. Cl.
CPC .......... *B65D 25/14* (2013.01); *A61M 5/3129* (2013.01); *C23C 16/045* (2013.01); *C23C 16/30* (2013.01);
(Continued)

(58) Field of Classification Search
CPC ......... B65D 25/14; C23C 16/30; C23C 16/36; C23C 16/401; C23C 16/045;
(Continued)

(56) References Cited

U.S. PATENT DOCUMENTS 3,274,267 A    9/1966    Chow
3,297,465 A    1/1967    Connell
(Continued)

FOREIGN PATENT DOCUMENTS

AT    414209 B    10/2006
AT    504533 A1   6/2008
(Continued)

OTHER PUBLICATIONS

US 5,645,643, 07/1997, Thomas (withdrawn)
(Continued)

*Primary Examiner* — Michael C Miggins
(74) *Attorney, Agent, or Firm* — McAndrews, Held & Malloy, Ltd.

(57) ABSTRACT

A method for providing a passivation layer or pH protective coating on a substrate surface by PECVD is provided, the method comprising generating a plasma from a gaseous reactant comprising polymerizing gases. The lubricity, passivation, pH protective, hydrophobicity, and/or barrier properties of the passivation layer or pH protective coating are
(Continued)

set by setting the ratio of the $O_2$ to the organosilicon precursor in the precursor feed, and/or by setting the electric power used for generating the plasma. In particular, a passivation layer or pH protective coating made by the method is provided. Pharmaceutical packages coated by the method and the use of such packages protecting a composition contained in the vessel against mechanical and/or chemical effects of the surface of the package without a passivation layer or pH protective coating material are also provided.

22 Claims, 17 Drawing Sheets

Related U.S. Application Data on Apr. 20, 2012, provisional application No. 61/558,885, filed on Nov. 11, 2011.

(51) Int. Cl.

| | | |
|---|---|---|
| C23C 16/36 | (2006.01) | |
| C23C 16/40 | (2006.01) | |
| C23C 16/04 | (2006.01) | |
| C23C 16/507 | (2006.01) | |
| A61M 5/31 | (2006.01) | |
| A61J 1/05 | (2006.01) | |

(52) U.S. Cl.
CPC ............ *C23C 16/36* (2013.01); *C23C 16/401* (2013.01); *C23C 16/507* (2013.01); *A61J 1/05* (2013.01); *A61M 2005/3109* (2013.01); *A61M 2005/3131* (2013.01)

(58) Field of Classification Search
CPC ........... C23C 16/507; A61J 1/05; A61M 1/05; A61M 5/3129; A61M 2005/3109; A61M 2005/3131
See application file for complete search history.

(56) References Cited

U.S. PATENT DOCUMENTS

| | | |
|---|---|---|
| 3,355,947 A | 12/1967 | Karlby |
| 3,442,686 A | 5/1969 | Jones |
| 3,448,614 A | 6/1969 | Muger |
| 3,590,634 A | 7/1971 | Pasternak |
| 3,838,598 A | 10/1974 | Tomkins |
| 3,957,653 A | 5/1976 | Blecher |
| 4,111,326 A | 9/1978 | Percarpio |
| 4,134,832 A | 1/1979 | Heimreid |
| 4,136,794 A | 1/1979 | Percapio |
| 4,162,528 A | 7/1979 | Maldonado |
| 4,168,330 A | 9/1979 | Kaganowicz |
| 4,186,840 A | 2/1980 | Percarpio |
| 4,187,952 A | 2/1980 | Percarpio |
| 4,226,333 A | 10/1980 | Percarpio |
| 4,289,726 A | 9/1981 | Potoczky |
| 4,290,534 A | 9/1981 | Percarpio |
| 4,293,078 A | 10/1981 | Percarpio |
| 4,338,764 A | 7/1982 | Percarpio |
| 4,391,128 A | 7/1983 | McWorter |
| 4,392,218 A | 7/1983 | Plunkett, Jr. |
| 4,422,896 A | 12/1983 | Class |
| 4,452,679 A | 6/1984 | Dunn |
| 4,478,873 A | 10/1984 | Masso |
| 4,481,229 A | 11/1984 | Suzuki |
| 4,483,737 A | 11/1984 | Mantei |
| 4,484,479 A | 11/1984 | Eckhardt |
| 4,486,378 A | 12/1984 | Hirata |
| 4,522,510 A | 6/1985 | Rosencwaig |
| 4,524,089 A | 6/1985 | Haque |
| 4,524,616 A | 6/1985 | Drexel |
| 4,552,791 A | 11/1985 | Hahn |
| 4,576,204 A | 3/1986 | Smallborn |
| 4,609,428 A | 9/1986 | Fujimura |
| 4,610,770 A | 9/1986 | Saito |
| 4,648,107 A | 3/1987 | Latter |
| 4,648,281 A | 3/1987 | Morita |
| 4,652,429 A | 3/1987 | Konrad |
| 4,664,279 A | 5/1987 | Obrist |
| 4,667,620 A | 5/1987 | White |
| 4,668,365 A | 5/1987 | Foster |
| 4,683,838 A | 8/1987 | Kimura |
| 4,697,717 A | 10/1987 | Grippi |
| 4,703,187 A | 10/1987 | Hofling |
| 4,716,491 A | 12/1987 | Ohno |
| 4,721,553 A | 1/1988 | Saito |
| 4,725,481 A | 2/1988 | Ostapchenko |
| 4,741,446 A | 5/1988 | Miller |
| 4,756,964 A | 7/1988 | Kincaid |
| 4,767,414 A | 8/1988 | Williams |
| 4,778,721 A | 10/1988 | Sliemers |
| 4,799,246 A | 1/1989 | Fischer |
| 4,808,453 A | 2/1989 | Romberg |
| 4,809,876 A | 3/1989 | Tomaswick |
| 4,824,444 A | 4/1989 | Nomura |
| 4,841,776 A | 6/1989 | Kawachi |
| 4,842,704 A | 6/1989 | Collins |
| 4,844,986 A | 7/1989 | Karakelle |
| 4,846,101 A | 7/1989 | Montgomery |
| 4,853,102 A | 8/1989 | Tateishi |
| 4,869,203 A | 9/1989 | Pinkhasov |
| 4,872,758 A | 10/1989 | Miyazaki |
| 4,874,497 A | 10/1989 | Matsuoka |
| 4,880,675 A | 11/1989 | Mehta |
| 4,883,686 A | 11/1989 | Doehler |
| 4,886,086 A | 12/1989 | Etchells |
| 4,894,256 A | 1/1990 | Gartner |
| 4,894,510 A | 1/1990 | Nakanishi |
| 4,897,285 A | 1/1990 | Wilhelm |
| 4,926,791 A | 5/1990 | Hirose |
| 4,948,628 A | 8/1990 | Montgomery |
| 4,973,504 A | 11/1990 | Romberg |
| 4,991,104 A | 2/1991 | Miller |
| 4,999,014 A | 3/1991 | Gold |
| 5,000,994 A | 3/1991 | Romberg |
| 5,016,564 A | 5/1991 | Nakamura |
| 5,021,114 A | 6/1991 | Saito |
| 5,028,566 A | 7/1991 | Lagendijk |
| 5,030,475 A | 7/1991 | Ackermann |
| 5,032,202 A | 7/1991 | Tsai |
| 5,039,548 A | 8/1991 | Hirose |
| 5,041,303 A | 8/1991 | Wertheimer |
| 5,042,951 A | 8/1991 | Gold |
| 5,044,199 A | 9/1991 | Drexel |
| 5,064,083 A | 11/1991 | Alexander |
| 5,067,491 A | 11/1991 | Taylor |
| 5,079,481 A | 1/1992 | Moslehi |
| 5,082,542 A | 1/1992 | Moslehi |
| 5,084,356 A | 1/1992 | Deak |
| 5,085,904 A | 2/1992 | Deak |
| 5,099,881 A | 3/1992 | Nakajima |
| 5,113,790 A | 5/1992 | Geisler |
| 5,120,966 A | 6/1992 | Kondo |
| 5,131,752 A | 7/1992 | Yu |
| 5,144,196 A | 9/1992 | Gegenwart |
| 5,147,678 A | 9/1992 | Foerch |
| 5,154,943 A | 10/1992 | Etzkorn |
| 5,189,446 A | 2/1993 | Barnes |
| 5,192,849 A | 3/1993 | Moslehi |
| 5,198,725 A | 3/1993 | Chen |
| 5,203,959 A | 4/1993 | Hirose |
| 5,204,141 A | 4/1993 | Roberts |
| 5,209,882 A | 5/1993 | Hattori |
| 5,216,329 A | 6/1993 | Pelleteir |
| 5,224,441 A | 7/1993 | Felts |
| 5,225,024 A | 7/1993 | Hanley |
| 5,232,111 A | 8/1993 | Bums |
| 5,252,178 A | 10/1993 | Moslehi |
| 5,260,095 A | 11/1993 | Affinito |

(56) References Cited

U.S. PATENT DOCUMENTS

| | | |
|---|---|---|
| 5,266,398 A | 11/1993 | Hioki |
| 5,271,274 A | 12/1993 | Khuri-Yakub |
| 5,272,417 A | 12/1993 | Ohmi |
| 5,272,735 A | 12/1993 | Bryan |
| 5,275,299 A | 1/1994 | Konrad |
| 5,286,297 A | 2/1994 | Moslehi |
| 5,292,370 A | 3/1994 | Tsai |
| 5,294,011 A | 3/1994 | Konrad |
| 5,294,464 A | 3/1994 | Geisler |
| 5,297,561 A | 3/1994 | Hulon |
| 5,298,587 A | 3/1994 | Hu |
| 5,300,901 A | 4/1994 | Krummel |
| 5,302,266 A | 4/1994 | Grabarz |
| 5,308,649 A | 5/1994 | Babacz |
| 5,314,561 A | 5/1994 | Komiya |
| 5,320,875 A | 6/1994 | Hu |
| 5,321,634 A | 6/1994 | Obata |
| 5,330,578 A | 7/1994 | Sakama |
| 5,333,049 A | 7/1994 | Ledger |
| 5,338,579 A | 8/1994 | Ogawa et al. |
| 5,346,579 A | 9/1994 | Cook |
| 5,354,286 A | 10/1994 | Mesa |
| 5,356,029 A | 10/1994 | Hogan |
| 5,361,921 A | 11/1994 | Bums |
| 5,364,665 A | 11/1994 | Felts |
| 5,364,666 A | 11/1994 | Williams |
| 5,372,851 A | 12/1994 | Ogawa et al. |
| 5,374,314 A | 12/1994 | Babacz |
| 5,378,510 A | 1/1995 | Thomas |
| 5,381,228 A | 1/1995 | Brace |
| 5,395,644 A | 3/1995 | Affinito |
| 5,396,080 A | 3/1995 | Hannotiau |
| 5,397,956 A | 3/1995 | Araki |
| 5,409,782 A | 4/1995 | Murayama |
| 5,413,813 A | 5/1995 | Cruse |
| 5,423,915 A | 6/1995 | Murata |
| 5,429,070 A | 7/1995 | Campbell |
| 5,433,786 A | 7/1995 | Hu |
| 5,434,008 A | 7/1995 | Felts |
| 5,439,736 A | 8/1995 | Nomura |
| 5,440,446 A | 8/1995 | Shaw |
| 5,443,645 A | 8/1995 | Otoshi |
| 5,444,207 A | 8/1995 | Sekine |
| 5,449,432 A | 9/1995 | Hanawa |
| 5,452,082 A | 9/1995 | Sanger |
| 5,468,520 A | 11/1995 | Williams |
| 5,470,388 A | 11/1995 | Goedicke |
| 5,472,660 A | 12/1995 | Fortin |
| 5,485,091 A | 1/1996 | Verkuil |
| 5,486,701 A | 1/1996 | Norton |
| 5,494,170 A | 2/1996 | Burns |
| 5,494,712 A | 2/1996 | Hu |
| 5,495,958 A | 3/1996 | Konrad |
| 5,508,075 A | 4/1996 | Roulin |
| 5,510,155 A | 4/1996 | Williams |
| 5,513,515 A | 5/1996 | Mayer |
| 5,514,276 A | 5/1996 | Babock |
| 5,521,351 A | 5/1996 | Mahoney |
| 5,522,518 A | 6/1996 | Konrad |
| 5,531,060 A | 7/1996 | Fayet |
| 5,531,683 A | 7/1996 | Kriesel |
| 5,536,253 A | 7/1996 | Haber |
| 5,543,919 A | 8/1996 | Mumola |
| 5,545,375 A | 8/1996 | Tropsha |
| 5,547,508 A | 8/1996 | Affinito |
| 5,547,723 A | 8/1996 | Williams |
| 5,554,223 A | 9/1996 | Imahashi |
| 5,555,471 A | 9/1996 | Xu |
| 5,565,248 A | 10/1996 | Piester |
| 5,569,810 A | 10/1996 | Tsuji |
| 5,571,366 A | 11/1996 | Ishii |
| 5,578,103 A | 11/1996 | Araujo |
| 5,591,898 A | 1/1997 | Mayer |
| 5,593,550 A | 1/1997 | Stewart |
| 5,597,456 A | 1/1997 | Maruyama |
| 5,616,369 A | 4/1997 | Williams |
| 5,620,523 A | 4/1997 | Maeda |
| 5,632,396 A | 5/1997 | Burns |
| 5,633,711 A | 5/1997 | Nelson |
| 5,643,638 A | 7/1997 | Otto |
| 5,652,030 A | 7/1997 | Delperier |
| 5,654,054 A | 8/1997 | Tropsha |
| 5,656,141 A | 8/1997 | Betz |
| 5,658,438 A | 8/1997 | Givens |
| 5,665,280 A | 9/1997 | Tropsha |
| 5,667,840 A | 9/1997 | Tingey |
| 5,674,321 A | 10/1997 | Pu |
| 5,677,010 A | 10/1997 | Esser |
| 5,679,412 A | 10/1997 | Kuehnle |
| 5,679,413 A | 10/1997 | Petrmichl |
| 5,683,771 A | 11/1997 | Tropsha |
| 5,686,157 A | 11/1997 | Harvey |
| 5,690,745 A | 11/1997 | Grunwald |
| 5,691,007 A | 11/1997 | Montgomery |
| 5,693,196 A | 12/1997 | Stewart |
| 5,699,923 A | 12/1997 | Burns |
| 5,702,770 A | 12/1997 | Martin |
| 5,704,983 A | 1/1998 | Thomas et al. |
| 5,716,683 A | 2/1998 | Harvey |
| 5,718,967 A | 2/1998 | Hu |
| 5,725,909 A | 3/1998 | Shaw |
| 5,733,405 A | 3/1998 | Taki |
| 5,736,207 A | 4/1998 | Walther |
| 5,737,179 A | 4/1998 | Shaw |
| 5,738,233 A | 4/1998 | Burns |
| 5,738,920 A | 4/1998 | Knors |
| 5,744,360 A | 4/1998 | Hu |
| 5,750,892 A | 5/1998 | Huang |
| 5,763,033 A | 6/1998 | Tropsha |
| 5,766,362 A | 6/1998 | Montgomery |
| 5,769,273 A | 6/1998 | Sasaki |
| 5,779,074 A | 7/1998 | Burns |
| 5,779,716 A | 7/1998 | Cano |
| 5,779,802 A | 7/1998 | Borghs |
| 5,779,849 A | 7/1998 | Blalock |
| 5,788,670 A | 8/1998 | Reinhard |
| 5,792,940 A | 8/1998 | Ghandhi |
| 5,798,027 A | 8/1998 | Lefebvre |
| 5,800,880 A | 9/1998 | Laurent |
| 5,807,343 A | 9/1998 | Tucker |
| 5,807,605 A | 9/1998 | Tingey |
| 5,812,261 A | 9/1998 | Nelson |
| 5,814,257 A | 9/1998 | Kawata |
| 5,814,738 A | 9/1998 | Pinkerton |
| 5,820,603 A | 10/1998 | Tucker |
| 5,823,373 A | 10/1998 | Sudo |
| 5,824,198 A | 10/1998 | Williams |
| 5,824,607 A | 10/1998 | Trow |
| 5,833,752 A | 11/1998 | Martin |
| 5,837,888 A | 11/1998 | Mayer |
| 5,837,903 A | 11/1998 | Weingand |
| 5,840,167 A | 11/1998 | Kim |
| 5,849,368 A | 12/1998 | Hostettler |
| 5,853,833 A | 12/1998 | Sudo |
| 5,855,686 A | 1/1999 | Rust |
| 5,861,546 A | 1/1999 | Sagi |
| 5,871,700 A | 2/1999 | Konrad |
| 5,877,895 A | 3/1999 | Shaw |
| 5,880,034 A | 3/1999 | Keller |
| 5,888,414 A | 3/1999 | Collins |
| 5,888,591 A | 3/1999 | Gleason |
| 5,897,508 A | 4/1999 | Konrad |
| 5,900,284 A | 5/1999 | Hu |
| 5,900,285 A | 5/1999 | Walther |
| 5,902,461 A | 5/1999 | Xu |
| 5,904,952 A | 5/1999 | Lopata |
| 5,913,140 A | 6/1999 | Roche |
| 5,914,189 A | 6/1999 | Hasz |
| 5,919,328 A | 7/1999 | Tropsha |
| 5,919,420 A | 7/1999 | Niermann |
| 5,935,391 A | 8/1999 | Nakahigashi |
| 5,945,187 A | 8/1999 | Buch-Rasmussen |
| 5,951,527 A | 9/1999 | Sudo |
| 5,952,069 A | 9/1999 | Tropsha |

(56) References Cited

U.S. PATENT DOCUMENTS

| | | |
|---|---|---|
| 5,955,161 A | 9/1999 | Tropsha |
| 5,961,911 A | 10/1999 | Hwang |
| 5,968,620 A | 10/1999 | Harvey |
| 5,972,297 A | 10/1999 | Niermann |
| 5,972,436 A | 10/1999 | Walther |
| 5,985,103 A | 11/1999 | Givens |
| 6,001,429 A | 12/1999 | Martin |
| 6,009,743 A | 1/2000 | Mayer |
| 6,013,337 A | 1/2000 | Knors |
| 6,017,317 A | 1/2000 | Newby |
| 6,018,987 A | 2/2000 | Mayer |
| 6,020,196 A | 2/2000 | Hu |
| 6,027,619 A | 2/2000 | Cathey |
| 6,032,813 A | 3/2000 | Niermann |
| 6,035,717 A | 3/2000 | Carodiskey |
| 6,050,400 A | 4/2000 | Taskis |
| 6,051,151 A | 4/2000 | Keller |
| 6,054,016 A | 4/2000 | Tuda |
| 6,054,188 A | 4/2000 | Tropsha |
| 6,068,884 A | 5/2000 | Rose |
| 6,077,403 A | 6/2000 | Kobayashi |
| 6,081,330 A | 6/2000 | Nelson |
| 6,082,295 A | 7/2000 | Lee |
| 6,083,313 A | 7/2000 | Venkatraman et al. |
| 6,085,927 A | 7/2000 | Kusz |
| 6,090,081 A | 7/2000 | Sudo |
| 6,106,678 A | 8/2000 | Shufflebotham |
| 6,110,395 A | 8/2000 | Gibson, Jr. |
| 6,110,544 A | 8/2000 | Yang |
| 6,112,695 A | 9/2000 | Felts |
| 6,116,081 A | 9/2000 | Ghandhi |
| 6,117,243 A | 9/2000 | Walther |
| 6,118,844 A | 9/2000 | Fischer |
| 6,124,212 A | 9/2000 | Fan |
| 6,125,687 A | 10/2000 | McClelland |
| 6,126,640 A | 10/2000 | Tucker |
| 6,136,275 A | 10/2000 | Niermann |
| 6,139,802 A | 10/2000 | Niermann |
| 6,143,140 A | 11/2000 | Wang |
| 6,149,982 A | 11/2000 | Plester |
| 6,153,269 A | 11/2000 | Gleason |
| 6,156,152 A | 12/2000 | Ogino |
| 6,156,399 A | 12/2000 | Spallek |
| 6,156,435 A | 12/2000 | Gleason |
| 6,160,350 A | 12/2000 | Sakemi |
| 6,161,712 A | 12/2000 | Savitz |
| 6,163,006 A | 12/2000 | Doughty |
| 6,165,138 A | 12/2000 | Miller |
| 6,165,542 A | 12/2000 | Jaworowski |
| 6,165,566 A | 12/2000 | Tropsha |
| 6,171,670 B1 | 1/2001 | Sudo |
| 6,175,612 B1 | 1/2001 | Sato |
| 6,177,142 B1 | 1/2001 | Felts |
| 6,180,185 B1 | 1/2001 | Felts |
| 6,180,191 B1 | 1/2001 | Felts |
| 6,188,079 B1 | 2/2001 | Juvinall |
| 6,189,484 B1 | 2/2001 | Yin |
| 6,190,992 B1 | 2/2001 | Sandhu |
| 6,193,853 B1 | 2/2001 | Yumshtyk |
| 6,196,155 B1 | 3/2001 | Setoyama |
| 6,197,166 B1 | 3/2001 | Moslehi |
| 6,200,658 B1 | 3/2001 | Walther |
| 6,200,675 B1 | 3/2001 | Neerinck |
| 6,204,922 B1 | 3/2001 | Chalmers |
| 6,210,791 B1 | 4/2001 | Skoog |
| 6,214,422 B1 | 4/2001 | Yializis |
| 6,217,716 B1 | 4/2001 | Fai Lai |
| 6,223,683 B1 | 5/2001 | Plester |
| 6,236,459 B1 | 5/2001 | Negandaripour |
| 6,245,190 B1 | 6/2001 | Masuda |
| 6,248,219 B1 | 6/2001 | Wellerdieck |
| 6,248,397 B1 | 6/2001 | Ye |
| 6,251,792 B1 | 6/2001 | Collins |
| 6,254,983 B1 | 7/2001 | Namiki |
| 6,261,643 B1 | 7/2001 | Hasz |
| 6,263,249 B1 | 7/2001 | Stewart |
| 6,271,047 B1 | 8/2001 | Ushio |
| 6,276,296 B1 | 8/2001 | Plester |
| 6,277,331 B1 | 8/2001 | Konrad |
| 6,279,505 B1 | 8/2001 | Plester |
| 6,284,986 B1 | 9/2001 | Dietze |
| 6,306,132 B1 | 10/2001 | Moorman |
| 6,308,556 B1 | 10/2001 | Sagi |
| 6,322,661 B1 | 11/2001 | Bailey, III |
| 6,331,174 B1 | 12/2001 | Reinhard et al. |
| 6,346,596 B1 | 2/2002 | Mallen |
| 6,348,967 B1 | 2/2002 | Nelson |
| 6,350,415 B1 | 2/2002 | Niermann |
| 6,351,075 B1 | 2/2002 | Barankova |
| 6,352,629 B1 | 3/2002 | Wang |
| 6,354,452 B1 | 3/2002 | DeSalvo |
| 6,355,033 B1 | 3/2002 | Moorman |
| 6,365,013 B1 | 4/2002 | Beele |
| 6,375,022 B1 | 4/2002 | Zurcher |
| 6,376,028 B1 | 4/2002 | Laurent |
| 6,379,757 B1 | 4/2002 | Iacovangelo |
| 6,382,441 B1 | 5/2002 | Carano |
| 6,394,979 B1 | 5/2002 | Sharp |
| 6,396,024 B1 | 5/2002 | Doughty |
| 6,399,944 B1 | 6/2002 | Vasilyev |
| 6,402,885 B2 | 6/2002 | Loewenhardt |
| 6,410,926 B1 | 6/2002 | Munro |
| 6,413,645 B1 | 7/2002 | Graff |
| 6,432,494 B1 | 8/2002 | Yang |
| 6,432,510 B1 | 8/2002 | Kim |
| 6,470,650 B1 | 10/2002 | Lohwasser |
| 6,471,822 B1 | 10/2002 | Yin |
| 6,475,622 B2 | 11/2002 | Namiki |
| 6,482,509 B2 | 11/2002 | Buch-Rasmussen et al. |
| 6,486,081 B1 | 11/2002 | Ishikawa |
| 6,500,500 B1 | 12/2002 | Okamura |
| 6,503,579 B1 | 1/2003 | Murakami |
| 6,518,195 B1 | 2/2003 | Collins |
| 6,524,448 B2 | 2/2003 | Brinkmann |
| 6,539,890 B1 | 4/2003 | Felts |
| 6,544,610 B1 | 4/2003 | Minami |
| 6,551,267 B1 | 4/2003 | Cohen |
| 6,558,679 B2 | 5/2003 | Flament-Garcia et al. |
| 6,562,189 B1 | 5/2003 | Quiles |
| 6,565,791 B1 | 5/2003 | Laurent |
| 6,582,426 B2 | 6/2003 | Moorman |
| 6,582,823 B1 | 6/2003 | Sakhrani et al. |
| 6,584,828 B2 | 7/2003 | Sagi |
| 6,595,961 B2 | 7/2003 | Hetzler |
| 6,597,193 B2 | 7/2003 | Lagowski |
| 6,599,569 B1 | 7/2003 | Humele |
| 6,599,594 B1 | 7/2003 | Walther |
| 6,602,206 B1 | 8/2003 | Niermann |
| 6,616,632 B2 | 9/2003 | Sharp |
| 6,620,139 B1 | 9/2003 | Plicchi |
| 6,620,334 B2 | 9/2003 | Kanno |
| 6,623,861 B2 | 9/2003 | Martin |
| 6,638,403 B1 | 10/2003 | Inaba |
| 6,638,876 B2 | 10/2003 | Levy |
| 6,645,354 B1 | 11/2003 | Gorokhovsky |
| 6,651,835 B2 | 11/2003 | Iskra |
| 6,652,520 B2 | 11/2003 | Moorman |
| 6,656,540 B2 | 12/2003 | Sakamoto |
| 6,658,919 B2 | 12/2003 | Chatard |
| 6,662,957 B2 | 12/2003 | Zurcher |
| 6,663,601 B2 | 12/2003 | Hetzler |
| 6,670,200 B2 | 12/2003 | Ushio |
| 6,673,199 B1 | 1/2004 | Yamartino |
| 6,680,091 B2 | 1/2004 | Buch-Rasmussen et al. |
| 6,680,621 B2 | 1/2004 | Savtchouk |
| 6,683,308 B2 | 1/2004 | Itagaki |
| 6,684,683 B2 | 2/2004 | Potyrailo |
| 6,702,898 B2 | 3/2004 | Hosoi |
| 6,706,412 B2 | 3/2004 | Yializis |
| 6,746,430 B2 | 6/2004 | Lubrecht |
| 6,749,078 B2 | 6/2004 | Iskra |
| 6,752,899 B2 | 6/2004 | Singh |
| 6,753,972 B1 | 6/2004 | Hirose |
| 6,757,056 B1 | 6/2004 | Meeks |

(56) References Cited

U.S. PATENT DOCUMENTS

| | | |
|---|---|---|
| 6,764,714 B2 | 7/2004 | Wei |
| 6,765,466 B2 | 7/2004 | Miyata |
| 6,766,682 B2 | 7/2004 | Engle |
| 6,774,018 B2 | 8/2004 | Mikhael |
| 6,796,780 B1 | 9/2004 | Chatard |
| 6,800,852 B2 | 10/2004 | Larson |
| 6,808,753 B2 | 10/2004 | Rule |
| 6,810,106 B2 | 10/2004 | Sato |
| 6,815,014 B2 | 11/2004 | Gabelnick |
| 6,818,310 B2 | 11/2004 | Namiki |
| 6,827,972 B2 | 12/2004 | Darras |
| 6,837,954 B2 | 1/2005 | Carano |
| 6,844,075 B1 | 1/2005 | Saak |
| 6,853,141 B2 | 2/2005 | Hoffman |
| 6,858,259 B2 | 2/2005 | Affinito |
| 6,863,731 B2 | 3/2005 | Elsayed-Ali |
| 6,864,773 B2 | 3/2005 | Perrin |
| 6,866,656 B2 | 3/2005 | Tingey |
| 6,872,428 B2 | 3/2005 | Yang |
| 6,876,154 B2 | 4/2005 | Appleyard |
| 6,885,727 B2 | 4/2005 | Tamura |
| 6,887,578 B2 | 5/2005 | Gleason |
| 6,891,158 B2 | 5/2005 | Larson |
| 6,892,567 B1 | 5/2005 | Morrow |
| 6,899,054 B1 | 5/2005 | Bardos |
| 6,905,769 B2 | 6/2005 | Komada |
| 6,910,597 B2 | 6/2005 | Iskra |
| 6,911,779 B2 | 6/2005 | Madocks |
| 6,919,107 B2 | 7/2005 | Schwarzenbach |
| 6,919,114 B1 | 7/2005 | Darras |
| 6,933,460 B2 | 8/2005 | Vanden Brande |
| 6,946,164 B2 | 9/2005 | Huang |
| 6,952,949 B2 | 10/2005 | Moore |
| 6,960,393 B2 | 11/2005 | Yializis |
| 6,962,671 B2 | 11/2005 | Martin |
| 6,965,221 B2 | 11/2005 | Lipcsei |
| 6,981,403 B2 | 1/2006 | Ascheman |
| 6,989,675 B2 | 1/2006 | Kesil |
| 6,995,377 B2 | 2/2006 | Darr |
| 7,029,755 B2 | 4/2006 | Terry |
| 7,029,803 B2 | 4/2006 | Becker |
| 7,039,158 B1 | 5/2006 | Janik |
| 7,052,736 B2 | 5/2006 | Wei |
| 7,052,920 B2 | 5/2006 | Ushio |
| 7,059,268 B2 | 6/2006 | Russell |
| 7,067,034 B2 | 6/2006 | Bailey, III |
| 7,074,501 B2 | 7/2006 | Czeremuszkin |
| 7,098,453 B2 | 8/2006 | Ando |
| 7,109,070 B2 | 9/2006 | Behle |
| 7,112,352 B2 | 9/2006 | Schaepkens |
| 7,112,541 B2 | 9/2006 | Xia |
| 7,115,310 B2 | 10/2006 | Jacoud |
| 7,118,538 B2 | 10/2006 | Konrad |
| 7,119,908 B2 | 10/2006 | Nomoto |
| 7,121,135 B2 | 10/2006 | Moore |
| 7,130,373 B2 | 10/2006 | Omote |
| 7,150,299 B2 | 12/2006 | Hertzler |
| 7,160,292 B2 | 1/2007 | Moorman |
| 7,180,849 B2 | 2/2007 | Hirokane |
| 7,183,197 B2 | 2/2007 | Won |
| 7,188,734 B2 | 3/2007 | Konrad |
| 7,189,290 B2 | 3/2007 | Hama |
| 7,193,724 B2 | 3/2007 | Isei |
| 7,198,685 B2 | 4/2007 | Hetzler |
| 7,206,074 B2 | 4/2007 | Fujimoto |
| 7,244,381 B2 | 7/2007 | Chatard |
| 7,253,892 B2 | 8/2007 | Semersky |
| 7,286,242 B2 | 10/2007 | Kim |
| 7,288,293 B2 | 10/2007 | Koulik |
| 7,297,216 B2 | 11/2007 | Hetzler |
| 7,297,640 B2 | 11/2007 | Xie |
| 7,300,684 B2 | 11/2007 | Boardman |
| 7,303,789 B2 | 12/2007 | Saito |
| 7,303,790 B2 | 12/2007 | Delaunay |
| 7,306,852 B2 | 12/2007 | Komada |
| 7,332,227 B2 | 2/2008 | Hardman |
| 7,338,576 B2 | 3/2008 | Ono |
| 7,339,682 B2 | 3/2008 | Aiyer |
| 7,344,766 B1 | 3/2008 | Sorensen |
| 7,348,055 B2 | 3/2008 | Chappa |
| 7,348,192 B2 | 3/2008 | Mikami |
| 7,362,425 B2 | 4/2008 | Meeks |
| 7,381,469 B2 | 6/2008 | Moelle |
| 7,390,573 B2 | 6/2008 | Korevaar |
| 7,399,500 B2 | 7/2008 | Bicker |
| 7,405,008 B2 | 7/2008 | Domine |
| 7,409,313 B2 | 8/2008 | Ringermacher |
| 7,411,685 B2 | 8/2008 | Takashima |
| RE40,531 E | 10/2008 | Graff |
| 7,431,989 B2 | 10/2008 | Sakhrani |
| 7,438,783 B2 | 10/2008 | Miyata |
| 7,444,955 B2 | 11/2008 | Boardman |
| 7,455,892 B2 | 11/2008 | Goodwin |
| 7,480,363 B2 | 1/2009 | Lasiuk |
| 7,488,683 B2 | 2/2009 | Kobayashi |
| 7,494,941 B2 | 2/2009 | Kasahara |
| 7,507,378 B2 | 3/2009 | Reichenbach |
| 7,513,953 B1 | 4/2009 | Felts |
| 7,520,965 B2 | 4/2009 | Wei |
| 7,521,022 B2 | 4/2009 | Konrad |
| 7,534,615 B2 | 5/2009 | Havens |
| 7,534,733 B2 | 5/2009 | Bookbinder |
| RE40,787 E | 6/2009 | Martin |
| 7,541,069 B2 | 6/2009 | Tudhope |
| 7,552,620 B2 | 6/2009 | DeRoos |
| 7,553,529 B2 | 6/2009 | Sakhrani |
| 7,555,934 B2 | 7/2009 | DeRoos |
| 7,569,035 B1 | 8/2009 | Wilmot |
| 7,579,056 B2 | 8/2009 | Brown |
| 7,586,824 B2 | 8/2009 | Hirokane |
| 7,582,868 B2 | 9/2009 | Jiang |
| 7,595,097 B2 | 9/2009 | Iacovangelo |
| 7,608,151 B2 | 10/2009 | Tudhope |
| 7,609,605 B2 | 10/2009 | Hirokane |
| 7,618,686 B2 | 11/2009 | Colpo |
| 7,624,622 B1 | 12/2009 | Mayer |
| 7,625,494 B2 | 12/2009 | Honda |
| 7,641,636 B2 | 1/2010 | Moesli |
| 7,645,696 B1 | 1/2010 | Dulkin |
| 7,648,481 B2 | 1/2010 | Geiger |
| 7,682,816 B2 | 3/2010 | Kim |
| 7,694,403 B2 | 4/2010 | Moulton |
| 7,699,933 B2 | 4/2010 | Lizenberg |
| 7,704,683 B2 | 5/2010 | Wittenberg |
| 7,713,638 B2 | 5/2010 | Moelle |
| 7,736,689 B2 | 6/2010 | Chappa |
| 7,740,610 B2 | 6/2010 | Moh |
| 7,744,567 B2 | 6/2010 | Glowacki |
| 7,744,790 B2 | 6/2010 | Behle |
| 7,745,228 B2 | 6/2010 | Schwind |
| 7,745,547 B1 | 6/2010 | Auerbach |
| 7,749,914 B2 | 7/2010 | Honda |
| 7,754,302 B2 | 7/2010 | Yamaski |
| 7,766,882 B2 | 8/2010 | Sudo |
| 7,780,866 B2 | 8/2010 | Miller |
| 7,785,862 B2 | 8/2010 | Kim |
| 7,790,475 B2 | 9/2010 | Galbraith |
| 7,798,993 B2 | 9/2010 | Lim |
| 7,803,305 B2 | 9/2010 | Ahern |
| 7,807,242 B2 | 10/2010 | Sorensen |
| 7,815,922 B2 | 10/2010 | Chaney |
| 7,846,293 B2 | 12/2010 | Iwasaki |
| 7,854,889 B2 | 12/2010 | Perot |
| 7,867,366 B1 | 1/2011 | McFarland |
| 7,901,783 B2 | 3/2011 | Rose |
| 7,905,866 B2 | 3/2011 | Haider |
| 7,922,880 B1 | 4/2011 | Pradhan |
| 7,922,958 B2 | 4/2011 | D'Arrigo |
| 7,931,955 B2 | 4/2011 | Behle |
| 7,932,678 B2 | 4/2011 | Madocks |
| 7,934,613 B2 | 5/2011 | Sudo |
| 7,943,205 B2 | 5/2011 | Schaepkens |
| 7,947,337 B2 | 5/2011 | Kuepper |
| 7,955,986 B2 | 6/2011 | Hoffman |

(56) References Cited

U.S. PATENT DOCUMENTS

| | | |
|---|---|---|
| 7,960,043 B2 | 6/2011 | Harris |
| 7,964,438 B2 | 6/2011 | Roca I Cabarrocas |
| 7,967,945 B2 | 6/2011 | Glukhoy |
| 7,975,646 B2 | 7/2011 | Rius |
| 7,985,188 B2 | 7/2011 | Felts |
| 8,025,915 B2 | 9/2011 | Haines |
| 8,038,858 B1 | 10/2011 | Bures |
| 8,039,524 B2 | 10/2011 | Chappa |
| 8,056,719 B2 | 11/2011 | Porret |
| 8,062,266 B2 | 11/2011 | McKinnon |
| 8,066,854 B2 | 11/2011 | Storey |
| 8,070,917 B2 | 12/2011 | Tsukamoto |
| 8,075,995 B2 | 12/2011 | Zhao |
| 8,092,605 B2 | 1/2012 | Shannon |
| 8,101,246 B2 | 1/2012 | Fayet |
| 8,197,452 B2 | 6/2012 | Harding |
| 8,227,025 B2 | 7/2012 | Lewis |
| 8,258,486 B2 | 9/2012 | Avnery |
| 8,268,410 B2 | 9/2012 | Moelle |
| 8,273,222 B2 | 9/2012 | Wei |
| 8,277,025 B2 | 10/2012 | Nakazawa et al. |
| 8,313,455 B2 | 11/2012 | DiGregorio |
| 8,323,166 B2 | 12/2012 | Haines |
| 8,389,958 B2 | 3/2013 | Vo-Dinh |
| 8,397,667 B2 | 3/2013 | Behle |
| 8,409,441 B2 | 4/2013 | Wilt |
| 8,418,650 B2 | 4/2013 | Goto |
| 8,435,605 B2 | 5/2013 | Aitken et al. |
| 8,475,886 B2 | 7/2013 | Chen et al. |
| 8,512,796 B2 | 8/2013 | Felts |
| 8,524,331 B2 | 9/2013 | Honda |
| 8,592,015 B2 | 11/2013 | Bicker |
| 8,603,638 B2 | 12/2013 | Liu |
| 8,618,509 B2 | 12/2013 | Vo-Dinh |
| 8,623,324 B2 | 1/2014 | Diwu |
| 8,633,034 B2 | 1/2014 | Troller |
| 8,747,962 B2 | 6/2014 | Bicker |
| 8,802,603 B2 | 8/2014 | D'Souza |
| 8,816,022 B2 | 8/2014 | Zhao |
| 9,068,565 B2 | 6/2015 | Alarcon |
| 2001/0000279 A1 | 4/2001 | Daniels |
| 2001/0021356 A1 | 9/2001 | Konrad |
| 2001/0038894 A1 | 11/2001 | Komada |
| 2001/0042510 A1 | 11/2001 | Plester |
| 2001/0043997 A1 | 11/2001 | Uddin |
| 2002/0006487 A1 | 1/2002 | O'Connor |
| 2002/0007796 A1 | 1/2002 | Gorokhovsky |
| 2002/0070647 A1 | 6/2002 | Ginovker |
| 2002/0117114 A1 | 8/2002 | Ikenaga |
| 2002/0125900 A1 | 9/2002 | Savtchouk |
| 2002/0130674 A1 | 9/2002 | Logowski |
| 2002/0141477 A1 | 10/2002 | Akahori |
| 2002/0153103 A1 | 10/2002 | Madocks |
| 2002/0155218 A1 | 10/2002 | Meyer |
| 2002/0170495 A1 | 11/2002 | Nakamura |
| 2002/0178947 A1 | 11/2002 | Darras |
| 2002/0182101 A1 | 12/2002 | Koulik |
| 2002/0185226 A1 | 12/2002 | Lea |
| 2002/0190207 A1 | 12/2002 | Levy |
| 2003/0010454 A1 | 1/2003 | Bailey, III |
| 2003/0013818 A1 | 1/2003 | Hakuta |
| 2003/0029837 A1 | 2/2003 | Trow |
| 2003/0031806 A1 | 2/2003 | Jinks |
| 2003/0046982 A1 | 3/2003 | Chartard |
| 2003/0102087 A1 | 6/2003 | Ito |
| 2003/0159654 A1 | 8/2003 | Arnold |
| 2003/0215652 A1 | 11/2003 | O'Connor |
| 2003/0219547 A1 | 11/2003 | Arnold |
| 2003/0232150 A1 | 12/2003 | Arnold |
| 2004/0024371 A1 | 2/2004 | Plicchi |
| 2004/0039401 A1 | 2/2004 | Chow |
| 2004/0040372 A1 | 3/2004 | Plester |
| 2004/0045811 A1 | 3/2004 | Wang |
| 2004/0050744 A1 | 3/2004 | Hama |
| 2004/0055538 A1 | 3/2004 | Gorokhovsky |
| 2004/0071960 A1 | 4/2004 | Weber |
| 2004/0082917 A1 | 4/2004 | Hetzler |
| 2004/0084151 A1 | 5/2004 | Kim |
| 2004/0125913 A1 | 7/2004 | Larson |
| 2004/0135081 A1 | 7/2004 | Larson |
| 2004/0149225 A1 | 8/2004 | Weikart |
| 2004/0175961 A1 | 9/2004 | Olsen |
| 2004/0177676 A1 | 9/2004 | Moore |
| 2004/0195960 A1 | 10/2004 | Czeremuszkin |
| 2004/0206309 A1 | 10/2004 | Bera |
| 2004/0217081 A1 | 11/2004 | Konrad |
| 2004/0247948 A1 | 12/2004 | Behle |
| 2004/0267194 A1 | 12/2004 | Sano |
| 2005/0000962 A1 | 1/2005 | Crawford |
| 2005/0010175 A1 | 1/2005 | Beedon |
| 2005/0019503 A1 | 1/2005 | Komada |
| 2005/0037165 A1 | 2/2005 | Ahern |
| 2005/0039854 A1 | 2/2005 | Matsuyama |
| 2005/0045472 A1 | 3/2005 | Nagata |
| 2005/0057754 A1 | 3/2005 | Smith |
| 2005/0073323 A1 | 4/2005 | Kohno |
| 2005/0075611 A1 | 4/2005 | Heltzer |
| 2005/0075612 A1 | 4/2005 | Lee |
| 2005/0161149 A1 | 7/2005 | Yokota |
| 2005/0169803 A1 | 8/2005 | Betz |
| 2005/0190450 A1 | 9/2005 | Becker |
| 2005/0196629 A1 | 9/2005 | Bariatinsky |
| 2005/0199571 A1 | 9/2005 | Geisler |
| 2005/0206907 A1 | 9/2005 | Fujimoto |
| 2005/0211383 A1 | 9/2005 | Miyata |
| 2005/0223988 A1 | 10/2005 | Behle |
| 2005/0227002 A1 | 10/2005 | Lizenberg |
| 2005/0227022 A1 | 10/2005 | Domine |
| 2005/0229850 A1 | 10/2005 | Behle |
| 2005/0233077 A1 | 10/2005 | Lizenberg |
| 2005/0233091 A1 | 10/2005 | Kumar |
| 2005/0236346 A1 | 10/2005 | Whitney |
| 2005/0260504 A1 | 11/2005 | Becker |
| 2005/0284550 A1 | 12/2005 | Bicker |
| 2006/0005608 A1 | 1/2006 | Kutzhoffer |
| 2006/0013997 A1 | 1/2006 | Kuepper |
| 2006/0014309 A1 | 1/2006 | Sachdev |
| 2006/0024849 A1 | 2/2006 | Zhu |
| 2006/0042755 A1 | 3/2006 | Holmberg |
| 2006/0046006 A1 | 3/2006 | Bastion |
| 2006/0051252 A1 | 3/2006 | Yuan |
| 2006/0051520 A1 | 3/2006 | Behle |
| 2006/0076231 A1 | 4/2006 | Wei |
| 2006/0086320 A1 | 4/2006 | Lizenberg |
| 2006/0099340 A1 | 5/2006 | Behle |
| 2006/0121222 A1 | 6/2006 | Audrich |
| 2006/0121613 A1 | 6/2006 | Havens |
| 2006/0121623 A1 | 6/2006 | He |
| 2006/0127699 A1 | 6/2006 | Moelle |
| 2006/0135945 A1 | 6/2006 | Bankiewicz |
| 2006/0138326 A1 | 6/2006 | Jiang |
| 2006/0150909 A1 | 7/2006 | Behle |
| 2006/0169026 A1 | 8/2006 | Kage |
| 2006/0178627 A1 | 8/2006 | Geiger |
| 2006/0183345 A1 | 8/2006 | Nguyen |
| 2006/0192973 A1 | 8/2006 | Aiyer |
| 2006/0196419 A1 | 9/2006 | Tudhope |
| 2006/0198903 A1 | 9/2006 | Storey |
| 2006/0198965 A1 | 9/2006 | Tudhope |
| 2006/0200078 A1 | 9/2006 | Konrad |
| 2006/0200084 A1 | 9/2006 | Ito |
| 2006/0210425 A1 | 9/2006 | Mirkarimi |
| 2006/0228497 A1 | 10/2006 | Kumar |
| 2006/0260360 A1 | 11/2006 | Dick |
| 2007/0003441 A1 | 1/2007 | Wohleb |
| 2007/0009673 A1 | 1/2007 | Fukazawa et al. |
| 2007/0017870 A1 | 1/2007 | Belov |
| 2007/0048456 A1 | 3/2007 | Keshner |
| 2007/0049048 A1 | 3/2007 | Rauf |
| 2007/0051629 A1 | 3/2007 | Donlik |
| 2007/0065680 A1 | 3/2007 | Schultheis |
| 2007/0076833 A1 | 4/2007 | Becker |
| 2007/0102344 A1 | 5/2007 | Konrad |
| 2007/0123920 A1 | 5/2007 | Inokuti |

(56) References Cited

U.S. PATENT DOCUMENTS

| | | |
|---|---|---|
| 2007/0148326 A1 | 6/2007 | Hatings |
| 2007/0168187 A1 | 7/2007 | Song |
| 2007/0184657 A1 | 8/2007 | Iijima |
| 2007/0187229 A1 | 8/2007 | Aksenov |
| 2007/0187280 A1 | 8/2007 | Haines |
| 2007/0205096 A1 | 9/2007 | Nagashima |
| 2007/0215009 A1 | 9/2007 | Shimazu |
| 2007/0215046 A1 | 9/2007 | Lupke |
| 2007/0218265 A1 | 9/2007 | Harris |
| 2007/0224236 A1 | 9/2007 | Boden |
| 2007/0229844 A1 | 10/2007 | Holz |
| 2007/0231655 A1 | 10/2007 | Ha |
| 2007/0232066 A1 | 10/2007 | Bicker |
| 2007/0235890 A1 | 10/2007 | Lewis |
| 2007/0243618 A1 | 10/2007 | Hatchett |
| 2007/0251458 A1 | 11/2007 | Mund |
| 2007/0258894 A1 | 11/2007 | Melker et al. |
| 2007/0259184 A1 | 11/2007 | Martin |
| 2007/0281108 A1 | 12/2007 | Weikart |
| 2007/0281117 A1 | 12/2007 | Kaplan |
| 2007/0287950 A1 | 12/2007 | Kjeken |
| 2007/0287954 A1 | 12/2007 | Zhao |
| 2007/0298189 A1 | 12/2007 | Straemke |
| 2008/0011232 A1 | 1/2008 | Ruis |
| 2008/0017113 A1 | 1/2008 | Goto |
| 2008/0023414 A1 | 1/2008 | Konrad |
| 2008/0027400 A1 | 1/2008 | Harding |
| 2008/0045880 A1 | 2/2008 | Kjeken |
| 2008/0050567 A1 | 2/2008 | Kawashima |
| 2008/0050932 A1 | 2/2008 | Lakshmanan |
| 2008/0053373 A1 | 3/2008 | Mund |
| 2008/0069970 A1 | 3/2008 | Wu |
| 2008/0071228 A1 | 3/2008 | Wu |
| 2008/0210550 A1 | 3/2008 | Mund |
| 2008/0081184 A1 | 4/2008 | Kubo |
| 2008/0090039 A1 | 4/2008 | Klein |
| 2008/0093245 A1 | 4/2008 | Periasamy |
| 2008/0102206 A1 | 5/2008 | Wagner |
| 2008/0109017 A1 | 5/2008 | Herweck |
| 2008/0110852 A1 | 5/2008 | Kuroda |
| 2008/0113109 A1 | 5/2008 | Moelle |
| 2008/0118734 A1 | 5/2008 | Goodwin |
| 2008/0131628 A1 | 6/2008 | Abensour |
| 2008/0131638 A1 | 6/2008 | Hutton |
| 2008/0139003 A1 | 6/2008 | Pirzada |
| 2008/0145271 A1 | 6/2008 | Kidambi |
| 2008/0187681 A1 | 8/2008 | Hofrichter |
| 2008/0202414 A1 | 8/2008 | Yan |
| 2008/0206477 A1 | 8/2008 | Leontaris |
| 2008/0220164 A1 | 9/2008 | Bauch |
| 2008/0223815 A1 | 9/2008 | Konrad |
| 2008/0233355 A1 | 9/2008 | Henze |
| 2008/0260966 A1 | 10/2008 | Hanawa |
| 2008/0277332 A1 | 11/2008 | Liu |
| 2008/0289957 A1 | 11/2008 | Takigawa |
| 2008/0292806 A1 | 11/2008 | Wei |
| 2008/0295772 A1 | 12/2008 | Park |
| 2008/0303131 A1 | 12/2008 | Mcelrea |
| 2008/0312607 A1 | 12/2008 | Delmotte |
| 2008/0314318 A1 | 12/2008 | Han |
| 2009/0004091 A1 | 1/2009 | Kang |
| 2009/0004363 A1 | 1/2009 | Keshner |
| 2009/0017217 A1 | 1/2009 | Hass |
| 2009/0022981 A1 | 1/2009 | Yoshida |
| 2009/0029402 A1 | 1/2009 | Papkovsky |
| 2009/0031953 A1 | 2/2009 | Ingle |
| 2009/0032393 A1 | 2/2009 | Madocks |
| 2009/0039240 A1 | 2/2009 | Van Nijnatten |
| 2009/0053491 A1 | 3/2009 | Laboda |
| 2009/0061237 A1 | 3/2009 | Gates |
| 2009/0065485 A1 | 3/2009 | O'Neill |
| 2009/0069790 A1 | 3/2009 | Yokley |
| 2009/0081797 A1 | 3/2009 | Fadeev |
| 2009/0099512 A1 | 4/2009 | Digregorio |
| 2009/0104392 A1 | 4/2009 | Takada |
| 2009/0117268 A1 | 5/2009 | Lewis |
| 2009/0117389 A1 | 5/2009 | Amberg-Schwab |
| 2009/0122832 A1 | 5/2009 | Feist |
| 2009/0134884 A1 | 5/2009 | Bosselmann |
| 2009/0137966 A1 | 5/2009 | Rueckert |
| 2009/0142227 A1 | 6/2009 | Fuchs |
| 2009/0142514 A1 | 6/2009 | O'Neill |
| 2009/0147719 A1 | 6/2009 | Rak |
| 2009/0149816 A1 | 6/2009 | Hetzler |
| 2009/0155490 A1 | 6/2009 | Bicker |
| 2009/0162571 A1 | 6/2009 | Haines |
| 2009/0166312 A1 | 7/2009 | Giraud |
| 2009/0176031 A1 | 7/2009 | Armellin |
| 2009/0214801 A1 | 8/2009 | Higashi |
| 2009/0220948 A1 | 9/2009 | Oviso et al. |
| 2009/0263668 A1 | 10/2009 | David |
| 2009/0274851 A1 | 11/2009 | Goudar |
| 2009/0280268 A1 | 11/2009 | Glukhoy |
| 2009/0297730 A1 | 12/2009 | Glukhoy |
| 2009/0306595 A1 | 12/2009 | Shih |
| 2009/0326517 A1 | 12/2009 | Bork |
| 2010/0021998 A1 | 1/2010 | Sanyal |
| 2010/0028238 A1 | 2/2010 | Maschwitz |
| 2010/0034985 A1 | 2/2010 | Krueger |
| 2010/0075077 A1 | 3/2010 | Bicker |
| 2010/0086808 A1 | 4/2010 | Nagata |
| 2010/0089097 A1 | 4/2010 | Brack |
| 2010/0104770 A1 | 4/2010 | Goudar |
| 2010/0105208 A1 | 4/2010 | Winniczek |
| 2010/0132762 A1 | 6/2010 | Graham, Jr. |
| 2010/0145284 A1 | 6/2010 | Togashi |
| 2010/0149540 A1 | 6/2010 | Boukherroub |
| 2010/0174239 A1 | 7/2010 | Yodfat |
| 2010/0174245 A1 | 7/2010 | Halverson |
| 2010/0178490 A1 | 7/2010 | Cerny |
| 2010/0186740 A1 | 7/2010 | Lewis |
| 2010/0190036 A1 | 7/2010 | Komvopoulos |
| 2010/0193461 A1 | 8/2010 | Boutroy |
| 2010/0195471 A1 | 8/2010 | Hirokane |
| 2010/0204648 A1 | 8/2010 | Stout |
| 2010/0230281 A1 | 9/2010 | Park |
| 2010/0231194 A1 | 9/2010 | Bauch |
| 2010/0237545 A1 | 9/2010 | Haury |
| 2010/0273261 A1 | 10/2010 | Chen |
| 2010/0275847 A1 | 11/2010 | Yamasaki |
| 2010/0279397 A1 | 11/2010 | Crawford |
| 2010/0298738 A1 | 11/2010 | Felts |
| 2010/0298779 A1 | 11/2010 | Hetzler |
| 2011/0037159 A1 | 2/2011 | Mcelerea |
| 2011/0046570 A1 | 2/2011 | Stout |
| 2011/0056912 A1 | 3/2011 | Magsuyama |
| 2011/0065798 A1 | 3/2011 | Hoang |
| 2011/0079582 A1 | 4/2011 | Yonesu |
| 2011/0093056 A1 | 4/2011 | Kaplan |
| 2011/0111132 A1 | 5/2011 | Wei |
| 2011/0117202 A1 | 5/2011 | Bourke, Jr. |
| 2011/0117288 A1 | 5/2011 | Honda |
| 2011/0137263 A1 | 6/2011 | Ashmead |
| 2011/0152820 A1 | 6/2011 | Chattaraj |
| 2011/0159101 A1 | 6/2011 | Kurdyumov et al. |
| 2011/0160662 A1 | 6/2011 | Stout |
| 2011/0160663 A1 | 6/2011 | Stout |
| 2011/0174220 A1 | 7/2011 | Laure |
| 2011/0186537 A1 | 8/2011 | Rodriguez San Juan et al. |
| 2011/0188537 A1 | 8/2011 | Rodriguez San Juan |
| 2011/0220490 A1 | 9/2011 | Wei |
| 2011/0253674 A1 | 10/2011 | Chung |
| 2011/0313363 A1 | 12/2011 | D'Souza et al. |
| 2011/0319758 A1 | 12/2011 | Wang |
| 2011/0319813 A1 | 12/2011 | Kamen |
| 2012/0003497 A1 | 1/2012 | Handy |
| 2012/0004339 A1 | 1/2012 | Chappa |
| 2012/0021136 A1 | 1/2012 | Dzengeleski |
| 2012/0031070 A1 | 2/2012 | Slough |
| 2012/0035543 A1 | 2/2012 | Kamen |
| 2012/0052123 A9 | 3/2012 | Kurdyumov et al. |
| 2012/0053530 A1 | 3/2012 | Zhao |
| 2012/0058351 A1 | 3/2012 | Zhao |
| 2012/0065612 A1 | 3/2012 | Stout |

(56) References Cited

U.S. PATENT DOCUMENTS

| | | | |
|---|---|---|---|
| 2012/0097527 A1 | 4/2012 | Kodaira | |
| 2012/0097870 A1 | 4/2012 | Leray | |
| 2012/0108058 A1 | 5/2012 | Ha | |
| 2012/0123345 A1 | 5/2012 | Felts | |
| 2012/0149871 A1 | 5/2012 | Saxena | |
| 2012/0141913 A1 | 6/2012 | Lee | |
| 2012/0143148 A1 | 6/2012 | Zhao | |
| 2012/0171386 A1 | 7/2012 | Bicker | |
| 2012/0174239 A1 | 7/2012 | Anderson et al. | |
| 2012/0175384 A1 | 7/2012 | Greter | |
| 2012/0183954 A1 | 7/2012 | Diwu | |
| 2012/0205374 A1 | 8/2012 | Klumpen | |
| 2012/0231182 A1 | 9/2012 | Stevens | |
| 2012/0234720 A1 | 9/2012 | Digregorio | |
| 2012/0252709 A1 | 10/2012 | Felts | |
| 2013/0041241 A1 | 2/2013 | Felts | |
| 2013/0046375 A1 | 2/2013 | Chen | |
| 2013/0057677 A1 | 3/2013 | Weil | |
| 2013/0072025 A1 | 3/2013 | Singh | |
| 2013/0081953 A1 | 4/2013 | Bruna et al. | |
| 2013/0190695 A1 | 7/2013 | Wu | |
| 2013/0209704 A1 | 8/2013 | Krueger | |
| 2013/0264303 A1 | 10/2013 | Andersen | |
| 2013/0296235 A1 | 11/2013 | Alarcon | |
| 2014/0010969 A1 | 1/2014 | Bicker | |
| 2014/0052076 A1 | 2/2014 | Zhao | |
| 2014/0054803 A1 | 2/2014 | Chen | |
| 2014/0099455 A1 | 4/2014 | Stanley | |
| 2014/0110297 A1 | 4/2014 | Trotter | |
| 2014/0147654 A1 | 5/2014 | Walthe | |
| 2014/0151320 A1 | 6/2014 | Chang | |
| 2014/0151370 A1 | 6/2014 | Chang | |
| 2014/0187666 A1 | 7/2014 | Aizenberg | |
| 2014/0190846 A1 | 7/2014 | Belt | |
| 2014/0221934 A1 | 8/2014 | Janvier | |
| 2014/0251856 A1 | 9/2014 | Larsson | |
| 2014/0251859 A1 | 9/2014 | Weikart | |
| 2014/0305830 A1 | 10/2014 | Bicker | |
| 2015/0165125 A1 | 6/2015 | Faucher | |
| 2015/0224263 A1 | 8/2015 | Dugand | |

FOREIGN PATENT DOCUMENTS

| | | |
|---|---|---|
| AU | 2002354470 B2 | 5/2007 |
| CA | 2085805 | 12/1992 |
| CA | 2277679 A1 | 7/1997 |
| CA | 2355681 | 7/2000 |
| CA | 2571380 A1 | 7/2006 |
| CA | 2718253 | 9/2009 |
| CA | 2268719 C | 8/2010 |
| CN | 2546041 Y | 4/2003 |
| CN | 1711310 A | 12/2005 |
| CN | 2766863 Y | 3/2006 |
| CN | 1898172 A | 1/2007 |
| CN | 201002786 Y | 1/2008 |
| CN | 101147813 A | 3/2008 |
| CN | 201056331 Y | 5/2008 |
| CN | 102581274 A | 7/2012 |
| DE | 1147836 | 4/1969 |
| DE | 1147838 | 4/1969 |
| DE | 3632748 A1 | 4/1988 |
| DE | 3908418 A1 | 9/1990 |
| DE | 4214401 C1 | 3/1993 |
| DE | 4204082 A1 | 8/1993 |
| DE | 4316349 A1 | 11/1994 |
| DE | 4438359 | 5/1996 |
| DE | 19707645 A1 | 8/1998 |
| DE | 19830794 A1 | 1/2000 |
| DE | 19912737 A1 | 6/2000 |
| DE | 10010831 A1 | 9/2001 |
| DE | 10154404 C1 | 6/2003 |
| DE | 10201110 A1 | 10/2003 |
| DE | 10242698 | 3/2004 |
| DE | 10246181 A1 | 4/2004 |
| DE | 10353540 A1 | 5/2004 |
| DE | 102004017236 A1 | 10/2005 |
| DE | 102006061585 A1 | 2/2008 |
| DE | 102008023027 A1 | 11/2009 |
| EP | 0121340 A2 | 10/1984 |
| EP | 0275965 A2 | 7/1988 |
| EP | 0284867 A2 | 10/1988 |
| EP | 0306307 | 3/1989 |
| EP | 0329041 A2 | 8/1989 |
| EP | 0343017 A2 | 11/1989 |
| EP | 0396919 A2 | 11/1990 |
| EP | 0482613 A1 | 10/1991 |
| EP | 0484746 A2 | 10/1991 |
| EP | 0495447 A1 | 7/1992 |
| EP | 0520519 A1 | 12/1992 |
| EP | 0535810 A1 | 4/1993 |
| EP | 0375778 B1 | 9/1993 |
| EP | 0571116 A1 | 11/1993 |
| EP | 0580094 A2 | 1/1994 |
| EP | 0603717 A2 | 6/1994 |
| EP | 0619178 | 10/1994 |
| EP | 0645470 A1 | 3/1995 |
| EP | 0697378 A2 | 2/1996 |
| EP | 0709485 B1 | 5/1996 |
| EP | 0719877 A1 | 7/1996 |
| EP | 0728676 A1 | 8/1996 |
| EP | 0787824 A2 | 8/1997 |
| EP | 0787828 A2 | 8/1997 |
| EP | 0814114 A1 | 12/1997 |
| EP | 0251812 A2 | 1/1998 |
| EP | 0833366 A2 | 4/1998 |
| EP | 0879611 A2 | 11/1998 |
| EP | 0940183 A2 | 9/1999 |
| EP | 0962229 A2 | 12/1999 |
| EP | 0992610 A2 | 4/2000 |
| EP | 1119034 A1 | 7/2001 |
| EP | 0954272 B1 | 3/2002 |
| EP | 1245694 A1 | 10/2002 |
| EP | 1388594 B1 | 1/2003 |
| EP | 1317937 A1 | 6/2003 |
| EP | 1365043 A1 | 11/2003 |
| EP | 1367145 | 12/2003 |
| EP | 1388593 A1 | 2/2004 |
| EP | 1439241 A2 | 7/2004 |
| EP | 1447459 A2 | 8/2004 |
| EP | 1990639 A1 | 2/2005 |
| EP | 1510595 A1 | 3/2005 |
| EP | 1522403 A2 | 4/2005 |
| EP | 1901067 A2 | 8/2005 |
| EP | 1507894 | 12/2005 |
| EP | 1507723 | 3/2006 |
| EP | 1653192 A1 | 5/2006 |
| EP | 1810758 A1 | 7/2007 |
| EP | 1356260 B1 | 12/2007 |
| EP | 1870117 A2 | 12/2007 |
| EP | 1881088 A1 | 1/2008 |
| EP | 1507887 | 7/2008 |
| EP | 1415018 | 10/2008 |
| EP | 2199264 A1 | 11/2009 |
| EP | 1388594 B1 | 1/2010 |
| EP | 2178109 A1 | 4/2010 |
| EP | 1507895 | 7/2010 |
| EP | 2218465 A1 | 8/2010 |
| EP | 2243751 A1 | 10/2010 |
| EP | 2251671 | 11/2010 |
| EP | 2261185 | 12/2010 |
| EP | 2369038 A2 | 9/2011 |
| EP | 1960279 B1 | 10/2011 |
| EP | 2602354 A1 | 6/2013 |
| EP | 2639330 A1 | 9/2013 |
| FR | 891892 A | 11/1942 |
| GB | 752822 | 7/1956 |
| GB | 1363762 | 8/1974 |
| GB | 1513426 A | 6/1978 |
| GB | 1566251 | 4/1980 |
| GB | 2210826 A | 6/1989 |
| GB | 2231197 A | 11/1990 |
| GB | 2246794 A | 2/1992 |
| GB | 2246795 A | 2/1992 |
| GB | 2387964 A | 10/2003 |

(56) References Cited

FOREIGN PATENT DOCUMENTS

| | | |
|---|---|---|
| JP | 56027330 A | 3/1981 |
| JP | 58154602 A | 9/1983 |
| JP | 59087307 A | 5/1984 |
| JP | 59154029 | 9/1984 |
| JP | S61183462 A | 8/1986 |
| JP | S62180069 A | 8/1987 |
| JP | S62290866 A | 12/1987 |
| JP | 63124521 A2 | 5/1988 |
| JP | 1023105 A | 1/1989 |
| JP | H01225775 A | 9/1989 |
| JP | 1279745 | 11/1989 |
| JP | 2501490 | 5/1990 |
| JP | 3183759 A2 | 8/1991 |
| JP | H03260065 A | 11/1991 |
| JP | H03271374 A | 12/1991 |
| JP | 4000373 A | 1/1992 |
| JP | 4000374 A | 1/1992 |
| JP | 4000375 A | 1/1992 |
| JP | 4014440 A | 1/1992 |
| JP | H04124273 A | 4/1992 |
| JP | H0578844 A | 3/1993 |
| JP | 05-006688 A | 4/1993 |
| JP | H05263223 A | 10/1993 |
| JP | 6010132 A | 1/1994 |
| JP | 6289401 | 10/1994 |
| JP | 7041579 A | 2/1995 |
| JP | 7068614 A | 3/1995 |
| JP | 7126419 A | 5/1995 |
| JP | 7-304127 | 11/1995 |
| JP | 8025244 A | 1/1996 |
| JP | 8084773 A | 4/1996 |
| JP | H08296038 A | 11/1996 |
| JP | 9005038 A | 1/1997 |
| JP | 10008254 A | 1/1998 |
| JP | 10-130844 | 5/1998 |
| JP | 11-108833 A | 4/1999 |
| JP | 11106920 | 4/1999 |
| JP | H11256331 A | 9/1999 |
| JP | 11344316 A | 12/1999 |
| JP | 2000064040 A | 2/2000 |
| JP | 2000109076 A | 4/2000 |
| JP | 2001033398 A | 2/2001 |
| JP | 2001231841 A | 8/2001 |
| JP | 2002177364 A | 6/2002 |
| JP | 2002206167 A | 7/2002 |
| JP | 2002371364 A | 12/2002 |
| JP | 2003171771 A | 6/2003 |
| JP | 2003-268550 A | 9/2003 |
| JP | 2003294431 A | 10/2003 |
| JP | 2003305121 A | 10/2003 |
| JP | 2004002928 A | 1/2004 |
| JP | 2004008509 A | 1/2004 |
| JP | 2004043789 A | 2/2004 |
| JP | 2004100036 A | 4/2004 |
| JP | 2004156444 A | 6/2004 |
| JP | 2004168359 A | 6/2004 |
| JP | 2004169087 A | 6/2004 |
| JP | 2004203682 A | 7/2004 |
| JP | 2004-253683 A | 9/2004 |
| JP | 2004307935 A | 11/2004 |
| JP | 2005035597 A | 2/2005 |
| JP | 2005043285 A | 2/2005 |
| JP | 2005132416 A | 5/2005 |
| JP | 2005160888 A | 6/2005 |
| JP | 2005-200044 | 7/2005 |
| JP | 2005200044 A | 7/2005 |
| JP | 2005-241524 A | 9/2005 |
| JP | 2005-290560 A | 10/2005 |
| JP | 2005271997 A | 10/2005 |
| JP | 2005290561 A | 10/2005 |
| JP | 2006-064416 A | 3/2006 |
| JP | 2006111967 A | 4/2006 |
| JP | 2006160268 A | 6/2006 |
| JP | 2006-224992 A | 8/2006 |
| JP | 2006249577 A | 9/2006 |
| JP | 2007050898 A | 3/2007 |
| JP | 2007231386 A | 9/2007 |
| JP | 2007246974 A | 9/2007 |
| JP | 2008-132766 A | 6/2008 |
| JP | 2008174793 A | 7/2008 |
| JP | 2009-062620 A | 3/2009 |
| JP | 2009062620 A | 3/2009 |
| JP | 2009079298 A | 4/2009 |
| JP | 2009084203 A | 4/2009 |
| JP | 2009185330 A | 8/2009 |
| JP | 2010155134 A | 7/2010 |
| JP | 2012210315 A | 11/2012 |
| JP | 5362941 B2 | 12/2013 |
| KR | 10-2005-0100367 A | 10/2005 |
| KR | 10-2006-0029694 | 4/2006 |
| KR | 10-0685594 B1 | 2/2007 |
| SU | 1530913 | 12/1989 |
| TW | 200703536 A | 1/2007 |
| WO | WO9324243 A1 | 12/1993 |
| WO | WO9400247 A1 | 1/1994 |
| WO | WO9426497 A1 | 11/1994 |
| WO | WO95/24275 | 9/1995 |
| WO | WO97/11482 | 3/1997 |
| WO | WO98-27926 | 7/1998 |
| WO | WO98/45871 | 10/1998 |
| WO | WO9917334 A1 | 4/1999 |
| WO | WO99/41425 | 8/1999 |
| WO | WO99/50471 | 10/1999 |
| WO | WO0038566 A2 | 7/2000 |
| WO | WO0104668 A1 | 1/2001 |
| WO | WO0125788 | 4/2001 |
| WO | WO0154816 A1 | 8/2001 |
| WO | WO0156706 A1 | 8/2001 |
| WO | WO0170403 A1 | 9/2001 |
| WO | WO02/43116 A2 | 5/2002 |
| WO | WO0249925 A1 | 6/2002 |
| WO | WO02/056333 A1 | 7/2002 |
| WO | WO02072914 | 9/2002 |
| WO | WO03033426 | 9/2002 |
| WO | WO02076709 A1 | 10/2002 |
| WO | WO03014415 A1 | 2/2003 |
| WO | WO03038143 | 5/2003 |
| WO | WO03040649 A1 | 5/2003 |
| WO | WO03044240 A1 | 5/2003 |
| WO | WO2005035147 A1 | 4/2005 |
| WO | WO2005/052555 A1 | 6/2005 |
| WO | WO2005051525 A1 | 6/2005 |
| WO | WO2005103605 A1 | 11/2005 |
| WO | WO2006012281 A1 | 2/2006 |
| WO | WO2006027568 A1 | 3/2006 |
| WO | WO2006029743 A1 | 3/2006 |
| WO | WO2006044254 A1 | 4/2006 |
| WO | WO2006/048650 | 5/2006 |
| WO | WO2006048276 | 5/2006 |
| WO | WO2006048277 A1 | 5/2006 |
| WO | WO2006069774 A1 | 7/2006 |
| WO | WO2006135755 A2 | 12/2006 |
| WO | WO2007028061 A2 | 3/2007 |
| WO | WO2007035741 A2 | 3/2007 |
| WO | WO2007036544 A1 | 4/2007 |
| WO | WO2007/081814 | 7/2007 |
| WO | WO2007/089216 A1 | 8/2007 |
| WO | WO2007112328 A2 | 10/2007 |
| WO | WO2007120507 A2 | 10/2007 |
| WO | WO2007133378 A1 | 11/2007 |
| WO | WO2007134347 A2 | 11/2007 |
| WO | WO2008014438 A2 | 1/2008 |
| WO | WO2008024566 A2 | 2/2008 |
| WO | WO2008040531 A1 | 4/2008 |
| WO | WO2008047541 A1 | 4/2008 |
| WO | WO2008067574 A1 | 6/2008 |
| WO | WO2008071458 A1 | 6/2008 |
| WO | WO2008093335 A2 | 8/2008 |
| WO | 2008/121478 A2 | 10/2008 |
| WO | WO2009/015862 A1 | 2/2009 |
| WO | WO2009020550 A2 | 2/2009 |
| WO | WO2009021257 A1 | 2/2009 |
| WO | WO2009030974 | 3/2009 |
| WO | WO2009030975 A1 | 3/2009 |

(56) References Cited

FOREIGN PATENT DOCUMENTS

| WO | WO2009030976 A1 | 3/2009 |
|---|---|---|
| WO | WO2009031838 A1 | 3/2009 |
| WO | WO2009040109 | 4/2009 |
| WO | WO2009053947 A2 | 4/2009 |
| WO | WO2009112053 A1 | 9/2009 |
| WO | WO2009117032 | 9/2009 |
| WO | WO2009118361 A1 | 10/2009 |
| WO | WO2009158613 | 12/2009 |
| WO | WO2010047825 A1 | 4/2010 |
| WO | WO2010095011 A1 | 8/2010 |
| WO | WO2010/132579 | 11/2010 |
| WO | WO2010/132581 | 11/2010 |
| WO | WO2010/132584 | 11/2010 |
| WO | WO2010/132585 | 11/2010 |
| WO | WO2010/132589 | 11/2010 |
| WO | WO2010/132591 | 11/2010 |
| WO | WO2010034004 A1 | 11/2010 |
| WO | WO2010132579 | 11/2010 |
| WO | WO2010132579 A2 | 11/2010 |
| WO | WO2010132589 | 11/2010 |
| WO | WO2010132591 | 11/2010 |
| WO | WO2011029628 | 3/2011 |
| WO | WO2011007055 A1 | 6/2011 |
| WO | WO2011080543 A1 | 7/2011 |
| WO | WO2011082296 A1 | 7/2011 |
| WO | WO2011090717 A1 | 7/2011 |
| WO | WO2011/143329 | 11/2011 |
| WO | WO2011/143509 | 11/2011 |
| WO | WO2011/143509 A1 | 11/2011 |
| WO | WO2011137437 | 11/2011 |
| WO | WO2011143329 | 11/2011 |
| WO | WO2011159975 A1 | 12/2011 |
| WO | WO2012003221 | 1/2012 |
| WO | WO2012009653 | 1/2012 |
| WO | WO2013045671 A1 | 4/2013 |
| WO | WO2013/071138 | 5/2013 |
| WO | WO2013/071138 A1 | 5/2013 |
| WO | WO2013/170044 | 11/2013 |
| WO | WO2013/170052 | 11/2013 |
| WO | WO2014/008138 | 1/2014 |
| WO | WO2014/059012 | 4/2014 |
| WO | WO2014/071061 | 5/2014 |
| WO | WO2014/078666 | 5/2014 |
| WO | WO2014/085346 | 6/2014 |
| WO | WO2014/085348 | 6/2014 |
| WO | WO2014/134577 | 9/2014 |
| WO | WO2014/144926 | 9/2014 |
| WO | WO2014/164928 | 10/2014 |

OTHER PUBLICATIONS

Japanese Patent Office, Notice of Reasons for Refusal, Patent Application No. 2013-510276, dated Mar. 8, 2016 (15 pages).
Australian Government, IP Australia, Patent Examination Report No. 1, in Application No. 2010249031, dated Mar. 13, 2014. (4 pages).
Australian Government, IP Australia, Patent Examination Report No. 1, in Application No. 2013202893, dated Mar. 13, 2014. (4 pages).
European Patent Office, Communication pursuant to Article 93(3) EPC, in Application No. 11 731 554.9 dated Apr. 15, 2014. (7 pages).
PCT, Notification Concerning Transmittal of International Preliminary Report on Patentability, in International application No. PCT/US2012/064489, dated May 22, 2014. (10 pages).
PCT, Notification of Transmittal of the International Search Report and the Written Opinion of the International Searching Authority, or the Declaration, in International application No. PCT/US2013/071750, dated Apr. 4, 2014. (13 pages).
PCT, Notification of Transmittal of the International Search Report and the Written Opinion of the International Searching Authority, or the Declaration, in International application No. PCT/US2014/019684, dated May 23, 2014. (16 pages).
PCT, Notification of Transmittal of the International Search Report and the Written Opinion of the International Searching Authority, or the Declaration, in International application No. PCT/US2014/023813, dated May 22, 2014. (11 pages).
European Patent Office, Communication pursuant to Article 94(3) EPC, in Application No. 11 736 511.4, dated Mar. 28, 2014.
PCT, Notification Concerning Transmittal of International Preliminary Report on Patentability, in International application No. PCT/US2011/042387, dated Jan. 17, 2013. (7 pages).
State Intellectual Property Office of the People's Republic of China, Notification of the First Office Action, in Application No. 201180032145.4, dated Jan. 30, 2014. (16 pages).
PCT, Notification Concerning Transmittal of International Preliminary Report on Patentability, in International application No. PCT/US2011/044215, dated Jan. 31, 2013. (14 pages).
Da Silva Sobrinho A S et al., "Transparent barrier coatings on polyethylene terephthalate by single-and dual-frequency plasma-enhanced chemical vapor deposition", Journal of Vacuum Science and Technology; Part A, AVS/AIP, Melville, NY, US, vol. 16, No. 6, Nov. 1, 1998 (Nov. 1, 1998), pp. 3190-3198, XP01200471, ISSN: 0734-2101, DOI: 10.1116/1.581519 (9 pages).
State Intellectual Property Office of the People's Republic of China, Notification of the Third Office Action, in Application No. 201080029201.4, dated Jul. 7, 2014 (15 pages).
PCT, Notification of Transmittal of the International Search Report and the Written Opinion of the International Searching Authority, or the Declaration, in International application No. PCT/US2014/029531, dated Jun. 20, 2014 (12 pages).
State Intellectual Property Office of the People's Republic of China, Notification of the Third Office Action, with translation, in Application No. 201080029199.0, dated Jun. 27, 2014 (19 pages).
Intellectual Property Office of Singapore, Invitation to Respond to Written Opinion, in Application No. 2012083077, dated Jun. 30, 2014 (12 pages).
PCT, Notification of Transmittal of International Preliminary Report on Patentability, in International application No. PCT/US13/40368, dated Jul. 16, 2014 (6 pages).
Australian Government, IP Australia, Patent Examination Report No. 1, in Application No. 2012318242, dated Apr. 30, 2014. (6 pages).
State Intellectual Property Office of the People's Republic of China, Notification of the First Office Action, in Application No. 201180023461.5, dated May 21, 2014. (25 pages).
European Patent Office, Communication pursuant to Article 94(3) EPC, in Application No. 10162758.6 dated May 27, 2014. (7 pages).
Australian Government, IP Australia, Patent Examination Report No. 1, in Application No. 2011252925, dated Sep. 6, 2013 (3 pages).
Patent Cooperation Treaty, Written Opinion of the International Searching Authority with International Search Report in Application No. PCT/US2012/064489, dated Jan. 25, 2013.
Danish Patent and Trademark Office, Singapore Written Opinion, in Application No. 201108308-6, dated Dec. 6, 2012.
Danish Patent and Trademark Office, Singapore Search Report, in Application No. 201108308-6, dated Dec. 12, 2012.
Tao, Ran et al., Condensationand Polymerization of Supersaturated Monomer Vapor, ACS Publications, 2012 American Chemical Society, ex.doi.org/10.1021/la303462q/Langmuir 2012, 28, 16580-16587.
State Intellectual Property Office of Teh People's Republic of China, Notification of First Office Action in Application No. 201080029201.4, dated Mar. 37, 2013. (15 pages).
PCT, Notification of Transmittal of the International Search Report and the Written Opinion of the International Searching Authority, or the Declaration, in International application No. PCT/US2013/040380, dated Sep. 3, 2013. (13 pages).
PCT, Notification of Transmittal of the International Search Report and the Written Opinion of the International Searching Authority, or the Declaration, in International application No. PCT/US2013/040368, dated Oct. 21, 2011 (21 pages).
PCT, Notification of Transmittal of the International Search Report and the Written Opinion of the International Searching Authority, or the Declaration, in International application No. PCT/US2013/048709, dated Oct. 2, 2011 (7 pages).

(56) References Cited

OTHER PUBLICATIONS

Coclite A.M. et al., "On the relationship between the structure and the barrier performance of plasma deposited silicon dioxide-like films", Surface and Coatings Technology, Elsevier, Amsterdam, NL, vol. 204, No. 24, Sep. 15, 2010 (Sep. 15, 2010), pp. 4012-4017, XP027113381, ISSN: 0257-8972 [retrieved on Jun. 16, 2010] abstract, p. 4014, right-hand col.—p. 4015, figures 2, 3.
Brunet-Bruneau A. et al., "Microstructural characterization of ion assisted Sio2 thin films by visible and infrared ellipsometry", Journal of Vacuum Science and Technology: Part A, AVS/AIP, Melville, NY, US, vol. 16, No. 4, Jul. 1, 1998 (Jul. 1, 1998), pp. 2281-2286, XP012004127, ISSN: 0734-2101, DOI: 10.1116/1.581341, p. 2283, right-hand col.—p. 2284, left-hand column, figures 2, 4.
Allison, H.L., The Real Markets for Transparent Barrier Films, 37th Annual Technical Conference Proceedings, 1994, ISBN 1-878068-13-X, pp. 458.
Bailey, R. et al., Thin-Film Multilayer Capacitors Using Pyrolytically Deposited Silicon Dioxide, IEEE Transactions on Parts, Hybrids, and Packaging, vol. PHP-12, No. 4, Dec. 1976, pp. 361-364.
Banks, B.A., et al., Fluoropolymer Filled SiO2 Coatings; Properties and Potential Applications, Society of Vacuum Coaters, 35th Annual Technical Conference Proceedings, 1992, ISBN 1-878068-11-3, pp. 89-93.
Baouchi, W., X-Ray Photoelectron Spectroscopy Study of Sodium Ion Migration through Thin Films of SiO2 Deposited on Sodalime Glass, 37th Annual Technical Conference Proceedings, 1994, ISBN 1-878068-13-X, pp. 419-422.
Boebel, F. et al., Simultaneous In Situ Measurement of Film Thickness and Temperature by Using Multiple Wavelengths Pyrometric Interferometry (MWPI), IEEE Transaction on Semiconductor Manufacturing, vol. 6, No. 2, May 1993, pp. 112-118.
Bush, V. et al., The Evolution of Evacuated Blood Collection Tubes, BD Diagnostics—Preanalytical Systems Newsletter, vol. 19, No. 1, 2009.
Chahroudi, D., Deposition Technology for Glass Barriers, 33rd Annual Technical Conference Proceedings, 1990, ISBN 1-878068-09-1, pp. 212-220.
Chahroudi, D., et al., Transparent Glass Barrier Coatings for Flexible Film Packaging, Society of Vacuum Coaters, 34th Annual Technical Conference Proceedings, 1991, ISBN 1-878068-10-5, pp. 130-133.
Chahroudi, D., Glassy Barriers from Electron Beam Web Coaters, 32nd Annual Technical Conference Proceedings, 1989, pp. 29-39.
Czeremuszkin, G. et al., Ultrathin Silicon-Compound Barrier Coatings for Polymeric Packaging Materials: An Industrial Perspective, Plasmas and Polymers, vol. 6, Nos. 1/2, Jun. 2001, pp. 107-120.
Ebihara, K. et al., Application of the Dielectric Barrier Discharge to Detect Defects in a Teflon Coated Metal Surface, 2003 J. Phys. D: Appl. Phys. 36 2883-2886, doi: 10.1088/0022-3727/36/23/003, IOP Electronic Journals, http://www.op.org/EJ/abstract/0022-3727/36/23/003, printed Jul. 14, 2009.
Egitto, F.D., et al., Plasma Modification of Polymer Surfaces, Society of Vacuum Coaters, 36th Annual Technical Conference Proceedings, 1993, ISBN 1-878068-12-1, pp. 10-21.
Erlat, A.G. et al., SIOx Gas Barrier Coatings on Polymer Substrates: Morphology and Gas Transport Considerations, ACS Publications, Journal of Physical Chemistry, published Jul. 2, 1999, http://pubs.acs.org/doi/abs/10.1021/jp990737e, printed Jul. 14, 2009.
Fayet, P., et al., Commercialism of Plasma Deposited Barrier Coatings for Liquid Food Packaging, 37th Annual Technical Conference Proceedings, 1995, ISBN 1-878068-13-X, pp. 15-16.
Felts, J., Hollow Cathode Based Multi-Component Depositions, Vacuum Technology & Coating, Mar. 2004, pp. 48-55.
Felts, J.T., Thickness Effects on Thin Film Gas Barriers: Silicon-Based Coatings, Society of Vacuum Coaters, 34th Annual Technical Conference Proceedings, 1991, ISBN 1-878068-10-5, pp. 99-104.
Felts, J.T., Transparent Barrier Coatings Update: Flexible Substrates, Society of Vacuum Coaters, 36th Annual Technical Conference Proceedings, 1993, ISBN 1-878068-12-1, pp. 324-331.
Felts, J.T., Transparent Gas Barrier Technologies, 33rd Annual Technical Conference Proceedings, 1990, ISBN 1-878068-09-1, pp. 184-193.
Finson, E., et al., Transparent SiO2 Barrier Coatings: Conversion and Production Status, 37th Annual Technical Conference Proceedings, 1994, ISBN 1-878068-13-X, pp. 139-143.
Flaherty, T. et al., Application of Spectral Reflectivity to the Measurement of Thin-Film Thickness, Opto-Ireland 2002: Optics and Photonics Technologies and Applications, Proceedings of SPIE vol. 4876, 2003, pp. 976-983.
Hora, R., et al., Plasma Polymerization: A New Technology for Functional Coatings on Plastics, 36th Annual Technical Conference Proceedings, 1993, ISBN 1-878068-12-1, pp. 51-55.
Izu, M., et al., High Performance Clear Coat™ Barrier Film, 36th Annual Technical Conference Proceedings, 1993, ISBN 1-878068-12-1, pp. 333-340.
Jost, S., Plasma Polymerized Organosilicon Thin Films on Reflective Coatings, 33rd Annual Technical Conference Proceedings, 1990, ISBN 1-878068-09-1, pp. 344-346.
Kaganowicz, G., et al., Plasma-Deposited Coatings—Properties and Applications, 23rd Annual Technical Conference Proceedings, 1980, pp. 24-30.
Kamineni, V. et al., Thickness Measurement of Thin Metal Films by Optical Metrology, College of Nanoscale Science and Engineering, University of Albany, Albany, NY.
Klemberg-Sapieha, J.E., et al., Transparent Gas Barrier Coatings Produced by Dual Frequency PECVD, 36th Annual Technical Conference Proceedings, 1993, ISBN 1-878068-12-1, pp. 445-449.
Krug, T., et al., New Developments in Transparent Barrier Coatings, 36th Annual Technical Conference Proceedings, 1993, ISBN 1-878068-12-1, pp. 302-305.
Kuhr, M. et al., Multifunktionsbeschichtungen für innovative Applikationen von Kunststoff-Substraten, HiCotec Smart Coating Solutions.
Kulshreshtha, D.S., Specifications of a Spectroscopic Ellipsometer, Department of Physics & Astrophysics, University of Delhi, Delhi-110007, Jan. 16, 2009.
Krug, T.G., Transparent Barriers for Food Packaging, 33rd Annual Technical Conference Proceedings, 1990, ISBN 1-878068-09-1, pp. 163-169.
Lee, K. et al., The Ellipsometric Measurements of a Curved Surface, Japanese Journal of Applied Physics, vol. 44, No. 32, 2005, pp. L1015-L1018.
Lelait, L. et al., Microstructural Investigations of EBPVD Thermal Barrier Coatings, Journal De Physique IV, Colloque C9, supplement au Journal de Physique III, vol. 3, Dec. 1993, pp. 645-654.
Masso, J.D., Evaluation of Scratch Resistant and Antireflective Coatings for Plastic Lenses, 32nd Annual Technical Conference Proceedings, 1989, p. 237-240.
Misiano, C., et al., New Colourless Barrier Coatings (Oxygen & Water Vapor Transmission Rate) on Plastic Substrates, 35th Annual Technical Conference Proceedings, 1992, ISBN 1-878068-11-3, pp. 28-40.
Misiano, C., et al., Silicon Oxide Barrier Improvements on Plastic Substrate, Society of Vacuum Coaters, 34th Annual Technical Conference Proceedings, 1991, ISBN 1-878068-10-5, pp. 105-112.
Mount, E., Measuring Pinhole Resistance of Packaging, Corotec Corporation website, http://www.convertingmagazine.com, printed Jul. 13, 2009.
Murray, L. et al., The Impact of Foil Pinholes and Flex Cracks on the Moisture and Oxygen Barrier of Flexible Packaging.
Nelson, R.J., et al., Double-Sided QLF® Coatings for Gas Barriers, Society of Vacuum Coaters, 34th Annual Technical Conference Proceedings, 1991, ISBN 1-878068-10-5, pp. 113-117.
Nelson, R.J., Scale-Up of Plasma Deposited SiOx Gas Diffusion Barrier Coatings, 35th Annual Technical Conference Proceedings, 1992, ISBN 1-878068-11-3, pp. 75-78.
Novotny, V. J., Ultrafast Ellipsometric Mapping of Thin Films, IBM Technical Disclosure Bulletin, vol. 37, No. 02A, Feb. 1994, pp. 187-188.
Rüger, M., Die Pulse Sind das Plus, PICVD-Beschichtungsverfahren.

(56) References Cited

OTHER PUBLICATIONS

Schultz, A. et al., Detection and Identification of Pinholes in Plasma-Polymerised Thin Film Barrier Coatings on Metal Foils, Surface & Coatings Technology 200, 2005, pp. 213-217.
Stchakovsky, M. et al., Characterization of Barrier Layers by Spectroscopic Ellipsometry for Packaging Applications, Horiba Jobin Yvon, Application Note, Spectroscopic Ellipsometry, SE 14, Nov. 2005.
Teboul, E., Thi-Film Metrology: Spectroscopic Ellipsometer Becomes Industrial Thin-Film Tool, LaserFocusWorld, http://www.laserfocusworld.com/display_article, printed Jul. 14, 2009.
Teyssedre, G. et al., Temperature Dependence of the Photoluminescence in Poly(Ethylene Terephthalate) Films, Polymer 42, 2001, pp. 8207-8216.
Tsung, L. et al., Development of Fast CCD Cameras for In-Situ Electron Microscopy, Microsc Microanal 14(Supp 2), 2008.
Wood, L. et al., A Comparison of SiO2 Barrier Coated Polypropylene to Other Coated Flexible Substrates, 35th Annual Technical Conference Proceedings, 1992, ISBN 1-878068-11-3, pp. 59-62.
Yang, et al., Microstructure and tribological properties of SiOx/DLC films grown by PECVD, Surface and Coatings Technology, vol. 194, Issue 1, Apr. 20, 2005, pp. 128-135.
AN 451, Accurate Thin Film Measurements by High-Resoluiton Transmission Electron Microscopy (HRTEM), Evans Alalytical Group, Version 1.0, Jun. 12, 2008, pp. 1-2.
Benefits of TriboGlide, TriboGlide Silicone-Free Lubrication Systems, http://www.triboglide.com/benfits.htm, printed Aug. 31, 2009.
Patent Cooperation Treaty, Notification of Transmittal of International Preliminary Report on Patentability, in Application No. PCT/US2010/034576, dated Sep. 14, 2011.
Patent Cooperation Treaty, Notification of Transmittal of International Preliminary Report on Patentability, in Application No. PCT/US2010/034568, dated Sep. 14, 2011.
Patent Cooperation Treaty, International Search Report and Written Opinion, in Application No. PCT/US2011/036358, dated Sep. 9, 2011.
Patent Cooperation Treaty, International Search Report and Written Opinion, in Application No. PCT/US2011/036340, dated Aug. 1, 2011.
MacDonald, Gareth, "West and Daikyo Seiko Launch Ready Pack", http://www.in-pharmatechnologist.com/Packaging/West-and-Daikyo-Seiko-launch-Ready-Pack, 2 pages, retrieved from the internet Sep. 22, 2011.
Kumer, Vijai, "Development of Terminal Sterilization Cycle for Pre-Filled Cyclic Olefin Polymer (COP) Syringes", http://abstracts.aapspharmaceutica.com/ExpoAAPS09/CC/forms/attendee/index.aspx?content=sessionInfo&sessionId=401, 1 page, retrieved from the internet Sep. 22, 2011.
Quinn, F.J., "Biotech Lights Up the Glass Packaging Picture", http://www.pharmaceuticalcommerce.com/frontEnd/main.php?idSeccion=840, 4 pages, retrieved from the internet Sep. 21, 2011.
Wen, Zai-Qing et al., Distribution of Silicone Oil in Prefilled Glass Syringes Probed with Optical and Spectroscopic Methods, PDA Journal of Pharmaceutical Science and Technology 2009, 63, pp. 149-158.
ZebraSci—Intelligent Inspection Products, webpage, http://zebrasci.com/index.html, retrieved from the internet Sep. 30, 2011.
Google search re "cyclic olefin polymer resin" syringe or vial, http://www.google.com/search?sclient=psy-ab&hl=en&lr=&source=hp&q=%22cyclic+olefin+polymer+resin%22+syringe+OR+vial&btnG=Search&pbx=1&oq=%22cyclic+olefin+polymer+resin%22+syringe+OR+vial&aq, 1 page, retrieved from the internet Sep. 22, 2011.
Taylor, Nick, "West to Add CZ Vials as Glass QC Issues Drive Interest", ttp://twitter.com/WestPharma/status/98804071874281988, 2 pages, retrieved from the internet Sep. 22, 2011.
Patent Cooperation Treaty, International Preliminary Examining Authority, Notification of Transmittal of International Preliminary Report on Patentability, in international application No. PCT/US2010/034571, dated Jun. 13, 2011.
Patent Cooperation Treaty, International Preliminary Examining Authority, Written Opinion of the International Preliminary Examining Authority, in international application No. PCT/US2010/034588, dated Aug. 23, 2011.
Patent Cooperation Treaty, International Preliminary Examining Authority, Written Opinion of the International Preliminary Examining Authority, in international application No. PCT/US2010/034588, dated May 30, 2011.
Silicone Oil Layer, Contract Testing, webpage, http://www.siliconization.com/downloads/siliconeoillayercontracttesting.pdf, retrieved from the internet Oct. 28, 2011.
Patent Cooperation Treaty, Notification of Transmittal of International Preliminary Report on Patentability, in PCT/US2010/034577, dated Nov. 24, 2011.
Patent Cooperation Treaty, Notification of Transmittal of International Preliminary Report on Patentability, in PCT/US2010/034582, dated Nov. 24, 2011.
Patent Cooperation Treaty, Notification of Transmittal of International Preliminary Report on Patentability, in PCT/US2010/034586, dated Dec. 20, 2011.
Patent Cooperation Treaty, Notification of Transmittal of the International Search Report and the Written Opinion of the International Searching Authority, in PCT/US2011/038097, dated Dec. 29, 2011.
"Oxford instruments plasmalab 80plus", XP55015205, retrieved from the Internet on Dec. 20, 2011, URL:http://www.oxfordplasma.de/pdf_inst/plas_80.pdf.
Patent Cooperation Treaty, Notification of Transmittal of the International Search Report and the Written Opinion of the International Searching Authority, in PCT/US2011/044215, dated Dec. 29, 2011.
European Patent Office, Communication pursuant to Article 94(3) EPC, in Application No. 10 162 758.6-1234, dated May 8, 2012 (6 pages).
Hanlon, Adriene Lepiane, Pak, Chung K., Pawlikowski, Beverly A., Decision on Appeal, Appeal No. 2005-1693, U.S. Appl. No. 10/192,333, dated Sep. 30, 2005.
Arganguren, Mirta I., Macosko, Christopher W., Thakkar, Bimal, and Tirrel, Matthew, "Interfacial Interactions in Silica Reinforced Silicones," Materials Research Society Symposium Proceedings, vol. 170, 1990, pp. 303-308.
Patent Cooperation Treaty, International Preliminary Examining Authority, Notification of Transmittal of International Preliminary Report on Patentability, in international application No. PCT/US2011/036097, dated Nov. 13, 2012.
Sahagian, Khoren; Larner, Mikki; Kaplan, Stephen L., "Altering Biological Interfaces with Gas Plasma: Example Applications", Plasma Technology Systems, Belmont, CA, In SurFACTS in Biomaterials, Surfaces in Biomaterials Foundation, Summer 2013, 18(3), p. 1-5.
Daikyo Cyrystal Zenith Insert Needle Syringe System, West Delivering Innovative Services, West Pharmaceutical Services, Inc., 2010.
Daikyo Crystal Zenigh Syringes, West Pharmaceutical Services, Inc., www. WestPFSsolutions.com, #5659, 2011.
Zhang, Yongchao and Heller, Adam, Reduction of the Nonspecific Binding of a Target Antibody and of Its Enzyme-Labeled Detection Probe Enabling Electrochemical Immunoassay of Antibody through the 7 pg/mL-100 ng/mL (40 fM-400 pM) Range, Department of Chemical Engineering and Texas Materials Institute, University of Texas at Austin, Anal. Chem. 2005, 7, 7758-7762. (6 pages).
Principles and Applications of Liquid Scintillation Counting, LSC Concepts—Fundamentals of Liquid Scintillation Counting, National Diagnostics, 2004, pp. 1-15.
Chikkaveeraiah, Bhaskara V. and Rusling, Dr. James, Non Specific Binding (NSB) in Antigen-Antibody Assays, University of Connecticut, Spring 2007. (13 pages).
Sahagian, Khoren; Larner, Mikki; Kaplan, Stephen L., "Cold Gas Plasma in Surface Modification of Vledical Plastics", Plasma Technology Systems, Belmont, CA, Publication pending. Presented at SPE Antec Medical Plastics Division, Apr. 23, 2013, Ohio.
Lipman, Melissa, "Jury Orders Becton to Pay $114M in Syringe Antitrust Case", © 2003-2013, Portfolio Media, Inc., Law360, New York (Sep. 20, 2013, 2:53 PM ET), http://www.law360.com/articles/474334/print?section=ip, [retrieved Sep. 23, 2013].

(56) References Cited

OTHER PUBLICATIONS

Wikipedia, the free encyclopedia, http://en.wikipedia.org/wiki/Birefringence, page last modified Sep. 18, 2013 at 11:39. [retrieved on Oct. 8, 2013]. (5 pages).
Wikipedia, the free encyclopedia, http://en.wikipedia.org/wiki/Confocal_microscopy, page last modified Aug. 28, 2013 at 11:12. [retrieved on Oct. 8, 2013]. (4 pages).
Wang, Jun et al., "Fluorocarbon thin film with superhydrophobic property prepared by pyrolysis of hexafluoropropylene oxide", Applied Surface Science, vol. 258, 2012, pp. 9782-9784 (4 pages).
Wang, Hong et al., "Ozone-Initiated Secondary Emission Rates of Aldehydes from Indoor surfaces in Four Homes", American Chemical Society, Environmental Science & Technology, vol. 40, No. 17, 2006, pp. 5263-5268 (6 pages).
Lewis, Hilton G. Pryce, et al., "HWCVD of Polymers: Commercialization and Scale-Up", Thin Solid Films 517, 2009, pp. 3551-3554.
Wolgemuth, Lonny, "Challenges With Prefilled Syringes: The Parylene Solution", Frederick Furness Publishing, www.ongrugdelivery.com, 2012, pp. 44-45.
History of Parylene (12 pages).
SCS Parylene HTX brochure, Stratamet Thin Film Corporation, Fremont, CA, 2012, retrieved from the Internet Feb. 13, 2013, http://www.stratametthinfilm.com/parylenes/htx. (2 pages).
SCS Parylene Properties, Specialty Coating Systems, Inc., Indianapolis, IN, 2011. (12 pages).
Werthheimer, M.R., Studies of the earliest stages of plasma-enhanced chemical vapor deposition of SiO2 on polymeric substrates, Thin Solid Films 382 (2001) 1-3, and references therein, United States Pharmacopeia 34. In General Chapters <1>, 2001.
Gibbins, Bruce and Warner, Lenna, The Role of Antimicrobial Silver Nanotechnology, Medical Device & Diagnostic Industry, Aug. 205, pp. 2-6.
MTI CVD Tube Furnace w Gas Delivery & Vacuum Pump, http://mtixtl.com/MiniCVDTubeFurnace2ChannelsGasVacuum-OTF-1200X-S50-2F.aspx (2 pages).
Lab-Built HFPO CVD Coater, HFPO Decomp to Give Thin Fluorocarbon Films, Applied Surface Science 2012 258 (24)9782.
Technical Report No. 10, Journal of Parenteral Science and Technology, 42, Supplement 1988, Parenteral Formulation of Proteins and Peptides: Stability and Stabilizers, Parenteral Drug Association, 1988.
Technical Report No. 12, Journal of Parenteral Science and Technology, 42, Supplement 1988, Siliconization of Parenteral Drug Packaging Components, Parenteral Drug Association, 1988.
European Patent Office, Communication under Rule 71(3) EPC, in Application No. 10 162 760.2-1353, dated Oct. 25, 2013. (366 pages).
Wikipedia, the free encyclopedia, http://en.wikipedia.org/wiki/Difluorocarbene, page last modified Feb. 20, 2012 at 14:41. [retrieved on Sep. 7, 2012]. (4 pages).
O'Shaughnessy, W.S., et al., "Initiated Chemical Vapor Deposition of a Siloxane Coating for Insulation of Neutral Probes", Thin Solid Films 517 (2008) 3612-3614. (3 pages).
Denler, et al., Investigations of SiOx-polymer "interphases" by glancing angle RBS with Li+ and Be+ ions, Nuclear Instruments and Methods in Physical Research B 208 (2003) 176-180, United States Pharmacopeia 34. In General Chapters <1>, 2003.
PCT, Invitation to Pay Additional Fees and Annex to Form PCT/ISA/206 Communication relating to the results of the partial international search in International application No. PCT/US2013/071750, dated Feb. 14, 2014. (6 pages).
PCT, Notification of Transmittal of the International Search Report and the Written Opinion of the International Searching Authority, or the Declaration, in International application No. PCT/US2013/62247, dated Dec. 30, 2013. (13 pages).
PCT, Notification of Transmittal of the International Search Report and the Written Opinion of the International Searching Authority, or the Declaration, in International application No. PCT/US2013/043642, dated Dec. 5, 2013. (21 pages).

Japanese Patent Office, Notice of Reason(s) for Rejection in Patent application No. 2012-510983, dated Jan. 7, 2014. (6 pages).
Chinese Patent Office, Notification of the Second Office Action in Application No. 201080029199.0, dated Jan. 6, 2014. (26 pages).
Chinese Patent Office, Notification of the First Office Action in Application No. 201180023474.2, dated Dec. 23, 2013. (18 pages).
PCT, Notification of Transmittal of the International Search Report and the Written Opinion of the International Searching Authority, or the Declaration, in International application No. PCT/US2013/067852, dated Jan. 22, 2014. (9 pages).
PCT, Notification of Transmittal of the International Search Report and the Written Opinion of the International Searching Authority, or the Declaration, in International application No. PCT/US2013/064121, dated Mar. 24, 2014. (8 pages).
PCT, Notification of Transmittal of the International Search Report and the Written Opinion of the International Searching Authority, or the Declaration, in International application No. PCT/US2013/070325, dated Mar. 24, 2014. (16 pages).
Coating Syringes, http://www.triboglide.com/syringes.htm, printed Aug. 31, 2009.
Coating/Production Process, http://www.triboglide.com/process.htm, printed Aug. 31, 2009.
Munich Exp, Materialica 2005: Fundierte Einblicke in den Werkstofsektor, Seite 1, von 4, ME095-6.
Schott Developing Syringe Production in United States, Apr. 14, 2009, http://www.schott.com/pharmaceutical_packaging, printed Aug. 31, 2009.
Sterile Prefillable Glass and Polymer Syringes, Schott forma vitrum, http://www.schott.com/pharmaceutical_packaging.
Transparent and recyclingfähig, neue verpackung, Dec. 2002, pp. 54-57.
European Patent Office, Communication with European Search Report, in Application No. 10162758.6, dated Aug. 19, 2010.
Griesser, Hans J., et al., Elimination of Stick-Slip of Elastomeric Sutures by Radiofrequency Glow Discharge Deposited Coatings, Biomed Mater. Res. Appl Biomater, 2000, vol. 53, 235-243, John Wiley & Sons, Inc.
European Patent Office, Communication with extended Search Report, in Application No. EP 10162761.0, dated Feb. 10, 2011.
European Patent Office, Communication with partial Search Report, in Application No. EP 10162758.6, dated Aug. 19, 2010.
European Patent Office, Communication with extended Search Report, in Application No. EP 10162758.6, dated Dec. 21, 2010.
Yang, et al., Microstructure and tribological properties of SiOx/DLC films grown by PECVD, Surface and Coatings Technology, vol. 194 (2005), Apr. 20, 2005, pp. 128-135.
European Patent Office, Communication with extended European search report, in Application No. EP10162756.0, dated Nov. 17, 2010.
Prasad, G.R. et al., "Biocompatible Coatings with Silicon and Titanium Oxides Deposited by PECVD", 3rd Mikkeli International Industrial Coating Seminar, Mikkeli, Finland, Mar. 16-18, 2006.
European Patent Office, Communication with extended European search report, in Application No. EP10162757.8, dated Nov. 10, 2010.
Patent Cooperation Treaty, Notification of Transmittal of the International Search Report and the Written Opinion of the International Searching Authority, in PCT/US2010/034568, dated Jan. 21, 2011.
Patent Cooperation Treaty, Notification of Transmittal of the International Search Report and the Written Opinion of the International Searching Authority, in PCT/US2010/034571, dated Jan. 26, 2011.
Patent Cooperation Treaty, Notification of Transmittal of the International Search Report and the Written Opinion of the International Searching Authority, in PCT/US2010/034576, dated Jan. 25, 2011.
Patent Cooperation Treaty, Notification of Transmittal of the International Search Report and the Written Opinion of the International Searching Authority, in PCT/US2010/034577, dated Jan. 21, 2011.
Patent Cooperation Treaty, Notification of Transmittal of the International Search Report and the Written Opinion of the International Searching Authority, in PCT/US2010/034582, dated Jan. 24, 2011.
European Patent Office, Communication with Extended Search Report, in Application No. EP 10162755.2, dated Nov. 9, 2010.

(56) References Cited

OTHER PUBLICATIONS

European Patent Office, Communication with Extended Search Report, in Application No. EP 10162760.2, dated Nov. 12, 2010.
PCT, Written Opinion of the International Searching Authority with International Search Report in Application No. PCT/US2010/034586, dated Mar. 15, 2011.
Shimojima, Atsushi et al., Structure and Properties of Multilayered Siloxane-Organic Hybrid Films Prepared Using Long-Chain Organotrialkoxysilanes Containing C=C Double Bonds, Journal of Materials Chemistry, 2007, vol. 17, pp. 658-663, © The Royal Society of Chemistry, 2007.
Sone, Hayato et al., Picogram Mass Sensor Using Resonance Frequency Shift of Cantilever, Japanese Journal of Applied Physics, vol. 43, No. 6A, 2004, pp. 3648-3651, © The Japan Society of Applied Physics.
Sone, Hayato et al., Femtogram Mass Sensor Using Self-Sensing Cantilever for Allergy Check, Japanese Journal of Applied Physics, vol. 45, No. 313, 2006, pp. 2301-2304, © The Japan Society of Applied Physics.
Mallikarjunan, Anupama et al, The Effect of Interfacial Chemistry on Metal Ion Penetration into Polymeric Films, Mat. Res. Soc. Symp. Proc. vol. 734, 2003, © Materials Research Society.
Schonher, H., et al., Friction and Surface Dynamics of Polymers on the Nanoscale by AFM, STM and AFM Studies on (Bio)molecular Systems: Unravelling the Nanoworld. Topics in Current Chemistry, 2008, vol. 285, pp. 103-156, © Springer-Verlag Berlin Heidelberg.
Lang, H.P., Gerber, C., Microcantilever Sensors, STM and AFM Studies on (Bio)molecular Systems: Unravelling the Nanoworld. Topics in Current Chemistry, 2008, vol. 285, pp. 1-28, © Springer-Verlag Berlin Heidelberg.
European Patent Office, Communication pursuant to Article 94(3) EPC, in Application No. 13 726 337.2, dated Dec. 2, 2016 (6 pages).
PCT, Written Opinion of the International Preliminary Examining Authority, in International application No. PCT/USUS13/048709, dated Sep. 30, 2014 (4 pages).
PCT, Notification of Transmittal of the International Preliminary Report on Patentability, in International application No. PCT/USUS13/048709, dated Oct. 15, 2014 (7 pages).
PCT, Written Opinion of the International Preliminary Examining Authority, in International application No. PCT/USUS13/064121, dated Nov. 19, 2014 (8 pages).
PCT, Written Opinion of the International Preliminary Examining Authority, in International application No. PCT/USUS13/064121, dated Nov. 21, 2014 (7 pages).
Intellectual Property Corporation of Malaysia, Substantive Examintion Adverse Report (section 30(1)/30(2)), in Application No. PI 2011005486, dated Oct. 31, 2014 (3 pages).
Patent Office of the Russian Federation, Official Action, in Application No. 2011150499, dated Sep. 25, 2014 (4 pages).
Instituto Mexicano de la Propiedad Indutrial, Official Action, in Application No. MX/a/2012/013129, dated Sep. 22, 2014 (5 pages).
Australian Government, Patent Examination Report No. 2 in Application No. 2010249031 dated Apr. 21, 2015.
Japanese Patent Office, Notice of Reasons for Refusal in application No. 2013-510276, dated Mar. 31, 2015.
Bose, Sagarika and Constable, Kevin, Advanced Delivery Devices, Design & Evaluation of a Polymer-Based Prefillable Syringe for Biopharmaceuticals With Improved Functionality & Performance, JR Automation Technologies, May 2015.
Hopwood J Ed—CRC Press: "Plasma-assisted deposition", Aug. 17, 1997 (Aug. 17, 1997), Handbook of Nanophase Materials, Chapter 6, pp. 141-197, XP008107730, ISBN: 978-0-8247-9469-9.
PCT, Written Opinion of the International Preliminary Examining Authority, International application No. PCT/SU2013/071752, dated May 6, 2015.
Hlobik, Plastic Pre-Fillable Syringe Systems (http://www.healthcarepackaging.com/package-type/Containers/plastic-prefillablesyringe-systems, Jun. 8, 2010).
PCT, Written Opinion of the International Preliminary Examining Authority, in International application No. PCT/US2013/071750, dated Jan. 20, 2015 (9 pages).
PCT, Written Opinion of the International Preliminary Examining Authority, in International application No. PCT/US2013/064121, dated Nov. 21, 2014 (7 pages).
Japanese Patent Office, Decision of Rejection in Application No. 2012-510983, dated Jan. 20, 2015 (4 pages).
Australian Government, IP Australia, Patent Examination Report No. 1, in Application No. 2010249033, dated Dec. 19, 2014 (7 pages).
Australian Government, IP Australia, Patent Examination Report No. 1, in Application No. 2011252925, dated Dec. 2, 2014 (3 pages).
State Intellectual Property Office of the People's Republic of China, Notification of the Fourth Office Action in Application No. 201080029199.0, dated Mar. 18, 2015 (15 pages).
Reh, et al., Evaluation of stationary phases for 2-dimensional HPLC of Proteins—Validation of commercial RP-columns, Published by Elsevier B.V., 2000.

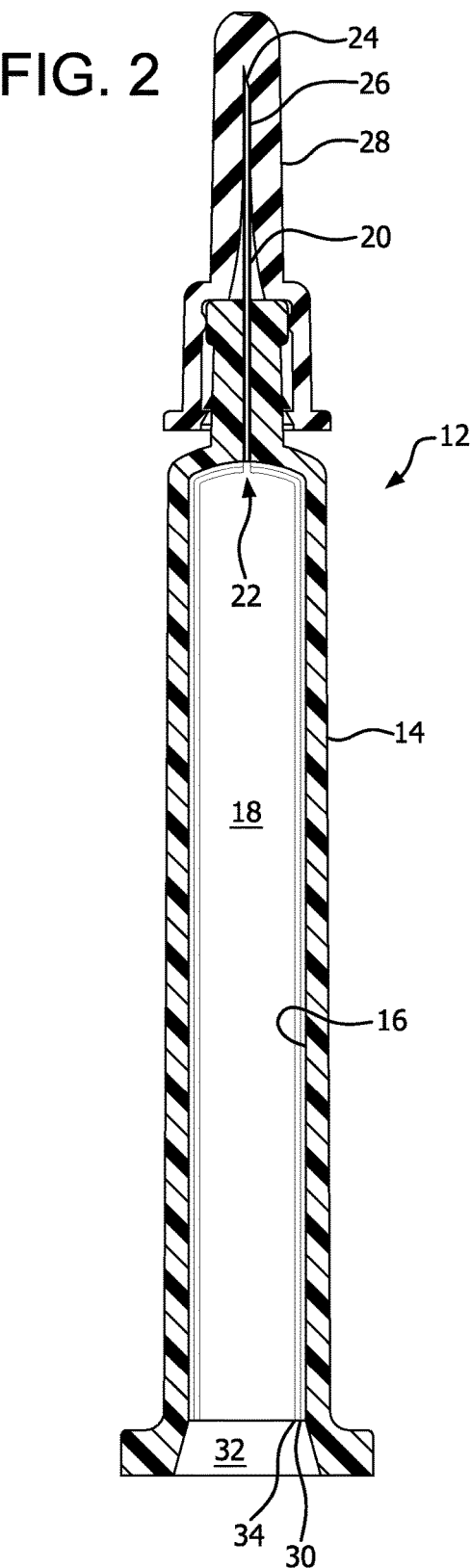
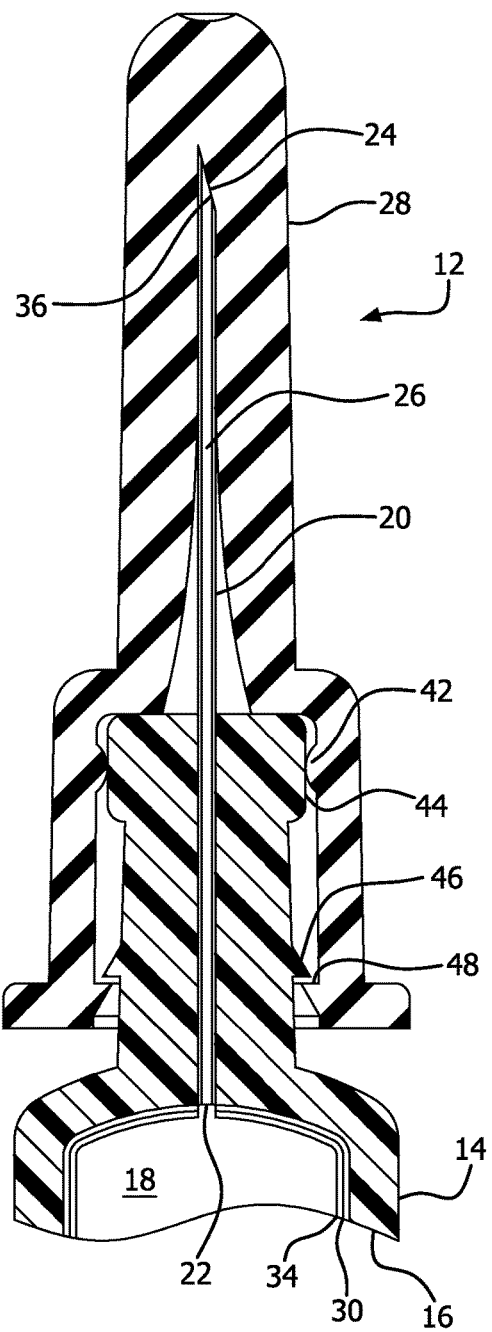
FIG. 2
FIG. 3

PASSIVATION, PH PROTECTIVE OR LUBRICITY COATING FOR PHARMACEUTICAL PACKAGE, COATING PROCESS AND APPARATUS

This application is a U.S. National Phase Application of International Application No. PCT/US2012/064489, filed Nov. 9, 2012 which claims priority from U.S. Provisional Application Ser. No. 61/558,885, filed Nov. 11, 2011; 61/636,377, filed Apr. 20, 2012; and U.S. Ser. No. 61/645, 003, filed May 9, 2012.

U.S. Provisional Ser. Nos. 61/177,984 filed May 13, 2009; 61/222,727, filed Jul. 2, 2009; 61/213,904, filed Jul. 24, 2009; 61/234,505, filed Aug. 17, 2009; 61/261,321, filed Nov. 14, 2009; 61/263,289, filed Nov. 20, 2009; 61/285,813, filed Dec. 11, 2009; 61/298,159, filed Jan. 25, 2010; 61/299, 888, filed Jan. 29, 2010; 61/318,197, filed Mar. 26, 2010; 61/333,625, filed May 11, 2010; 61/413,334, filed Nov. 12, 2010; Ser. No. 12/779,007, filed May 12, 2010, now U.S. Pat. No. 7,985,188; International Application PCT/US11/ 36097, filed May 11, 2011; U.S. Ser. No. 61/558,885, filed Nov. 11, 2011; U.S. Ser. No. 61/636,377, filed Apr. 20, 2012; U.S. Ser. No. 61/645,003, filed May 9, 2012; and U.S. Ser. No. 61/716,381, filed Oct. 19, 2012; are all incorporated here by reference in their entirety.

Also incorporated by reference in their entirety are the following European patent applications: EP10162755.2 filed May 12, 2010; EP10162760.2 filed May 12, 2010; EP10162756.0 filed May 12, 2010; EP10162758.6 filed May 12, 2010; EP10162761.0 filed May 12, 2010; and EP10162757.8 filed May 12, 2010.

FIELD OF THE INVENTION

The present invention relates to the technical field of coated surfaces, for example interior surfaces of pharmaceutical packages or other vessels for storing or other contact with fluids. Examples of suitable fluids include foods or biologically active compounds or body fluids, for example blood. The present invention also relates to a pharmaceutical package or other vessel and to a method for coating an inner or interior surface of a pharmaceutical package or other vessel. The present invention also relates more generally to medical devices, including devices other than packages or vessels, for example catheters.

The present disclosure also relates to improved methods for processing pharmaceutical packages or other vessels, for example multiple identical pharmaceutical packages or other vessels used for pharmaceutical preparation storage and delivery, venipuncture and other medical sample collection, and other purposes. Such pharmaceutical packages or other vessels are used in large numbers for these purposes, and must be relatively economical to manufacture and yet highly reliable in storage and use.

BACKGROUND OF THE INVENTION

One important consideration in manufacturing pharmaceutical packages or other vessels for storing or other contact with fluids, for example vials and pre-filled syringes, is that the contents of the pharmaceutical package or other vessel desirably will have a substantial shelf life. During this shelf life, it can be important to isolate the material filling the pharmaceutical package or other vessel from the vessel wall containing it, or from barrier coatings or layers or other functional layers applied to the pharmaceutical package or other vessel wall to avoid leaching material from the pharmaceutical package or other vessel wall, barrier coating or layer, or other functional layers into the prefilled contents or vice versa.

Since many of these pharmaceutical packages or other vessels are inexpensive and used in large quantities, for certain applications it will be useful to reliably obtain the necessary shelf life without increasing the manufacturing cost to a prohibitive level.

For decades, most parenteral therapeutics have been delivered to end users in Type I medical grade borosilicate glass vessels such as vials or pre-filled syringes. The relatively strong, impermeable and inert surface of borosilicate glass has performed adequately for most drug products. However, the recent advent of costly, complex and sensitive biologics as well as such advanced delivery systems as auto injectors has exposed the physical and chemical shortcomings of glass pharmaceutical packages or other vessels, including possible contamination from metals, flaking, delamination, and breakage, among other problems. Moreover, glass contains several components which can leach out during storage and cause damage to the stored material.

In more detail, borosilicate pharmaceutical packages or other vessels exhibit a number of drawbacks.

Glass is manufactured from sand containing a heterogeneous mixture of many elements (silicon, oxygen, boron, aluminum, sodium, calcium) with trace levels of other alkali and earth metals. Type I borosilicate glass consists of approximately 76% $SiO_2$, 10.5% $B_2O_3$, 5% $Al_2O_3$, 7% $Na_2O$ and 1.5% CaO and often contains trace metals such as iron, magnesium, zinc, copper and others. The heterogeneous nature of borosilicate glass creates a non-uniform surface chemistry at the molecular level. Glass forming processes used to create glass vessels expose some portions of the vessels to temperatures as great as 1200° C. Under such high temperatures alkali ions migrate to the local surface and form oxides. The presence of ions extracted from borosilicate glass devices may be involved in degradation, aggregation and denaturation of some biologics. Many proteins and other biologics must be lyophilized (freeze dried), because they are not sufficiently stable in solution in glass vials or syringes.

In glass syringes, silicone oil is typically used as a lubricant to allow the plunger tip, piston, stopper, or seal to slide in the barrel. Silicone oil has been implicated in the precipitation of protein solutions such as insulin and some other biologics. Additionally, the silicone oil coating or layer is often non-uniform, resulting in syringe failures in the market.

Glass pharmaceutical packages or other vessels are prone to breakage or degradation during manufacture, filling operations, shipping and use, which means that glass particulates may enter the drug. The presence of glass particles has led to many FDA Warning Letters and to product recalls.

Glass-forming processes do not yield the tight dimensional tolerances required for some of the newer auto-injectors and delivery systems.

As a result, some companies have turned to plastic pharmaceutical packages or other vessels, which provide tighter dimensional tolerances and less breakage than glass.

Although plastic is superior to glass with respect to breakage, dimensional tolerances and surface uniformity, its use for primary pharmaceutical packaging remains limited due to the following shortcomings:

Gas (oxygen) permeability: Plastic allows small molecule gases to permeate into (or out of) the device. The permeability of plastics to gases can be significantly greater than that of glass and, in many cases (as with oxygen-sensitive drugs such as epinephrine), plastics previously have been unacceptable for that reason.

Water vapor transmission: Plastics allow water vapor to pass through devices to a greater degree than glass. This can be detrimental to the shelf life of a solid (lyophilized) drug. Alternatively, a liquid product may lose water in an arid environment.

Leachables and extractables: Plastic pharmaceutical packages or other vessels contain organic compounds that can leach out or be extracted into the drug product. These compounds can contaminate the drug and/or negatively impact the drug's stability.

Clearly, while plastic and glass pharmaceutical packages or other vessels each offer certain advantages in pharmaceutical primary packaging, neither is optimal for all drugs, biologics or other therapeutics. Thus, there can be a desire for plastic pharmaceutical packages or other vessels, in particular plastic syringes, with gas and solute barrier properties which approach the properties of glass. Moreover, there can be a need for plastic syringes with sufficient lubricity and/or passivation or protective properties and a lubricity and/or passivation layer or pH protective coating which can be compatible with the syringe contents. There also can be a need for glass vessels with surfaces that do not tend to delaminate or dissolve or leach constituents when in contact with the vessel contents.

There are additional considerations to be taken into account when manufacturing a prefilled syringe. Prefilled syringes are commonly prepared and sold so the syringe does not need to be filled before use, and can be disposed of after use. The syringe can be prefilled with saline solution, a dye for injection, or a pharmaceutically active preparation, for some examples.

Commonly, the prefilled syringe can be capped at the distal end, as with a cap (or, if the hypodermic needle is preinstalled, a needle shield that can also be a cap), and can be closed at the proximal end by its drawn plunger tip, piston, stopper, or seal. The prefilled syringe can be wrapped in a sterile package before use. To use the prefilled syringe, the packaging and cap are removed, optionally a hypodermic needle or another delivery conduit can be attached to the distal end of the barrel, the delivery conduit or syringe can be moved to a use position (such as by inserting the hypodermic needle into a patient's blood vessel or into apparatus to be rinsed with the contents of the syringe), and the plunger tip, piston, stopper, or seal can be advanced in the barrel to inject the contents of the barrel.

An important consideration regarding medical syringes can be to ensure that the plunger tip, piston, stopper, or seal can move at a constant speed and with a constant force when it is pressed into the barrel. A similar consideration applies to vessels such as pharmaceutical vials which have to be closed by a stopper, and to the stopper itself, and more generally to any surface which is to provide smooth operation of moving parts and/or be passivated or protectively coated.

A non-exhaustive list of documents of possible relevance includes U.S. Pat. Nos. 7,901,783; 6,068,884; 4,844,986; and 8,067,070 and U.S. Publ. Appl. Nos. 2008/0090039, 2011/0152820, 2006/0046006 and 2004/0267194. These documents are all incorporated by reference.

SUMMARY OF THE INVENTION

An aspect of the invention is a filled package comprising a vessel, a barrier coating or layer, and a passivation layer or pH protective coating on the vessel, and a fluid composition contained in the vessel. The calculated shelf life of the package can be more than six months at a storage temperature of 4° C.

The vessel can have a lumen defined at least in part by a wall. The wall can have an interior surface facing the lumen and an outer surface.

The barrier coating or layer comprises $SiO_x$, wherein x is from 1.5 to 2.9, from 2 to 1000 nm thick. The barrier coating or layer of $SiO_x$ can have an interior surface facing the lumen and an outer surface facing the wall interior surface.

The passivation layer or pH protective coating comprises $SiO_xC_y$ or $SiN_xC_y$, wherein x is from about 0.5 to about 2.4 and y is from about 0.6 to about 3. Optionally in one embodiment, x can be about 1.1 and y can be about 1.1. The passivation layer or pH protective coating can have an interior surface facing the lumen and an outer surface facing the interior surface of the barrier coating or layer. The passivation layer or pH protective coating can be effective to increase the calculated shelf life of the package (total Si/Si dissolution rate).

The fluid composition can be contained in the lumen and can have a pH between 4 and 10, alternatively between 5 and 9.

Another aspect of the invention can be a filled package comprising a vessel, a passivation layer or pH protective coating on the vessel, and a fluid composition contained in the vessel.

The vessel can have a lumen defined at least in part by a wall. The wall can have an interior surface comprising glass facing the lumen and an outer surface.

The passivation layer or pH protective coating comprises $SiO_xC_y$ or $SiN_xC_y$, wherein x is from about 0.5 to about 2.4 and y is from about 0.6 to about 3. The passivation layer or pH protective coating can have an interior surface facing the lumen and an outer surface facing the interior surface of the barrier coating or layer. The passivation layer or pH protective coating can be effective to decrease the Si dissolution rate of the glass interior surface.

The fluid composition can be contained in the lumen and can have a pH between 4 and 10, alternatively between 5 and 9.

Still another aspect of the invention can be an article comprising a wall, a barrier coating or layer, and a passivation layer or pH protective coating.

The wall can have an interior surface facing the lumen.

The barrier coating or layer comprises $SiO_x$, wherein x is from 1.5 to 2.9, from 2 to 1000 nm thick. The barrier coating or layer of $SiO_x$ can have an interior surface facing the lumen and an outer surface facing the wall interior surface. The barrier coating or layer can be effective to reduce the ingress of atmospheric gas through the wall compared to an uncoated wall.

The passivation layer or pH protective coating can be on the barrier coating or layer, optionally with one or more intervening layers, and comprises $SiO_xC_y$ or $SiN_xC_y$ wherein x is from about 0.5 to about 2.4 and y is from about 0.6 to about 3. The passivation layer or pH protective coating can be formed by chemical vapor deposition of a precursor selected from a linear siloxane, a monocyclic siloxane, a polycyclic siloxane, a polysilsesquioxane, a linear silazane, a monocyclic silazane, a polycyclic silazane, a polysilsesquiazane, a silatrane, a silquasilatrane, a silproatrane, an azasilatrane, an azasilquasiatrane, an azasilproatrane, or a combination of any two or more of these precursors. The rate of erosion of the passivation layer or pH protective coating, if directly contacted by a fluid composition having a pH between 4 and 10, alternatively between 5 and 9, can be less than the rate of erosion of the barrier coating or layer, if directly contacted by the fluid composition.

Even another aspect of the invention can be a vessel comprising a wall, a fluid contained in the vessel, a barrier coating or layer, and a passivation layer or pH protective coating.

The wall can be a thermoplastic wall having an interior surface enclosing a lumen.

The fluid can be disposed in the lumen and can have a pH greater than 5.

The barrier coating or layer comprises $SiO_x$, in which x is between 1.5 and 2.9. The barrier coating or layer can be applied by PECVD. The barrier coating or layer can be positioned between the interior surface of the thermoplastic wall and the fluid, and supported by the thermoplastic wall. The barrier coating or layer commonly can have the characteristic of being subject to being measurably diminished in barrier improvement factor in less than six months as a result of attack by the fluid, although this is not a required feature of the invention.

The passivation layer or pH protective coating comprises $SiO_xC_y$, in which x is between 0.5 and 2.4 and y is between 0.6 and 3. The passivation layer or pH protective coating can be applied by PECVD, and can be positioned between the barrier coating or layer and the fluid. The passivation layer or pH protective coating can be supported by the thermoplastic wall. The passivation layer or pH protective coating can be effective to keep the barrier coating or layer at least substantially undissolved as a result of attack by the fluid for a period of at least six months.

Yet another aspect of the invention can be a composite material comprising a substrate, a barrier coating or layer over the substrate, and a passivation layer or pH protective coating (which can have the same function as the passivation layer referred to in U.S. Pat. No. 8,067,070) over the barrier coating or layer. The passivation layer or pH protective coating shows an FTIR absorbance ratio of greater than 0.75 between: (1) the maximum amplitude of the Si—O—Si symmetrical stretch peak of an FTIR spectrum between about 1000 and 1040 cm$^{-1}$, and (2) the maximum amplitude of the Si—O—Si assymmetric stretch peak of the FTIR spectrum between about 1060 and about 1100 cm$^{-1}$.

Optionally, the vessel further includes an opening communicating with the lumen and a closure. The method optionally further includes placing a fluid in the lumen via the opening and closing the opening with the closure. The fluid can be a pharmaceutical fluid such as a drug, for example.

Other aspects of the invention will become apparent to a person of ordinary skill in the art after reviewing the present disclosure and claims.

BRIEF DESCRIPTION OF THE DRAWINGS

FIG. 2 is a longitudinal section of the capped pre-assembly of FIG. 1.

FIG. 3 is an enlarged fragmentary view of the capped pre-assembly of FIGS. 1 and 2.

Figure 1:
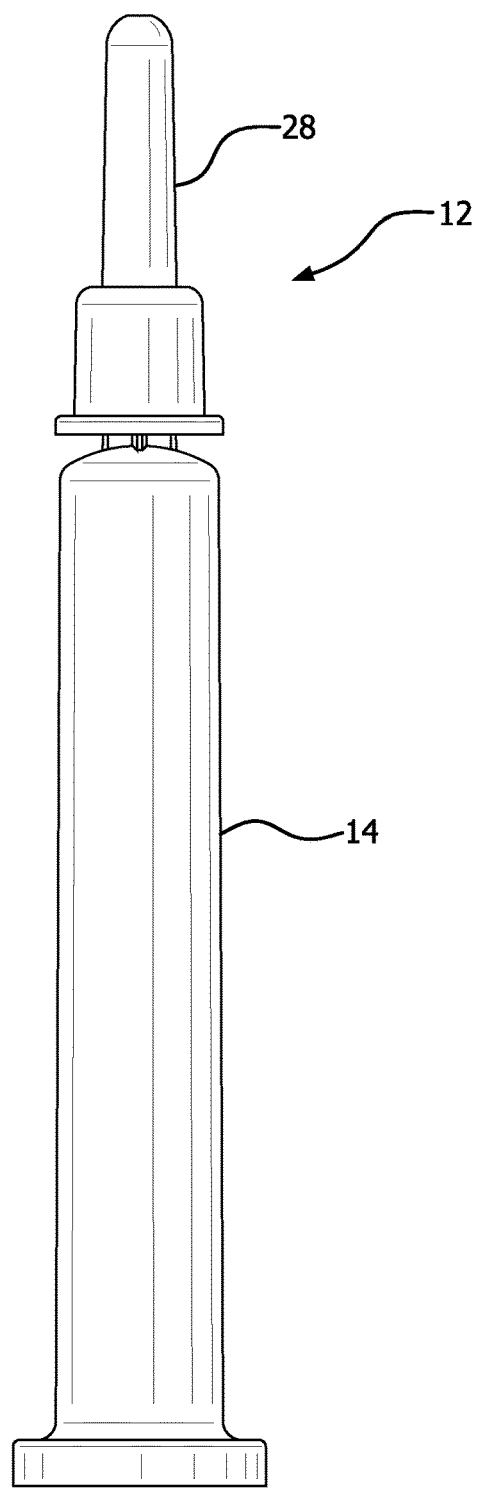
FIG. 1 is an elevation view of a capped pre-assembly according to an embodiment of the disclosure.

The following reference characters are used in the drawing figures:

| | |
|---|---|
| 12 | Capped pre-assembly |
| 14 | Barrel |
| 16 | Internal wall |
| 18 | Barrel lumen |
| 20 | Dispensing portion |
| 22 | Proximal opening |
| 24 | Distal opening |
| 26 | Dispensing portion lumen |
| 27 | Shield |
| 30 | Barrier coating or layer |
| 32 | Opening |
| 34 | Passivation layer or pH protective coating |
| 36 | plunger tip, piston, stopper, or seal |
| 38 | Push rod |
| 40 | Fluid material |
| 42 | Rib |
| 44 | Cylindrical surface |
| 46 | Barb |
| 48 | Catch |
| 50 | Vessel holder |
| 52 | Plot |
| 54 | Plot |
| 60 | coating station |
| 82 | Opening |
| 84 | Closed end |
| 92 | Vessel port |
| 94 | Vacuum duct |
| 96 | Vacuum port |
| 98 | Vacuum source |
| 100 | O-ring (of 92) |
| 102 | O-ring (of 96) |
| 104 | Gas inlet port |
| 106 | O-ring (of 100) |
| 108 | Probe (counter electrode) |
| 110 | Gas delivery port (of 108) |
| 114 | Housing (of 50 or 112) |
| 116 | Collar |
| 118 | Exterior surface (of 80) |
| 144 | PECVD gas source |
| 152 | Pressure gauge |
| 160 | Electrode |
| 162 | Power supply |
| 164 | Sidewall (of 160) |
| 166 | Sidewall (of 160) |
| 168 | Closed end (of 160) |
| 200 | Electrode |
| 210 | Pharmaceutical package |
| 404 | Exhaust |
| 574 | Main vacuum valve |
| 576 | Vacuum line |
| 578 | Manual bypass valve |
| 580 | Bypass line |
| 582 | Vent valve |
| 584 | Main reactant gas valve |
| 586 | Main reactant feed line |
| 588 | Organosilicon liquid reservoir |
| 590 | Organosilicon feed line (capillary) |
| 592 | Organosilicon shut-off valve |
| 594 | Oxygen tank |
| 596 | Oxygen feed line |
| 598 | Mass flow controller |
| 600 | Oxygen shut-off valve |
| 602 | Additional reservoir |
| 604 | Feed line |
| 606 | Shut-off valve |
| 614 | Headspace |
| 616 | Pressure source |
| 618 | Pressure line |
| 620 | Capillary connection |

Definition Section

In the context of the present invention, the following definitions and abbreviations are used:

RF is radio frequency.

The term "at least" in the context of the present invention means "equal or more" than the integer following the term. The word "comprising" does not exclude other elements or steps, and the indefinite article "a" or "an" does not exclude a plurality unless indicated otherwise. Whenever a parameter range is indicated, it is intended to disclose the parameter values given as limits of the range and all values of the parameter falling within said range.

"First" and "second" or similar references to, for example, processing stations or processing devices refer to the minimum number of processing stations or devices that are present, but do not necessarily represent the order or total number of processing stations and devices. These terms do not limit the number of processing stations or the particular processing carried out at the respective stations.

For purposes of the present invention, an "organosilicon precursor" is a compound having at least one of the linkages:

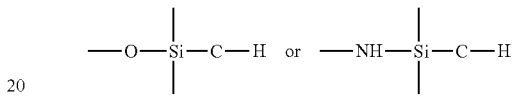

which is a tetravalent silicon atom connected to an oxygen or nitrogen atom and an organic carbon atom (an organic carbon atom being a carbon atom bonded to at least one hydrogen atom). A volatile organosilicon precursor, defined as such a precursor that can be supplied as a vapor in a PECVD apparatus, can be an optional organosilicon precursor. Optionally, the organosilicon precursor can be selected from the group consisting of a linear siloxane, a monocyclic siloxane, a polycyclic siloxane, a polysilsesquioxane, an alkyl trimethoxysilane, a linear silazane, a monocyclic silazane, a polycyclic silazane, a polysilsesquiazane, and a combination of any two or more of these precursors.

The feed amounts of PECVD precursors, gaseous reactant or process gases, and carrier gas are sometimes expressed in "standard volumes" in the specification and claims. The standard volume of a charge or other fixed amount of gas is the volume the fixed amount of the gas would occupy at a standard temperature and pressure (without regard to the actual temperature and pressure of delivery). Standard volumes can be measured using different units of volume, and still be within the scope of the present disclosure and claims. For example, the same fixed amount of gas could be expressed as the number of standard cubic centimeters, the number of standard cubic meters, or the number of standard cubic feet. Standard volumes can also be defined using different standard temperatures and pressures, and still be within the scope of the present disclosure and claims. For example, the standard temperature might be 0° C. and the standard pressure might be 760 Torr (as is conventional), or the standard temperature might be 20° C. and the standard pressure might be 1 Torr. But whatever standard is used in a given case, when comparing relative amounts of two or more different gases without specifying particular parameters, the same units of volume, standard temperature, and standard pressure are to be used relative to each gas, unless otherwise indicated.

The corresponding feed rates of PECVD precursors, gaseous reactant or process gases, and carrier gas are expressed in standard volumes per unit of time in the specification. For example, in the working examples the flow rates are expressed as standard cubic centimeters per minute, abbreviated as sccm. As with the other parameters, other units of time can be used, such as seconds or hours, but consistent parameters are to be used when comparing the flow rates of two or more gases, unless otherwise indicated.

A "vessel" in the context of the present invention can be any type of article with at least one opening and a wall defining an inner or interior surface. The substrate can be the inside wall of a vessel having a lumen. Though the invention is not necessarily limited to pharmaceutical packages or other vessels of a particular volume, pharmaceutical packages or other vessels are contemplated in which the lumen can have a void volume of from 0.5 to 50 mL, optionally from 1 to 10 mL, optionally from 0.5 to 5 mL, optionally from 1 to 3 mL. The substrate surface can be part or all of the inner or interior surfaceinner or interior surface of a vessel having at least one opening and an inner or interior surfaceinner or interior surface.

A vessel in the context of the present invention can have one or more openings. One or two openings, like the openings of a sample tube (one opening) or a syringe barrel (two openings) are preferred. If the vessel has two openings, they can be the same size or different sizes. If there is more than one opening, one opening can be used for the gas inlet for a PECVD coating method according to the present invention, while the other openings are either capped or open. A vessel according to the present invention can be a sample tube, for example for collecting or storing biological fluids like blood or urine, a syringe (or a part thereof, for example a syringe barrel) for storing or delivering a biologically active compound or composition, for example a medicament or pharmaceutical composition, a vial for storing biological materials or biologically active compounds or compositions, a pipe, for example a catheter for transporting biological materials or biologically active compounds or compositions, or a cuvette for holding fluids, for example for holding biological materials or biologically active compounds or compositions.

The vessel can be provided with a reagent or preservative for sample collection or analysis. For example, a vessel for blood collection can have an inner or interior surface defining a lumen and an exterior surface, the passivation layer or pH protective coating can be on the inner or interior surface, and the vessel can contain a compound or composition in its lumen, for example citrate or a citrate containing composition.

A vessel can be of any shape, a vessel having a substantially cylindrical wall adjacent to at least one of its open ends being preferred. Generally, the interior wall of the vessel can be cylindrically shaped, like, for example in a sample tube or a syringe barrel. Sample tubes and syringes or their parts (for example syringe barrels) are contemplated.

A "hydrophobic layer" in the context of the present invention means that the coating or layer lowers the wetting tension of a surface coated with the coating or layer, compared to the corresponding uncoated surface. Hydrophobicity can be thus a function of both the uncoated substrate and the coating or layer. The same applies with appropriate alterations for other contexts wherein the term "hydrophobic" is used. The term "hydrophilic" means the opposite, i.e. that the wetting tension is increased compared to reference sample. The present hydrophobic layers are primarily defined by their hydrophobicity and the process conditions providing hydrophobicity. Suitable hydrophobic coatings or layers and their application, properties, and use are described in U.S. Pat. No. 7,985,188. Dual functional passivation layers or pH protective coatings that also have the properties of hydrophobic coatings or layers can be provided for any embodiment of the present invention.

The values of w, x, y, and z are applicable to the empirical composition $Si_wO_xC_yH_z$ throughout this specification. The values of w, x, y, and z used throughout this specification should be understood as ratios or an empirical formula (for example for a coating or layer), rather than as a limit on the number or type of atoms in a molecule. For example, octamethylcyclotetrasiloxane, which has the molecular composition $Si_4O_4C_8H_{24}$, can be described by the following empirical formula, arrived at by dividing each of w, x, y, and z in the molecular formula by 4, the largest common factor: $Si_1O_1C_2H_6$. The values of w, x, y, and z are also not limited to integers. For example, (acyclic) octamethyltrisiloxane, molecular composition $Si_3O_2C_8H_{24}$, is reducible to $Si_1O_{0.67}C_{2.67}H_8$. Also, although $SiO_xC_yH_z$ can be described as equivalent to $SiO_xC_y$, it is not necessary to show the presence of hydrogen in any proportion to show the presence of $SiO_xC_y$.

"Wetting tension" is a specific measure for the hydrophobicity or hydrophilicity of a surface. An optional wetting tension measurement method in the context of the present invention is ASTM D 2578 or a modification of the method described in ASTM D 2578. This method uses standard wetting tension solutions (called dyne solutions) to determine the solution that comes nearest to wetting a plastic film surface for exactly two seconds. This is the film's wetting tension. The procedure utilized can be varied herein from ASTM D 2578 in that the substrates are not flat plastic films, but are tubes made according to the Protocol for Forming PET Tube and (except for controls) coated according to the Protocol for coating Tube Interior with Hydrophobic Coating or Layer (see Example 9 of EP2251671 A2).

A "lubricity coating or layer" according to the present invention is a coating or layer which has a lower frictional resistance than the uncoated surface.

A "passivation layer or pH protective coating" according to the present invention passivates or protects an underlying surface or layer from a fluid composition contacting the layer (as more extensively defined elsewhere in this specification).

"Frictional resistance" can be static frictional resistance and/or kinetic frictional resistance.

One of the optional embodiments of the present invention can be a syringe part, for example a syringe barrel or plunger tip, piston, stopper, or seal, coated with a lubricity and/or passivation layer or pH protective coating. In this contemplated embodiment, the relevant static frictional resistance in the context of the present invention is the breakout force as defined herein, and the relevant kinetic frictional resistance in the context of the present invention is the plunger sliding force as defined herein. For example, the plunger sliding force as defined and determined herein is suitable to determine the presence or absence and the lubricity and/or passivating or protective characteristics of a lubricity and/or passivation layer or pH protective coating in the context of the present invention whenever the coating or layer is applied to any syringe or syringe part, for example to the inner wall of a syringe barrel. The breakout force can be of particular relevance for evaluation of the coating or layer effect on a prefilled syringe, i.e. a syringe which can be filled after coating and can be stored for some time, for example several months or even years, before the plunger tip, piston, stopper, or seal is moved again (has to be "broken out").

The "plunger sliding force" (synonym to "glide force," "maintenance force", or $F_m$, also used in this description) in the context of the present invention is the force required to maintain movement of a plunger tip, piston, stopper, or seal in a syringe barrel, for example during aspiration or dispense. It can advantageously be determined using the ISO 7886-1:1993 test described herein and known in the art. A synonym for "plunger sliding force" often used in the art is "plunger force" or "pushing force".

The "plunger breakout force" (synonym to "breakout force", "break loose force", "initiation force", Fi, also used in this description) in the context of the present invention is the initial force required to move the plunger tip, piston, stopper, or seal in a syringe, for example in a prefilled syringe.

Both "plunger sliding force" and "plunger breakout force" and methods for their measurement are described in more detail in subsequent parts of this description. These two forces can be expressed in N, lbs or kg and all three units are used herein. These units correlate as follows: 1N=0.102 kg=0.2248 lbs (pounds).

Sliding force and breakout force are sometimes used herein to describe the forces required to advance a stopper or other closure into a pharmaceutical package or other vessel, such as a medical sample tube or a vial, to seat the stopper in a vessel to close the vessel. Its use can be analogous to use in the context of a syringe and its plunger tip, piston, stopper, or seal, and the measurement of these forces for a vessel and its closure are contemplated to be analogous to the measurement of these forces for a syringe, except that at least in most cases no liquid is ejected from a vessel when advancing the closure to a seated position.

"Slidably" means that the plunger tip, piston, stopper, or seal or other removable part can be permitted to slide in a syringe barrel or other vessel.

Coatings of $SiO_x$ are deposited by plasma enhanced chemical vapor deposition (PECVD) or other chemical vapor deposition processes on the vessel of a pharmaceutical package, in particular a thermoplastic package, to serve as a barrier coating or layer preventing oxygen, air, carbon dioxide, or other gases from entering the vessel and/or to prevent leaching of the pharmaceutical material into or through the package wall. The barrier coating or layer can be effective to reduce the ingress of atmospheric gas, for example oxygen, into the lumen compared to a vessel without a passivation layer or pH protective coating.

In any embodiment the vapor-deposited coating or layer optionally can also, or alternatively, be a solute barrier coating or layer. A concern of converting from glass to plastic syringes centers around the potential for leachable materials from plastics. With plasma coating technology, the coatings or layers derived from non-metal gaseous precursors, for example HMDSO or OMCTS or other organosilicon compounds, will contain no trace metals and function as a barrier coating or layer to inorganic, metals and organic solutes, preventing leaching of these species from the coated substrate into syringe fluids. In addition to leaching control of plastic syringes, the same plasma passivation layer or pH protective coating technology offers potential to provide a solute barrier to the plunger tip, piston, stopper, or seal, typically made of elastomeric plastic compositions containing even higher levels of leachable organic oligomers and catalysts.

Moreover, certain syringes prefilled with synthetic and biological pharmaceutical formulations are very oxygen and moisture sensitive. A critical factor in the conversion from glass to plastic syringe barrels will be the improvement of plastic oxygen and moisture barrier performance. The plasma passivation layer or pH protective coating technology can be suitable to maintain the $SiO_x$ barrier coating or layer or layer for protection against oxygen and moisture over an extended shelf life.

Examples of solutes in drugs usefully excluded by a barrier layer in any embodiment include antibacterial preservatives, antioxidants, chelating agents, pH buffers, and combinations of any of these. In any embodiment the vapor-deposited coating or layer optionally can be a solvent barrier coating or layer for a solvent comprising a co-solvent used to increase drug solubilization.

In any embodiment the vapor-deposited coating or layer optionally can be a barrier coating or layer for water, glycerin, propylene glycol, methanol, ethanol, n-propanol, isopropanol, acetone, benzyl alcohol, polyethylene glycol, cotton seed oil, benzene, dioxane, or combinations of any two or more of these.

In any embodiment the vapor-deposited coating or layer optionally can be a metal ion barrier coating or layer.

In any embodiment the vapor-deposited coating or layer optionally can be a barrel wall material barrier coating or layer, to prevent or reduce the leaching of barrel material such as any of the base barrel resins mentioned previously and any other ingredients in their respective compositions.

The inventors have found, however, that such barrier coatings or layers or coatings of $SiO_x$ are eroded or dissolved by some fluid compositions, for example aqueous compositions having a pH above about 5. Since coatings applied by chemical vapor deposition can be very thin—tens to hundreds of nanometers thick—even a relatively slow rate of erosion can remove or reduce the effectiveness of the barrier coating or layer in less time than the desired shelf life of a product package. This can be particularly a problem for fluid pharmaceutical compositions, since many of them have a pH of roughly 7, or more broadly in the range of 5 to 9, similar to the pH of blood and other human or animal fluids. The higher the pH of the pharmaceutical preparation, the more quickly it erodes or dissolves the $SiO_x$ coating.

The inventors have further found that without a protective coating borosilicate glass surfaces are eroded or dissolved by some fluid compositions, for example aqueous compositions having a pH above about 5. This can be particularly a problem for fluid pharmaceutical compositions, since many of them have a pH of roughly 7, or more broadly in the range of 5 to 9, similar to the pH of blood and other human or animal fluids. The higher the pH of the pharmaceutical preparation, the more quickly it erodes or dissolves the glass. Delamination of the glass can also result from such erosion or dissolution, as small particles of glass are undercut by the aqueous compositions having a pH above about 5.

The inventors have further found that certain passivation layers or pH protective coatings of $SiO_xC_y$ or $SiN_xC_y$ formed from cyclic polysiloxane precursors, which passivation layers or pH protective coatings have a substantial organic component, do not erode quickly when exposed to fluid compositions, and in fact erode or dissolve more slowly when the fluid compositions have higher pHs within the range of 5 to 9. For example, at pH 8, the dissolution rate of a passivation layer or pH protective coating made from the precursor octamethylcyclotetrasiloxane, or OMCTS, can be quite slow. These passivation layers or pH protective coatings of $SiO_xC_y$ or $SiN_xC_y$ can therefore be used to cover a barrier coating or layer of $SiO_x$, retaining the benefits of the barrier coating or layer by passivating or protecting it from the fluid composition in the pharmaceutical package. These passivation layers or pH protective coatings of $SiO_xC_y$ or $SiN_xC_y$ also can be used to cover a glass surface, for example a borosilicate glass surface, preventing delamination, erosion and dissolution of the glass, by passivating or protecting it from the fluid composition in the pharmaceutical package.

Although the present invention does not depend upon the accuracy of the following theory, it is believed that the material properties of an effective $SiO_xC_y$ passivation layer or pH protective coating and those of an effective lubricity layer as described in U.S. Pat. No. 7,985,188 and in International Application PCT/US11/36097 are similar in some instances, such that a coating having the characteristics of a lubricity layer as described in certain working examples of this specification, U.S. Pat. No. 7,985,188, or International Application PCT/US11/36097 will also in certain cases serve as well as a passivation layer or pH protective coating to passivate or protect the barrier coating or layer of the package and vice versa.

Although the present invention does not depend upon the accuracy of the following theory, it is further believed that the most effective lubricity and/or passivation layers or pH protective coatings are those made from cyclic siloxanes and silazanes as described in this disclosure. $SiO_xC_y$ or $SiN_xC_y$ coatings deposited from linear siloxane or linear silazane precursors, for example hexamethyldisiloxane (HMDSO), are believed to contain fragments of the original precursor to a large degree and low organic content. Such $SiO_xC_y$ or $SiN_xC_y$ coatings have a degree of water miscibility or swellability, allowing them to be attacked by aqueous solutions. $SiO_xC_y$ or $SiN_xC_y$ coatings deposited from cyclic siloxane or linear silazane precursors, for example octamethylcyclotetrasiloxane (OMCTS), however, are believed to include more intact cyclic siloxane rings and longer series of repeating units of the precursor structure. These coatings are believed to be nanoporous but structured and hydrophobic, and these properties are believed to contribute to their success as passivation layers or pH protective coatings. This is shown, for example, in U.S. Pat. No. 7,901,783.

DETAILED DESCRIPTION

The present invention will now be described more fully, with reference to the accompanying drawings, in which several embodiments are shown. This invention can, however, be embodied in many different forms and should not be construed as limited to the embodiments set forth here. Rather, these embodiments are examples of the invention, which has the full scope indicated by the language of the claims. Like numbers refer to like or corresponding elements throughout. The following disclosure relates to all embodiments unless specifically limited to a certain embodiment.

PECVD Treated Pharmaceutical Packages or Other Vessels

A vessel with a passivation layer or pH protective coating as described herein and/or prepared according to a method described herein can be used for reception and/or storage and/or delivery of a compound or composition. The compound or composition can be sensitive, for example air-sensitive, oxygen-sensitive, sensitive to humidity and/or sensitive to mechanical influences. It can be a biologically active compound or composition, for example a pharmaceutical preparation or medicament like insulin or a composition comprising insulin. A prefilled syringe can be especially considered which contains injectable or other liquid drugs like insulin.

In another aspect, the compound or composition can be a biological fluid, optionally a bodily fluid, for example blood or a blood fraction. In certain aspects of the present invention, the compound or composition can be a product to be administered to a subject in need thereof, for example a product to be injected, like blood (as in transfusion of blood from a donor to a recipient or reintroduction of blood from a patient back to the patient) or insulin.

A vessel with a passivation layer or pH protective coating as described herein and/or prepared according to a method described herein can further be used for protecting a compound or composition contained in its interior space against mechanical and/or chemical effects of the surface of the vessel material. For example, it can be used for preventing or reducing precipitation and/or clotting or platelet activation of the compound or a component of the composition, for example insulin precipitation or blood clotting or platelet activation.

It can further be used for protecting a compound or composition contained in its interior against the environment outside of the pharmaceutical package or other vessel, for example by preventing or reducing the entry of one or more compounds from the environment surrounding the vessel into the interior space of the vessel. Such environmental compound can be a gas or liquid, for example an atmospheric gas or liquid containing oxygen, air, and/or water vapor.

Figure 7:
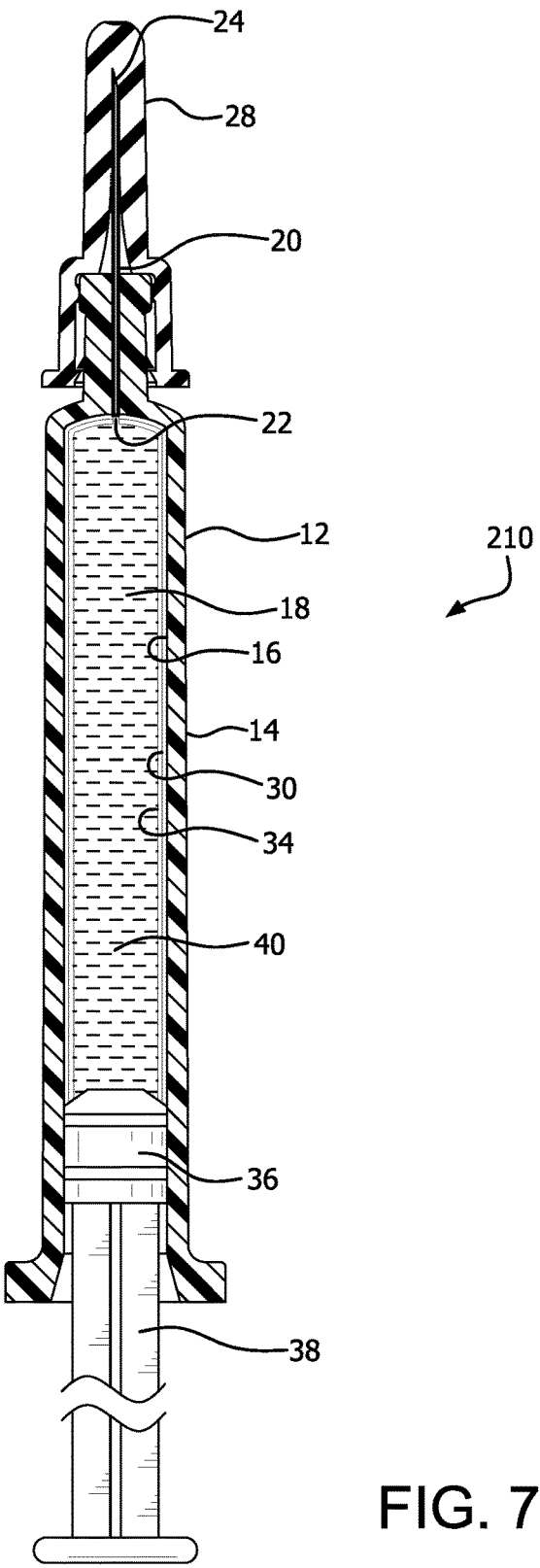
FIG. 7 is a view similar to FIG. 2 of the capped pre-assembly of FIGS. 1-6, filled with a pharmaceutical preparation and fitted with a plunger tip, piston, stopper, or seal to define a pre-filled syringe. In the option shown, a plunger tip, piston, stopper, or seal and plunger push rod are installed.
Figure 8:
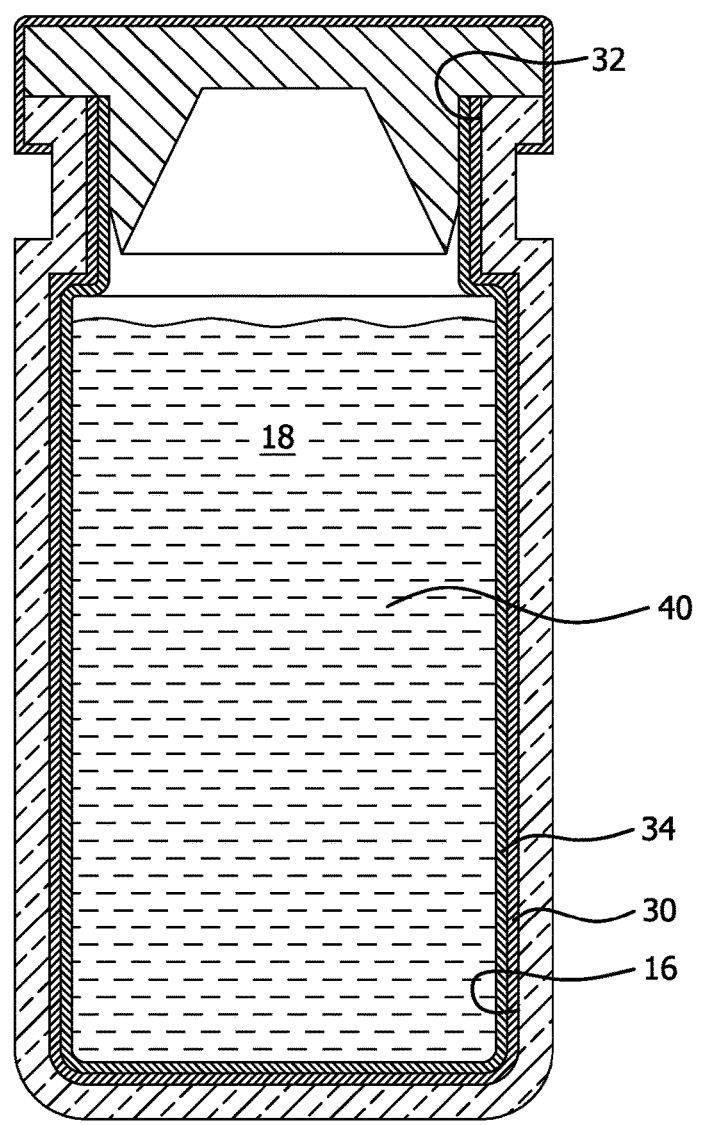
FIG. 8 is a longitudinal section of a vial fitted with a septum and crimp and having the same barrier coating or layer, passivation layer or pH protective coating, and other common features of FIG. 7.

Referring to the Figures, an aspect of the invention can be a method in which a barrier coating or layer 30 and a passivation layer or pH protective coating 34 are applied directly or indirectly applied to at least a portion of the interior wall 16 of a vessel, such as any of the pharmaceutical packages 210 of FIGS. 7-8, a sample collection tube, for example a blood collection tube and/or a closed-ended sample collection tube; a conduit; a cuvette; or a vessel part, for example a plunger tip, piston, stopper, or seal for contact with and/or storage and/or delivery of a compound or composition.

Vessel Wall Construction

Optionally for any of the embodiments of FIGS. 7-8, at least a portion of the internal wall 16 of the pharmaceutical package 210 comprises or consists essentially of a polymer, for example a polyolefin (for example a cyclic olefin polymer, a cyclic olefin copolymer, or polypropylene), a polyester, for example polyethylene terephthalate or polyethylene naphthalate, a polycarbonate, polylactic acid, or any combination, composite or blend of any two or more of the above materials.

Optionally for any of the embodiments of FIGS. 7-8, at least a portion of the internal wall 16 of the pharmaceutical package 210 comprises or consists essentially of glass, for example borosilicate glass.

As an optional feature of any of the foregoing embodiments the polymeric material can be a silicone elastomer or a thermoplastic polyurethane, as two examples, or any material suitable for contact with blood, or with insulin. For example, the use of a coated substrate according to any described embodiment is contemplated for storing insulin.

Optionally, as for the embodiments of FIG. 7, the pharmaceutical package 210 comprises a syringe barrel.

Optionally, the pharmaceutical package comprises a cartridge.

Optionally, as for the embodiments of FIG. 8, the pharmaceutical package 210 comprises a vial.

Optionally, as for the embodiments of FIGS. 7-8, the pharmaceutical package 210 comprises a blister package.

Optionally, the pharmaceutical package comprises an ampoule.

Alternatively, the vessel can be a length of tubing from about 1 cm to about 200 cm, optionally from about 1 cm to about 150 cm, optionally from about 1 cm to about 120 cm, optionally from about 1 cm to about 100 cm, optionally from about 1 cm to about 80 cm, optionally from about 1 cm to about 60 cm, optionally from about 1 cm to about 40 cm, optionally from about 1 cm to about 30 cm long, and processing it with a probe electrode as described below. Particularly for the longer lengths in the above ranges, it is contemplated that relative motion between the PECVD or other chemical vapor deposition probe and the vessel can be useful during passivation layer or pH protective coating formation. This can be done, for example, by moving the vessel with respect to the probe or moving the probe with respect to the vessel.

In these embodiments, it is contemplated that the barrier coating or layer discussed below can be thinner or less complete than would be preferred to provide the high gas barrier integrity needed in an evacuated blood collection tube, and thus the long shelf life needed to store a liquid material in contact with the barrier coating or layer for an extended period.

As an optional feature of any of the foregoing embodiments the vessel can have a central axis. As an optional feature of any of the foregoing embodiments the vessel wall can be sufficiently flexible to be flexed at least once at 20° C., without breaking the wall, over a range from at least substantially straight to a bending radius at the central axis of not more than 100 times as great as the outer diameter of the vessel.

As an optional feature of any of the foregoing embodiments the bending radius at the central axis can be, for example, not more than 90 times as great as, or not more than 80 times as great as, or not more than 70 times as great as, or not more than 60 times as great as, or not more than 50 times as great as, or not more than 40 times as great as, or not more than 30 times as great as, or not more than 20 times as great as, or not more than 10 times as great as, or not more than 9 times as great as, or not more than 8 times as great as, or not more than 7 times as great as, or not more than 6 times as great as, or not more than 5 times as great as, or not more than 4 times as great as, or not more than 3 times as great as, or not more than 2 times as great as, or not more than, the outer diameter of the vessel.

As an optional feature of any of the foregoing embodiments the vessel wall can be a fluid-contacting surface made of flexible material.

As an optional feature of any of the foregoing embodiments the vessel lumen can be the fluid flow passage of a pump.

As an optional feature of any of the foregoing embodiments the vessel can be a blood containing vessel. The passivation layer or pH protective coating can be effective to reduce the clotting or platelet activation of blood exposed to the inner or interior surface, compared to the same type of wall uncoated with a hydrophobic layer.

It is contemplated that the incorporation of a hydrophobic layer will reduce the adhesion or clot forming tendency of the blood, as compared to its properties in contact with an unmodified polymeric or $SiO_x$ surface. This property is contemplated to reduce or potentially eliminate the need for treating the blood with heparin, as by reducing the necessary blood concentration of heparin in a patient undergoing surgery of a type requiring blood to be removed from the patient and then returned to the patient, as when using a heart-lung machine during cardiac surgery. It is contemplated that this will reduce the complications of surgery involving the passage of blood through such a pharmaceutical package or other vessel, by reducing the bleeding complications resulting from the use of heparin.

Another embodiment can be a vessel including a wall and having an inner or interior surface defining a lumen. The inner or interior surface can have an at least partial passivation layer or pH protective coating that presents a hydrophobic surface, the thickness of the passivation layer or pH protective coating being from monomolecular thickness to about 1000 nm thick on the inner or interior surface, the passivation layer or pH protective coating being effective to reduce the clotting or platelet activation of blood exposed to the inner or interior surface.

Several non-limiting examples of such a vessel are a blood transfusion bag, a blood sample collection vessel in which a sample has been collected, the tubing of a heart-lung machine, a flexible-walled blood collection bag, or tubing used to collect a patient's blood during surgery and reintroduce the blood into the patient's vasculature. If the vessel includes a pump for pumping blood, a particularly suitable pump can be a centrifugal pump or a peristaltic pump. The vessel can have a wall; the wall can have an inner or interior surface defining a lumen. The inner or interior surface of the wall can have an at least partial passivation layer or pH protective coating of a protective layer, which optionally also presents a hydrophobic surface. The passivation layer or pH protective coating can be as thin as monomolecular thickness or as thick as about 1000 nm. Optionally, the vessel can contain blood viable for return to the vascular system of a patient disposed within the lumen in contact with the hydrophobic layer.

An embodiment can be a blood containing vessel including a wall and having an inner or interior surface defining a lumen. The inner or interior surface can have an at least partial passivation layer or pH protective coating that optionally also presents a hydrophobic surface. The passivation layer or pH protective coating can also comprise or consist essentially of $SiO_xC_y$, where x and y are as defined in this specification. The vessel contains blood viable for return to the vascular system of a patient disposed within the lumen in contact with the hydrophobic coating or layer.

An embodiment can be carried out under conditions effective to form a hydrophobic passivation layer or pH protective coating on the substrate. Optionally, the hydrophobic characteristics of the passivation layer or pH protective coating can be set by setting the ratio of the oxidizing gas to the organosilicon precursor in the gaseous reactant, and/or by setting the electric power used for generating the plasma. Optionally, the passivation layer or pH protective coating can have a lower wetting tension than the uncoated surface, optionally a wetting tension of from 20 to 72 dyne/cm, optionally from 30 to 60 dynes/cm, optionally from 30 to 40 dynes/cm, optionally 34 dyne/cm. Optionally, the passivation layer or pH protective coating can be more hydrophobic than the uncoated surface.

In an optional embodiment, the vessel can have an inner diameter of at least 2 mm, or at least 4 mm.

As an optional feature of any of the foregoing embodiments the vessel can be a tube.

As an optional feature of any of the foregoing embodiments the lumen can have at least two open ends.

Syringe

The vessel of FIGS. 1-7 is a syringe, which is a contemplated type of vessel provided with a passivation layer or pH protective coating. The syringe can comprise a syringe barrel 14 and a plunger tip, piston, stopper, or seal 36. The internal wall 16 can define at least a portion of the syringe barrel 250. The plunger tip, piston, stopper, or seal 36 can be a relatively sliding part of the syringe, with respect to the syringe barrel 250. The term "syringe" is broadly defined to include cartridges, injection "pens," and other types of barrels or reservoirs adapted to be assembled with one or more other components to provide a functional syringe. A "syringe" is also broadly defined to include related articles such as auto-injectors, which provide a mechanism for dispensing the contents.

As one non-limiting way to make the syringe, a capped pre-assembly 12 can be provided comprising a barrel 14, a dispensing portion 20, and a shield 28. The capped pre-assembly 12 can be a complete article or it can be a portion of a complete article adapted to dispense fluid, such as a syringe, a cartridge, a catheter, or other article.

The barrel 14 can have an internal wall 16 defining a barrel lumen 18. Optionally in any embodiment, the barrel 14 can further include an opening 32 spaced from the dispensing portion 20 and communicating through the internal wall 16. Such an opening can be conventional, for example, in a syringe or cartridge, where a typical example can be the back opening 32 of a prefilled syringe barrel, through which the plunger tip, piston, stopper, or seal 36 can be inserted after the barrel lumen 18 is filled with a suitable pharmaceutical preparation or other fluid material 40 to be dispensed.

The barrel 14 can be formed, for example, by molding, although the manner of its formation is not critical and it can also be formed, for example, by machining a solid preform. Preferably, the barrel can be molded by injection molding thermoplastic material, although it can also be formed by blow molding or a combined method.

As one preferred example, the barrel 14 can be formed by placing a dispensing portion 20 as described below in an injection mold and injection molding thermoplastic material about the dispensing portion, thus forming the barrel and securing the dispensing portion to the barrel. Alternatively, the dispensing portion and the barrel can be molded or otherwise formed as a single piece, or can be formed separately and joined in other ways. The barrel of any embodiment can be made of any suitable material. Several barrel materials particularly contemplated are COC (cyclic olefin copolymer), COP (cyclic olefin polymer), PET (polyethylene terephthalate), and polypropylene.

The dispensing portion 20 of the capped pre-assembly 12 can be provided to serve as an outlet for fluid dispensed from the barrel lumen 18 of a completed article made from the capped pre-assembly 12. One example of a suitable dispensing portion illustrated in the Figures can be a hypodermic needle 20.

Alternatively, in any embodiment the dispensing portion 20 can instead be a needle-free dispenser. One example of a suitable needle-free dispenser can be a blunt or flexible dispensing portion intended to be received in a complementary coupling to transfer fluid material 40. Such blunt or flexible dispensing portions are well known for use in syringes, intravenous infusion systems, and other systems and equipment to dispense material while avoiding the hazard of working with a sharp needle that may accidentally stick a health professional or other person. Another example of a needle-free dispenser can be a fluid jet or spray injection system that injects a free jet or spray of fluid directly through a patient's skin, without the need for an intermediate needle. Any type of dispensing portion 20, whether a hypodermic needle or any form of needle-free dispenser, is contemplated for use according to any embodiment of the present invention.

The dispensing portion 20 is or can be secured to the barrel 14 and includes a proximal opening 22, a distal opening 24, and a dispensing portion lumen 26. The proximal opening 22 communicates with the barrel lumen 18. The distal opening 24 can be located outside the barrel 14. The dispensing portion lumen 26 communicates between the proximal and distal openings 22, 24 of the dispensing portion 20. In the illustrated embodiment, the distal opening 24 can be at the sharpened tip of a hypodermic needle 20.

The shield 28 can be secured to the barrel 14 and at least substantially isolates the distal opening 24 of the dispensing portion 20 from pressure conditions outside the shield 28. Optionally in any embodiment, the shield 28 sufficiently isolates portions of the assembly 12 to provide a sufficient bio-barrier to facilitate safe use of the capped pre-assembly 12 for transdermal injections.

The shield 28 can isolate the distal opening 24 in various ways. Effective isolation can be provided at least partially due to contact between the shield 28 and the distal opening 24, as shown in present FIGS. 2, 3, 4, and 7. In the illustrated embodiment, the tip of the dispensing portion 20 can be buried in the material of the shield 28. Alternatively in any embodiment, effective isolation can be provided at least partially due to contact between the shield 28 and the barrel 14, as also shown in present FIGS. 2, 3, 4, and 7. In the illustrated embodiment, the primary line of contact between the shield 28 and the barrel 14 can be at a rib 42 (best seen in FIG. 3) encircling and seated against a generally cylindrical surface 44 at the nose of the barrel 14. Alternatively in any embodiment, effective isolation can be provided due to both of these types of contact as illustrated in FIGS. 2-3, or in other ways, without limitation.

The shield 28 of any embodiment optionally can have a latching mechanism, best shown in FIG. 3, including a barb 46 and a catch 48 which engage to hold the shield 28 in place. The catch 48 can be made of sufficiently resilient material to allow the shield 28 to be removed and replaced easily.

If the dispensing portion 20 is a hypodermic needle, the shield 28 can be a specially formed needle shield. The original use of a needle shield is to cover the hypodermic needle before use, preventing accidental needle sticks and preventing contamination of the needle before it is injected in a patient or an injection port. A comparable shield preferably is used, even if the dispensing portion 20 is a needle-free dispenser, to prevent contamination of the dispenser during handling.

The shield 28 can be formed in any suitable way. For example, the shield 28 can be formed by molding thermoplastic material. Optionally in any embodiment, the thermoplastic material can be elastomeric material or other material that can be suitable for forming a seal. One suitable category of elastomeric materials is known generically as thermoplastic elastomer (TPE). An example of a suitable thermoplastic elastomer for making a shield 28 is Stelmi® Formulation 4800 (flexible shield formulation). Any other material having suitable characteristics can instead be used in any embodiment.

As another optional feature in any embodiment the shield 28 can be sufficiently permeable to a sterilizing gas to sterilize the portions of the assembly 12 isolated by the shield. One example of a suitable sterilizing gas is ethylene oxide. Shields 28 are available that are sufficiently permeable to the sterilizing gas that parts isolated by the shield can nonetheless be sterilized. An example of a shield formulation sufficiently permeable to accommodate ethylene oxide gas sterilization can be Stelmi® Formulation 4800.

Three embodiments of the invention having many common features are those of FIGS. 7-8. Some of their common features are the following, indicated in many cases by common reference characters or names. The nature of the features of each embodiment can be as described later in the specification.

The pharmaceutical packages of FIGS. 7-8 each include a vessel 210, a fluid composition 40, an $SiO_x$ barrier coating or layer 30, and a passivation layer or pH protective coating 34. Each vessel 210 can have a lumen 18 defined at least in part by a wall interior portion 16 made of thermoplastic material.

The internal wall 16 can have an interior surface 254 facing the lumen 18 and an outer surface 216.

The fluid composition 40 can be contained in the lumen 18 and can have a pH between 4 and 10, alternatively between 5 and 9.

Barrier Coating or Layer

In the filled pharmaceutical package or other vessel 210 the barrier coating or layer 30 can be located between the inner or interior surface of the thermoplastic internal wall 16 and the fluid material 40. The barrier coating or layer 286 of $SiO_x$ can be supported by the thermoplastic internal wall 16. The barrier coating or layer 286 can have the characteristic of being subject to being measurably diminished in barrier improvement factor in less than six months as a result of attack by the fluid material 40. The barrier coating or layer 286 as described elsewhere in this specification, or in U.S. Pat. No. 7,985,188, can be used in any embodiment.

The barrier coating or layer 30 can be effective to reduce the ingress of atmospheric gas into the lumen 18, compared to an uncoated container otherwise the same as the pharmaceutical package or other vessel 210. The barrier coating or layer for any embodiment defined in this specification (unless otherwise specified in a particular instance) is optionally applied by PECVD as indicated in U.S. Pat. No. 7,985,188.

The barrier improvement factor (BIF) of the barrier coating or layer can be determined by providing two groups of identical containers, adding a barrier coating or layer to one group of containers, testing a barrier property (such as the rate of outgassing in micrograms per minute or another suitable measure) on containers having a barrier coating or layer, doing the same test on containers lacking a barrier coating or layer, and taking a ratio of the properties of the materials with versus without a barrier coating or layer. For example, if the rate of outgassing through the barrier coating or layer is one-third the rate of outgassing without a barrier coating or layer, the barrier coating or layer has a BIF of 3.

The barrier coating or layer optionally can be characterized as an "$SiO_x$" coating, and contains silicon, oxygen, and optionally other elements, in which x, the ratio of oxygen to silicon atoms, can be from about 1.5 to about 2.9, or 1.5 to about 2.6, or about 2. These alternative definitions of x apply to any use of the term $SiO_x$ in this specification. The barrier coating or layer can be applied, for example to the interior of a pharmaceutical package or other vessel, for example a sample collection tube, a syringe barrel, a vial, or another type of vessel.

The barrier coating or layer 30 comprises or consists essentially of $SiO_x$, from 2 to 1000 nm thick, the barrier coating or layer 30 of $SiO_x$ having an interior surface facing the lumen 18 and an outer surface facing the internal wall 16. The barrier coating or layer 30 can be effective to reduce the ingress of atmospheric gas into the lumen 18 compared to an uncoated pharmaceutical package 210. One suitable barrier composition can be one where x is 2.3, for example.

For example, the barrier coating or layer such as 30 of any embodiment can be applied at a thickness of at least 2 nm, or at least 4 nm, or at least 7 nm, or at least 10 nm, or at least 20 nm, or at least 30 nm, or at least 40 nm, or at least 50 nm, or at least 100 nm, or at least 150 nm, or at least 200 nm, or at least 300 nm, or at least 400 nm, or at least 500 nm, or at least 600 nm, or at least 700 nm, or at least 800 nm, or at least 900 nm. The barrier coating or layer can be up to 1000 nm, or at most 900 nm, or at most 800 nm, or at most 700 nm, or at most 600 nm, or at most 500 nm, or at most 400 nm, or at most 300 nm, or at most 200 nm, or at most 100 nm, or at most 90 nm, or at most 80 nm, or at most 70 nm, or at most 60 nm, or at most 50 nm, or at most 40 nm, or at most 30 nm, or at most 20 nm, or at most 10 nm, or at most 5 nm thick. Specific thickness ranges composed of any one of the minimum thicknesses expressed above, plus any equal or greater one of the maximum thicknesses expressed above, are expressly contemplated. The thickness of the $SiO_x$ or other barrier coating or layer can be measured, for example, by transmission electron microscopy (TEM), and its composition can be measured by X-ray photoelectron spectroscopy (XPS). The passivation layer or pH protective coating described herein can be applied to a variety of pharmaceutical packages or other vessels made from plastic or glass, for example to plastic tubes, vials, and syringes.

Passivation Layer or pH Protective Coating

A passivation layer or pH protective coating 34 of $SiO_xC_y$, can be applied, for example, by PECVD directly or indirectly to the barrier coating or layer 30 so it can be located between the barrier coating or layer 30 and the fluid material 40 in the finished article. The passivation layer or pH protective coating 34 can have an interior surface facing the lumen 18 and an outer surface facing the interior surface of the barrier coating or layer 30. The passivation layer or pH protective coating 34 can be supported by the thermoplastic internal wall 16. The passivation layer or pH protective coating 34 can be effective to keep the barrier coating or layer 30 at least substantially undissolved as a result of attack by the fluid material 40 for a period of at least six months, in one non-limiting embodiment.

Optionally, the passivation layer or pH protective coating can be composed of $Si_wO_xC_yH_z$ (or its equivalent $SiO_xC_y$) or $Si_wN_xC_yH_z$ or its equivalent $SiN_xC_y$), each as defined in this specification. Taking into account the H atoms, the passivation layer or pH protective coating may thus in one aspect have the formula $Si_wO_xC_yH_z$, or its equivalent $SiO_xC_y$, for example where w is 1, x is from about 0.5 to about 2.4, y is from about 0.6 to about 3, and z (if defined) is from about 2 to about 9.

The atomic ratio can be determined by XPS (X-ray photoelectron spectroscopy). XPS does not detect hydrogen atoms, so it is customary, when determining the atomic ratio by XPS, to omit hydrogen from the stated formulation. The formulation thus can be typically expressed as $Si_wO_xC_y$, where w is 1, x is from about 0.5 to about 2.4, and y is from about 0.6 to about 3, with no limitation on z.

The atomic ratios of Si, O, and C in the "lubricity and/or passivation layer or pH protective coating" can be, as several options:

Si 100:O 50-150:C 90-200 (i.e. w=1, x=0.5 to 1.5, y=0.9 to 2);

Si 100:O 70-130:C 90-200 (i.e. w=1, x=0.7 to 1.3, y=0.9 to 2)

Si 100:O 80-120:C 90-150 (i.e. w=1, x=0.8 to 1.2, y=0.9 to 1.5)

Si 100:O 90-120:C 90-140 (i.e. w=1, x=0.9 to 1.2, y=0.9 to 1.4), or

Si 100:O 92-107:C 116-133 (i.e. w=1, x=0.92 to 1.07, y=1.16 to 1.33)

Typically, such a coating or layer would contain 36% to 41% carbon normalized to 100% carbon plus oxygen plus silicon. Alternatively, the passivation layer or pH protective coating can have atomic concentrations normalized to 100% carbon, oxygen, and silicon, as determined by X-ray photoelectron spectroscopy (XPS) of less than 50% carbon and more than 25% silicon. Alternatively, the atomic concentrations can be from 25 to 45% carbon, 25 to 65% silicon, and 10 to 35% oxygen. Alternatively, the atomic concentrations can be from 30 to 40% carbon, 32 to 52% silicon, and 20 to 27% oxygen. Alternatively, the atomic concentrations can be from 33 to 37% carbon, 37 to 47% silicon, and 22 to 26% oxygen.

Optionally, the atomic concentration of carbon in the protective layer, normalized to 100% of carbon, oxygen, and silicon, as determined by X-ray photoelectron spectroscopy (XPS), can be greater than the atomic concentration of carbon in the atomic formula for the organosilicon precursor. For example, embodiments are contemplated in which the atomic concentration of carbon increases by from 1 to 80 atomic percent, alternatively from 10 to 70 atomic percent, alternatively from 20 to 60 atomic percent, alternatively from 30 to 50 atomic percent, alternatively from 35 to 45 atomic percent, alternatively from 37 to 41 atomic percent.

Optionally, the atomic ratio of carbon to oxygen in the passivation layer or pH protective coating can be increased in comparison to the organosilicon precursor, and/or the atomic ratio of oxygen to silicon can be decreased in comparison to the organosilicon precursor.

Optionally, the passivation layer or pH protective coating can have an atomic concentration of silicon, normalized to 100% of carbon, oxygen, and silicon, as determined by X-ray photoelectron spectroscopy (XPS), less than the atomic concentration of silicon in the atomic formula for the feed gas. For example, embodiments are contemplated in which the atomic concentration of silicon decreases by from 1 to 80 atomic percent, alternatively by from 10 to 70 atomic percent, alternatively by from 20 to 60 atomic percent, alternatively by from 30 to 55 atomic percent, alternatively by from 40 to 50 atomic percent, alternatively by from 42 to 46 atomic percent.

As another option, a passivation layer or pH protective coating is contemplated that can be characterized by a sum formula wherein the atomic ratio C:O can be increased and/or the atomic ratio Si:O can be decreased in comparison to the sum formula of the organosilicon precursor.

The passivation layer or pH protective coating can have a density between 1.25 and 1.65 g/cm$^3$, alternatively between 1.35 and 1.55 g/cm$^3$, alternatively between 1.4 and 1.5 g/cm$^3$, alternatively between 1.4 and 1.5 g/cm$^3$, alternatively between 1.44 and 1.48 g/cm$^3$, as determined by X-ray reflectivity (XRR). Optionally, the organosilicon compound can be octamethylcyclotetrasiloxane and the passivation layer or pH protective coating can have a density which can be higher than the density of a passivation layer or pH protective coating made from HMDSO as the organosilicon compound under the same PECVD reaction conditions.

The passivation layer or pH protective coating optionally can have an RMS surface roughness value (measured by AFM) of from about 2 to about 9, optionally from about 6 to about 8, optionally from about 6.4 to about 7.8. The $R_a$ surface roughness value of the passivation layer or pH protective coating, measured by AFM, can be from about 4 to about 6, optionally from about 4.6 to about 5.8. The $R_{max}$ surface roughness value of the passivation layer or pH protective coating, measured by AFM, can be from about 70 to about 160, optionally from about 84 to about 142, optionally from about 90 to about 130.

The rate of erosion, dissolution, or leaching (different names for related concepts) of the construction including a passivation layer or pH protective coating 34, if directly contacted by the fluid material 40, can be less than the rate of erosion, dissolution, or leaching of the barrier coating or layer 30, if directly contacted by the fluid material 40.

The passivation layer or pH protective coating 34 can be effective to isolate or protect the barrier coating or layer 30 from the fluid material 40 at least for sufficient time to allow the barrier coating or layer to act as a barrier during the shelf life of the pharmaceutical package or other vessel 210.

Optionally an FTIR absorbance spectrum of the passivation layer or pH protective coating 34 of any embodiment of FIGS. 7-8 can have a ratio greater than 0.75 between the maximum amplitude of the Si—O—Si symmetrical stretch peak normally located between about 1000 and 1040 cm$^{-1}$, and the maximum amplitude of the Si—O—Si assymetric stretch peak normally located between about 1060 and about 1100 cm$^{-1}$. Alternatively in any embodiment, this ratio can be at least 0.8, or at least 0.9, or at least 1.0, or at least 1.1, or at least 1.2. Alternatively in any embodiment, this ratio can be at most 1.7, or at most 1.6, or at most 1.5, or at most 1.4, or at most 1.3. Any minimum ratio stated here can be combined with any maximum ratio stated here, as an alternative embodiment of the invention of FIGS. 7-8.

Optionally, in any embodiment of FIGS. 7-8 the passivation layer or pH protective coating, in the absence of the medicament, can have a non-oily appearance. This appearance has been observed in some instances to distinguish an effective passivation layer or pH protective coating from a lubricity layer, which in some instances has been observed to have an oily (i.e. shiny) appearance.

Optionally, in any embodiment of FIGS. 7-8 the silicon dissolution rate by a 50 mM potassium phosphate buffer diluted in water for injection, adjusted to pH 8 with concentrated nitric acid, and containing 0.2 wt. % polysorbate-80 surfactant, (measured in the absence of the medicament, to avoid changing the dissolution reagent), at 40° C., can be less than 170 ppb/day. (Polysorbate-80 is a common ingredient of pharmaceutical preparations, available for example as Tween®-80 from Uniqema Americas LLC, Wilmington Del.) As will be seen from the working examples, the silicon dissolution rate can be measured by determining the total silicon leached from the vessel into its contents, and does not distinguish between the silicon derived from the passivation layer or pH protective coating 34, the lubricity layer 287, the barrier coating or layer 30, or other materials present.

Optionally, in any embodiment of FIGS. 7-8 the silicon dissolution rate can be less than 160 ppb/day, or less than 140 ppb/day, or less than 120 ppb/day, or less than 100 ppb/day, or less than 90 ppb/day, or less than 80 ppb/day. Optionally, in any embodiment of FIGS. 7-8 the silicon dissolution rate can be more than 10 ppb/day, or more than 20 ppb/day, or more than 30 ppb/day, or more than 40 ppb/day, or more than 50 ppb/day, or more than 60 ppb/day. Any minimum rate stated here can be combined with any maximum rate stated here, as an alternative embodiment of the invention of FIGS. 7-8.

Optionally, in any embodiment of FIGS. 7-8 the total silicon content of the passivation layer or pH protective coating and barrier coating or layer, upon dissolution into a test composition with a pH of 8 from the vessel, can be less than 66 ppm, or less than 60 ppm, or less than 50 ppm, or less than 40 ppm, or less than 30 ppm, or less than 20 ppm.

Optionally, in any embodiment of FIGS. 7-8 the calculated shelf life of the package (total Si/Si dissolution rate) can be more than six months, or more than 1 year, or more than 18 months, or more than 2 years, or more than 2½ years, or more than 3 years, or more than 4 years, or more than 5 years, or more than 10 years, or more than 20 years.

Optionally, in any embodiment of FIGS. 7-8 the calculated shelf life of the package (total Si/Si dissolution rate) can be less than 60 years.

Any minimum time stated here can be combined with any maximum time stated here, as an alternative embodiment of the invention of FIGS. 7-8.

O-Parameter or P-Parameters of Passivation Coating or Protective Layer

The passivation layer or pH protective coating 34 optionally can have an O-Parameter measured with attenuated total reflection (ATR) of less than 0.4, measured as:

$$\text{O-Parameter} = \frac{\text{Intensity at 1253 cm}^{-1}}{\text{Maximum intensity in the range 1000 to 1100 cm}^{-1}}.$$

Figure 24:
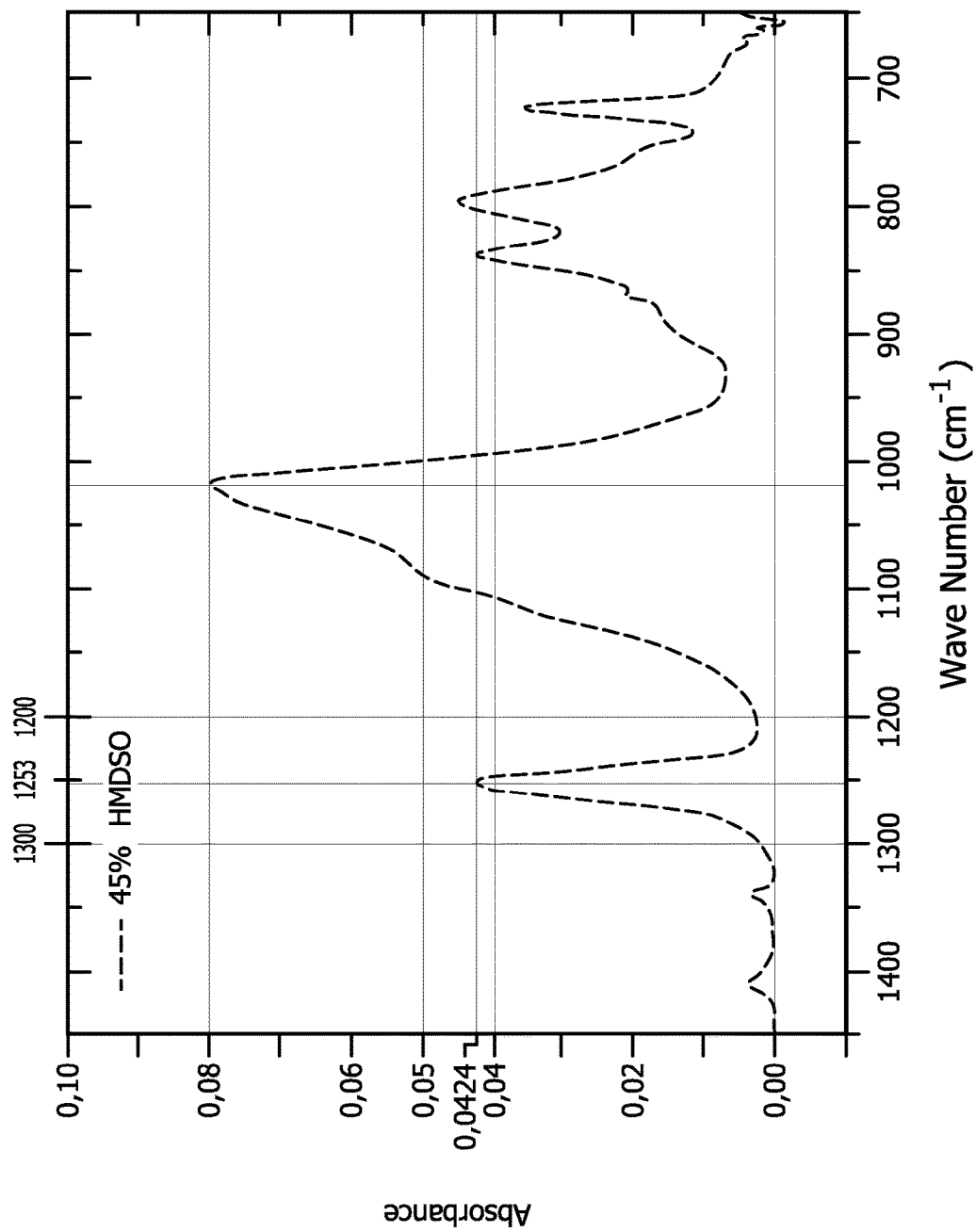
FIG. 24 is a Fourier Transform Infrared Spectrophotometer (FTIR) absorbance spectrum of a PECVD coating, originally presented as FIG. 5 of U.S. Pat. No. 8,067,070, annotated to show the calculation of the O-Parameter referred to in that patent.

The O-Parameter is defined in U.S. Pat. No. 8,067,070, which claims an O-parameter value of most broadly from 0.4 to 0.9. It can be measured from physical analysis of an FTIR amplitude versus wave number plot to find the numerator and denominator of the above expression, as shown in FIG. 24, which is the same as FIG. 5 of U.S. Pat. No. 8,067,070, except annotated to show interpolation of the wave number and absorbance scales to arrive at an absorbance at 1253 cm$^{-1}$ of 0.0424 and a maximum absorbance at 1000 to 1100 cm$^{-1}$ of 0.08, resulting in a calculated O-parameter of 0.53. The O-Parameter can also be measured from digital wave number versus absorbance data.

U.S. Pat. No. 8,067,070 asserts that its claimed O-parameter range provides a superior passivation layer or pH protective coating, relying on experiments only with HMDSO and HMDSN, which are both non-cyclic siloxanes. Surprisingly, it has been found by the present inventors that if the PECVD precursor is a cyclic siloxane, for example OMCTS, O-parameters outside the ranges claimed in U.S. Pat. No. 8,067,070, using OMCTS, can provide better results than are obtained in U.S. Pat. No. 8,067,070 with HMDSO.

Alternatively in the embodiment of FIGS. 7-8, the O-parameter can have a value of from 0.1 to 0.39, or from 0.15 to 0.37, or from 0.17 to 0.35.

Even another aspect of the invention can be a composite material as just described, exemplified in FIGS. 7-8, wherein the passivation layer or pH protective coating shows an N-Parameter measured with attenuated total reflection (ATR) of less than 0.7, measured as:

$$\text{N-Parameter} = \frac{\text{Intensity at 840 cm}^{-1}}{\text{Intensity at 799 cm}^{-1}}.$$

The N-Parameter is also described in U.S. Pat. No. 8,067,070, and can be measured analogously to the O-Parameter except that intensities at two specific wave numbers are used—neither of these wave numbers is a range. U.S. Pat. No. 8,067,070 claims a passivation layer or pH protective coating with an N-Parameter of 0.7 to 1.6. Again, the present inventors have made better coatings employing a passivation layer or pH protective coating 34 having an N-Parameter lower than 0.7, as described above. Alternatively, the N-parameter can have a value of 0.3 to lower than 0.7, or from 0.4 to 0.6, or from at least 0.53 to lower than 0.7.

Theory of Operation

The inventors offer the following theory of operation of the passivation layer or pH protective coating described here. The invention is not limited by the accuracy of this theory or to the embodiments predictable by use of this theory.

The dissolution rate of the SiO$_x$ barrier coating or layer, or of glass, is believed to be dependent on SiO bonding within the layer or glass. Oxygen bonding sites (silanols) are believed to increase the dissolution rate.

It is believed that the OMCTS-based passivation layer or pH protective coating bonds with the silanol sites on the SiO barrier coating or layer, or glass, to "heal" or passivate the SiO surface or glass and thus dramatically reduce the dissolution rate. In this hypothesis, the thickness of the OMCTS layer is not the primary means of protection—the primary means can be passivation of the SiO or glass surface. It is contemplated that a passivation layer or pH protective coating as described in this specification can be improved by increasing the crosslink density of the passivation layer or pH protective coating.

Optional Graded Composite Layers

The passivation layer or pH protective coating 34 and lubricity layers of any embodiment of FIGS. 7-8 can be either separate layers with a sharp transition or a single, graduated layer that transitions between the passivation layer or pH protective coating 34 and the lubricity layer, without a sharp interface between them. Another optional expedient contemplated here, for adjacent layers of SiO$_x$ and a passivation layer or pH protective coating, can be a graded composite of SiO$_x$ and Si$_w$O$_x$C$_y$, or its equivalent SiO$_x$C$_y$, as defined in the Definition Section.

A graded composite can be separate layers of a lubricity and/or protective and/or barrier coating or layer or coating with a transition or interface of intermediate composition between them, or separate layers of a lubricity and/or protective and/or hydrophobic layer and SiO$_x$ with an intermediate distinct passivation layer or pH protective coating of intermediate composition between them, or a single coating or layer that changes continuously or in steps from a composition of a lubricity and/or protective and/or hydrophobic layer to a composition more like SiO$_x$, going through the passivation layer or pH protective coating in a normal direction.

The grade in the graded composite can go in either direction. For example, the composition of SiO$_x$ can be applied directly to the substrate and graduate to a composition further from the surface of a passivation layer or pH protective coating, and optionally can further graduate to another type of coating or layer, such as a hydrophobic coating or layer or a lubricity coating or layer. Additionally, in any embodiment an adhesion coating or layer, for example Si$_w$O$_x$C$_y$, or its equivalent SiO$_x$C$_y$, optionally can be applied directly to the substrate before applying the barrier coating or layer.

A graduated passivation layer or pH protective coating is particularly contemplated if a layer of one composition is better for adhering to the substrate than another, in which case the better-adhering composition can, for example, be applied directly to the substrate. It is contemplated that the more distant portions of the graded passivation layer or pH protective coating can be less compatible with the substrate than the adjacent portions of the graded passivation layer or pH protective coating, since at any point the passivation layer or pH protective coating can be changing gradually in properties, so adjacent portions at nearly the same depth of the passivation layer or pH protective coating have nearly identical composition, and more widely physically separated portions at substantially different depths can have more diverse properties. It is also contemplated that a passivation layer or pH protective coating portion that forms a better barrier against transfer of material to or from the substrate can be directly against the substrate, to prevent the more remote passivation layer or pH protective coating portion that forms a poorer barrier from being contaminated with the material intended to be barred or impeded by the barrier.

The applied coatings or layers, instead of being graded, optionally can have sharp transitions between one layer and the next, without a substantial gradient of composition. Such passivation layer or pH protective coating can be made, for example, by providing the gases to produce a layer as a steady state flow in a non-plasma state, then energizing the system with a brief plasma discharge to form a coating or layer on the substrate. If a subsequent passivation layer or pH protective coating is to be applied, the gases for the previous passivation layer or pH protective coating are cleared out and the gases for the next passivation layer or pH protective coating are applied in a steady-state fashion before energizing the plasma and again forming a distinct layer on the surface of the substrate or its outermost previous passivation layer or pH protective coating, with little if any gradual transition at the interface.

PECVD Apparatus

The low-pressure PECVD process described in U.S. Pat. No. 7,985,188 can be used to provide the barrier coating or layer, lubricity coating or layer, and/or passivation layer or pH protective coating described in this specification. A brief synopsis of that process follows, with reference to present FIGS. 4-6.

A PECVD apparatus or coating station 60 suitable for the present purpose includes a vessel holder 50, an inner electrode defined by the probe 108, an outer electrode 160, and a power supply 162. The pre-assembly 12 seated on the vessel holder 50 defines a plasma reaction chamber, which optionally can be a vacuum chamber. Optionally, a source of vacuum 98, a reactant gas source 144, a gas feed (probe 108) or a combination of two or more of these can be supplied.

The PECVD apparatus can be used for atmospheric-pressure PECVD, in which case the plasma reaction chamber defined by the pre-assembly 12 does not need to function as a vacuum chamber.

Figure 4:
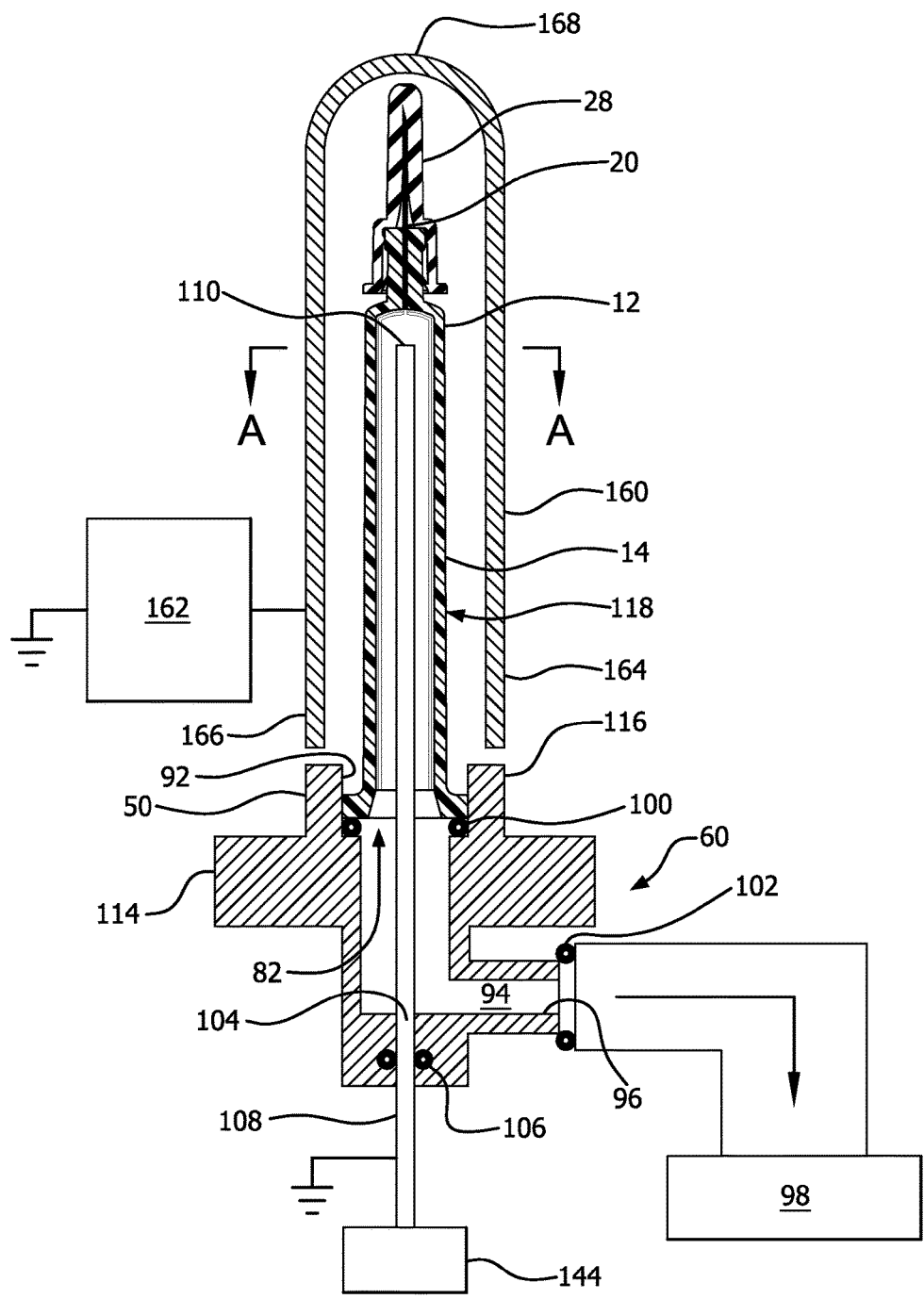
FIG. 4 is a schematic longitudinal section of the capped pre-assembly of FIGS. 1 and 2 seated on a chemical vapor deposition coating station.
Figure 5:
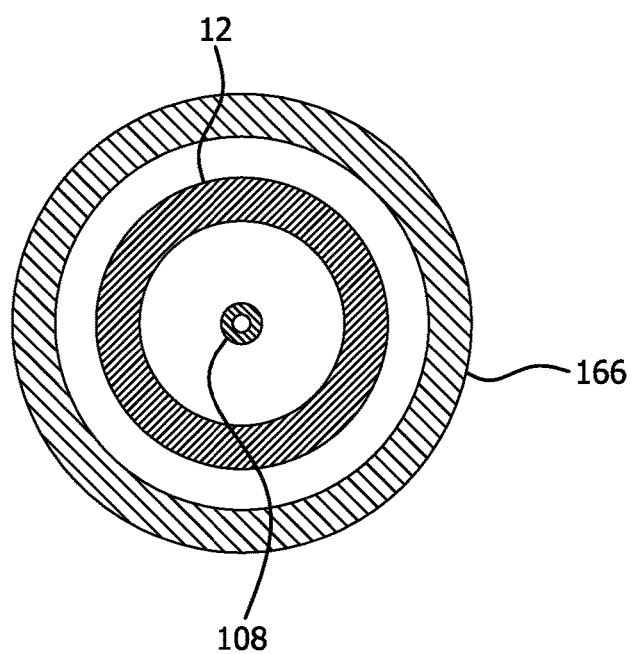
FIG. 5 is a section taken along section lines A-A of FIG. 4.
Figure 6:
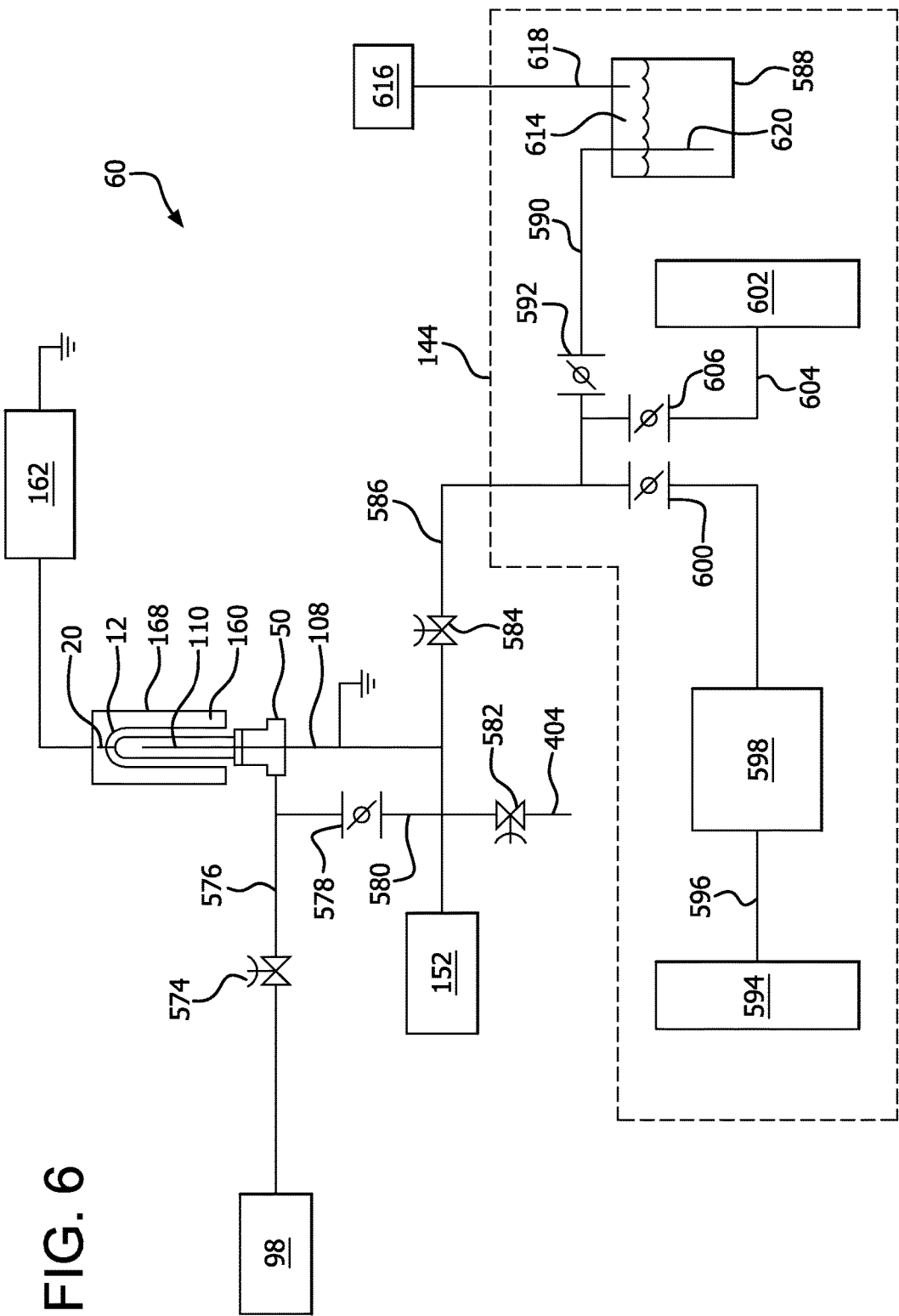
FIG. 6 is a schematic view showing more details of the chemical vapor deposition coating station shown in FIGS. 4 and 5.

Referring to FIGS. 4-6, the vessel holder 50 comprises a gas inlet port 104 for conveying a gas into the pre-assembly 12 seated on the opening 82. The gas inlet port 104 can have a sliding seal provided for example by at least one O-ring 106, or two O-rings in series, or three O-rings in series, which can seat against a cylindrical probe 108 when the probe 108 is inserted through the gas inlet port 104. The probe 108 can be a gas inlet conduit that extends to a gas delivery port at its distal end 110. The distal end 110 of the illustrated embodiment can be inserted at an appropriate depth in the pre-assembly 12 for providing one or more PECVD reactants and other precursor feed or process gases.

FIG. 6 shows additional optional details of the coating station 60 that are usable, for example, with all the illustrated embodiments. The coating station 60 can also have a main vacuum valve 574 in its vacuum line 576 leading to the pressure sensor 152. A manual bypass valve 578 can be provided in the bypass line 580. A vent valve 582 controls flow at the vent 404.

Flow out of the PECVD gas or precursor source 144 can be controlled by a main reactant gas valve 584 regulating flow through the main reactant feed line 586. One component of the gas source 144 can be the organosilicon liquid reservoir 588, containing the precursor. The contents of the reservoir 588 can be drawn through the organosilicon capillary line 590, which optionally can be provided at a suitable length to provide the desired flow rate. Flow of organosilicon vapor can be controlled by the organosilicon shut-off valve 592. Pressure can be applied to the headspace 614 of the liquid reservoir 588, for example a pressure in the range of 0-15 psi (0 to 78 cm. Hg), from a pressure source 616 such as pressurized air connected to the headspace 614 by a pressure line 618 to establish repeatable organosilicon liquid delivery that is not dependent on atmospheric pressure (and the fluctuations therein). The reservoir 588 can be sealed and the capillary connection 620 can be at the bottom of the reservoir 588 to ensure that only neat organosilicon liquid (not the pressurized gas from the headspace 614) flows through the capillary tube 590. The organosilicon liquid optionally can be heated above ambient temperature, if necessary or desirable to cause the organosilicon liquid to evaporate, forming an organosilicon vapor. To accomplish this heating, the apparatus can advantageously include heated delivery lines from the exit of the precursor reservoir to as close as possible to the gas inlet into the syringe. Preheating can be useful, for example, when feeding OMCTS.

Oxidant gas can be provided from the oxidant gas tank 594 via an oxidant gas feed line 596 controlled by a mass flow controller 598 and provided with an oxidant shut-off valve 600.

Optionally in any embodiment, other precursor, oxidant, and/or carrier gas reservoirs such as 602 can be provided to supply additional materials if needed for a particular deposition process. Each such reservoir such as 602 can have an appropriate feed line 604 and shut-off valve 606.

Referring especially to FIG. 4, the processing station 60 can include an electrode 160 fed by a radio frequency power supply 162 for providing an electric field for generating plasma within the pre-assembly 12 during processing. In this embodiment, the probe 108 can be electrically conductive and can be grounded, thus providing a counter-electrode within the pre-assembly 12. Alternatively, in any embodiment the outer electrode 160 can be grounded and the probe 108 can be directly connected to the power supply 162.

In the embodiment of FIGS. 4-6, the outer electrode 160 can either be generally cylindrical as illustrated in FIGS. 4 and 5 or a generally U-shaped elongated channel as illustrated in FIG. 6 (FIG. 5 being an alternative embodiment of the section taken along section line A-A of FIG. 4). Each illustrated embodiment can have one or more sidewalls, such as 164 and 166, and optionally a top end 168, disposed about the pre-assembly 12 in close proximity.

Application of Barrier Coating or Layer

When carrying out the present method, a barrier coating or layer 30 can be applied directly or indirectly to at least a portion of the internal wall 16 of the barrel 14. In the illustrated embodiment, the barrier coating or layer 30 can be applied while the pre-assembly 12 is capped, though this is not a requirement. The barrier coating or layer 30 can be an $SiO_x$ barrier coating or layer applied by plasma enhanced chemical vapor deposition (PECVD), under conditions substantially as described in U.S. Pat. No. 7,985,188. The barrier coating or layer 30 can be applied under conditions effective to maintain communication between the barrel lumen 18 and the dispensing portion lumen 26 via the proximal opening 22 at the end of the applying step.

In any embodiment the barrier coating or layer 30 optionally can be applied through the opening 32.

In any embodiment the barrier coating or layer 30 optionally can be applied by introducing a vapor-phase precursor material through the opening and employing chemical vapor deposition to deposit a reaction product of the precursor material on the internal wall of the barrel.

In any embodiment the precursor material for forming the barrier coating optionally can be any of the precursors described in U.S. Pat. No. 7,985,188 or in this specification for formation of the passivating layer or pH protective coating.

In any embodiment the reactant vapor material optionally can comprise an oxidant gas.

In any embodiment the reactant vapor material optionally can comprise oxygen.

In any embodiment the reactant vapor material optionally can comprise a carrier gas.

In any embodiment the reactant vapor material optionally can include helium, argon, krypton, xenon, neon, or a combination of two or more of these.

In any embodiment the reactant vapor material optionally can include argon.

In any embodiment the reactant vapor material optionally can be a precursor material mixture with one or more oxidant gases and a carrier gas in a partial vacuum through the opening and employing chemical vapor deposition to deposit a reaction product of the precursor material mixture on the internal wall of the barrel.

In any embodiment the reactant vapor material optionally can be passed through the opening at sub-atmospheric pressure.

In any embodiment plasma optionally can be generated in the barrel lumen 18 by placing an inner electrode into the barrel lumen 18 through the opening 32, placing an outer electrode outside the barrel 14 and using the electrodes to apply plasma-inducing electromagnetic energy which optionally can be radio frequency energy, in the barrel lumen 18. If a different arrangement is used, the plasma-inducing electromagnetic energy can be microwave energy or other forms of electromagnetic energy.

In any embodiment the electromagnetic energy optionally can be direct current.

In any embodiment the electromagnetic energy optionally can be alternating current. The alternating current optionally can be modulated at frequencies including audio, or microwave, or radio, or a combination of two or more of audio, microwave, or radio.

In any embodiment the electromagnetic energy optionally can be applied across the barrel lumen (18).

Application of Passivation Layer or pH Protective Coating

In any embodiment, in addition to applying a first coating or layer as described above, the method optionally can include applying second or further coating or layer of the same material or a different material. As one example useful in any embodiment, particularly contemplated if the first coating or layer is an $SiO_x$ barrier coating or layer, a further coating or layer can be placed directly or indirectly over the barrier coating or layer. One example of such a further coating or layer useful in any embodiment is a passivation layer or pH protective coating 34.

Precursors

The organosilicon precursor for any of the processes for forming the barrier coating or layer, the passivation layer or pH protective coating, or a lubricity coating or layer can include any of the following precursors.

The precursor for the passivation layer or pH protective coating of the present invention is broadly defined as an organometallic precursor. An organometallic precursor is defined in this specification as comprehending compounds of metal elements from Group III and/or Group IV of the Periodic Table having organic residues, for example hydrocarbon, aminocarbon or oxycarbon residues. Organometallic compounds as presently defined include any precursor having organic moieties bonded to silicon or other Group III/IV metal atoms directly, or optionally bonded through oxygen or nitrogen atoms. The relevant elements of Group III of the Periodic Table are Boron, Aluminum, Gallium, Indium, Thallium, Scandium, Yttrium, and Lanthanum, Aluminum and Boron being preferred. The relevant elements of Group IV of the Periodic Table are Silicon, Germanium, Tin, Lead, Titanium, Zirconium, Hafnium, and Thorium, with Silicon and Tin being preferred. Other volatile organic compounds can also be contemplated. However, organosilicon compounds are preferred for performing present invention.

An organosilicon precursor is contemplated, where an "organosilicon precursor" is defined throughout this specification most broadly as a compound having at least one of the linkages:

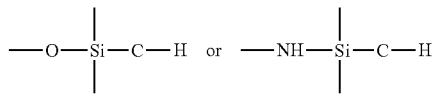

The first structure immediately above is a tetravalent silicon atom connected to an oxygen atom and an organic carbon atom (an organic carbon atom being a carbon atom bonded to at least one hydrogen atom). The second structure immediately above is a tetravalent silicon atom connected to an —NH— linkage and an organic carbon atom (an organic carbon atom being a carbon atom bonded to at least one hydrogen atom).

Optionally, the organosilicon precursor can be selected from the group consisting of a linear siloxane, a monocyclic siloxane, a polycyclic siloxane, a polysilsesquioxane, a linear silazane, a monocyclic silazane, a polycyclic silazane, a polysilsesquiazane, and a combination of any two or more of these precursors. Also contemplated as a precursor, though not within the two formulas immediately above, can be an alkyl trimethoxysilane.

If an oxygen-containing precursor (for example a Siloxane) is used, a representative predicted empirical composition resulting from PECVD under conditions forming a hydrophobic or lubricating passivation layer or pH protective coating would be $Si_wO_xC_yH_z$ or its equivalent $SiO_xC_y$, as defined in the Definition Section, while a representative predicted empirical composition resulting from PECVD under conditions forming a barrier coating or layer would be $SiO_x$, where x in this formula is from about 1.5 to about 2.9. If a nitrogen-containing precursor (for example a silazane) is used, the predicted composition would be $Si_{w*}N_{x*}C_{y*}H_{z*}$, i.e. in $Si_wO_xC_yH_z$ or its equivalent $SiO_xC_y$ as specified in the Definition Section, O is replaced by N and the indices for H are adapted to the higher valency of N as compared to O (3 instead of 2). The latter adaptation will generally follow the ratio of w, x, y and z in a Siloxane to the corresponding indices in its aza counterpart. In a particular aspect of the invention, $Si_{w*}N_{x*}C_{y*}H_{z*}$ (or its equivalent $SiN_{x*}C_{y*}$) in which w*, x*, y*, and z* are defined the same as w, x, y, and z for the siloxane counterparts, but for an optional deviation in the number of hydrogen atoms.

One type of precursor starting material having the above empirical formula can be a linear siloxane, for example a material having the following formula:

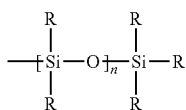

in which each R can be independently selected from alkyl, for example methyl, ethyl, propyl, isopropyl, butyl, isobutyl, t-butyl, vinyl, alkyne, or others, and n can be 1, 2, 3, 4, or greater, optionally two or greater. Several examples of contemplated linear siloxanes are
hexamethyldisiloxane (HMDSO) (particularly for forming the barrier coating or layer 30 of a vessel),
octamethyltrisiloxane,
decamethyltetrasiloxane,
dodecamethylpentasiloxane,
or combinations of two or more of these. The analogous silazanes in which —NH— can be substituted for the oxygen atom in the above structure are also useful for making analogous passivation layers or pH protective coatings or layers. Several examples of contemplated linear silazanes are octamethyltrisilazane, decamethyltetrasilazane, or combinations of two or more of these.

Another type of precursor starting material, among the preferred starting materials in the present context, can be a monocyclic siloxane, for example a material having the following structural formula:

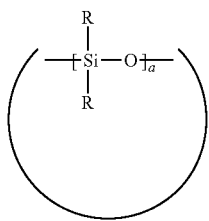

in which R can be defined as for the linear structure and "a" can be from 3 to about 10, or the analogous monocyclic silazanes. Several examples of contemplated hetero-substituted and unsubstituted monocyclic siloxanes and silazanes include:
1,3,5-trimethyl-1,3,5-tris(3,3,3-trifluoropropyl)methyl]cyclotrisiloxane
2,4,6,8-tetramethyl-2,4,6,8-tetravinylcyclotetrasiloxane,
pentamethylcyclopentasiloxane,
pentavinylpentamethylcyclopentasiloxane,
hexamethylcyclotrisiloxane,
hexaphenylcyclotrisiloxane (HMCTS,
octamethylcyclotetrasiloxane (OMCTS),
decamethylcyclopentasiloxane (DMCPS),
2,2,4,4,6,6,8,8-octamethyl-1,5-dimethano-3,7-dioxa-2,4,6,8-tetrasiloxane octaphenylcyclotetrasiloxane,
decamethylcyclopentasiloxane
dodecamethylcyclohexasiloxane,
methyl(3,3,3-trifluoropropl)cyclosiloxane,
Cyclic organosilazanes are also contemplated, such as
Octamethylcyclotetrasilazane,
1,3,5,7-tetravinyl-1,3,5,7-tetramethylcyclotetrasilazane
hexamethylcyclotrisilazane,
octamethylcyclotetrasilazane,
decamethylcyclopentasilazane,
dodecamethylcyclohexasilazane, or
combinations of any two or more of these.

Another type of precursor starting material, among the preferred starting materials in the present context, can be a polycyclic siloxane, for example a material having one of the following structural formulas:

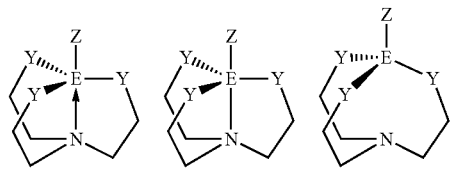

in which Y can be oxygen or nitrogen, E is silicon, and Z is a hydrogen atom or an organic substituent, for example alkyl such as methyl, ethyl, propyl, isopropyl, butyl, isobutyl, t-butyl, vinyl, alkyne, or others. When each Y is oxygen, the respective structures, from left to right, are a Silatrane, a Silquasilatrane, and a Silproatrane. When Y is nitrogen, the respective structures are an azasilatrane, an azasilquasiatrane, and an azasilproatrane.

Another type of polycyclic siloxane precursor starting material, among the preferred starting materials in the present context, can be a polysilsesquioxane, with the empirical formula $RSiO_{1.5}$ and the structural formula:

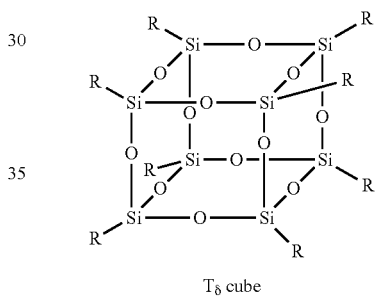

T$_8$ cube in which each R is a hydrogen atom or an organic substituent, for example alkyl such as methyl, ethyl, propyl, isopropyl, butyl, isobutyl, t-butyl, vinyl, alkyne, or others. Two commercial materials of this sort are SST-eM01 poly(methylsilsesquioxane), in which each R can be methyl, and SST-3MH1.1 poly(Methyl-Hydridosilsesquioxane), in which 90% of the R groups are methyl, 10% are hydrogen atoms. This material is available in a 10% solution in tetrahydrofuran, for example. Combinations of two or more of these are also contemplated. Other examples of a contemplated precursor are methylsilatrane, CAS No. 2288-13-3, in which each Y is oxygen and Z is methyl, methylazasilatrane, poly(methylsilsesquioxane) (for example SST-eM01 poly(methylsilsesquioxane)), in which each R optionally can be methyl, SST-3MH1.1 poly(Methyl-Hydridosilsesquioxane) (for example SST-3MH1.1 poly(Methyl-Hydridosilsesquioxane)), in which 90% of the R groups are methyl and 10% are hydrogen atoms, or a combination of any two or more of these.

The analogous polysilsesquiazanes in which —NH— can be substituted for the oxygen atom in the above structure are also useful for making analogous passivation layer or pH protective coating. Examples of contemplated polysilsesquiazanes are a poly(methylsilsesquiazane), in which each R can be methyl, and a poly(Methyl-Hydridosilsesquiazane, in which 90% of the R groups are methyl, 10% are hydrogen atoms. Combinations of two or more of these are also contemplated.

One particularly contemplated precursor for the barrier coating or layer according to the present invention can be a linear siloxane, for example hexamethyldisiloxane or HMDSO. One particularly contemplated precursor for the lubricity coating or layer and the passivation layer or pH protective coating according to the present invention can be a cyclic siloxane, for example octamethylcyclotetrasiloxane (OMCTS).

It is believed that the OMCTS or other cyclic siloxane molecule provides several advantages over other siloxane materials. First, its ring structure is believed to result in a less dense passivation layer or pH protective coating (as compared to passivation layer or pH protective coating prepared from HMDSO). The molecule also is believed to allow selective ionization so that the final structure and chemical composition of the passivation layer or pH protective coating can be directly controlled through the application of the plasma power. Other organosilicon molecules are readily ionized (fractured) so that it can be more difficult to retain the original structure of the molecule.

In any of the PECVD methods according to the present invention, the applying step optionally can be carried out by vaporizing the precursor and providing it in the vicinity of the substrate. For example, OMCTS can be vaporized by heating it to about 50° C. before applying it to the PECVD apparatus.

Cyclic organosilicon precursors, in particular monocyclic organosilicon precursors (like the monocyclic precursors listed elsewhere in present description), and specifically OMCTS, are particularly suitable to achieve a passivation layer or pH protective coating.

The organosilicon precursor can be delivered at a rate of equal to or less than 10 sccm, optionally equal to or less than 6 sccm, optionally equal to or less than 2.5 sccm, optionally equal to or less than 1.5 sccm, optionally equal to or less than 1.25 sccm. Larger pharmaceutical packages or other vessels or other changes in conditions or scale may require more or less of the precursor.

Other Components of PECVD Reaction Mixture and Ratios of Components for Passivation Layer or pH Protective Coating Generally, for a passivation layer or pH protective coating, $O_2$ can be present in an amount (which can, for example be expressed by the flow rate in sccm) which can be less than one order of magnitude greater than the organosilicon amount. In contrast, in order to achieve a barrier coating or layer, the amount of $O_2$ typically can be at least one order of magnitude higher than the amount of organosilicon precursor.

As some specific examples of suitable proportions of the respective constituents, the volume ratio (in sccm) of organosilicon precursor to $O_2$ for a passivation layer or pH protective coating can be in the range from 0.1:1 to 10:1, optionally in the range from 0.3:1 to 8:1, optionally in the range from 0.5:1 to 5:1, optionally from 1:1 to 3:1. Some non-exhaustive alternative selections and suitable proportions of the precursor gas, oxygen, and a carrier gas are provided below.

The process gas can contain this ratio of gases for preparing a lubricity and/or passivation layer or pH protective coating:
  from 0.5 to 10 standard volumes of the precursor;
  from 1 to 100 standard volumes of a carrier gas,
  from 0.1 to 10 standard volumes of an oxidizing agent.
alternatively this ratio:
  from 1 to 6 standard volumes of the precursor;
  from 1 to 80 standard volumes of a carrier gas,
  from 0.1 to 2 standard volumes of an oxidizing agent.
alternatively this ratio:
  from 2 to 4 standard volumes, of the precursor;
  from 1 to 100 standard volumes of a carrier gas,
  from 0.1 to 2 standard volumes of an oxidizing agent.
alternatively this ratio:
  from 1 to 6 standard volumes of the precursor;
  from 3 to 70 standard volumes, of a carrier gas,
  from 0.1 to 2 standard volumes of an oxidizing agent.
alternatively this ratio:
  from 2 to 4 standard volumes, of the precursor;
  from 3 to 70 standard volumes of a carrier gas,
  from 0.1 to 2 standard volumes of an oxidizing agent.
alternatively this ratio:
  from 1 to 6 standard volumes of the precursor;
  from 1 to 100 standard volumes of a carrier gas,
  from 0.2 to 1.5 standard volumes of an oxidizing agent.
alternatively this ratio:
  from 2 to 4 standard volumes, of the precursor;
  from 1 to 100 standard volumes of a carrier gas,
  from 0.2 to 1.5 standard volumes of an oxidizing agent.
alternatively this ratio:
  from 1 to 6 standard volumes of the precursor;
  from 3 to 70 standard volumes of a carrier gas,
  from 0.2 to 1.5 standard volumes of an oxidizing agent.
alternatively this ratio:
  from 2 to 4 standard volumes of the precursor;
  from 3 to 70 standard volumes of a carrier gas,
  from 0.2 to 1.5 standard volumes of an oxidizing agent.
alternatively this ratio:
  from 1 to 6 standard volumes of the precursor;
  from 1 to 100 standard volumes of a carrier gas,
  from 0.2 to 1 standard volumes of an oxidizing agent.
alternatively this ratio:
  from 2 to 4 standard volumes of the precursor;
  from 1 to 100 standard volumes of a carrier gas,
  from 0.2 to 1 standard volumes of an oxidizing agent.
alternatively this ratio:
  from 1 to 6 standard volumes of the precursor;
  from 3 to 70 standard volumes of a carrier gas,
  from 0.2 to 1 standard volumes of an oxidizing agent.
alternatively this ratio:
  2 to 4 standard volumes, of the precursor;
  from 3 to 70 standard volumes of a carrier gas,
  from 0.2 to 1 standard volumes of an oxidizing agent.
alternatively this ratio:
  from 1 to 6 standard volumes of the precursor;
  from 5 to 100 standard volumes of a carrier gas,
  from 0.1 to 2 standard volumes of an oxidizing agent.
alternatively this ratio:
  from 2 to 4 standard volumes, of the precursor;
  from 5 to 100 standard volumes of a carrier gas,
  from 0.1 to 2 standard volumes
  of an oxidizing agent.
alternatively this ratio:
  from 1 to 6 standard volumes of the precursor;
  from 10 to 70 standard volumes, of a carrier gas,
  from 0.1 to 2 standard volumes of an oxidizing agent.
alternatively this ratio:
  from 2 to 4 standard volumes, of the precursor;
  from 10 to 70 standard volumes of a carrier gas,
  from 0.1 to 2 standard volumes of an oxidizing agent.
alternatively this ratio:
  from 1 to 6 standard volumes of the precursor;
  from 5 to 100 standard volumes of a carrier gas, from 0.5 to 1.5 standard volumes of an oxidizing agent. alternatively this ratio:
from 2 to 4 standard volumes, of the precursor;
from 5 to 100 standard volumes of a carrier gas,
from 0.5 to 1.5 standard volumes of an oxidizing agent. alternatively this ratio:
from 1 to 6 standard volumes of the precursor;
from 10 to 70 standard volumes, of a carrier gas,
from 0.5 to 1.5 standard volumes of an oxidizing agent. alternatively this ratio:
from 2 to 4 standard volumes of the precursor;
from 10 to 70 standard volumes of a carrier gas,
from 0.5 to 1.5 standard volumes of an oxidizing agent. alternatively this ratio:
from 1 to 6 standard volumes of the precursor;
from 5 to 100 standard volumes of a carrier gas,
from 0.8 to 1.2 standard volumes of an oxidizing agent. alternatively this ratio:
from 2 to 4 standard volumes of the precursor;
from 5 to 100 standard volumes of a carrier gas,
from 0.8 to 1.2 standard volumes of an oxidizing agent. alternatively this ratio:
from 1 to 6 standard volumes of the precursor;
from 10 to 70 standard volumes of a carrier gas,
from 0.8 to 1.2 standard volumes of an oxidizing agent. alternatively this ratio:
2 to 4 standard volumes, of the precursor;
from 10 to 70 standard volumes of a carrier gas,
from 0.8 to 1.2 standard volumes of an oxidizing agent.

Exemplary reaction conditions for preparing a passivation layer or pH protective coating according to the present invention in a 3 ml sample size syringe with a ⅛" diameter tube (open at the end) are as follows:
Flow rate ranges:
OMCTS: 0.5-10 sccm
Oxygen: 0.1-10 sccm
Argon: 1.0-200 sccm
Power: 0.1-500 watts In another contemplated embodiment the proportions of precursor, oxygen, and Argon can be, for example:
OMCTS: 0.5-5.0 sccm
Oxygen: 0.1-5.0 sccm
Argon: 1.0-20 sccm In yet another contemplated embodiment the proportions of precursor, oxygen, and Argon and the power level can be, for example:
Specific Flow rates:
OMCTS: 2.0 sccm
Oxygen: 0.7 sccm
Argon: 7.0 sccm
Power: 3.5 watts The coatings can vary from the above proportions, however. For example, to provide a coating with lubricity which also serves as a passivation layer or pH protection coating, the following proportions of gases can be used:
from 0.5 to 10 standard volumes, optionally from 1 to 6 standard volumes, optionally from 2 to 4 standard volumes, optionally equal to or less than 6 standard volumes, optionally equal to or less than 2.5 standard volumes, optionally equal to or less than 1.5 standard volumes, optionally equal to or less than 1.25 standard volumes of the precursor, for example OMCTS or one of the other precursors of any embodiment;
from 0 to 100 standard volumes, optionally from 1 to 80 standard volumes, optionally from 5 to 100 standard volumes, optionally from 10 to 70 standard volumes, of a carrier gas of any embodiment;
from 0.1 to 10 standard volumes, optionally from 0.1 to 2 standard volumes, optionally from 0.2 to 1.5 standard volumes, optionally from 0.2 to 1 standard volumes, optionally from 0.5 to 1.5 standard volumes, optionally from 0.8 to 1.2 standard volumes of an oxidizing agent.

The presence of the precursor and $O_2$ in the volume ratios as given in Tables 9-11 can be specifically suitable to achieve a passivation layer or pH protective coating.

In one aspect of the invention, a carrier gas can be absent in the reaction mixture; in another aspect of the invention, it can be present. Suitable carrier gases include any noble gas, for example Argon, Helium, Neon, Xenon or combinations of two or more of these. When the carrier gas is present in the reaction mixture, it is typically present in a volume (in sccm) exceeding the volume of the organosilicon precursor. For example, the ratio of the organosilicon precursor to carrier gas can be from 1:1 to 1:50, optionally from 1:5 to 1:40, optionally from 1:10 to 1:30. One function of the carrier gas can be to dilute the reactants in the plasma, encouraging the formation of a coating on the substrate instead of powdered reaction products that do not adhere to the substrate and are largely removed with the exhaust gases.

The addition of Argon gas has been found to improve the performance of the passivation layer or pH protective coating 34. It is believed that additional ionization of the molecule in the presence of Argon contributes to this performance. The Si—O—Si bonds of the molecule have a high bond energy followed by the Si—C, with the C—H bonds being the weakest. Passivation or pH protection appear to be achieved when a portion of the C—H bonds are broken. This allows the connecting (cross-linking) of the structure as it grows. Addition of oxygen (with the Argon) is understood to enhance this process. A small amount of oxygen can also provide C—O bonding to which other molecules can bond. The combination of breaking C—H bonds and adding oxygen all at low pressure and power leads to a chemical structure that can be solid while providing passivation or pH protection.

In any of the disclosed embodiments, one preferred combination of process gases includes octamethylcyclotetrasiloxane (OMCTS) or another cyclic siloxane as the precursor; $O_2$, nitrous oxide ($N_2O$), ozone ($O_3$), or another oxidizing gas, which means any other gas that oxidizes the precursor during PECVD at the conditions employed, preferably $O_2$; and a carrier gas, for example a noble carrier gas, for example Argon (Ar). The gaseous reactant or process gas can be at least substantially free of nitrogen. This combination is contemplated to improve the resulting passivation layer or pH protective coating.

Application Method

A passivation layer or pH protective coating 34 optionally can be applied directly or indirectly over the barrier coating or layer 30, and optionally can be applied to a pre-assembly such as 12 while the pre-assembly is capped, under conditions effective to maintain communication between the barrel lumen 18 and the dispensing portion lumen 26 via the proximal opening 22 at the end of applying the passivation layer or pH protective coating 34.

Vessel Made of Glass

Optionally in any embodiment, the passivation layer or pH protective coating 34 can be applied as the first or sole vapor-deposited coating or layer 30, instead of or in addition to its application as a further layer. This expedient may be useful, for example, where the barrel is made of glass, as described below. The presently disclosed passivation layer or pH protective coating also can reduce the dissolution of glass by contents having the pH values indicated as attacking $SiO_x$ coatings or layers.

A pharmaceutical package 210 is contemplated as shown in any embodiment, for example FIGS. 7-8, comprising a vessel or vessel part made of glass; optionally a barrier coating or layer or layer such as 30 on the vessel or vessel part; a passivation layer or pH protective coating such as 34 on the vessel, vessel part, or barrier coating or layer or layer; and a pharmaceutical composition or preparation contained within the vessel.

In this glass embodiment the barrier coating or layer or layer can be optional because a glass vessel wall in itself is an extremely good barrier coating or layer. It is contemplated to optionally provide a barrier coating or layer primarily to provide isolation: in other words, to prevent contact and interchange of material of any kind, such as ions of the glass or constituents of the pharmaceutical composition or preparation between the vessel wall and the contents of the vessel. The protective layer as defined in this specification can be contemplated to perform the isolation function independently, at least to a degree. This passivation coating or pH protection layer can be contemplated to provide a useful function on glass in contact with the pharmaceutical composition or preparation, as the present working examples show that borosilicate glass, commonly used today for pharmaceutical packaging, can be dissolved by a fluid composition having a pH exceeding 5. Particularly in applications where such dissolution can be disadvantageous or perceived to be disadvantageous, the present passivation layers or protective coatings or layers will find utility.

The vessel can be made, for example of glass of any type used in medical or laboratory applications, such as soda-lime glass, borosilicate glass, or other glass formulations. One function of a passivation layer or pH protective coating on a glass vessel can be to reduce the ingress of ions in the glass, either intentionally or as impurities, for example sodium, calcium, or others, from the glass to the contents of the pharmaceutical package or other vessel, such as a reagent or blood in an evacuated blood collection tube. Alternatively, a dual functional protective/lubricity coating or layer can be used on a glass vessel in whole or in part, such as selectively at surfaces contacted in sliding relation to other parts, to provide lubricity, for example to ease the insertion or removal of a stopper or passage of a sliding element such as a piston in a syringe, as well as to provide the isolation of a passivation layer or pH protective coating. Still another reason to coat a glass vessel, for example with a dual functional hydrophobic and passivation layer or pH protective coating, can be to prevent a reagent or intended sample for the pharmaceutical package or other vessel, such as blood, from sticking to the wall of the vessel or an increase in the rate of coagulation of the blood in contact with the wall of the vessel, as well as to provide the isolation of a passivation layer or pH protective coating.

A related embodiment can be a vessel as described in the previous paragraphs, in which the barrier coating or layer or layer can be made of soda lime glass, borosilicate glass, or another type of glass coating or layer on a substrate.

Plasma Conditions for Passivation Layer or pH Protective Coating

The precursor can be contacted with a plasma made by energizing the vicinity of the precursor with electrodes powered at radio frequency, optionally a frequency of 10 kHz to 2.45 GHz, optionally from 10 kHz to less than 300 MHz, optionally from 1 to 50 MHz, optionally from 10 to 15 MHz, alternatively from about 13 to about 14 MHz, optionally at or about 13.56 MHz. Typically, the plasma in the PECVD process can be generated at RF frequency, although microwave or other electromagnetic energy can also be used. For providing a protective layer on the interior of a vessel by a plasma reaction carried out within the vessel, the plasma of any embodiment can be generated with an electric power of from 0.1 to 500 W, optionally from 0.1 to 400 W, optionally from 0.1 to 300 W, optionally from 1 to 250 W, optionally from 1 to 200 W, even optionally from 10 to 150 W, optionally from 20 to 150 W, for example of 40 W, optionally from 40 to 150 W, even optionally from 60 to 150 W.

For any PECVD process in any embodiment herein, PECVD can be initiated by applying an initial higher power level within the stated range, followed by a subsequent lower power level within the stated range. The initial higher power level can be applied, for example, for from 1 to 3 seconds. The subsequent lower power level can applied, for example, for the remainder of PECVD.

For forming a coating intended to provide lubricity in addition to passivation or pH protection, the precursor can be contacted with a plasma made by energizing the vicinity of the precursor with electrodes supplied with electric power at from 0.1 to 25 W, optionally from 1 to 22 W, optionally from 1 to 10 W, even optionally from 1 to 5 W, optionally from 2 to 4 W, for example of 3 W, optionally from 3 to 17 W, even optionally from 5 to 14 W, for example 6 or 7.5 W, optionally from 7 to 11 W, for example of 8 W.

The ratio of the electrode power to the plasma volume can be less than 100 W/ml, optionally can be from 0.1 to 100 W/mL, optionally can be from 5 W/ml to 75 W/ml, optionally can be from 6 W/ml to 60 W/ml, optionally can be from 10 W/ml to 50 W/ml, optionally from 20 W/ml to 40 W/ml. These power levels are suitable for applying passivation layers or protective coatings or layers to syringes and sample tubes and pharmaceutical packages or other vessels of similar geometry having a void volume of 5 mL in which PECVD plasma can be generated. It is contemplated that for larger or smaller objects the power applied, in Watts, should be increased or reduced accordingly to scale the process to the size of the substrate.

For forming a coating intended to provide lubricity in addition to passivation or pH protection, the precursor can be contacted with a plasma made by energizing the vicinity of the precursor with electrodes supplied with electric power density at less than 10 W/ml of plasma volume, alternatively from 6 W/ml to 0.1 W/ml of plasma volume, alternatively from 5 W/ml to 0.1 W/ml of plasma volume, alternatively from 4 W/ml to 0.1 W/ml of plasma volume, alternatively from 2 W/ml to 0.2 W/ml of plasma volume, alternatively from 10 W/ml to 50 W/ml, optionally from 20 W/ml to 40 W/ml.

Optionally, in any embodiment of FIGS. 7-8 the passivation layer or pH protective coating can be applied by PECVD at a power level per of more than 22,000 kJ/kg of mass of precursor, or more than 30,000 kJ/kg of mass of precursor, or more than 40,000 kJ/kg of mass of precursor, or more than 50,000 kJ/kg of mass of precursor, or more than 60,000 kJ/kg of mass of precursor, or more than 62,000 kJ/kg of mass of precursor, or more than 70,000 kJ/kg of mass of precursor, or more than 80,000 kJ/kg of mass of precursor, or more than 100,000 kJ/kg of mass of precursor, or more than 200,000 kJ/kg of mass of precursor, or more than 300,000 kJ/kg of mass of precursor, or more than 400,000 kJ/kg of mass of precursor, or more than 500,000 kJ/kg of mass of precursor.

Optionally, in any embodiment of FIGS. 7-8 the passivation layer or pH protective coating 34 can be applied by PECVD at a power level per of less than 2,000,000 kJ/kg of mass of precursor, or less than 1,000,000 kJ/kg of mass of precursor, or less than 700,000 kJ/kg of mass of precursor, or less than 500,000 kJ/kg of mass of precursor, or less than 100,000 kJ/kg of mass of precursor, or less than 90,000 kJ/kg of mass of precursor, or less than 81,000 kJ/kg of mass of precursor.

For a PECVD process the deposition time can be from 1 to 30 sec, alternatively from 2 to 10 sec, alternatively from 3 to 9 sec. The purposes for optionally limiting deposition time can be to avoid overheating the substrate, to increase the rate of production, and to reduce the use of process gas and its constituents. The purposes for optionally extending deposition time can be to provide a thicker passivation layer or pH protective coating for particular deposition conditions.

Other methods can be used to apply the passivation layer or pH protective coating. For example, hexamethylene disilazane (HMDZ) can be used as the precursor. HMDZ has the advantage of containing no oxygen in its molecular structure. This passivation layer or pH protective coating treatment is contemplated to be a surface treatment of the $SiO_x$ barrier coating or layer with HMDZ. It is contemplated that HMDZ will react with the —OH sites that are present in the silicon dioxide coating, resulting in the evolution of $NH_3$ and bonding of S—$CH_3)_3$ to the silicon (it is contemplated that hydrogen atoms will be evolved and bond with nitrogen from the HMDZ to produce $NH_3$).

It is contemplated that this HMDZ passivation layer or pH protective coating can be accomplished through several possible paths.

One contemplated path can be dehydration/vaporization of the HMDZ at ambient temperature. First, an $SiO_x$ surface can be deposited, for example using hexamethylene disiloxane (HMDSO). The as-coated silicon dioxide surface then can be reacted with HMDZ vapor. In an embodiment, as soon as the $SiO_x$ surface is deposited onto the article of interest, the vacuum can be maintained. The HMDSO and oxygen are pumped away and a base vacuum is achieved. Once base vacuum is achieved, HMDZ vapor can be flowed over the surface of the silicon dioxide (as coated on the part of interest) at pressures from the mTorr range to many Torr. The HMDZ then can be pumped away (with the resulting $NH_3$ that is a byproduct of the reaction). The amount of $NH_3$ in the gas stream can be monitored (with a residual gas analyzer—RGA—as an example) and when there is no more $NH_3$ detected, the reaction is complete. The part then can be vented to atmosphere (with a clean dry gas or nitrogen). The resulting surface then can be found to have been passivated or protected. It is contemplated that this method optionally can be accomplished without forming a plasma.

Alternatively, after formation of the $SiO_x$ barrier coating or layer, the vacuum can be broken before dehydration/vaporization of the HMDZ. Dehydration/vaporization of the HMDZ can then be carried out in either the same apparatus used for formation of the $SiO_x$ barrier coating or layer or different apparatus.

Dehydration/vaporization of HMDZ at an elevated temperature is also contemplated. The above process can alternatively be carried out at an elevated temperature exceeding room temperature up to about 150° C. The maximum temperature can be determined by the material from which the coated part is constructed. An upper temperature should be selected that will not distort or otherwise damage the part being coated.

Dehydration/vaporization of HMDZ with a plasma assist is also contemplated. After carrying out any of the above embodiments of dehydration/vaporization, once the HMDZ vapor is admitted into the part, plasma can be generated. The plasma power can range from a few watts to 100+ watts (similar powers as used to deposit the $SiO_x$). The above is not limited to HMDZ and could be applicable to any molecule that will react with hydrogen, for example any of the nitrogen-containing precursors described in this specification.

Surprisingly, it has been found that the above stated coatings or layers can be applied to the capped pre-assembly 12 with substantially no deposition of the vapor-deposited coating 30 in the dispensing portion lumen 26. This is shown by a working example below.

In certain embodiments, the generation of uniform plasma throughout the portion of the vessel to be coated is contemplated, as it has been found in certain instances to generate a better passivation layer or pH protective coating. Uniform plasma means regular plasma that does not include a substantial amount of hollow cathode plasma (which has higher emission intensity than regular plasma and can be manifested as a localized area of higher intensity interrupting the more uniform intensity of the regular plasma).

It is further contemplated that any embodiment of the passivation layer or pH protective coating processes described in this specification can also be carried out without using the article to be coated to contain the plasma. For example, external surfaces of medical devices, for example catheters, surgical instruments, closures, and others can be passivated or protected by sputtering the coating, employing a radio frequency target.

Non-Organosilicon Passivation Layer or pH Protective Coating

Another way of applying the passivation layer or pH protective coating can be to apply as the passivation layer or pH protective coating an amorphous carbon or fluorinated polymer coating, or a combination of the two.

Amorphous carbon coatings can be formed by PECVD using a saturated hydrocarbon, (e.g. methane, ethane, ethylene or propane), or an unsaturated hydrocarbon (e.g. ethylene, acetylene), or a combination of two or more of these as a precursor for plasma polymerization.

Fluorinated polymer coatings can be applied by chemically modifying a precursor, while on or in the vicinity of the fluid receiving interior surface.

Optionally, the precursor comprises:
dimeric tetrafluoroparaxylylene,
difluorocarbene,
monomeric tetrafluoroethylene,
oligomeric tetrafluoroethylene having the formula $F_2C=CF(CF_2)xF$ in which x can be from 1 to 100, optionally 2 to 50, optionally 2-20, optionally 2-10,
sodium chlorodifluoroacetate,
chlorodifluoromethane,
bromodifluoromethane,
hexafluoropropylene oxide,
1H,1H,2H,2H-perfluorodecyl acrylate (FDA),
a bromofluoroalkane in which the alkane moiety can have from 1 to 6 carbon atoms,
an iodofluoroalkane in which the alkane moiety can have from 1 to 6 carbon atoms, or
a combination of any two or more of these.

The fluorinated polymer is:
optionally from at least 0.01 micrometer to at most 100 micrometers thick, optionally from at least 0.05 micrometers to at most 90 micrometers thick,
optionally from at least 0.1 micrometers to at most 80 micrometers thick,
optionally from at least 0.1 micrometers to at most 70 micrometers thick,
optionally from at least 0.1 micrometers to at most 60 micrometers thick,
optionally from at least 0.1 micrometers to at most 50 micrometers thick,
optionally from at least 0.1 micrometers to at most 40 micrometers thick,
optionally from at least 0.1 micrometers to at most 30 micrometers thick,
optionally from at least 0.1 micrometers to at most 20 micrometers thick,
optionally from at least 0.1 micrometers to at most 15 micrometers thick,
optionally from at least 0.1 micrometers to at most 12 micrometers thick,
optionally from at least 0.1 micrometers to at most 10 micrometers thick
optionally from at least 0.1 micrometers to at most 8 micrometers thick,
optionally from at least 0.1 micrometers to at most 6 micrometers thick,
optionally from at least 0.1 micrometers to at most 4 micrometers thick,
optionally from at least 0.1 micrometers to at most 2 micrometers thick,
optionally from at least 0.1 micrometers to at most 1 micrometers thick,
optionally from at least 0.1 micrometers to at most 0.9 micrometers thick,
optionally from at least 0.1 micrometers to at most 0.8 micrometers thick,
optionally from at least 0.1 micrometers to at most 0.7 micrometers thick,
optionally from at least 0.1 micrometers to at most 0.6 micrometers thick,
optionally from at least 0.1 micrometers to at most 0.5 micrometers thick,
optionally from at least 0.5 micrometers to at most 5 micrometers thick,
optionally from at least 0.5 micrometers to at most 4 micrometers thick,
optionally from at least 0.5 micrometers to at most 3 micrometers thick,
optionally from at least 0.5 micrometers to at most 2 micrometers thick,
optionally from at least 0.5 micrometers to at most 1 micrometer thick,
optionally about 10 micrometers thick,
optionally about 2 micrometers thick.

The fluorinated polymer optionally can be applied by vapor deposition, for example chemical vapor deposition. Optionally, the fluorinated polymer can be applied by chemical vapor deposition of dimeric tetrafluoroparaxylylene. An example of a suitable fluorinated polymer can be polytetrafluoroparaxylylene. Optionally, the fluorinated polymer consists essentially of polytetrafluoroparaxylylene.

Optionally in any embodiment, the fluorinated polymer coating or layer comprises polytetrafluoroethylene. Optionally in any embodiment, the fluorinated polymer coating or layer consists essentially of polytetrafluoroethylene.

For example, in any embodiment, the fluorinated polymer coating or layer can be applied by chemically modifying a precursor, while on or in the vicinity of the fluid receiving interior surface, to produce the fluorinated polymer coating or layer on the fluid receiving interior surface. Optionally in any embodiment, the fluorinated polymer coating or layer can be applied by chemical vapor deposition. For one example, in any embodiment, the fluorinated polymer coating or layer can be applied by heated wire chemical vapor deposition (HWCVD). For another example, in any embodiment, the fluorinated polymer coating or layer can be applied by plasma enhanced chemical vapor deposition (PECVD). Mixed processes or other processes for applying a suitable coating are also contemplated, in any embodiment.

Another example of a suitable HWCVD process for applying the fluorinated polymer coating can be the process described in Hilton G. Pryce Lewis, Neeta P. Bansal, Aleksandr J. White, Erik S. Handy, HWCVD of Polymers: Commercialization and Scale-up, THIN SOLID FILMS 517 2009) 3551-3554; US Publ. Appl. 2012/0003497 A1, published Jan. 5, 2012; and US Publ. Appl. 2011/0186537, published Aug. 4, 2011, which are incorporated here by reference in their entirety for their description of fluorinated polymer coatings and their application.

It is contemplated that that amorphous carbon and/or fluorinated polymer coatings will provide better passivation or protection of an $SiO_x$ barrier coating or layer than a siloxane coating since an amorphous carbon and/or fluorinated polymer coating will not contain silanol bonds.

It is further contemplated that fluorosilicon precursors can be used to provide a passivation layer or pH protective coating over an $SiO_x$ barrier coating or layer. This can be carried out by using as a precursor a fluorinated silane precursor such as hexafluorosilane and a PECVD process. The resulting coating would also be expected to be a non-wetting coating.

Liquid-Applied Passivation Layer or pH Protective Coating

Another example of a suitable barrier or other type of passivation layer or pH protective coating, usable in conjunction with the PECVD-applied passivation layer or pH protective coating or other PECVD treatment as disclosed here, can be a liquid barrier, lubricant, surface energy tailoring, or passivation layer or pH protective coating 90 applied to the inner or interior surface of a pharmaceutical package or other vessel, either directly or with one or more intervening PECVD-applied coatings or layers described in this specification, for example $SiO_x$, a lubricity coating or layer and/or a passivation layer or pH protective coating, or both.

A suitable liquid barrier, lubricity, or passivation layer or pH protective coating 90 also optionally can be applied, for example, by applying a liquid monomer or other polymerizable or curable material to the inner or interior surface of the vessel 80 and curing, polymerizing, or crosslinking the liquid monomer to form a solid polymer, or by applying a solvent-dispersed polymer to the surface 88 and removing the solvent.

Any of the above methods can include as a step forming a passivation layer or pH protective coating 90 on the interior 88 of a vessel 80 via the vessel port 92 at a processing station or device 28. One example can be applying a liquid passivation layer or pH protective coating, for example of a curable monomer, prepolymer, or polymer dispersion, to the inner or interior surface 88 of a vessel 80 and curing it to form a film that physically isolates the contents of the vessel 80 from its inner or interior surface 88. The prior art describes polymer passivation layer or pH protective coating technology as suitable for treating plastic blood collection tubes. For example, the acrylic and polyvinylidene chloride (PVdC) passivation layer or pH protective coating materials and methods described in U.S. Pat. No. 6,165,566, which is hereby incorporated by reference, optionally can be used.

Any of the above methods can also include as a step forming a coating or layer on the exterior outer wall of a vessel 80. The exterior coating or layer optionally can be a barrier coating or layer or layer, optionally an oxygen barrier coating or layer or layer, or optionally a water barrier coating or layer or layer. The exterior coating or layer can also be an armor layer that protects the outer wall of a vessel 80. One example of a suitable exterior coating or layer can be polyvinylidene chloride, which functions both as a water barrier and an oxygen barrier. Optionally, the exterior coating or layer can be applied as a water-based coating or layer. The exterior coating or layer optionally can be applied by dipping the vessel in it, spraying it on the pharmaceutical package or other vessel, or other expedients.

Yet another coating modality contemplated for protecting or passivating an $SiO_x$ barrier coating or layer can be coating the barrier coating or layer using a polyamidoamine epichlorohydrin resin. For example, the barrier coating or layer can be applied by dip coating in a fluid polyamidoamine epichlorohydrin resin melt, solution or dispersion and cured by autoclaving or other heating at a temperature between 60 and 100° C.

It is contemplated that a coating of polyamidoamine epichlorohydrin resin can be preferentially used in aqueous environments between pH 5-8, as such resins are known to provide high wet strength in paper in that pH range. Wet strength is the ability to maintain mechanical strength of paper subjected to complete water soaking for extended periods of time, so it is contemplated that a coating of polyamidoamine epichlorohydrin resin on an $SiO_x$ barrier coating or layer will have similar resistance to dissolution in aqueous media. It is also contemplated that, because polyamidoamine epichlorohydrin resin imparts a lubricity improvement to paper, it will also provide lubricity in the form of a coating on a thermoplastic surface made of, for example, COC or COP.

Fluid Material

Optionally for any of the embodiments of FIGS. 7-8, the fluid material 40 can have a pH between 5 and 6, optionally between 6 and 7, optionally between 7 and 8, optionally between 8 and 9, optionally between 6.5 and 7.5, optionally between 7.5 and 8.5, optionally between 8.5 and 9.

Optionally for any of the embodiments of FIGS. 7-8, the fluid material 40 can be a liquid at 20° C. and ambient pressure at sea level, which is defined as a pressure of 760 mm Hg.

Optionally for any of the embodiments of FIGS. 7-8, the fluid material 40 can be an aqueous liquid.

Optionally for any of the embodiments of FIGS. 7-8, the fluid material 40 comprises a member or a combination of two or more members selected from the group consisting of:
Inhalation Anesthetics
Aliflurane
Chloroform
Cyclopropane
Desflurane (Suprane)
Diethyl Ether
Enflurane (Ethrane)
Ethyl Chloride
Ethylene
Halothane (Fluothane)
Isoflurane (Forane, Isoflo)
Isopropenyl vinyl ether
Methoxyflurane
methoxyflurane,
Methoxypropane
Nitrous Oxide
Roflurane
Sevoflurane (Sevorane, Ultane, Sevoflo)
Teflurane
Trichloroethylene
Vinyl Ether
Xenon
Injectable Drugs
Ablavar (Gadofosveset Trisodium Injection)
Abarelix Depot
Abobotulinumtoxin A Injection (Dysport)
ABT-263
ABT-869
ABX-EFG
Accretropin (Somatropin Injection)
Acetadote (Acetylcysteine Injection)
Acetazolamide Injection (Acetazolamide Injection)
Acetylcysteine Injection (Acetadote)
Actemra (Tocilizumab Injection)
Acthrel (Corticorelin Ovine Triflutate for Injection)
Actummune
Activase
Acyclovir for Injection (Zovirax Injection)
Adacel
Adalimumab
Adenoscan (Adenosine Injection)
Adenosine Injection (Adenoscan)
Adrenaclick
AdreView (Iobenguane I 123 Injection for Intravenous Use)
Afluria
Ak-Fluor (Fluorescein Injection)
Aldurazyme (Laronidase)
Alglucerase Injection (Ceredase)
Alkeran Injection (Melphalan Hcl Injection)
Allopurinol Sodium for Injection (Aloprim)
Aloprim (Allopurinol Sodium for Injection)
Alprostadil
Alsuma (Sumatriptan Injection)
ALTU-238
Amino Acid Injections
Aminosyn
Apidra
Apremilast
Alprostadil Dual Chamber System for Injection (Caverject Impulse)
AMG 009
AMG 076
AMG 102
AMG 108
AMG 114
AMG 162
AMG 220
AMG 221
AMG 222
AMG 223
AMG 317
AMG 379
AMG 386
AMG 403
AMG 477
AMG 479
AMG 517
AMG 531
AMG 557

AMG 623
AMG 655
AMG 706
AMG 714
AMG 745
AMG 785
AMG 811
AMG 827
AMG 837
AMG 853
AMG 951
Amiodarone HCl Injection (Amiodarone HCl Injection)
Amobarbital Sodium Injection (Amytal Sodium)
Amytal Sodium (Amobarbital Sodium Injection)
Anakinra
Anti-Abeta
Anti-Beta7
Anti-Beta20
Anti-CD4
Anti-CD20
Anti-CD40
Anti-IFNalpha
Anti-IL13
Anti-OX40L
Anti-oxLDS
Anti-NGF
Anti-NRP1
Arixtra
Amphadase (Hyaluronidase Inj)
Ammonul (Sodium Phenylacetate and Sodium Benzoate Injection)
Anaprox
Anzemet Injection (Dolasetron Mesylate Injection)
Apidra (Insulin Glulisine [rDNA origin] Inj)
Apomab
Aranesp (darbepoetin alfa)
Argatroban (Argatroban Injection)
Arginine Hydrochloride Injection (R-Gene 10
Aristocort
Aristospan
Arsenic Trioxide Injection (Trisenox)
Articane HCl and Epinephrine Injection (Septocaine)
Arzerra (Ofatumumab Injection)
Asclera (Polidocanol Injection)
Ataluren
Ataluren-DMD
Atenolol lnj (Tenormin I.V. Injection)
Atracurium Besylate Injection (Atracurium Besylate Injection)
Avastin
Azactam Injection (Aztreonam Injection)
Azithromycin (Zithromax Injection)
Aztreonam Injection (Azactam Injection)
Baclofen Injection (Lioresal Intrathecal)
Bacteriostatic Water (Bacteriostatic Water for Injection)
Baclofen Injection (Lioresal Intrathecal)
Bal in Oil Ampules (Dimercarprol Injection)
BayHepB
BayTet
Benadryl
Bendamustine Hydrochloride Injection (Treanda)
Benztropine Mesylate Injection (Cogentin)
Betamethasone Injectable Suspension (Celestone Soluspan)
Bexxar
Bicillin C-R 900/300 (Penicillin G Benzathine and Penicillin G Procaine Injection)
Blenoxane (Bleomycin Sulfate Injection)
Bleomycin Sulfate Injection (Blenoxane)
Boniva Injection (Ibandronate Sodium Injection)
Botox Cosmetic (OnabotulinumtoxinA for Injection)
BR3-FC
Bravelle (Urofollitropin Injection)
Bretylium (Bretylium Tosylate Injection)
Brevital Sodium (Methohexital Sodium for Injection)
Brethine
Briobacept
BTT-1023
Bupivacaine HCl
Byetta
Ca-DTPA (Pentetate Calcium Trisodium Inj)
Cabazitaxel Injection (Jevtana)
Caffeine Alkaloid (Caffeine and Sodium Benzoate Injection)
Calcijex Injection (Calcitrol)
Calcitrol (Calcijex Injection)
Calcium Chloride (Calcium Chloride Injection 10%)
Calcium Disodium Versenate (Edetate Calcium Disodium Injection)
Campath (Altemtuzumab)
Camptosar Injection (Irinotecan Hydrochloride)
Canakinumab Injection (Ilaris)
Capastat Sulfate (Capreomycin for Injection)
Capreomycin for Injection (Capastat Sulfate)
Cardiolite (Prep kit for Technetium Tc99 Sestamibi for Injection)
Carticel
Cathflo
Cefazolin and Dextrose for Injection (Cefazolin Injection)
Cefepime Hydrochloride
Cefotaxime
Ceftriaxone
Cerezyme
Carnitor Injection
Caverject
Celestone Soluspan
Celsior
Cerebyx (Fosphenytoin Sodium Injection)
Ceredase (Alglucerase Injection)
Ceretec (Technetium Tc99m Exametazime Injection)
Certolizumab
CF-101
Chloramphenicol Sodium Succinate (Chloramphenicol Sodium Succinate Injection)
Chloramphenicol Sodium Succinate Injection (Chloramphenicol Sodium Succinate)
Cholestagel (Colesevelam HCL)
Choriogonadotropin Alfa Injection (Ovidrel)
Cimzia
Cisplatin (Cisplatin Injection)
Clolar (Clofarabine Injection)
Clomiphine Citrate
Clonidine Injection (Duraclon)
Cogentin (Benztropine Mesylate Injection)
Colistimethate Injection (Coly-Mycin M)
Coly-Mycin M (Colistimethate Injection)
Compath
Conivaptan Hcl Injection (Vaprisol)
Conjugated Estrogens for Injection (Premarin Injection)
Copaxone
Corticorelin Ovine Triflutate for Injection (Acthrel)
Corvert (Ibutilide Fumarate Injection)
Cubicin (Daptomycin Injection)
CF-101
Cyanokit (Hydroxocobalamin for Injection)
Cytarabine Liposome Injection (DepoCyt)

Cyanocobalamin
Cytovene (ganciclovir)
D.H.E. 45
Dacetuzumab
Dacogen (Decitabine Injection)
Dalteparin
Dantrium IV (Dantrolene Sodium for Injection)
Dantrolene Sodium for Injection (Dantrium IV)
Daptomycin Injection (Cubicin)
Darbepoietin Alfa
DDAVP Injection (Desmopressin Acetate Injection)
Decavax
Decitabine Injection (Dacogen)
Dehydrated Alcohol (Dehydrated Alcohol Injection)
Denosumab Injection (Prolia)
Delatestryl
Delestrogen
Delteparin Sodium
Depacon (Valproate Sodium Injection)
Depo Medrol (Methylprednisolone Acetate Injectable Suspension)
DepoCyt (Cytarabine Liposome Injection)
DepoDur (Morphine Sulfate XR Liposome Injection)
Desmopressin Acetate Injection (DDAVP Injection)
Depo-Estradiol
Depo-Provera 104 mg/ml
Depo-Provera 150 mg/ml
Depo-Testosterone
Dexrazoxane for Injection, Intravenous Infusion Only (Totect)
Dextrose/Electrolytes
Dextrose and Sodium Chloride lnj (Dextrose 5% in 0.9% Sodium Chloride)
Dextrose
Diazepam Injection (Diazepam Injection)
Digoxin Injection (Lanoxin Injection)
Dilaudid-HP (Hydromorphone Hydrochloride Injection)
Dimercarprol Injection (Bal in Oil Ampules)
Diphenhydramine Injection (Benadryl Injection)
Dipyridamole Injection (Dipyridamole Injection)
DMOAD
Docetaxel for Injection (Taxotere)
Dolasetron Mesylate Injection (Anzemet Injection)
Doribax (Doripenem for Injection)
Doripenem for Injection (Doribax)
Doxercalciferol Injection (Hectorol Injection)
Doxil (Doxorubicin Hcl Liposome Injection)
Doxorubicin Hcl Liposome Injection (Doxil)
Duraclon (Clonidine Injection)
Duramorph (Morphine Injection)
Dysport (Abobotulinumtoxin A Injection)
Ecallantide Injection (Kalbitor)
EC-Naprosyn (naproxen)
Edetate Calcium Disodium Injection (Calcium Disodium Versenate)
Edex (Alprostadil for Injection)
Engerix
Edrophonium Injection (Enlon)
Eliglustat Tartate
Eloxatin (Oxaliplatin Injection)
Emend Injection (Fosaprepitant Dimeglumine Injection)
Enalaprilat Injection (Enalaprilat Injection)
Enlon (Edrophonium Injection)
Enoxaparin Sodium Injection (Lovenox)
Eovist (Gadoxetate Disodium Injection)
Enbrel (etanercept)
Enoxaparin
Epicel
Epinepherine
Epipen
Epipen Jr.
Epratuzumab
Erbitux
Ertapenem Injection (Invanz)
Erythropoieten
Essential Amino Acid Injection (Nephramine)
Estradiol Cypionate
Estradiol Valerate
Etanercept
Exenatide Injection (Byetta)
Evlotra
Fabrazyme (Adalsidase beta)
Famotidine Injection
FDG (Fludeoxyglucose F 18 Injection)
Feraheme (Ferumoxytol Injection)
Feridex I.V. (Ferumoxides Injectable Solution)
Fertinex
Ferumoxides Injectable Solution (Feridex I.V.)
Ferumoxytol Injection (Feraheme)
Flagyl Injection (Metronidazole Injection)
Fluarix
Fludara (Fludarabine Phosphate)
Fludeoxyglucose F 18 Injection (FDG)
Fluorescein Injection (Ak-Fluor)
Follistim AQ Cartridge (Follitropin Beta Injection)
Follitropin Alfa Injection (Gonal-f RFF)
Follitropin Beta Injection (Follistim AQ Cartridge)
Folotyn (Pralatrexate Solution for Intravenous Injection)
Fondaparinux
Forteo (Teriparatide (rDNA origin) Injection)
Fostamatinib
Fosaprepitant Dimeglumine Injection (Emend Injection)
Foscarnet Sodium Injection (Foscavir)
Foscavir (Foscarnet Sodium Injection)
Fosphenytoin Sodium Injection (Cerebyx)
Fospropofol Disodium Injection (Lusedra)
Fragmin
Fuzeon (enfuvirtide)
GA101
Gadobenate Dimeglumine Injection (Multihance)
Gadofosveset Trisodium Injection (Ablavar)
Gadoteridol Injection Solution (ProHance)
Gadoversetamide Injection (OptiMARK)
Gadoxetate Disodium Injection (Eovist)
Ganirelix (Ganirelix Acetate Injection)
Gardasil
GC1008
GDFD
Gemtuzumab Ozogamicin for Injection (Mylotarg)
Genotropin
Gentamicin Injection
GENZ-112638
Golimumab Injection (Simponi Injection)
Gonal-f RFF (Follitropin Alfa Injection)
Granisetron Hydrochloride (Kytril Injection)
Gentamicin Sulfate
Glatiramer Acetate
Glucagen
Glucagon
HAE1
Haldol (Haloperidol Injection)
Havrix
Hectorol Injection (Doxercalciferol Injection)
Hedgehog Pathway Inhibitor Heparin
Herceptin
hG-CSF
Humalog
Human Growth Hormone
Humatrope
HuMax
Humegon
Humira
Humulin
Ibandronate Sodium Injection (Boniva Injection)
Ibuprofen Lysine Injection (NeoProfen)
Ibutilide Fumarate Injection (Corvert)
Idamycin PFS (Idarubicin Hydrochloride Injection)
Idarubicin Hydrochloride Injection (Idamycin PFS)
Ilaris (Canakinumab Injection)
Imipenem and Cilastatin for Injection (Primaxin I.V.)
Imitrex
Incobotulinumtoxin A for Injection (Xeomin)
Increlex (Mecasermin [rDNA origin] Injection)
Indocin IV (Indomethacin Inj)
Indomethacin lnj (Indocin IV)
Infanrix
Innohep
Insulin
Insulin Aspart [rDNA origin] lnj (NovoLog)
Insulin Glargine [rDNA origin] Injection (Lantus)
Insulin Glulisine [rDNA origin] lnj (Apidra)
Interferon alfa-2b, Recombinant for Injection (Intron A)
Intron A (Interferon alfa-2b, Recombinant for Injection)
Invanz (Ertapenem Injection)
Invega Sustenna (Paliperidone Palmitate Extended-Release Injectable Suspension)
Invirase (saquinavir mesylate)
lobenguane I 123 Injection for Intravenous Use (AdreView)
Iopromide Injection (Ultravist)
Ioversol Injection (Optiray Injection)
Iplex (Mecasermin Rinfabate [rDNA origin] Injection)
Iprivask
Irinotecan Hydrochloride (Camptosar Injection)
Iron Sucrose Injection (Venofer)
Istodax (Romidepsin for Injection)
Itraconazole Injection (Sporanox Injection)
Jevtana (Cabazitaxel Injection)
Jonexa
Kalbitor (Ecallantide Injection)
KCL in D5NS (Potassium Chloride in 5% Dextrose and Sodium Chloride Injection)
KCL in D5W
KCL in NS
Kenalog 10 Injection (Triamcinolone Acetonide Injectable Suspension)
Kepivance (Palifermin)
Keppra Injection (Levetiracetam)
Keratinocyte
KFG
Kinase Inhibitor
Kineret (Anakinra)
Kinlytic (Urokinase Injection)
Kinrix
Klonopin (clonazepam)
Kytril Injection (Granisetron Hydrochloride)
lacosamide Tablet and Injection (Vimpat)
Lactated Ringer's
Lanoxin Injection (Digoxin Injection)
Lansoprazole for Injection (Prevacid I.V.)
Lantus
Leucovorin Calcium (Leucovorin Calcium Injection)
Lente (L)
Leptin
Levemir
Leukine Sargramostim
Leuprolide Acetate
Levothyroxine
Levetiracetam (Keppra Injection)
Lovenox
Levocarnitine Injection (Carnitor Injection)
Lexiscan (Regadenoson Injection)
Lioresal Intrathecal (Baclofen Injection)
Liraglutide [rDNA] Injection (Victoza)
Lovenox (Enoxaparin Sodium Injection)
Lucentis (Ranibizumab Injection)
Lumizyme
Lupron (Leuprolide Acetate Injection)
Lusedra (Fospropofol Disodium Injection)
Maci
Magnesium Sulfate (Magnesium Sulfate Injection)
Mannitol Injection (Mannitol IV)
Marcaine (Bupivacaine Hydrochloride and Epinephrine Injection)
Maxipime (Cefepime Hydrochloride for Injection)
MDP Multidose Kit of Technetium Injection (Technetium Tc99m Medronate Injection)
Mecasermin [rDNA origin] Injection (Increlex)
Mecasermin Rinfabate [rDNA origin] Injection (Iplex)
Melphalan Hcl Injection (Alkeran Injection)
Methotrexate
Menactra
Menopur (Menotropins Injection)
Menotropins for Injection (Repronex)
Methohexital Sodium for Injection (Brevital Sodium)
Methyldopate Hydrochloride Injection, Solution (Methyldopate Hcl)
Methylene Blue (Methylene Blue Injection)
Methylprednisolone Acetate Injectable Suspension (Depo Medrol)
MetMab
Metoclopramide Injection (Reglan Injection)
Metrodin (Urofollitropin for Injection)
Metronidazole Injection (Flagyl Injection)
Miacalcin
Midazolam (Midazolam Injection)
Mimpara (Cinacalet)
Minocin Injection (Minocycline Inj)
Minocycline lnj (Minocin Injection)
Mipomersen
Mitoxantrone for Injection Concentrate (Novantrone)
Morphine Injection (Duramorph)
Morphine Sulfate XR Liposome Injection (DepoDur)
Morrhuate Sodium (Morrhuate Sodium Injection)
Motesanib
Mozobil (Plerixafor Injection)
Multihance (Gadobenate Dimeglumine Injection)
Multiple Electrolytes and Dextrose Injection
Multiple Electrolytes Injection
Mylotarg (Gemtuzumab Ozogamicin for Injection)
Myozyme (Alglucosidase alfa)
Nafcillin Injection (Nafcillin Sodium)
Nafcillin Sodium (Nafcillin Injection)
Naltrexone XR Inj (Vivitrol)
Naprosyn (naproxen)
NeoProfen (Ibuprofen Lysine Injection)
Nandrol Decanoate Neostigmine Methylsulfate (Neostigmine Methylsulfate Injection)
NEO-GAA
NeoTect (Technetium Tc 99m Depreotide Injection)
Nephramine (Essential Amino Acid Injection)
Neulasta (pegfilgrastim)
Neupogen (Filgrastim)
Novolin
Novolog
NeoRecormon
Neutrexin (Trimetrexate Glucuronate Inj)
NPH (N)
Nexterone (Amiodarone HCl Injection)
Norditropin (Somatropin Injection)
Normal Saline (Sodium Chloride Injection)
Novantrone (Mitoxantrone for Injection Concentrate)
Novolin 70/30 Innolet (70% NPH, Human Insulin Isophane Suspension and 30% Regular, Human Insulin Injection)
NovoLog (Insulin Aspart [rDNA origin] Inj)
Nplate (romiplostim)
Nutropin (Somatropin (rDNA origin) for Inj)
Nutropin AQ
Nutropin Depot (Somatropin (rDNA origin) for Inj)
Octreotide Acetate Injection (Sandostatin LAR)
Ocrelizumab
Ofatumumab Injection (Arzerra)
Olanzapine Extended Release Injectable Suspension (Zyprexa Relprevv)
Omnitarg
Omnitrope (Somatropin [rDNA origin] Injection)
Ondansetron Hydrochloride Injection (Zofran Injection)
OptiMARK (Gadoversetamide Injection)
Optiray Injection (Ioversol Injection)
Orencia
Osmitrol Injection in Aviva (Mannitol Injection in Aviva Plastic Pharmaceutical package 210)
Osmitrol Injection in Viaflex (Mannitol Injection in Viaflex Plastic Pharmaceutical package 210)
Osteoprotegrin
Ovidrel (Choriogonadotropin Alfa Injection)
Oxacillin (Oxacillin for Injection)
Oxaliplatin Injection (Eloxatin)
Oxytocin Injection (Pitocin)
Paliperidone Palmitate Extended-Release Injectable Suspension (Invega Sustenna)
Pamidronate Disodium Injection (Pamidronate Disodium Injection)
Panitumumab Injection for Intravenous Use (Vectibix)
Papaverine Hydrochloride Injection (Papaverine Injection)
Papaverine Injection (Papaverine Hydrochloride Injection)
Parathyroid Hormone
Paricalcitol Injection Fliptop Vial (Zemplar Injection)
PARP Inhibitor
Pediarix
PEGIntron
Peginterferon
Pegfilgrastim
Penicillin G Benzathine and Penicillin G Procaine
Pentetate Calcium Trisodium Inj (Ca-DTPA)
Pentetate Zinc Trisodium Injection (Zn-DTPA)
Pepcid Injection (Famotidine Injection)
Pergonal
Pertuzumab
Phentolamine Mesylate (Phentolamine Mesylate for Injection)
Physostigmine Salicylate (Physostigmine Salicylate (injection))
Physostigmine Salicylate (injection) (Physostigmine Salicylate)
Piperacillin and Tazobactam Injection (Zosyn)
Pitocin (Oxytocin Injection)
Plasma-Lyte 148 (Multiple Electrolytes Inj)
Plasma-Lyte 56 and Dextrose (Multiple Electrolytes and Dextrose Injection in Viaflex Plastic Pharmaceutical package 210)
PlasmaLyte
Plerixafor Injection (Mozobil)
Polidocanol Injection (Asclera)
Potassium Chloride
Pralatrexate Solution for Intravenous Injection (Folotyn)
Pramlintide Acetate Injection (Symlin)
Premarin Injection (Conjugated Estrogens for Injection)
Prep kit for Technetium Tc99 Sestamibi for Injection (Cardiolite)
Prevacid I.V. (Lansoprazole for Injection)
Primaxin I.V. (Imipenem and Cilastatin for Injection)
Prochymal
Procrit
Progesterone
ProHance (Gadoteridol Injection Solution)
Prolia (Denosumab Injection)
Promethazine HCl Injection (Promethazine Hydrochloride Injection)
Propranolol Hydrochloride Injection (Propranolol Hydrochloride Injection)
Quinidine Gluconate Injection (Quinidine Injection)
Quinidine Injection (Quinidine Gluconate Injection)
R-Gene 10 (Arginine Hydrochloride Injection)
Ranibizumab Injection (Lucentis)
Ranitidine Hydrochloride Injection (Zantac Injection)
Raptiva
Reclast (Zoledronic Acid Injection)
Recombivarix HB
Regadenoson Injection (Lexiscan)
Reglan Injection (Metoclopramide Injection)
Remicade
Renagel
Renvela (Sevelamer Carbonate)
Repronex (Menotropins for Injection)
Retrovir IV (Zidovudine Injection)
rhApo2L/TRAIL
Ringer's and 5% Dextrose Injection (Ringers in Dextrose)
Ringer's Injection (Ringers Injection)
Rituxan
Rituximab
Rocephin (ceftriaxone)
Rocuronium Bromide Injection (Zemuron)
Roferon-A (interferon alfa-2a)
Romazicon (flumazenil)
Romidepsin for Injection (Istodax)
Saizen (Somatropin Injection)
Sandostatin LAR (Octreotide Acetate Injection)
Sclerostin Ab
Sensipar (cinacalcet)
Sensorcaine (Bupivacaine HCl Injections)
Septocaine (Articane HCl and Epinephrine Injection)
Serostim LQ (Somatropin (rDNA origin) Injection)
Simponi Injection (Golimumab Injection)
Sodium Acetate (Sodium Acetate Injection)
Sodium Bicarbonate (Sodium Bicarbonate 5% Injection)
Sodium Lactate (Sodium Lactate Injection in AVIVA)
Sodium Phenylacetate and Sodium Benzoate Injection (Ammonul)
Somatropin (rDNA origin) for Inj (Nutropin)

Sporanox Injection (Itraconazole Injection)
Stelara Injection (Ustekinumab)
Stemgen
Sufenta (Sufentanil Citrate Injection)
Sufentanil Citrate Injection (Sufenta)
Sumavel
Sumatriptan Injection (Alsuma)
Symlin
Symlin Pen
Systemic Hedgehog Antagonist
Synvisc-One (Hylan G-F 20 Single Intra-articular Injection)
Tarceva
Taxotere (Docetaxel for Injection)
Technetium Tc 99m
Telavancin for Injection (Vibativ)
Temsirolimus Injection (Torisel)
Tenormin I.V. Injection (Atenolol Inj)
Teriparatide (rDNA origin) Injection (Forteo)
Testosterone Cypionate
Testosterone Enanthate
Testosterone Propionate
Tev-Tropin (Somatropin, rDNA Origin, for Injection)
tgAAC94
Thallous Chloride
Theophylline
Thiotepa (Thiotepa Injection)
Thymoglobulin (Anti-Thymocyte Globulin (Rabbit)
Thyrogen (Thyrotropin Alfa for Injection)
Ticarcillin Disodium and Clavulanate Potassium Galaxy (Timentin Injection)
Tigan Injection (Trimethobenzamide Hydrochloride Injectable)
Timentin Injection (Ticarcillin Disodium and Clavulanate Potassium Galaxy)
TNKase
Tobramycin Injection (Tobramycin Injection)
Tocilizumab Injection (Actemra)
Torisel (Temsirolimus Injection)
Totect (Dexrazoxane for Injection, Intravenous Infusion Only)
Trastuzumab-DM1
Travasol (Amino Acids (Injection))
Treanda (Bendamustine Hydrochloride Injection)
Trelstar (Triptorelin Pamoate for Injectable Suspension)
Triamcinolone Acetonide
Triamcinolone Diacetate
Triamcinolone Hexacetonide Injectable Suspension (Aristospan Injection 20 mg)
Triesence (Triamcinolone Acetonide Injectable Suspension)
Trimethobenzamide Hydrochloride Injectable (Tigan Injection)
Trimetrexate Glucuronate Inj (Neutrexin)
Triptorelin Pamoate for Injectable Suspension (Trelstar)
Twinject
Trivaris (Triamcinolone Acetonide Injectable Suspension)
Trisenox (Arsenic Trioxide Injection)
Twinrix
Typhoid Vi
Ultravist (Iopromide Injection)
Urofollitropin for Injection (Metrodin)
Urokinase Injection (Kinlytic)
Ustekinumab (Stelara Injection)
Ultralente (U)
Valium (diazepam)
Valproate Sodium Injection (Depacon)
Valtropin (Somatropin Injection)
Vancomycin Hydrochloride (Vancomycin Hydrochloride Injection)
Vancomycin Hydrochloride Injection (Vancomycin Hydrochloride)
Vaprisol (Conivaptan Hcl Injection)
VAQTA
Vasovist (Gadofosveset Trisodium Injection for Intravenous Use)
Vectibix (Panitumumab Injection for Intravenous Use)
Venofer (Iron Sucrose Injection)
Verteporfin Inj (Visudyne)
Vibativ (Telavancin for Injection)
Victoza (Liraglutide [rDNA] Injection)
Vimpat (lacosamide Tablet and Injection)
Vinblastine Sulfate (Vinblastine Sulfate Injection)
Vincasar PFS (Vincristine Sulfate Injection)
Victoza
Vincristine Sulfate (Vincristine Sulfate Injection)
Visudyne (Verteporfin Inj)
Vitamin B-12
Vivitrol (Naltrexone XR Inj)
Voluven (Hydroxyethyl Starch in Sodium Chloride Injection)
Xeloda
Xenical (orlistat)
Xeomin (Incobotulinumtoxin A for Injection)
Xolair
Zantac Injection (Ranitidine Hydrochloride Injection)
Zemplar Injection (Paricalcitol Injection Fliptop Vial)
Zemuron (Rocuronium Bromide Injection)
Zenapax (daclizumab)
Zevalin
Zidovudine Injection (Retrovir IV)
Zithromax Injection (Azithromycin)
Zn-DTPA (Pentetate Zinc Trisodium Injection)
Zofran Injection (Ondansetron Hydrochloride Injection)
Zingo
Zoledronic Acid for Inj (Zometa)
Zoledronic Acid Injection (Reclast)
Zometa (Zoledronic Acid for Inj)
Zosyn (Piperacillin and Tazobactam Injection)
Zyprexa Relprevv (Olanzapine Extended Release Injectable Suspension)
Liquid Drugs (Non-Injectable)
Abilify
AccuNeb (Albuterol Sulfate Inhalation Solution)
Actidose Aqua (Activated Charcoal Suspension)
Activated Charcoal Suspension (Actidose Aqua)
Advair
Agenerase Oral Solution (Amprenavir Oral Solution)
Akten (Lidocaine Hydrochloride Ophthalmic Gel)
Alamast (Pemirolast Potassium Ophthalmic Solution)
Albumin (Human) 5% Solution (Buminate 5%)
Albuterol Sulfate Inhalation Solution
Alinia
Alocril
Alphagan
Alrex
Alvesco
Amprenavir Oral Solution
Analpram-HC
Arformoterol Tartrate Inhalation Solution (Brovana)
Aristospan Injection 20 mg (Triamcinolone Hexacetonide Injectable Suspension)
Asacol
Asmanex
Astepro Astepro (Azelastine Hydrochloride Nasal Spray)
Atrovent Nasal Spray (Ipratropium Bromide Nasal Spray)
Atrovent Nasal Spray 0.06
Augmentin ES-600
Azasite (Azithromycin Ophthalmic Solution)
Azelaic Acid (Finacea Gel)
Azelastine Hydrochloride Nasal Spray (Astepro)
Azelex (Azelaic Acid Cream)
Azopt (Brinzolamide Ophthalmic Suspension)
Bacteriostatic Saline
Balanced Salt
Bepotastine
Bactroban Nasal
Bactroban
Beclovent
Benzac W
Betimol
Betoptic S
Bepreve
Bimatoprost Ophthalmic Solution
Bleph 10 (Sulfacetamide Sodium Ophthalmic Solution 10%)
Brinzolamide Ophthalmic Suspension (Azopt)
Bromfenac Ophthalmic Solution (Xibrom)
Bromhist
Brovana (Arformoterol Tartrate Inhalation Solution)
Budesonide Inhalation Suspension (Pulmicort Respules)
Cambia (Diclofenac Potassium for Oral Solution)
Capex
Carac
Carboxine-PSE
Carnitor
Cayston (Aztreonam for Inhalation Solution)
Cellcept
Centany
Cerumenex
Ciloxan Ophthalmic Solution (Ciprofloxacin HCL Ophthalmic Solution)
Ciprodex
Ciprofloxacin HCL Ophthalmic Solution (Ciloxan Ophthalmic Solution)
Clemastine Fumarate Syrup (Clemastine Fumarate Syrup)
CoLyte (PEG Electrolytes Solution)
Combiven
Comtan
Condylox
Cordran
Cortisporin Ophthalmic Suspension
Cortisporin Otic Suspension
Cromolyn Sodium Inhalation Solution (Intal Nebulizer Solution)
Cromolyn Sodium Ophthalmic Solution (Opticrom)
Crystalline Amino Acid Solution with Electrolytes (Aminosyn Electrolytes)
Cutivate
Cuvposa (Glycopyrrolate Oral Solution)
Cyanocobalamin (CaloMist Nasal Spray)
Cyclosporine Oral Solution (Gengraf Oral Solution)
Cyclogyl
Cysview (Hexaminolevulinate Hydrochloride Intravesical Solution)
DermOtic Oil (Fluocinolone Acetonide Oil Ear Drops)
Desmopressin Acetate Nasal Spray
DDAVP
Derma-Smoothe/FS
Dexamethasone Intensol
Dianeal Low Calcium
Dianeal PD
Diclofenac Potassium for Oral Solution (Cambia)
Didanosine Pediatric Powder for Oral Solution (Videx)
Differin
Dilantin 125 (Phenytoin Oral Suspension)
Ditropan
Dorzolamide Hydrochloride Ophthalmic Solution (Trusopt)
Dorzolamide Hydrochloride-Timolol Maleate Ophthalmic Solution (Cosopt)
Dovonex Scalp (Calcipotriene Solution)
Doxycycline Calcium Oral Suspension (Vibramycin Oral)
Efudex
Elaprase (Idursulfase Solution)
Elestat (Epinastine HCl Ophthalmic Solution)
Elocon
Epinastine HCl Ophthalmic Solution (Elestat)
Epivir HBV
Epogen (Epoetin alfa)
Erythromycin Topical Solution 1.5% (Staticin)
Ethiodol (Ethiodized Oil)
Ethosuximide Oral Solution (Zarontin Oral Solution)
Eurax
Extraneal (Icodextrin Peritoneal Dialysis Solution)
Felbatol
Feridex I.V. (Ferumoxides Injectable Solution)
Flovent
Floxin Otic (Ofloxacin Otic Solution)
Flo-Pred (Prednisolone Acetate Oral Suspension)
Fluoroplex
Flunisolide Nasal Solution (Flunisolide Nasal Spray 0.025%)
Fluorometholone Ophthalmic Suspension (FML)
Flurbiprofen Sodium Ophthalmic Solution (Ocufen)
FML
Foradil
Formoterol Fumarate Inhalation Solution (Perforomist)
Fosamax
Furadantin (Nitrofurantoin Oral Suspension)
Furoxone
Gammagard Liquid (Immune Globulin Intravenous (Human) 10%)
Gantrisin (Acetyl Sulfisoxazole Pediatric Suspension)
Gatifloxacin Ophthalmic Solution (Zymar)
Gengraf Oral Solution (Cyclosporine Oral Solution)
Glycopyrrolate Oral Solution (Cuvposa)
Halcinonide Topical Solution (Halog Solution)
Halog Solution (Halcinonide Topical Solution)
HEP-LOCK U/P (Preservative-Free Heparin Lock Flush Solution)
Heparin Lock Flush Solution (Hepflush 10
Hexaminolevulinate Hydrochloride Intravesical Solution (Cysview)
Hydrocodone Bitartrate and Acetaminophen Oral Solution (Lortab Elixir)
Hydroquinone 3% Topical Solution (Melquin-3 Topical Solution)
IAP Antagonist
Isopto
Ipratropium Bromide Nasal Spray (Atrovent Nasal Spray)
Itraconazole Oral Solution (Sporanox Oral Solution)
Ketorolac Tromethamine Ophthalmic Solution (Acular LS)
Kaletra
Lanoxin
Lexiva
Leuprolide Acetate for Depot Suspension (Lupron Depot 11.25 mg)

Levobetaxolol Hydrochloride Ophthalmic Suspension (Betaxon)
Levocarnitine Tablets, Oral Solution, Sugar-Free (Carnitor)
Levofloxacin Ophthalmic Solution 0.5% (Quixin)
Lidocaine HCl Sterile Solution (Xylocaine MPF Sterile Solution)
Lok Pak (Heparin Lock Flush Solution)
Lorazepam Intensol
Lortab Elixir (Hydrocodone Bitartrate and Acetaminophen Oral Solution)
Lotemax (Loteprednol Etabonate Ophthalmic Suspension)
Loteprednol Etabonate Ophthalmic Suspension (Alrex)
Low Calcium Peritoneal Dialysis Solutions (Dianeal Low Calcium)
Lumigan (Bimatoprost Ophthalmic Solution 0.03% for Glaucoma)
Lupron Depot 11.25 mg (Leuprolide Acetate for Depot Suspension)
Megestrol Acetate Oral Suspension (Megestrol Acetate Oral Suspension)
MEK Inhibitor
Mepron
Mesnex
Mestinon
Mesalamine Rectal Suspension Enema (Rowasa)
Melquin-3 Topical Solution (Hydroquinone 3% Topical Solution)
MetMab
Methyldopate Hcl (Methyldopate Hydrochloride Injection, Solution)
Methylin Oral Solution (Methylphenidate HCl Oral Solution 5 mg/5 mL and 10 mg/5 mL)
Methylprednisolone Acetate Injectable Suspension (Depo Medrol)
Methylphenidate HCl Oral Solution 5 mg/5 mL and 10 mg/5 mL (Methylin Oral Solution)
Methylprednisolone sodium succinate (Solu Medrol)
Metipranolol Ophthalmic Solution (Optipranolol)
Migranal
Miochol-E (Acetylcholine Chloride Intraocular Solution)
Micro-K for Liquid Suspension (Potassium Chloride Extended Release Formulation for Liquid Suspension)
Minocin (Minocycline Hydrochloride Oral Suspension)
Nasacort
Neomycin and Polymyxin B Sulfates and Hydrocortisone
Nepafenac Ophthalmic Suspension (Nevanac)
Nevanac (Nepafenac Ophthalmic Suspension)
Nitrofurantoin Oral Suspension (Furadantin)
Noxafil (Posaconazole Oral Suspension)
Nystatin (oral) (Nystatin Oral Suspension)
Nystatin Oral Suspension (Nystatin (oral))
Ocufen (Flurbiprofen Sodium Ophthalmic Solution)
Ofloxacin Ophthalmic Solution (Ofloxacin Ophthalmic Solution)
Ofloxacin Otic Solution (Floxin Otic)
Olopatadine Hydrochloride Ophthalmic Solution (Pataday)
Opticrom (Cromolyn Sodium Ophthalmic Solution)
Optipranolol (Metipranolol Ophthalmic Solution)
Patanol
Pediapred
PerioGard
Phenytoin Oral Suspension (Dilantin 125)
Phisohex
Posaconazole Oral Suspension (Noxafil)
Potassium Chloride Extended Release Formulation for Liquid Suspension (Micro-K for Liquid Suspension)
Pataday (Olopatadine Hydrochloride Ophthalmic Solution)
Patanase Nasal Spray (Olopatadine Hydrochloride Nasal Spray)
PEG Electrolytes Solution (CoLyte)
Pemirolast Potassium Ophthalmic Solution (Alamast)
Penlac (Ciclopirox Topical Solution)
PENNSAID (Diclofenac Sodium Topical Solution)
Perforomist (Formoterol Fumarate Inhalation Solution)
Peritoneal Dialysis Solution
Phenylephrine Hydrochloride Ophthalmic Solution (Neo-Synephrine)
Phospholine Iodide (Echothiophate Iodide for Ophthalmic Solution)
Podofilox (Podofilox Topical Solution)
Pred Forte (Prednisolone Acetate Ophthalmic Suspension)
Pralatrexate Solution for Intravenous Injection (Folotyn)
Pred Mild
Prednisone Intensol
Prednisolone Acetate Ophthalmic Suspension (Pred Forte)
Prevacid
PrismaSol Solution (Sterile Hemofiltration Hemodiafiltration Solution)
ProAir
Proglycem
ProHance (Gadoteridol Injection Solution)
Proparacaine Hydrochloride Ophthalmic Solution (Alcaine)
Propine
Pulmicort
Pulmozyme
Quixin (Levofloxacin Ophthalmic Solution 0.5%)
QVAR
Rapamune
Rebetol
Relacon-HC
Rotarix (Rotavirus Vaccine, Live, Oral Suspension)
Rotavirus Vaccine, Live, Oral Suspension (Rotarix)
Rowasa (Mesalamine Rectal Suspension Enema)
Sabril (Vigabatrin Oral Solution)
Sacrosidase Oral Solution (Sucraid)
Sandimmune
Sepra
Serevent Diskus
Solu Cortef (Hydrocortisone Sodium Succinate)
Solu Medrol (Methylprednisolone sodium succinate)
Spiriva
Sporanox Oral Solution (Itraconazole Oral Solution)
Staticin (Erythromycin Topical Solution 1.5%)
Stalevo
Starlix
Sterile Hemofiltration Hemodiafiltration Solution (PrismaSol Solution)
Stimate
Sucralfate (Carafate Suspension)
Sulfacetamide Sodium Ophthalmic Solution 10% (Bleph 10
Synarel Nasal Solution (Nafarelin Acetate Nasal Solution for Endometriosis)
Taclonex Scalp (Calcipotriene and Betamethasone Dipropionate Topical Suspension)
Tamiflu
Tobi
TobraDex
Tobradex ST (Tobramycin/Dexamethasone Ophthalmic Suspension 0.3%/0.05%)
Tobramycin/Dexamethasone Ophthalmic Suspension 0.3%/0.05% (Tobradex ST)
Timolol
Timoptic
Travatan Z Treprostinil Inhalation Solution (Tyvaso)
Trusopt (Dorzolamide Hydrochloride Ophthalmic Solution)
Tyvaso (Treprostinil Inhalation Solution)
Ventolin
Vfend
Vibramycin Oral (Doxycycline Calcium Oral Suspension)
Videx (Didanosine Pediatric Powder for Oral Solution)
Vigabatrin Oral Solution (Sabril)
Viokase
Viracept
Viramune
Vitamin K1 (Fluid Colloidal Solution of Vitamin K1)
Voltaren Ophthalmic (Diclofenac Sodium Ophthalmic Solution)
Zarontin Oral Solution (Ethosuximide Oral Solution)
Ziagen
Zyvox
Zymar (Gatifloxacin Ophthalmic Solution)
Zymaxid (Gatifloxacin Ophthalmic Solution)
Drug Classes
5-alpha-reductase inhibitors
5-aminosalicylates
5HT3 receptor antagonists
adamantane antivirals
adrenal cortical steroids
adrenal corticosteroid inhibitors
adrenergic bronchodilators
agents for hypertensive emergencies
agents for pulmonary hypertension
aldosterone receptor antagonists
alkylating agents
alpha-adrenoreceptor antagonists
alpha-glucosidase inhibitors
alternative medicines
amebicides
aminoglycosides
aminopenicillins
aminosalicylates
amylin analogs
Analgesic Combinations
Analgesics
androgens and anabolic steroids
angiotensin converting enzyme inhibitors
angiotensin II inhibitors
anorectal preparations
anorexiants
antacids
anthelmintics
anti-angiogenic ophthalmic agents
anti-CTLA-4 monoclonal antibodies
anti-infectives
antiadrenergic agents, centrally acting
antiadrenergic agents, peripherally acting
antiandrogens
antianginal agents
antiarrhythmic agents
antiasthmatic combinations
antibiotics/antineoplastics
anticholinergic antiemetics
anticholinergic antiparkinson agents
anticholinergic bronchodilators
anticholinergic chronotropic agents
anticholinergics/antispasmodics
anticoagulants
anticonvulsants
antidepressants
antidiabetic agents
antidiabetic combinations
antidiarrheals
antidiuretic hormones
antidotes
antiemetic/antivertigo agents
antifungals
antigonadotropic agents
antigout agents
antihistamines
antihyperlipidemic agents
antihyperlipidemic combinations
antihypertensive combinations
antihyperuricemic agents
antimalarial agents
antimalarial combinations
antimalarial quinolines
antimetabolites
antimigraine agents
antineoplastic detoxifying agents
antineoplastic interferons
antineoplastic monoclonal antibodies
antineoplastics
antiparkinson agents
antiplatelet agents
antipseudomonal penicillins
antipsoriatics
antipsychotics
antirheumatics
antiseptic and germicides
antithyroid agents
antitoxins and antivenins
antituberculosis agents
antituberculosis combinations
antitussives
antiviral agents
antiviral combinations
antiviral interferons
anxiolytics, sedatives, and hypnotics
aromatase inhibitors
atypical antipsychotics
azole antifungals
bacterial vaccines
barbiturate anticonvulsants
barbiturates
BCR-ABL tyrosine kinase inhibitors
benzodiazepine anticonvulsants
benzodiazepines
beta-adrenergic blocking agents
beta-lactamase inhibitors
bile acid sequestrants
biologicals
bisphosphonates
bone resorption inhibitors
bronchodilator combinations
bronchodilators
calcitonin
calcium channel blocking agents
carbamate anticonvulsants
carbapenems
carbonic anhydrase inhibitor anticonvulsants
carbonic anhydrase inhibitors
cardiac stressing agents
cardioselective beta blockers
cardiovascular agents
catecholamines
CD20 monoclonal antibodies
CD33 monoclonal antibodies CD52 monoclonal antibodies
central nervous system agents
cephalosporins
cerumenolytics
chelating agents
chemokine receptor antagonist
chloride channel activators
cholesterol absorption inhibitors
cholinergic agonists
cholinergic muscle stimulants
cholinesterase inhibitors
CNS stimulants
coagulation modifiers
colony stimulating factors
contraceptives
corticotropin
coumarins and indandiones
cox-2 inhibitors
decongestants
dermatological agents
diagnostic radiopharmaceuticals
dibenzazepine anticonvulsants
digestive enzymes
dipeptidyl peptidase 4 inhibitors
diuretics
dopaminergic antiparkinsonism agents
drugs used in alcohol dependence
echinocandins
EGFR inhibitors
estrogen receptor antagonists
estrogens
expectorants
factor Xa inhibitors
fatty acid derivative anticonvulsants
fibric acid derivatives
first generation cephalosporins
fourth generation cephalosporins
functional bowel disorder agents
gallstone solubilizing agents
gamma-aminobutyric acid analogs
gamma-aminobutyric acid reuptake inhibitors
gamma-aminobutyric acid transaminase inhibitors
gastrointestinal agents
general anesthetics
genitourinary tract agents
GI stimulants
glucocorticoids
glucose elevating agents
glycopeptide antibiotics
glycoprotein platelet inhibitors
glycylcyclines
gonadotropin releasing hormones
gonadotropin-releasing hormone antagonists
gonadotropins
group I antiarrhythmics
group II antiarrhythmics
group III antiarrhythmics
group IV antiarrhythmics
group V antiarrhythmics
growth hormone receptor blockers
growth hormones
*H. pylori* eradication agents
H2 antagonists
hematopoietic stem cell mobilizer
heparin antagonists
heparins
HER2 inhibitors
herbal products
histone deacetylase inhibitors
hormone replacement therapy
hormones
hormones/antineoplastics
hydantoin anticonvulsants
illicit (street) drugs
immune globulins
immunologic agents
immunosuppressive agents
impotence agents
in vivo diagnostic biologicals
incretin mimetics
inhaled anti-infectives
inhaled corticosteroids
inotropic agents
insulin
insulin-like growth factor
integrase strand transfer inhibitor
interferons
intravenous nutritional products
iodinated contrast media
ionic iodinated contrast media
iron products
ketolides
laxatives
leprostatics
leukotriene modifiers
lincomycin derivatives
lipoglycopeptides
local injectable anesthetics
loop diuretics
lung surfactants
lymphatic staining agents
lysosomal enzymes
macrolide derivatives
macrolides
magnetic resonance imaging contrast media
mast cell stabilizers
medical gas
meglitinides
metabolic agents
methylxanthines
mineralocorticoids
minerals and electrolytes
miscellaneous agents
miscellaneous analgesics
miscellaneous antibiotics
miscellaneous anticonvulsants
miscellaneous antidepressants
miscellaneous antidiabetic agents
miscellaneous antiemetics
miscellaneous antifungals
miscellaneous antihyperlipidemic agents
miscellaneous antimalarials
miscellaneous antineoplastics
miscellaneous antiparkinson agents
miscellaneous antipsychotic agents
miscellaneous antituberculosis agents
miscellaneous antivirals
miscellaneous anxiolytics, sedatives and hypnotics
miscellaneous biologicals
miscellaneous bone resorption inhibitors
miscellaneous cardiovascular agents
miscellaneous central nervous system agents
miscellaneous coagulation modifiers
miscellaneous diuretics miscellaneous genitourinary tract agents
miscellaneous GI agents
miscellaneous hormones
miscellaneous metabolic agents
miscellaneous ophthalmic agents
miscellaneous otic agents
miscellaneous respiratory agents
miscellaneous sex hormones
miscellaneous topical agents
miscellaneous uncategorized agents
miscellaneous vaginal agents
mitotic inhibitors
monoamine oxidase inhibitors
monoclonal antibodies
mouth and throat products
mTOR inhibitors
mTOR kinase inhibitors
mucolytics
multikinase inhibitors
muscle relaxants
mydriatics
narcotic analgesic combinations
narcotic analgesics
nasal anti-infectives
nasal antihistamines and decongestants
nasal lubricants and irrigations
nasal preparations
nasal steroids
natural penicillins
neuraminidase inhibitors
neuromuscular blocking agents
next generation cephalosporins
nicotinic acid derivatives
nitrates
NNRTIs
non-cardioselective beta blockers
non-iodinated contrast media
non-ionic iodinated contrast media
non-sulfonylureas
nonsteroidal anti-inflammatory agents
norepinephrine reuptake inhibitors
norepinephrine-dopamine reuptake inhibitors
nucleoside reverse transcriptase inhibitors (NRTIs)
nutraceutical products
nutritional products
ophthalmic anesthetics
ophthalmic anti-infectives
ophthalmic anti-inflammatory agents
ophthalmic antihistamines and decongestants
ophthalmic diagnostic agents
ophthalmic glaucoma agents
ophthalmic lubricants and irrigations
ophthalmic preparations
ophthalmic steroids
ophthalmic steroids with anti-infectives
ophthalmic surgical agents
oral nutritional supplements
otic anesthetics
otic anti-infectives
otic preparations
otic steroids
otic steroids with anti-infectives
oxazolidinedione anticonvulsants
parathyroid hormone and analogs
penicillinase resistant penicillins
penicillins
peripheral opioid receptor antagonists
peripheral vasodilators
peripherally acting antiobesity agents
phenothiazine antiemetics
phenothiazine antipsychotics
phenylpiperazine antidepressants
plasma expanders
platelet aggregation inhibitors
platelet-stimulating agents
polyenes
potassium-sparing diuretics
probiotics
progesterone receptor modulators
progestins
prolactin inhibitors
prostaglandin D2 antagonists
protease inhibitors
proton pump inhibitors
psoralens
psychotherapeutic agents
psychotherapeutic combinations
purine nucleosides
pyrrolidine anticonvulsants
quinolones
radiocontrast agents
radiologic adjuncts
radiologic agents
radiologic conjugating agents
radiopharmaceuticals
RANK ligand inhibitors
recombinant human erythropoietins
renin inhibitors
respiratory agents
respiratory inhalant products
rifamycin derivatives
salicylates
sclerosing agents
second generation cephalosporins
selective estrogen receptor modulators
selective serotonin reuptake inhibitors
serotonin-norepinephrine reuptake inhibitors
serotoninergic neuroenteric modulators
sex hormone combinations
sex hormones
skeletal muscle relaxant combinations
skeletal muscle relaxants
smoking cessation agents
somatostatin and somatostatin analogs
spermicides
statins
sterile irrigating solutions
*streptomyces* derivatives
succinimide anticonvulsants
sulfonamides
sulfonylureas
synthetic ovulation stimulants
tetracyclic antidepressants
tetracyclines
therapeutic radiopharmaceuticals
thiazide diuretics
thiazolidinediones
thioxanthenes
third generation cephalosporins
thrombin inhibitors
thrombolytics
thyroid drugs
tocolytic agents
topical acne agents topical agents
topical anesthetics
topical anti-infectives
topical antibiotics
topical antifungals
topical antihistamines
topical antipsoriatics
topical antivirals
topical astringents
topical debriding agents
topical depigmenting agents
topical emollients
topical keratolytics
topical steroids
topical steroids with anti-infectives
toxoids
triazine anticonvulsants
tricyclic antidepressants
trifunctional monoclonal antibodies
tumor necrosis factor (TNF) inhibitors
tyrosine kinase inhibitors
ultrasound contrast media
upper respiratory combinations
urea anticonvulsants
urinary anti-infectives
urinary antispasmodics
urinary pH modifiers
uterotonic agents
vaccine
vaccine combinations
vaginal anti-infectives
vaginal preparations
vasodilators
vasopressin antagonists
vasopressors
VEGF/VEGFR inhibitors
viral vaccines
viscosupplementation agents
vitamin and mineral combinations
vitamins
Diagnostic Tests
17-Hydroxyprogesterone
ACE (Angiotensin I converting enzyme)
Acetaminophen
Acid phosphatase
ACTH
Activated clotting time
Activated protein C resistance
Adrenocorticotropic hormone (ACTH)
Alanine aminotransferase (ALT)
Albumin
Aldolase
Aldosterone
Alkaline phosphatase
Alkaline phosphatase (ALP)
Alpha1-antitrypsin
Alpha-fetoprotein
Alpha-fetoprotien
Ammonia levels
Amylase
ANA (antinuclear antbodies)
ANA (antinuclear antibodies)
Angiotensin-converting enzyme (ACE)
Anion gap
Anticardiolipin antibody
Anticardiolipin antivbodies (ACA)
Anti-centromere antibody
Antidiuretic hormone
Anti-DNA
Anti-Dnase-B
Anti-Gliadin antibody
Anti-glomerular basement membrane antibody
Anti-HBc (Hepatitis B core antibodies)
Anti-HBs (Hepatitis B surface antibody)
Antiphospholipid antibody
Anti-RNA polymerase
Anti-Smith (Sm) antibodies
Anti-Smooth Muscle antibody
Antistreptolysin O (ASO)
Antithrombin III
Anti-Xa activity
Anti-Xa assay
Apolipoproteins
Arsenic
Aspartate aminotransferase (AST)
B12
Basophil
Beta-2-Microglobulin
Beta-hydroxybutyrate
B-HCG
Bilirubin
Bilirubin, direct
Bilirubin, indirect
Bilirubin, total
Bleeding time
Blood gases (arterial)
Blood urea nitrogen (BUN)
BUN
BUN (blood urea nitrogen)
CA 125
CA 15-3
CA 19-9
Calcitonin
Calcium
Calcium (ionized)
Carbon monoxide (CO)
Carcinoembryonic antigen (CEA)
CBC
CEA
CEA (carcinoembryonic antigen)
Ceruloplasmin
CH50Chloride
Cholesterol
Cholesterol, HDL
Clot lysis time
Clot retraction time
CMP
CO2
Cold agglutinins
Complement C3
Copper
Corticotrophin releasing hormone (CRH) stimulation test
Cortisol
Cortrosyn stimulation test
C-peptide
CPK (Total)
CPK-MB
C-reactive protein
Creatinine
Creatinine kinase (CK)
Cryoglobulins
DAT (Direct antiglobulin test)
D-Dimer
Dexamethasone suppression test DHEA-S
Dilute Russell viper venom
Elliptocytes
Eosinophil
Erythrocyte sedimentation rate (ESR)
Estradiol
Estriol
Ethanol
Ethylene glycol
Euglobulin lysis
Factor V Leiden
Factor VIII inhibitor
Factor VIII level
Ferritin
Fibrin split products
Fibrinogen
Folate
Folate (serum
Fractional excretion of sodium (FENA)
FSH (follicle stimulating factor)
FTA-ABS
Gamma glutamyl transferase (GGT)
Gastrin
GGTP (Gamma glutamyl transferase)
Glucose
Growth hormone
Haptoglobin
HBeAg (Hepatitis Be antigen)
HBs-Ag (Hepatitis B surface antigen)
*Helicobacter pylori*
Hematocrit
Hematocrit (HCT)
Hemoglobin
Hemoglobin A1C
Hemoglobin electrophoresis
Hepatitis A antibodies
Hepatitis C antibodies
IAT (Indirect antiglobulin test)
Immunofixation (IFE)
Iron
Lactate dehydrogenase (LDH)
Lactic acid (lactate)
LDH
LH (Leutinizing hormone
Lipase
Lupus anticoagulant
Lymphocyte
Magnesium
MCH (mean corpuscular hemoglobin
MCHC (mean corpuscular hemoglobin concentration)
MCV (mean corpuscular volume)
Methylmalonate
Monocyte
MPV (mean platelet volume)
Myoglobin
Neutrophil
Parathyroid hormone (PTH)
Phosphorus
Platelets (plt)
Potassium
Prealbumin
Prolactin
Prostate specific antigen (PSA)
Protein C
Protein S
PSA (prostate specific antigen)
PT (Prothrombin time)
PTT (Partial thromboplastin time)
RDW (red cell distribution width)
Renin
Rennin
Reticulocyte count
reticulocytes
Rheumatoid factor (RF)
Sed Rate
Serum glutamic-pyruvic transaminase (SGPT
Serum protein electrophoresis (SPEP)
Sodium
T3-resin uptake (T3RU)
T4, Free
Thrombin time
Thyroid stimulating hormone (TSH)
Thyroxine (T4
Total iron binding capacity (TIBC)
Total protein
Transferrin
Transferrin saturation
Triglyceride (TG)
Troponin
Uric acid
Vitamin B12
White blood cells (WBC)
Widal test As several examples, the fluid material 40 can be an inhalation anesthetic, a drug, or a diagnostic test material. Any of these fluid materials 40 can be an injectable material, a volatile material capable of being inhaled, or otherwise capable of being introduced into a subject.

Other Uses of the Passivation Layer or pH Protective Coating

A vessel with a passivation layer or pH protective coating as described herein can also be evacuated and stored in an evacuated state. For example, the passivation layer or pH protective coating allows better maintenance of the vacuum in comparison to a corresponding vessel without a passivation layer or pH protective coating. In one aspect of this embodiment, the vessel with a passivation layer or pH protective coating can be a blood collection tube. The tube can also contain an agent for preventing blood clotting or platelet activation, for example EDTA or heparin.

Even another embodiment can be a medical or diagnostic kit including a vessel having a passivation layer or pH protective coating as defined in any embodiment herein on a substrate as defined in any embodiment herein. Optionally, the kit additionally includes a medicament or diagnostic agent as defined in any embodiment herein which is contained in the vessel with a passivation layer or pH protective coating in contact with the coating or layer; and/or a hypodermic needle, double-ended needle, or other delivery conduit; and/or an instruction sheet.

Use of the passivation layer or pH protective coating according to any described embodiment is contemplated for preventing or reducing precipitation and/or clotting or platelet activation of a compound or a component of the composition in contact with the coating or layer.

The use of a coated substrate according to any described embodiment is contemplated for storing insulin. As one option, precipitation of the insulin can be prevented or reduced by providing vessel to contain the insulin having a contact surface including a passivation layer or pH protective coating.

As another option, the compound or a component of the composition can be blood or a blood fraction, and blood clotting or platelet activation can be prevented or reduced by storing the blood in the blood collection tube in contact with a passivation layer or pH protective coating. Optionally, the blood collection tube can contain an agent for preventing blood clotting or platelet activation, for example ethylenediamineteetraacetic acid (EDTA), a sodium salt thereof, or heparin. The blood collection tube can include a passivation layer or pH protective coating for preventing the agent from attacking an $SiO_x$ barrier coating or layer in the vessel. The use of a coated substrate according to any described embodiment is contemplated for storing blood. Optionally, the stored blood can be viable for return to the vascular system of a patient.

Use of a coating or layer according to any described embodiment can be contemplated as (i) a lubricity coating having a lower frictional resistance than the uncoated surface; and/or (ii) a passivation layer or pH protective coating preventing dissolution of the barrier coating or layer in contact with a fluid, and/or (iii) a hydrophobic layer that can be more hydrophobic than the uncoated surface.

Measurement of Coating Thickness

Figure 11:
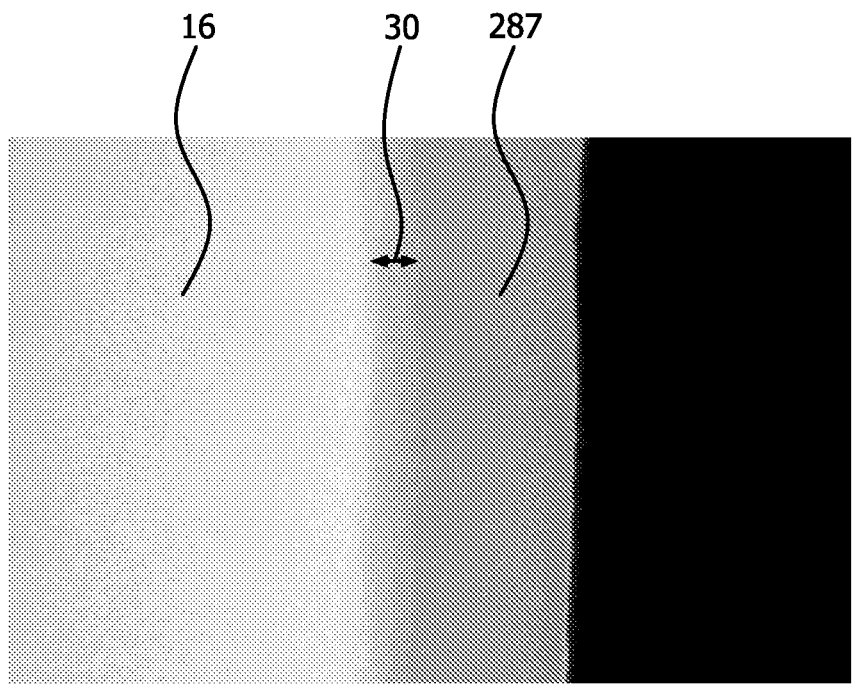
FIG. 11 shows a TEM image of a passivation layer or pH protective coating according to the invention coated on an $SiO_x$ barrier coating or layer, which in turn is coated on a COC substrate.
Figure 12:
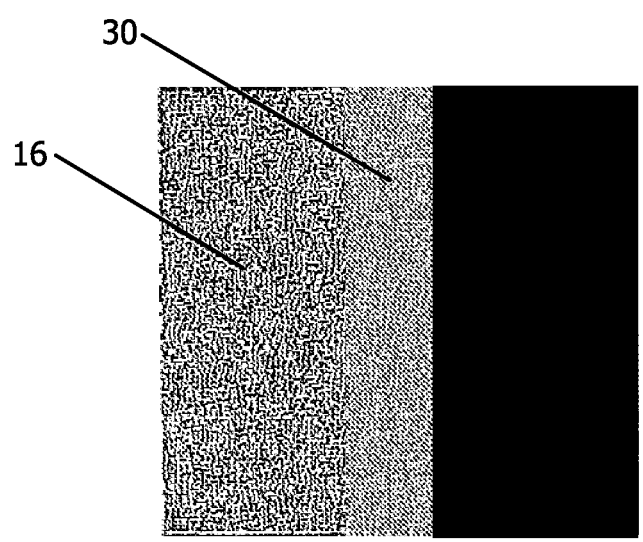
FIG. 12 shows a TEM image of an $SiO_2$ barrier coating or layer which is coated on a COC substrate.
Figure 13:
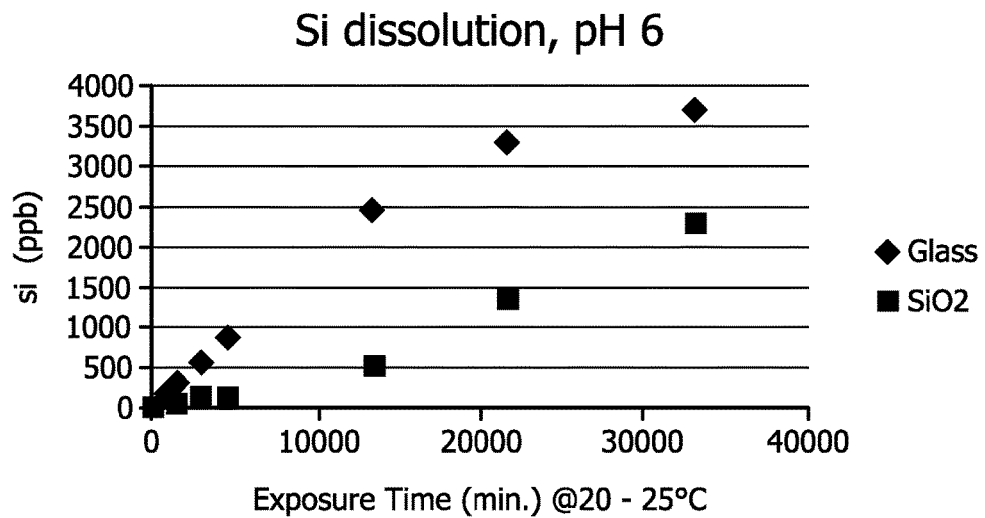
FIG. 13 is a plot of silicon dissolution versus exposure time at pH 6 for a glass container versus a plastic container having an $SiO_x$ barrier coating or layer coated in the inside wall.

The thickness of a PECVD coating or layer such as the passivation layer or pH protective coating, the barrier coating or layer, the lubricity coating or layer, and/or a composite of any two or more of these layers can be measured, for example, by transmission electron microscopy (TEM). An exemplary TEM image for a lubricity and/or passivation layer or pH protective coating on an $SiO_x$ barrier coating or layer is shown in FIG. 11. An exemplary TEM image for an $SiO_x$ barrier coating or layer on a substrate is shown in FIG. 12.

The TEM can be carried out, for example, as follows. Samples can be prepared for Focused Ion Beam (FIB) cross-sectioning in two ways. Either the samples can be first coated with a thin layer of carbon (50-100 nm thick) and then coated with a sputtered coating or layer of platinum (50-100 nm thick) using a K575X Emitech passivation layer or pH protective coating system, or the samples can be coated directly with the protective sputtered Pt layer. The coated samples can be placed in an FEI FIB200 FIB system. An additional coating or layer of platinum can be FIB-deposited by injection of an organometallic gas while rastering the 30 kV gallium ion beam over the area of interest. The area of interest for each sample can be chosen to be a location half way down the length of the syringe barrel. Thin cross sections measuring approximately 15 μm ("micrometers") long, 2 μm wide and 15 μm deep can be extracted from the die surface using an in-situ FIB lift-out technique. The cross sections can be attached to a 200 mesh copper TEM grid using FIB-deposited platinum. One or two windows in each section, measuring about 8 μm wide, can be thinned to electron transparency using the gallium ion beam of the FEI FIB.

Cross-sectional image analysis of the prepared samples can be performed utilizing either a Transmission Electron Microscope (TEM), or a Scanning Transmission Electron Microscope (STEM), or both. All imaging data can be recorded digitally. For STEM imaging, the grid with the thinned foils can be transferred to a Hitachi HD2300 dedicated STEM. Scanning transmitted electron images can be acquired at appropriate magnifications in atomic number contrast mode (ZC) and transmitted electron mode (TE). The following instrument settings can be used.

| Instrument | Scanning Transmission Electron Microscope |
|---|---|
| Manufacturer/Model | Hitachi HD2300 |
| Accelerating Voltage | 200 kV |
| Objective Aperture | #2 |
| Condenser Lens 1 Setting | 1.672 |
| Condenser Lens 2 Setting | 1.747 |
| Approximate Objective Lens Setting | 5.86 |
| ZC Mode Projector Lens | 1.149 |
| TE Mode Projector Lens | 0.7 |
| Image Acquisition | |
| Pixel Resolution | 1280 × 960 |
| Acquisition Time | 20 sec.(×4 |

For TEM analysis the sample grids can be transferred to a Hitachi HF2000 transmission electron microscope. Transmitted electron images can be acquired at appropriate magnifications. The relevant instrument settings used during image acquisition can be those given below.

| Instrument | Transmission Electron Microscope |
|---|---|
| Manufacturer/Model | Hitachi HF2000 |
| Accelerating Voltage | 200 kV |
| Condenser Lens 1 | 0.78 |
| Condenser Lens 2 | 0 |
| Objective Lens | 6.34 |
| Condenser Lens Aperture | #1 |
| Objective Lens Aperture for imaging | #3 |
| Selective Area Aperture for SAD | N/A |

Basic Protocols for Forming and Coating Syringe Barrels

The pharmaceutical packages or other vessels tested in the subsequent working examples were formed and coated according to the following exemplary protocols, except as otherwise indicated in individual examples. Particular parameter values given in the following basic protocols, for example the electric power and gaseous reactant or process gas flow, are typical values. When parameter values were changed in comparison to these typical values, this will be indicated in the subsequent working examples. The same applies to the type and composition of the gaseous reactant or process gas.

In some instances, the reference characters and Figures mentioned in the following protocols and additional details can be found in U.S. Pat. No. 7,985,188.

Protocol for Coating Syringe Barrel Interior with $SiO_x$

The apparatus and protocol generally as found in U.S. Pat. No. 7,985,188 were used for coating syringe barrel interiors with an $SiO_x$ barrier coating or layer, in some cases with minor variations. A similar apparatus and protocol were used for coating vials with an $SiO_x$ barrier coating or layer, in some cases with minor variations.

Protocol for Coating Syringe Barrel Interior with OMCTS Passivation Layer or pH Protective Coating Syringe barrels already interior coated with a barrier coating or layer of $SiO_x$, as previously identified, are further interior coated with a passivation layer or pH protective coating as previously identified, generally following the protocols of U.S. Pat. No. 7,985,188 for applying the lubricity coating or layer, except with modified conditions in certain instances as noted in the working examples. The conditions given here are for a COC syringe barrel, and can be modified as appropriate for syringe barrels made of other materials. The apparatus as generally shown in FIG. 4 can be used to hold a syringe barrel with butt sealing at the base of the syringe barrel.

The syringe barrel is carefully moved into the sealing position over the extended probe or counter electrode 108 and pushed against a plasma screen. The plasma screen is fit snugly around the probe or counter electrode 108 insuring good electrical contact. The probe or counter electrode 108 is grounded to the casing of the RF matching network.

The gas delivery port 110 is connected to a manual ball valve or similar apparatus for venting, a thermocouple pressure gauge and a bypass valve connected to the vacuum pumping line. In addition, the gas system is connected to the gas delivery port 110 allowing the gaseous reactant or process gas, octamethylcyclotetrasiloxane (OMCTS) (or the specific gaseous reactant or process gas reported for a particular example) to be flowed through the gas delivery port 110 (under process pressures) into the interior of the syringe barrel.

The gas system is comprised of a commercially available heated mass flow vaporization system that heats the OMCTS to about 100° C. The heated mass flow vaporization system is connected to liquid octamethylcyclotetrasiloxane (Alfa Aesar® Part Number A12540, 98%). The OMCTS flow rate is set to the specific organosilicon precursor flow reported for a particular example. To ensure no condensation of the vaporized OMCTS flow past this point, the gas stream is diverted to the pumping line when it is not flowing into the interior of the COC syringe barrel for processing.

Once the syringe barrel is installed, the vacuum pump valve is opened to the vessel holder 50 and the interior of the COC syringe barrel. A vacuum pump and blower comprise the vacuum pump system. The pumping system allows the interior of the COC syringe barrel to be reduced to pressure(s) of less than 100 mTorr while the gaseous reactant or process gases is flowing at the indicated rates.

Once the base vacuum level is achieved, the vessel holder 50 assembly is moved into the electrode 160 assembly. The gas stream (OMCTS vapor) is flowed into the gas delivery port 110 (by adjusting the 3-way valve from the pumping line to the gas delivery port 110. The plasma for PECVD, if used, can be generated at reduced pressure and the reduced pressure can be less than 300 mTorr, optionally less than 200 mTorr, even optionally less than 100 mTorr. Pressure inside the COC syringe barrel can be, as one example, approximately 140 mTorr as measured by a capacitance manometer (MKS) installed on the pumping line near the valve that controls the vacuum. In addition to the COC syringe barrel pressure, the pressure inside the gas delivery port 110 and gas system is also measured with the thermocouple vacuum gauge that is connected to the gas system. This pressure is typically less than 6 Torr.

Once the gas is flowing to the interior of the COC syringe barrel, the RF power supply is turned on to its fixed power level or as otherwise indicated in a specific example or description. The physical and chemical properties of the passivation layer or pH protective coating can be set by setting the ratio of oxidizing gas to the organosilicon precursor in the gaseous reactant, and/or by setting the electric power used for generating the plasma. A 600 Watt RF power supply is used (at 13.56 MHz) at a fixed power level or as otherwise indicated in a specific example or description. The RF power supply is connected to an auto match which matches the complex impedance of the plasma (to be created in the vessel) to the output impedance of the RF power supply. The forward power is as stated and the reflected power is 0 Watts so that the stated power is delivered to the interior of the vessel. The RF power supply is controlled by a laboratory timer and the power on time set to 10 seconds (or a different time stated in a given example).

Upon initiation of the RF power, uniform plasma is established inside the interior of the vessel. The plasma is maintained for the entire passivation layer or pH protective coating time, until the RF power is terminated by the timer. The plasma produces a passivation layer or pH protective coating on the interior of the vessel.

After applying the passivation layer or pH protective coating, the gas flow is diverted back to the vacuum line and the vacuum valve is closed. The vent valve is then opened, returning the interior of the COC syringe barrel to atmospheric pressure (approximately 760 Torr). The treated vessel is then carefully removed from the vessel holder 50 assembly (after moving the vessel holder 50 assembly out of the electrode 160 assembly).

A similar protocol is used, except using apparatus generally like that of FIG. 1, for applying a passivation layer or pH protective coating to vials.

Protocol for Total Silicon Measurement

This protocol is used to determine the total amount of silicon coatings present on the entire vessel wall. A supply of 0.1 N potassium hydroxide (KOH) aqueous solution is prepared, taking care to avoid contact between the solution or ingredients and glass. The water used is purified water, 18 MΩ quality. A Perkin Elmer Optima Model 7300DV ICP-OES instrument is used for the measurement except as otherwise indicated.

Each device (vial, syringe, tube, or the like) to be tested and its cap and crimp (in the case of a vial) or other closure are weighed empty to 0.001 g, then filled completely with the KOH solution (with no headspace), capped, crimped, and reweighed to 0.001 g. In a digestion step, each vial is placed in a sonicating water bath at 40° C. for a minimum of 8-10 hours. The digestion step is carried out to quantitatively remove the silicon coatings from the vessel wall into the KOH solution. After this digestion step, the vials are removed from the sonicating water bath and allowed to cool to room temperature. The contents of the vials are transferred into 15 ml ICP tubes. The total Si concentration is run on each solution by ICP/OES following the operating procedure for the ICP/OES.

The total Si concentration is reported as parts per billion of Si in the KOH solution. This concentration represents the total amount of silicon coatings that were on the vessel wall before the digestion step was used to remove it.

The total Si concentration can also be determined for fewer than all the silicon layers on the vessel, as when an $SiO_x$ barrier coating or layer is applied, an $SiO_xC_y$ second layer (for example, a lubricity layer or a passivation layer or pH protective coating) is then applied, and it is desired to know the total silicon concentration of just the $SiO_xC_y$ layer. This determination is made by preparing two sets of vessels, one set to which only the $SiO_x$ layer is applied and the other set to which the same $SiO_x$ layer is applied, followed by the $SiO_xC_y$ layer or other layers of interest. The total Si concentration for each set of vessels is determined in the same manner as described above. The difference between the two Si concentrations is the total Si concentration of the $SiO_xC_y$ second layer.

Protocol for Measuring Dissolved Silicon in a Vessel

In some of the working examples, the amount of silicon dissolved from the wall of the vessel by a test solution is determined, in parts per billion (ppb), for example to evaluate the dissolution rate of the test solution. This determination of dissolved silicon is made by storing the test solution in a vessel provided with an $SiO_x$ and/or $SiO_xC_y$ coating or layer under test conditions, then removing a sample of the solution from the vessel and testing the Si concentration of the sample. The test is done in the same manner as the Protocol for Total Silicon Measurement, except that the digestion step of that protocol is replaced by storage of the test solution in the vessel as described in this protocol. The total Si concentration is reported as parts per billion of Si in the test solution Protocol for Determining Average Dissolution Rate The average dissolution rates reported in the working examples are determined as follows. A series of test vessels having a known total silicon measurement are filled with the desired test solution analogous to the manner of filling the vials with the KOH solution in the Protocol for Total Silicon Measurement. (The test solution can be a physiologically inactive test solution as employed in the present working examples or a physiologically active pharmaceutical preparation intended to be stored in the vessels to form a pharmaceutical package). The test solution is stored in respective vessels for several different amounts of time, then analyzed for the Si concentration in parts per billion in the test solution for each storage time. The respective storage times and Si concentrations are then plotted. The plots are studied to find a series of substantially linear points having the steepest slope.

The plot of dissolution amount (ppb Si) versus days decreases in slope with time. It is believed that the dissolution rate is not flattening out because the Si layer has been fully digested by the test solution.

For the PC194 test data in Table 10 below, linear plots of dissolution versus time data are prepared by using a least squares linear regression program to find a linear plot corresponding to the first five data points of each of the experimental plots. The slope of each linear plot is then determined and reported as representing the average dissolution rate applicable to the test, measured in parts per billion of Si dissolved in the test solution per unit of time.

Protocol for Determining Calculated Shelf Life

The calculated shelf life values reported in the working examples below are determined by extrapolation of the total silicon measurements and average dissolution rates, respectively determined as described in the Protocol for Total Silicon Measurement and the Protocol for Determining Average Dissolution Rate. The assumption is made that under the indicated storage conditions the $SiO_xC_y$ passivation layer or pH protective coating will be removed at the average dissolution rate until the coating is entirely removed. Thus, the total silicon measurement for the vessel, divided by the dissolution rate, gives the period of time required for the test solution to totally dissolve the $SiO_xC_y$ coating. This period of time is reported as the calculated shelf life. Unlike commercial shelf life calculations, no safety factor is calculated. Instead, the calculated shelf life is the calculated time to failure.

It should be understood that because the plot of ppb Si versus hours decreases in slope with time, an extrapolation from relatively short measurement times to relatively long calculated shelf lives is believed to be a "worst case" test that tends to underestimate the calculated shelf life actually obtainable.

SEM Procedure

SEM Sample Preparation: Each syringe sample was cut in half along its length (to expose the inner or interior surface). The top of the syringe (Luer end) was cut off to make the sample smaller.

The sample was mounted onto the sample holder with conductive graphite adhesive, then put into a Denton Desk IV SEM Sample Preparation System, and a thin (approximately 50 Å) gold passivation layer or pH protective coating was sputtered onto the inner or interior surface of the syringe. The gold passivation layer or pH protective coating is required to eliminate charging of the surface during measurement.

The sample was removed from the sputter system and mounted onto the sample stage of a Jeol JSM 6390 SEM (Scanning Electron Microscope). The sample was pumped down to at least $1\times10^{-6}$ Torr in the sample compartment. Once the sample reached the required vacuum level, the slit valve was opened and the sample was moved into the analysis station.

The sample was imaged at a coarse resolution first, then higher magnification images were accumulated. The SEM images provided in the Figures are 5 μm edge-to-edge (horizontal and vertical).

AFM (Atomic Force Microscopy) Procedure.

AFM images were collected using a NanoScope III Dimension 3000 machine (Digital Instruments, Santa Barbara, Calif., USA). The instrument was calibrated against a NIST traceable standard. Etched silicon scanning probe microscopy (SPM) tips were used. Image processing procedures involving auto-flattening, plane fitting or convolution were employed. One 10 μm×10 μm area was imaged. Roughness analyses were performed and were expressed in: (1) Root-Mean-Square Roughness, RMS; 2 Mean Roughness, Ra; and (3) Maximum Height (Peak-to-Valley), $R_{max}$, all measured in nm (see Table 5). For the roughness analyses, each sample was imaged over the 10 μm×10 μm area, followed by three cross sections selected by the analyst to cut through features in the 10 μm×10 μm images. The vertical depth of the features was measures using the cross section tool. For each cross section, a Root-Mean-Square Roughness (RMS) in nanmeters was reported. These RMS values along with the average of the three cross sections for each sample are listed in Table 5.

Additional analysis of the 10 μm×10 μm images represented by Examples Q, T and V was carried out. For this analysis three cross sections were extracted from each image. The locations of the cross sections were selected by the analyst to cut through features in the images. The vertical depth of the features was measured using the cross section tool.

The Digital Instruments Nanoscope III AFM/STM acquires and stores 3-dimensional representations of surfaces in a digital format. These surfaces can be analyzed in a variety of ways.

The Nanoscope III software can perform a roughness analysis of any AFM or STM image. The product of this analysis is a single page reproducing the selected image in top view. To the upper right of the image is the "Image Statistics" box, which lists the calculated characteristics of the whole image minus any areas excluded by a stopband (a box with an X through it). Similar additional statistics can be calculated for a selected portion of the image and these are listed in the "Box Statistics" in the lower right portion of the page. What follows is a description and explanation of these statistics.

Image Statistics:

Z Range ($R_p$): The difference between the highest and lowest points in the image. The value is not corrected for tilt in the plane of the image; therefore, plane fitting or flattening the data will change the value.

Mean: The average of all of the Z values in the imaged area. This value is not corrected for the tilt in the plane of the image; therefore, plane fitting or flattening the data will change this value.

RMS($R_q$): This is the standard deviation of the Z values (or RMS roughness) in the image. It is calculated according to the formula:

$$R_q = \{\Sigma(Z_1 - Z_{avg})2/N\}$$

where $Z_{avg}$ is the average Z value within the image; $Z_1$ is the current value of Z; and N is the number of points in the image. This value is not corrected for tilt in the plane of the image; therefore, plane fitting or flattening the data will change this value.

Mean roughness ($R_a$): This is the mean value of the surface relative to the Center Plane and is calculated using the formula:

$$R_a = [1/(L_x L_y)] \int_o^{Ly} \int_o^{Lx} \{f(x,y)\} dx dy$$

where f(x,y) is the surface relative to the Center plane, and $L_x$ and $L_y$ are the dimensions of the surface.

Max height ($R_{max}$): This is the difference in height between the highest and lowest points of the surface relative to the Mean Plane.

Surface area: (Optical calculation): This is the area of the 3-dimensional surface of the imaged area. It is calculated by taking the sum of the areas of the triangles formed by 3 adjacent data points throughout the image.

Surface area diff: (Optional calculation) This is the amount that the Surface area is in excess of the imaged area. It is expressed as a percentage and is calculated according to the formula:

Surface area diff=100[(Surface area/$S_1$2−1]

where $S_1$ is the length (and width) of the scanned area minus any areas excluded by stopbands.

Center Plane: A flat plane that is parallel to the Mean Plane. The volumes enclosed by the image surface above and below the center plane are equal.

Mean Plane: The image data has a minimum variance about this flat plane. It results from a first order least squares fit on the Z data.

WORKING EXAMPLES

The working examples follow. While much of the testing is carried out using thermoplastic vessels, instead of glass vessels, and protecting barrier coatings, instead of preventing glass delamination, the testing of the passivation layer or pH protective coating is analogous in either type of vessel.

Examples A-D

Syringe samples were produced as follows. A COC 8007 extended barrel syringe was produced according to the Protocol for Forming COC Syringe Barrel. An SiO$_x$ coating or layer was applied to some of the syringes according to the Protocol for coating COC Syringe Barrel Interior with SiO$_x$. A lubricity and/or passivation layer or pH protective coating was applied to the SiO$_x$ coated syringes according to the Protocol for Coating COC Syringe Barrel Interior with OMCTS Lubricity Coating, modified as follows. The OMCTS was supplied from a vaporizer, due to its low volatility. Argon carrier gas was used. The process conditions were set to the following:
OMCTS-3 sccm
Argon gas-65 sccm
Power-6 watts
Time-10 seconds The coater was later determined to have a small leak while producing the L2 samples identified in the Table, which resulted in an estimated oxygen flow of 1.0 sccm. The L3 samples were produced without introducing oxygen.

Several syringes were then tested for lubricity using a Genesis Packaging Plunger Force Tester (Model SFT-01 Syringe Force Tester, manufactured by Genesis Machinery, Lionville, Pa.) according to the Protocol for Lubricity Testing. Both the initiation force and maintenance forces (in Newtons) were noted relative to an uncoated sample, and are reported in Table 1.

Syringes coated with silicone oil were included as a reference since this is the current industry standard.

The lubricity coatings produced according to these working examples are also contemplated to function as passivation layers or pH protective coatings or layers to increase the shelf life of the vessels, compared to similar vessels provided with a barrier coating or layer but no lubricity coating or layer.

Examples E-H

Syringe samples were produced as follows. A COC 8007 extended barrel syringe was produced according to the Protocol for Forming COC Syringe Barrel. An SiO$_x$ passivation layer or pH protective coating was applied to the syringe barrels according to the Protocol for Coating COC Syringe Barrel Interior with SiO$_x$. A lubricity and/or passivation layer or pH protective coating was applied to the SiO$_x$ coated syringes according to the Protocol for Coating COC Syringe Barrel Interior with OMCTS, modified as follows. Argon carrier gas and oxygen were used where noted in Table 2. The process conditions were set to the following, or as indicated in Table 2:
OMCTS-3 sccm (when used)
Argon gas-7.8 sccm (when used)
Oxygen 0.38 sccm (when used)
Power-3 watts
Power on time-10 seconds Syringes E and F prepared under these conditions, Syringes G prepared under these conditions except without a lubricity layer or a passivation layer or pH protective coating, and Syringes H (a commercial syringe coated with silicone oil) were then tested for lubricity using a Genesis Packaging Plunger Force Tester according to the Protocol for Lubricity Testing. Both the initiation force and maintenance forces (in Newtons) were noted relative to an uncoated sample, and are reported in Table 2. Syringes coated with silicone oil were included as a reference since this is the current industry standard.

The lubricity results are shown in Table 2 (Initiation Force and Maintenance Force), illustrating under these test conditions as well that the lubricity and/or passivation layer or pH protective coating on Syringes E and F markedly improved their lubricity compared to Syringes G which lacked any lubricity and/or passivation layer or pH protective coating. The lubricity and/or passivation layer or pH protective coating on Syringes E and F also markedly improved their lubricity compared to Syringes H which contained the standard lubricity coating or layer in the industry.

Syringes E, F, and G were also tested to determine total extractable silicon levels (representing extraction of the organosilicon-based PECVD passivation layer or pH protective coating) using the Protocol for Measuring Dissolved Silicon in a Vessel, modified and supplemented as shown in this example.

The silicon was extracted using saline water digestion. The tip of each syringe plunger tip, piston, stopper, or seal was covered with PTFE tape to prevent extracting material from the elastomeric tip material, then inserted into the syringe barrel base. The syringe barrel was filled with two milliliters of 0.9% aqueous saline solution via a hypodermic needle inserted through the Luer tip of the syringe. This is an appropriate test for extractables because many prefilled syringes are used to contain and deliver saline solution. The Luer tip was plugged with a piece of PTFE beading of appropriate diameter. The syringe was set into a PTFE test stand with the Luer tip facing up and placed in an oven at 50° C. for 72 hours.

Then, either a static or a dynamic mode was used to remove the saline solution from the syringe barrel. According to the static mode indicated in Table 2, the syringe plunger tip, piston, stopper, or seal was removed from the test stand, and the fluid in the syringe was decanted into a vessel. According to the dynamic mode indicated in Table 2, the Luer tip seal was removed and the plunger tip, piston, stopper, or seal was depressed to push fluid through the syringe barrel and expel the contents into a vessel. In either case, the fluid obtained from each syringe barrel was brought to a volume of 50 ml using 18.2 MΩ-cm deionized water and further diluted 2× to minimize sodium background during analysis. The CVH barrels contained two milliliters and the commercial barrels contained 2.32 milliliters.

Next, the fluid recovered from each syringe was tested for extractable silicon using the Protocol for Measuring Dissolved Silicon in a Vessel. The instrument used was a Perkin Elmer Elan DRC II equipped with a Cetac ASX-520 autosampler. The following ICP-MS conditions were employed:

Nebulizer: Quartz Meinhardt
Spray Chamber: Cyclonic
RF (radio frequency) power: 1550 Watts
Argon (Ar) Flow: 15.0 L/min
Auxiliary Ar Flow: 1.2 L/min
Nebulizer Gas Flow: 0.88 L/min
Integration time: 80 sec
Scanning mode: Peak hopping
RPq (The RPq is a rejection parameter) for Cerium as CeO (m/z 156: <2%

Aliquots from aqueous dilutions obtained from Syringes E, F, and G were injected and analyzed for Si in concentration units of micrograms per liter. The results of this test are shown in Table 2. While the results are not quantitative, they do indicate that extractables from the lubricity and/or passivation layer or pH protective coating are not clearly higher than the extractables for the $SiO_x$ barrier coating or layer only. Also, the static mode produced far less extractables than the dynamic mode, which was expected.

Examples I-K

Syringe samples I, J, and K, employing three different lubricity and/or passivation layers or pH protective coatings or layers, were produced in the same manner as for Examples E-H except as follows or as indicated in Table 3:
OMCTS-2.5 sccm
Argon gas-7.6 sccm (when used)
Oxygen 0.38 sccm (when used)
Power-3 watts
Power on time-10 seconds Syringe I had a three-component passivation layer or pH protective coating employing OMCTS, oxygen, and carrier gas. Syringe J had a two component passivation layer or pH protective coating employing OMCTS and oxygen, but no carrier gas. Syringe K had a one-component passivation layer or pH protective coating (OMCTS only). Syringes I, J, and K were then tested for lubricity as described for Examples E-H.

The lubricity results are shown in Table 3 (Initiation Force and Maintenance Force). Syringe I with a three-component passivation layer or pH protective coating employing OMCTS, oxygen, and carrier gas provided the best lubricity results for both initiation force and maintenance force. Syringe J omitting the carrier gas yielded intermediate results. Syringe K had a one-component passivation layer or pH protective coating (OMCTS only), and provided the lowest lubricity. This example shows that the addition of both a carrier gas and oxygen to the process gas improved lubricity under the tested conditions.

The lubricity coatings produced according to these working examples are also contemplated to function as passivation layers or pH protective coatings or layers to increase the shelf life of the vessels, compared to similar vessels provided with a barrier coating or layer but no lubricity coating or layer.

Examples L-N

Examples I-K using an OMCTS precursor gas were repeated in Examples L-N, except that HMDSO was used as the precursor in Examples L-N. The results are shown in Table 3. The results show that for the tested three-component, two-component, and one-component lubricity coating or layer, the OMCTS passivation layer or pH protective coating provided lower resistance, thus better lubricity, than the HMDSO passivation layer or pH protective coating, demonstrating the value of OMCTS as the precursor gas for lubricity.

The lubricity coatings produced according to these working examples are also contemplated to function as passivation layers or pH protective coatings or layers to increase the shelf life of the vessels, compared to similar vessels provided with a barrier coating or layer but no lubricity coating or layer.

Examples O-Y

In these examples the surface roughness of the lubricity and/or passivation layer or pH protective coating was correlated with lubricity and/or protective performance.

Figure 10:
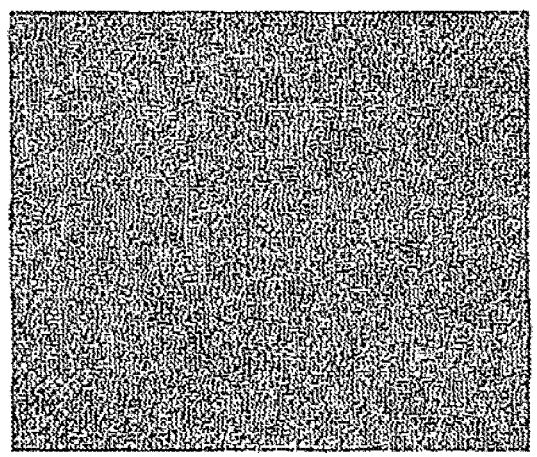
FIG. 10 shows a SEM image of Example S. The horizontal edge-to-edge scale is 5 μm.

OMCTS lubricity coatings or layers were applied with previously described equipment with the indicated specific process conditions (Table 5) onto one milliliter COC 6013 molded syringe barrels. Plunger force measurements ($F_i$, $F_m$) (Table 5) were performed with previously described equipment under the same protocols. Scanning electron spectroscopy (SEM) photomicrographs (Table 5, FIGS. 10 and 11) and atomic force microscopy (AFM) Root Mean Square (RMS) and other roughness determinations (Tables 5 and 6) were made using the procedures indicated below. Average RMS values are taken from three different RMS readings on the surface. The plunger force tests, AFM and SEM tests reported in table 5 were performed on different samples due to the nature of the individual tests which prohibited a performance of all tests on one sample.

Comparison of $F_i/F_m$ to SEM photomicrograph to AFM Average RMS values clearly indicates that lower plunger forces are realized with non-continuous, rougher OMCTS plasma-coated surfaces (cf. Samples O to Q vs. R to V).

Further testing was carried out on sister samples Examples W, X, and Y, respectively made under conditions similar to Example Q, T, and V, to show the $F_i$ and $F_m$ values corresponding to the AFM roughness data. Example W which has a higher surface roughness (compare Example Q in Table 5) has much lower $F_i$ and $F_m$ friction values (Table 6) than Example X or Y. The $F_m$ test shown in Table 6 was interrupted before reaching the measured value of $F_m$ for Examples X and Y because the $F_m$ value was too high.

The lubricity coatings produced according to these working examples are also contemplated to function as passivation layers or pH protective coatings or layers to increase the shelf life of the vessels, compared to similar vessels provided with a barrier coating or layer but no lubricity coating or layer.

Summary of Lubricity and/or Protective Measurements

Table 8 shows a summary of the above OMCTS coatings or layers and their $F_i$ and $F_m$ values. It should be understood that the initial lubricity and/or passivation layer or pH protective coating work (C-K; roughness not known) was to identify the lowest possible plunger tip, piston, stopper, or seal advancing force attainable. From subsequent market input, it was determined that the lowest achievable force was not necessarily most desirable, for reasons explained in the generic description (for example premature release). Thus, the PECVD reaction parameters were varied to obtain a plunger tip, piston, stopper, or seal force of practical market use.

Example Z: Lubricity and/or Passivation Layer or pH Protective Coating Extractables Silicon extractables from syringes were measured using ICP-MS analysis as described in the Protocol for Measuring Dissolved Silicon in a Vessel. The syringes were evaluated in both static and dynamic situations. The Protocol for Measuring Dissolved Silicon in a Vessel, modified as follows, describes the test procedure:
Syringe filled with 2 ml of 0.9% saline solution
Syringe placed in a stand—stored at 50° C. for 72 hours.
After 72 hours saline solution test for dissolved silicon
Dissolved silicon measured before and after saline solution expelled through syringe.

The extractable Silicon Levels from a silicone oil coated glass syringe and a Lubricity and/or protective coated and $SiO_x$ coated COC syringe are shown in Table 7. Precision of the ICP-MS total silicon measurement is +/−3%.

Comparative Example AA: Dissolution of $SiO_x$ Coating Versus pH

The Protocol for Measuring Dissolved Silicon in a Vessel is followed, except as modified here. Test solutions—50 mM buffer solutions at pH 3, 6, 7, 8, 9, and 12 are prepared. Buffers are selected having appropriate pKa values to provide the pH values being studied. A potassium phosphate buffer is selected for pH 3, 7, 8 and 12, a sodium citrate buffer is utilized for pH 6 and tris buffer is selected for pH 9. 3 ml of each test solution is placed in borosilicate glass 5 ml pharmaceutical vials and $SiO_x$ coated 5 ml thermoplastic pharmaceutical vials. The vials are all closed with standard coated stoppers and crimped. The vials are placed in storage at 20-25° C. and pulled at various time points for inductively coupled plasma spectrometer (ICP) analysis of Si content in the solutions contained in the vials, in parts per billion (ppb) by weight, for different storage times.

Figure 14:
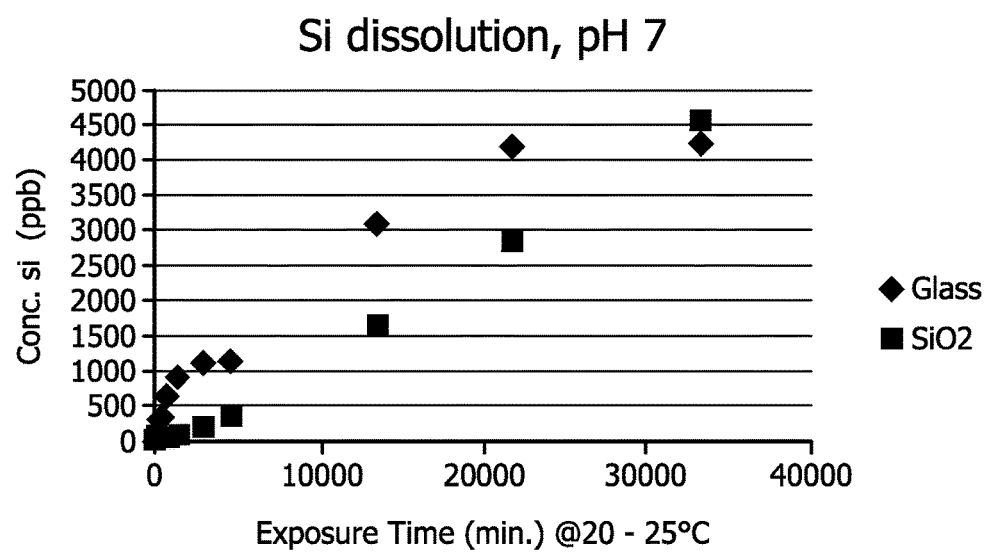
FIG. 14 is a plot of silicon dissolution versus exposure time at pH 7 for a glass container versus a plastic container having an $SiO_x$ barrier coating or layer coated in the inside wall.
Figure 15:
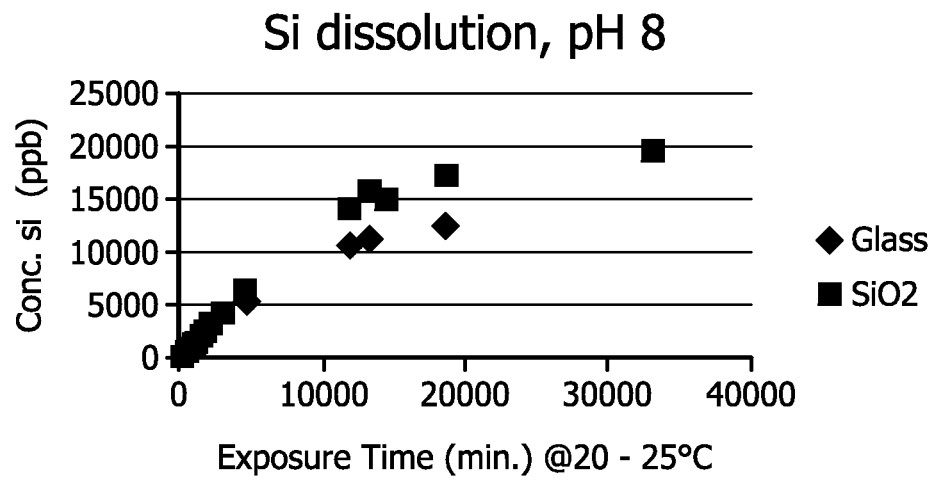
FIG. 15 is a plot of silicon dissolution versus exposure time at pH 8 for a glass container versus a plastic container having an $SiO_x$ barrier coating or layer coated in the inside wall.

The Protocol for Determining Average Dissolution Rate Si content is used to monitor the rate of glass dissolution, except as modified here. The data is plotted to determine an average rate of dissolution of borosilicate glass or $SiO_x$ coating at each pH condition. Representative plots at pH 6 through 8 are FIGS. 14-16.

Figure 16:
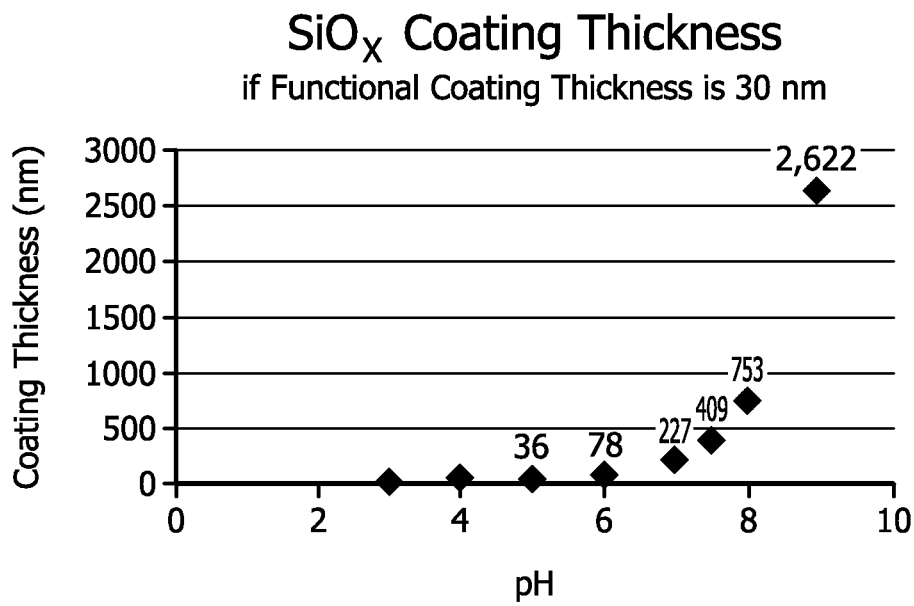
FIG. 16 is a plot of the $SiO_x$ coating thickness necessary initially to leave a 30 nm residual coating thickness when stored with solutions at different nominal pH values from 3 to 9.

The rate of Si dissolution in ppb is converted to a predicted thickness (nm) rate of Si dissolution by determining the total weight of Si removed, then using a surface area calculation of the amount of vial surface (11.65 $cm^2$) exposed to the solution and a density of $SiO_x$ of 2.2 $g/cm^3$. FIG. 16 shows the predicted initial thickness of the $SiO_x$ coating required, based on the conditions and assumptions of this example (assuming a residual $SiO_x$ coating of at least 30 nm at the end of the desired shelf life of two years, and assuming storage at 20 to 25° C.). As FIG. 16 shows, the predicted initial thickness of the coating is about 36 nm at pH 5, about 80 nm at pH 6, about 230 nm at pH 7, about 400 nm at pH 7.5, about 750 nm at pH 8, and about 2600 nm at pH 9.

The coating thicknesses in FIG. 16 represent atypically harsh case scenarios for pharma and biotech products. Most biotech products and many pharma products are stored at refrigerated conditions and none are typically recommended for storage above room temperature. As a general rule of thumb, storage at a lower temperature reduces the thickness required, all other conditions being equivalent.

The following conclusions are reached, based on this test. First, the amount of dissolved Si in the $SiO_x$ coating or glass increases exponentially with increasing pH. Second, the $SiO_x$ coating dissolves more slowly than borosilicate glass at a pH lower than 8. The $SiO_x$ coating shows a linear, monophasic dissolution over time, whereas borosilicate glass tends to show a more rapid dissolution in the early hours of exposure to solutions, followed by a slower linear dissolution. This may be due to surface accumulation of some salts and elements on borosilicate during the forming process relative to the uniform composition of the $SiO_x$ coating. This result incidentally suggests the utility of an $SiO_x$ coating on the wall of a borosilicate glass vial to reduce dissolution of the glass at a pH lower than 8. Third, PECVD applied barrier coatings or layers for vials in which pharmaceutical preparations are stored will need to be adapted to the specific pharmaceutical preparation and proposed storage conditions (or vice versa), at least in some instances in which the pharmaceutical preparation interacts with the barrier coating or layer significantly.

Example BB

An experiment is conducted with vessels coated with $SiO_x$ coating+OMCTS lubricity layer, to test the lubricity layer for its functionality as a passivation layer or pH protective coating. The vessels are 5 mL vials (the vials are normally filled with product to 5 mL; their capacity without headspace, when capped, is about 7.5 mL) composed of cyclic olefin co-polymer (COC, Topas® 6013M-07).

Sixty vessels are coated on their interior surfaces with an $SiO_x$ coating produced in a plasma enhanced chemical vapor deposition (PECVD) process using a HMDSO precursor gas according to the Protocol for Coating Tube Interior with $SiO_x$ set forth above, except that equipment suitable for coating a vial is used. The following conditions are used.
HMDSO flow rate: 0.47 sccm
Oxygen flow rate: 7.5 sccm
RF power: 70 Watts
Coating time: 12 seconds (includes a 2-sec RF power ramp-up time)

Next the $SiO_x$ coated vials are coated over the $SiO_x$ with an $SiO_xC_y$ coating produced in a PECVD process using an OMCTS precursor gas according to the Protocol for Coating COC Syringe Barrel Interior with OMCTS Lubricity Coating set forth above, except that the same coating equipment is used as for the $SiO_x$ coating. Thus, the special adaptations in the protocol for coating a syringe are not used. The following conditions are used.

OMCTS flow rate: 2.5 sccm

Argon flow rate: 10 sccm

Oxygen flow rate: 0.7 sccm

RF power: 3.4 Watts

Coating time: 5 seconds

Eight vials are selected and the total deposited quantity of PECVD coating ($SiO_x + SiO_xC_y$) is determined with a Perkin Elmer Optima Model 7300DV ICP-OES instrument, using the Protocol for Total Silicon Measurement set forth above. This measurement determines the total amount of silicon in both coatings, and does not distinguish between the respective $SiO_x$ and $SiO_xC_y$ coatings. The results are shown below.

| Quantity of $SiO_x$ + Lubricity layer on Vials | |
|---|---|
| Vial | Total Silicon ug/L |
| 1 | 13844 |
| 2 | 14878 |
| 3 | 14387 |
| 4 | 13731 |
| 5 | 15260 |
| 6 | 15017 |
| 7 | 15118 |
| 8 | 12736 |
| Mean | 14371 |
| StdDev | 877 |

In the following work, except as indicated otherwise in this example, the Protocol for Determining Average Dissolution Rate is followed. Two buffered pH test solutions are used in the remainder of the experiment, respectively at pH 4 and pH 8 to test the effect of pH on dissolution rate. Both test solutions are 50 mM buffers using potassium phosphate as the buffer, diluted in water for injection (WFI) (0.1 um sterilized, filtered). The pH is adjusted to pH 4 or 8, respectively, with concentrated nitric acid.

25 vials are filled with 7.5 ml per vial of pH 4 buffered test solution and 25 other vials are filled with 7.5 ml per vial of pH 4 buffered test solution (note the fill level is to the top of the vial—no head space). The vials are closed using pre-washed butyl stoppers and aluminum crimps. The vials at each pH are split into two groups. One group at each pH containing 12 vials is stored at 4° C. and the second group of 13 vials is stored at 23° C.

The vials are sampled at Days 1, 3, 6, and 8. The Protocol for Measuring Dissolved Silicon in a Vessel is used, except as otherwise indicated in this example. The analytical result is reported on the basis of parts per billion of silicon in the buffered test solutions of each vial. A dissolution rate is calculated in terms of parts per billion per day as described above in the Protocol for Determining Average Dissolution Rate. The results at the respective storage temperatures follow:

|  | Vial SiOx + Lubricity Coating at pH 4 | Vial SiOx + Lubricity Coating at pH 8 |
|---|---|---|
|  | Shelf Life Conditions 23° C. | |
| Si Dissolution Rate (PPB/day) | 31 | 7 |
|  | Shelf Life Conditions 4° C. | |
| Si Dissolution Rate (PPB/day) | 7 | 11 |

The observations of Si dissolution versus time for the OMCTS-based coating at pH8 and pH 4 indicate the pH 4 rates are higher at ambient conditions. Thus, the pH 4 rates are used to determine how much material would need to be initially applied to leave a coating of adequate thickness at the end of the shelf life, taking account of the amount of the initial coating that would be dissolved. The results of this calculation are:

| Shelf Life Calculation | |
|---|---|
|  | Vial with SiOx + Lubricity Coating at pH 4 |
| Si Dissolution Rate (PPB/day) | 31 |
| Mass of Coating Tested (Total Si) | 14,371 |
| Shelf Life (days) at 23° C. | 464 |
| Shelf Life (years) at 23° C. | 1.3 |
| Required Mass of Coating (Total Si)--2-years | 22,630 |
| Required Mass of Coating (Total Si)--3-years | 33,945 |

Based on this calculation, the OMCTS lubricity layer needs to be about 2.5 times thicker—resulting in dissolution of 33945 ppb versus the 14,371 ppb representing the entire mass of coating tested—to achieve a 3-year calculated shelf life.

Example CC

The results of Comparative Example AA and Example BB above can be compared as follows, where the "lubricity layer" is the coating of $SiO_xC_y$ referred to in Example BB.

| | Shelf Life Conditions--pH 8 and 23° C. | |
|---|---|---|
|  | Vial with SiOx | Vial with SiOx + Lubricity Coating |
| Si Dissolution Rate (PPB/day) | 1,250 | 7 |

This data shows that the silicon dissolution rate of $SiO_x$ alone is reduced by more than 2 orders of magnitude at pH 8 in vials also coated with $SiO_xC_y$ coatings.

Figure 17:
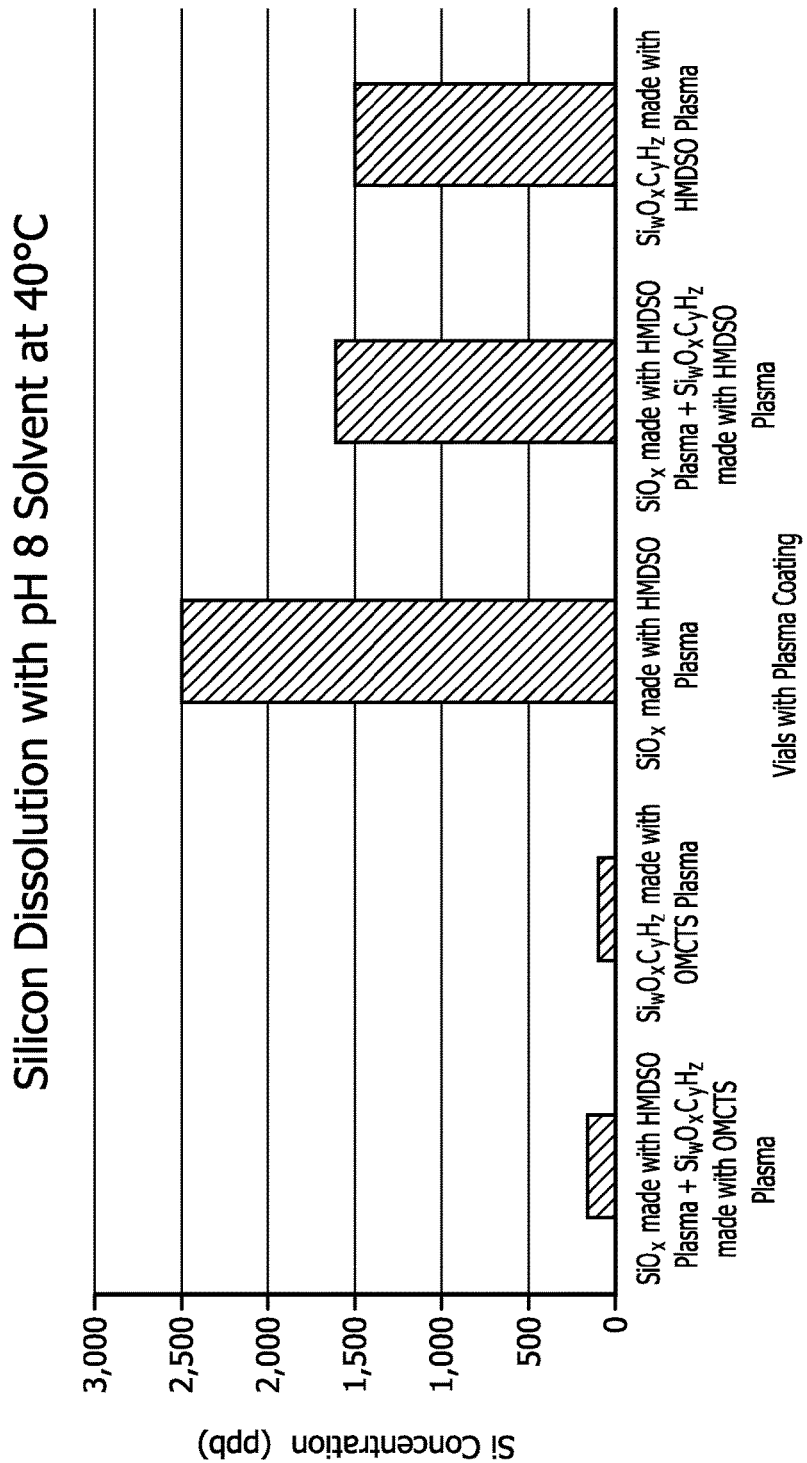
FIG. 17 shows the silicon dissolution rates at pH 8 and 40° C. of various PECVD coatings.
Figure 18:
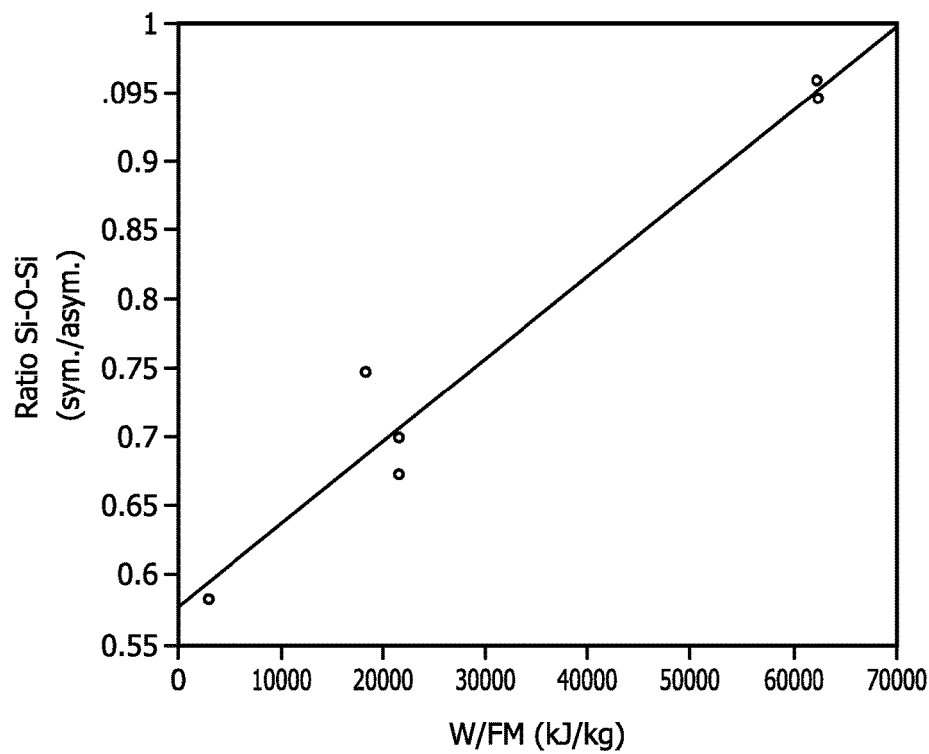
FIG. 18 is a plot of the ratio of Si—O—Si symmetric/asymmetric stretching mode versus energy input per unit mass (W/FM or KJ/kg) of a PECVD coating using as the reactive precursor gases OMCTS and oxygen.

Another comparison is shown by the following data from several different experiments carried out under similar accelerated dissolution conditions, of which the 1-day data is also presented in FIG. 17.

| Vial Coating Description | Silicon Dissolution with pH 8 at 40° C. (ug/L) | | | | | | |
|---|---|---|---|---|---|---|---|
| | 1 day | 2 days | 3 days | 4 days | 7 days | 10 days | 15 days |
| A. SiO$_x$ made with HMDSO Plasma + Si$_w$O$_x$C$_y$ or its equivalent SiO$_x$C$_y$ made with OMCTS Plasma | 165 | 211 | 226 | 252 | 435 | 850 | 1,364 |
| B. Si$_w$O$_x$C$_y$ or its equivalent SiO$_x$C$_y$ made with OMCTS Plasma | 109 | 107 | 76 | 69 | 74 | 158 | 198 |
| C. SiO$_x$ made with HMDSO Plasma | 2,504 | 4,228 | 5,226 | 5,650 | 9,292 | 10,177 | 9,551 |
| D. SiO$_x$ made with HMDSO Plasma + Si$_w$O$_x$C$_y$ or its equivalent SiO$_x$C$_y$ made with HMDSO Plasma | 1,607 | 1,341 | 3,927 | 10,182 | 18,148 | 20,446 | 21,889 |
| E. Si$_w$O$_x$C$_y$ or its equivalent SiO$_x$C$_y$ made with HMDSO Plasma | 1,515 | 1,731 | 1,813 | 1,743 | 2,890 | 3,241 | 3,812 |

FIG. 17 and Row A (SiO$_x$ with OMCTS coating) versus C (SiO$_x$ without OMCTS coating) show that the OMCTS lubricity layer is also an effective passivation layer or pH protective coating to the SiO$_x$ coating at pH 8. The OMCTS coating reduced the one-day dissolution rate from 2504 ug/L ("u" or µ or the Greek letter "mu" as used herein are identical, and are abbreviations for "micro") to 165 ug/L. This data also shows that an HMDSO-based Si$_w$O$_x$C$_y$ (or its equivalent SiO$_x$C$_y$) overcoat (Row D) provided a far higher dissolution rate than an OMCTS-based Si$_w$O$_x$C$_y$ (or its equivalent SiO$_x$C$_y$) overcoat (Row A). This data shows that a substantial benefit can be obtained by using a cyclic precursor versus a linear one.

Example DD

Samples 1-6 as listed in Table 9 were prepared as described in Example AA, with further details as follows.

A cyclic olefin copolymer (COC) resin was injection molded to form a batch of 5 ml vials. Silicon chips were adhered with double-sided adhesive tape to the internal walls of the vials. The vials and chips were coated with a two layer coating by plasma enhanced chemical vapor deposition (PECVD). The first layer was composed of SiO$_x$ with barrier coating or layer properties as defined in the present disclosure, and the second layer was an SiO$_x$C$_y$ passivation layer or pH protective coating.

A precursor gas mixture comprising OMCTS, argon, and oxygen was introduced inside each vial. The gas inside the vial was excited between capacitively coupled electrodes by a radio-frequency (13.56 MHz) power source as described in connection with FIGS. 4-6. The monomer flow rate (F$_m$) in units of sccm, oxygen flow rate (F$_o$) in units of sccm, argon flowrate in sccm, and power (W) in units of watts are shown in Table 9.

A composite parameter, W/FM in units of kJ/kg, was calculated from process parameters W, F$_m$, F$_o$ and the molecular weight, M in g/mol, of the individual gas species. W/FM is defined as the energy input per unit mass of polymerizing gases. Polymerizing gases are defined as those species that are incorporated into the growing coating such as, but not limited to, the monomer and oxygen. Non-polymerizing gases, by contrast, are those species that are not incorporated into the growing coating, such as but not limited to argon, helium and neon.

In this test, PECVD processing at high W/FM is believed to have resulted in higher monomer fragmentation, producing organosiloxane coatings with higher cross-link density. PECVD processing at low W/FM, by comparison, is believed to have resulted in lower monomer fragmentation producing organosiloxane coatings with a relatively lower cross-link density.

Figure 19:
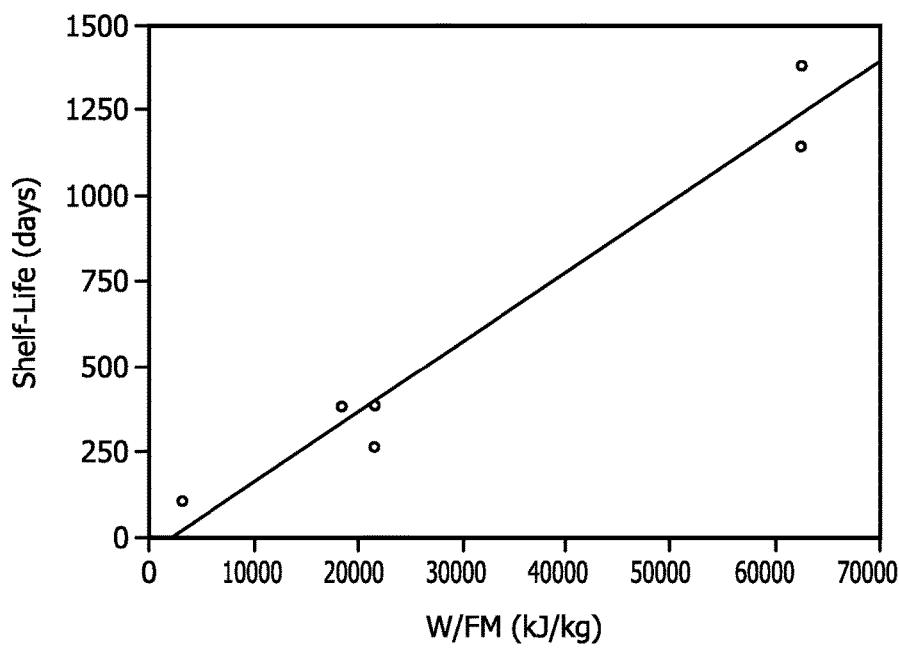
FIG. 19 is a plot of silicon shelf life (days) versus energy input per unit mass (W/FM or KJ/kg) of a PECVD coating using as the reactive precursor gases OMCTS and oxygen.
Figure 20:
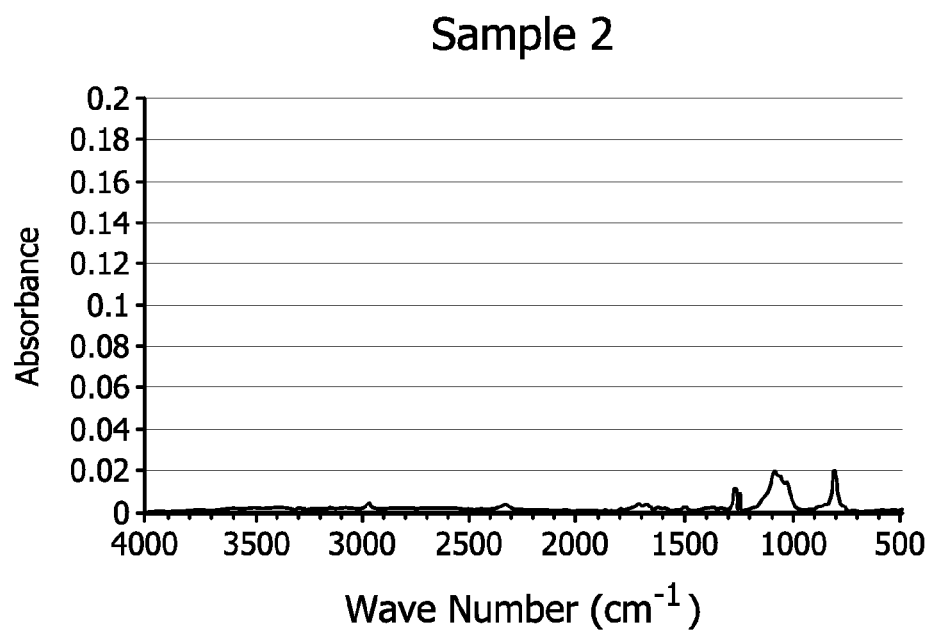
FIG. 20 is a Fourier Transform Infrared Spectrophotometer (FTIR) absorbance spectrum of a PECVD coating.
Figure 21:
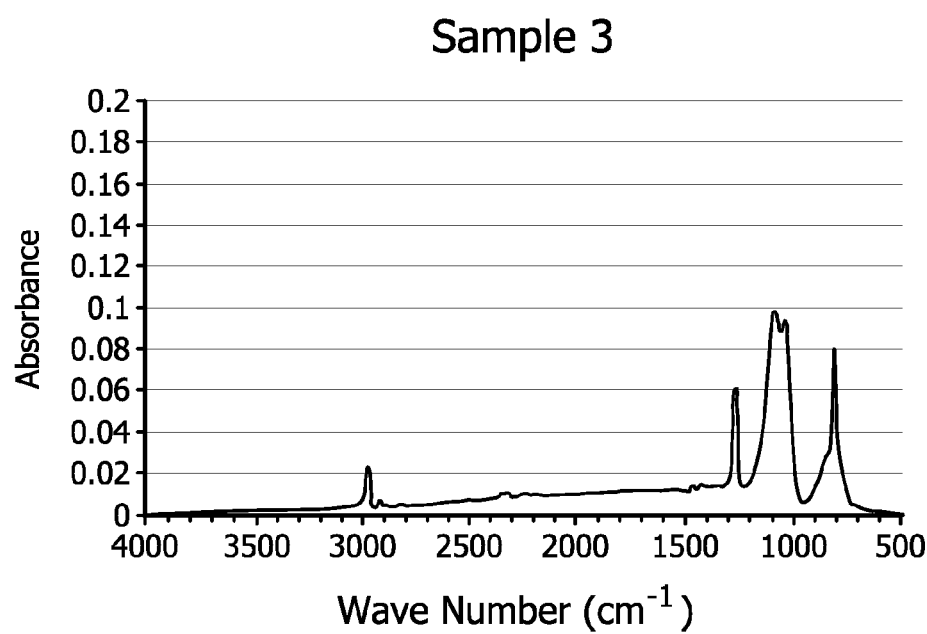
FIG. 21 is a Fourier Transform Infrared Spectrophotometer (FTIR) absorbance spectrum of a PECVD coating.
Figure 22:
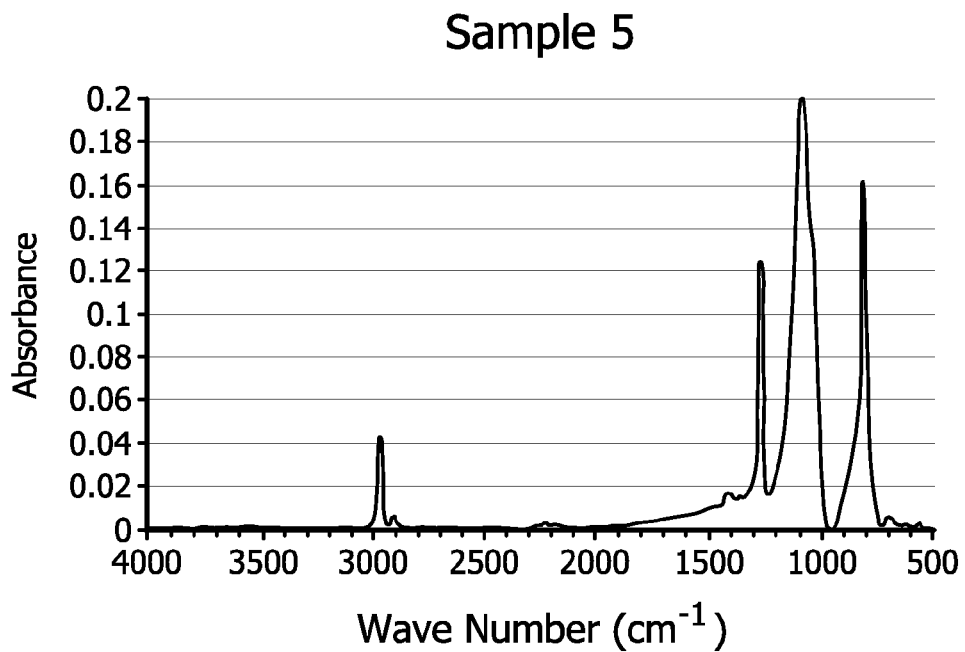
FIG. 22 is a Fourier Transform Infrared Spectrophotometer (FTIR) absorbance spectrum of a PECVD coating.
Figure 23:
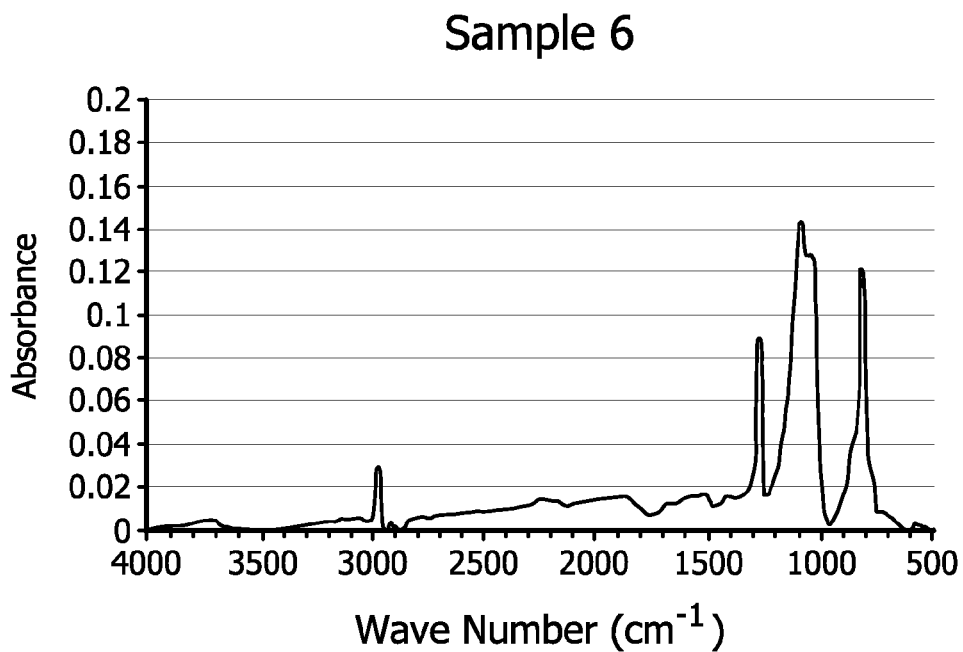
FIG. 23 is a Fourier Transform Infrared Spectrophotometer (FTIR) absorbance spectrum of a PECVD coating.

The relative cross-link density of samples 5, 6, 2, and 3 was compared between different coatings by measuring FTIR absorbance spectra. The spectra of samples 5, 6, 2, and 3 are provided in FIGS. 21-24. In each spectrum, the ratio of the peak absorbance at the symmetric stretching mode (1000-1040 cm$^{-1}$) versus the peak absorbance at the asymmetric stretching mode (1060-1100 cm$^{-1}$) of the Si—O—Si bond was measured, and the ratio of these two measurements was calculated, all as shown in Table 9. The respective ratios were found to have a linear correlation to the composite parameter W/FM as shown in FIGS. 19 and 20.

A qualitative relation—whether the coating appeared oily (shiny, often with irridescence) or non-oily (non-shiny) when applied on the silicon chips—was also found to correlate with the W/FM values in Table 9. Oily appearing coatings deposited at lower W/FM values, as confirmed by Table 9, are believed to have a lower crosslink density, as determined by their lower sym/asym ratio, relative to the non-oily coatings that were deposited at higher W/FM and a higher cross-link density. The only exception to this general rule of thumb was sample 2 in Table 9. It is believed that the coating of sample 2 exhibited a non-oily appearance because it was too thin to see. Thus, an oilyness observation was not reported in Table 9 for sample 2. The chips were analyzed by FTIR in transmission mode, with the infrared spectrum transmitted through the chip and sample coating, and the transmission through an uncoated null chip subtracted.

Non-oily organosiloxane layers produced at higher W/FM values, which protect the underlying SiO$_x$ coating from aqueous solutions at elevated pH and temperature, were preferred because they provided lower Si dissolution and a longer shelf life, as confirmed by Table 9. For example, the calculated silicon dissolution by contents of the vial at a pH of 8 and 40° C. was reduced for the non-oily coatings, and the resulting shelf life was 1381 days in one case and 1147 days in another, as opposed to the much shorter shelf lives and higher rates of dissolution for oily coatings. Calculated shelf life was determined as shown for Example AA. The calculated shelf life also correlated linearly to the ratio of symmetric to asymmetric stretching modes of the Si—O—Si bond in organosiloxane passivation layers or pH protective coatings.

Sample 6 can be particularly compared to Sample 5. An organosiloxane, pH passivation layer or pH protective coating was deposited according to the process conditions of sample 6 in Table 9. The coating was deposited at a high W/FM. This resulted in a non-oily coating with a high Si—O—Si sym/asym ratio of 0.958, which resulted in a low rate of dissolution of 84.1 ppb/day (measured by the Protocol for Determining Average Dissolution Rate) and long shelf life of 1147 days (measured by the Protocol for Determining Calculated Shelf Life). The FTIR spectra of this coating is shown in FIG. 35, which exhibits a relatively similar asymmetric Si—O—Si peak absorbance compared to the symmetric Si—O—Si peak absorbance. This is an indication of a higher cross-link density coating, which is a preferred characteristic for pH protection and long shelf life.

An organosiloxane pH passivation layer or pH protective coating was deposited according to the process conditions of sample 5 in Table 9. The coating was deposited at a moderate W/FM. This resulted in an oily coating with a low Si—O—Si sym/asym ratio of 0.673, which resulted in a high rate of dissolution of 236.7 ppb/day (following the Protocol for Determining Average Dissolution Rate) and shorter shelf life of 271 days (following the Protocol for Determining Calculated Shelf Life). The FTIR spectrum of this coating is shown in FIG. 20, which exhibits a relatively high asymmetric Si—O—Si peak absorbance compared to the symmetric Si—O—Si peak absorbance. This is an indication of a lower cross-link density coating, which is contemplated to be an unfavorable characteristic for pH protection and long shelf life.

Sample 2 can be particularly compared to Sample 3. A passivation layer or pH protective coating was deposited according to the process conditions of sample 2 in Table 9. The coating was deposited at a low W/FM. This resulted in a coating that exhibited a low Si—O—Si sym/asym ratio of 0.582, which resulted in a high rate of dissolution of 174 ppb/day and short shelf life of 107 days. The FTIR spectrum of this coating is shown in FIG. 36, which exhibits a relatively high asymmetric Si—O—Si peak absorbance compared to the symmetric Si—O—Si peak absorbance. This is an indication of a lower cross-link density coating, which is an unfavorable characteristic for pH protection and long shelf life.

An organosiloxane, pH passivation layer or pH protective coating was deposited according to the process conditions of sample 3 in Table 9. The coating was deposited at a high W/FM. This resulted in a non-oily coating with a high Si—O—Si sym/asym ratio of 0.947, which resulted in a low rate of Si dissolution of 79.5 ppb/day (following the Protocol for Determining Average Dissolution Rate) and long shelf life of 1381 days (following the Protocol for Determining Calculated Shelf Life). The FTIR spectrum of this coating is shown in FIG. 37, which exhibits a relatively similar asymmetric Si—O—Si peak absorbance compared to the symmetric Si—O—Si peak absorbance. This is an indication of a higher cross-link density coating, which is a preferred characteristic for pH protection and long shelf life.

Example EE

An experiment similar to Example BB was carried out, modified as indicated in this example and in Table 10 (where the results are tabulated). 100 5 mL COP vials were made and coated with an $SiO_x$ barrier coating or layer and an OMCTS-based passivation layer or pH protective coating as described previously, except that for Sample PC194 only the passivation layer or pH protective coating was applied. The coating quantity was again measured in parts per billion extracted from the surfaces of the vials to remove the entire passivation layer or pH protective coating, as reported in Table 10.

In this example, several different coating dissolution conditions were employed. The test solutions used for dissolution contained either 0.02 or 0.2 wt. % polysorbate-80 surfactant, as well as a buffer to maintain a pH of 8. Dissolution tests were carried out at either 23° C. or 40° C.

Multiple syringes were filled with each test solution, stored at the indicated temperature, and analyzed at several intervals to determine the extraction profile and the amount of silicon extracted. An average dissolution rate for protracted storage times was then calculated by extrapolating the data obtained according to the Protocol for Determining Average Dissolution Rate. The results were calculated as described previously and are shown in Table 10. Of particular note, as shown on Table 10, were the very long calculated shelf lives of the filled packages provided with a PC 194 passivation layer or pH protective coating:

21045 days (over 57 years) based on storage at a pH of 8, 0.02 wt. % polysorbate-80 surfactant, at 23° C.;

38768 days (over 100 years) based on storage at a pH of 8, 0.2 wt. % polysorbate-80 surfactant, at 23° C.;

8184 days (over 22 years) based on storage at a pH of 8, 0.02 wt. % polysorbate-80 surfactant, at 40° C.; and 14732 days (over 40 years) based on storage at a pH of 8, 0.2 wt. % polysorbate-80 surfactant, at 40° C.

Referring to Table 10, the longest calculated shelf lives corresponded with the use of an RF power level of 150 Watts and a corresponding high W/FM value. It is believed that the use of a higher power level causes higher cross-link density of the passivation layer or pH protective coating.

Example FF

Another series of experiments similar to those of Example EE are run, showing the effect of progressively increasing the RF power level on the FTIR absorbance spectrum of the passivation layer or pH protective coating. The results are tabulated in Table 11, which in each instance shows a symmetric/assymmetric ratio greater than 0.75 between the maximum amplitude of the Si—O—Si symmetrical stretch peak normally located between about 1000 and 1040 cm$^{-1}$, and the maximum amplitude of the Si—O—Si assymmetric stretch peak normally located between about 1060 and about 1100 cm$^{-1}$. Thus, the symmetric/assymmetric ratio is 0.79 at a power level of 20 W, 1.21 or 1.22 at power levels of 40, 60, or 80 W, and 1.26 at 100 Watts under otherwise comparable conditions.

The 150 Watt data in Table 11 is taken under somewhat different conditions than the other data, so it is not directly comparable with the 20-100 Watt data discussed above. The FTIR data of samples 6 and 8 of Table 11 was taken from the upper portion of the vial and the FTIR data of samples 7 and 9 of Table 11 was taken from the lower portion of the vial. Also, the amount of OMCTS was cut in half for samples 8 and 9 of Table 11, compared to samples 6 and 7. Reducing the oxygen level while maintaining a power level of 150 W raised the symmetric/asymmetric ratio still further, as shown by comparing samples 6 and 7 to samples 8 and 9 in Table 11.

It is believed that, other conditions being equal, increasing the symmetric/asymmetric ratio increases the shelf life of a vessel filled with a material having a pH exceeding 5.

Table 12 shows the calculated O-Parameters and N-Parameters (as defined in U.S. Pat. No. 8,067,070) for the experiments summarized in Table 11. As Table 12 shows, the O-Parameters ranged from 0.134 to 0.343, and the N-Parameters ranged from 0.408 to 0.623—all outside the ranges claimed in U.S. Pat. No. 8,067,070.

Example GG—Measurement of Contact Angle

The test purpose was to determine the contact angle or surface energy on the inside surface of two kinds of plastic vials and one kind of glass vial The specimens that underwent testing and analysis reported here are three kinds of vials. The specimens are (A) an uncoated COP vial, (B) an $SiO_x$+passivation layer or pH protective coating on a COP vial prepared according to the above Protocol for Coating Syringe Barrel Interior with $SiO_x$, followed by the Protocol for Coating Syringe Barrel Interior with OMCTS Passivation layer or pH protective coating, and (C) a glass vial. Small pieces were obtained by cutting the plastic vials or crushing the glass vial in order to test the inside surface.

The analysis instrument for the contact angle tests is the Contact Angle Meter model DM-701, made by Kyowa Interface Science Co., Ltd. (Tokyo, Japan). To obtain the contact angle, five water droplets were deposited on the inside surface of small pieces obtained from each specimen. The testing conditions and parameters are summarized below. Both plastic vials were cut and trimmed, while the glass vial needed to be crushed. The best representative pieces for each specimen were selected for testing. A drop-size of 1 μL (one microliter) was used for all samples. Due to the curvature of the specimens, a curvature correction routine was used to accurately measure the contact angle. The second table below contains the values for the radius of curvature used for each specimen.

Contact Angle Testing Conditions and Parameters

| Test instrument- | DM-701 Contact Angle Meter |
|---|---|
| Liquid Dispenser- | 22 gauge stainless steel needle |
| Drop Size- | 1 μL |
| Test liquid | Distilled water |
| Environment | Ambient air, room temperature |

Radius of Curvature for each Vial Specimen

| Specimen | Radius of Curvature (μm, micrometers) |
|---|---|
| COP | 9240 |
| COP plus passivation layer or pH protective coating | 9235 |
| Glass | 9900 |

The contact angle results for each specimen are provided below.

The specimen made from COP plus passivation layer or pH protective coating had the highest average contact angle of all tested specimens. The average contact angle for specimen made from COP plus passivation layer or pH protective coating was 99.1°. The average contact angle for the uncoated COP specimen was 90.5°. The glass specimen had a significantly lower average contact angle at 10.6°. This data shows the utility of the passivation layer or pH protective coating to raise the contact angle of the uncoated COP vessel. It is expected that an $SiO_x$ coated vessel without the passivation layer or pH protective coating would exhibit a result similar to glass, which shows a hydrophilic coating relative to the relative to the passivation layer or pH protective coating.

TABLE

Contact Angle Results for Each Tested Specimen (degrees)

| Specimen | Test 1 | Test 2 | Test 3 | Test 4 | Test 5 | Ave. | Std. Dev. |
|---|---|---|---|---|---|---|---|
| COP | 88.9 | 91.9 | 89.1 | 91.4 | 91.1 | 90.5 | 1.4 |
| COP/Pass. | 98.9 | 96.8 | 102.2 | 98.3 | 99.5 | 99.1 | 2.0 |
| Glass | 11.6 | 10.6 | 10.1 | 10.4 | 10.4 | 10.6 | 0.6 |

Note:
"Pass." means passivation layer or pH protective coating.

Example HH

The purpose of this example was to evaluate the recoverability or drainage of a slightly viscous aqueous solution from glass, COP and coated vials, This study evaluated the recovery of a 30 cps (centipoise) carbohydrate solution in water-for-injection from (A) an uncoated COP vial, (B) an $SiO_x$+passivation layer or pH protective coating on a COP vial prepared according to the above Protocol for Coating Syringe Barrel Interior with $SiO_x$, followed by the Protocol for Coating Syringe Barrel Interior with OMCTS Passivation layer or pH protective coating, and (C) a glass vial.

2.0 ml of the carbohydrate solution was pipetted into 30 vials each of glass, COP and vials coated with a passivation layer or pH protective coating. The solution was aspirated from the vials with a 10 ml syringe, through a 23 gauge, 1.5" needle. The vials were tipped to one side as the solution was aspirated to maximize the amount recovered. The same technique and similar withdrawal time was used for all vials. The vials were weighed empty, after placing 2.0 ml of the solution to the vial and at the conclusion of aspirating the solution from the vial. The amount delivered to the vial (A) was determined by subtracting the weight of the empty vial from the weight of the vial with the 2.0 ml of solution. The weight of solution not recovered (B) was determined by subtracting the weight of the empty vial from the weight of the vials after aspirating the solution from the vial. The percent unrecovered was determined by dividing B by A and multiplying by 100.

It was observed during the aspiration of drug product that the glass vials remained wetted with the solution. The COP vial repelled the liquid and as the solution was aspirated from the vials. This helped with recovery but droplets were observed to bead on the sidewalls of the vials during the aspiration. The vials coated with a passivation layer or pH protective coating also repelled the liquid during aspiration but no beading of solution on the sidewalls was observed.

The conclusion was that vials coated with a passivation layer or pH protective coating do not wet with aqueous solutions as do glass vials, leading to superior recovery of drug product relative to glass. Vials coated with a passivation layer or pH protective coating were not observed to cause beading of solution on sidewall during aspiration of aqueous products therefore coated vials performed better than uncoated COP vials in product recovery experiments.

Example II—Glass Delamination

Bi-layer coated ($SiO_x$ barrier coating or layer plus passivation layer or pH protective coating) glass vials were subjected to a wide range of chemical and physical challenges:

pH 2.5 to 9.5
Water for Injection (WFI) contained in the vial;
Variety of buffers—acetate, citrate, phosphate and HEPES contained in the vial;
4-(2-hydroxyethyl)-1-piperazineethanesulfonic acid contained in the vial.
Ionic strengths from 0 to 600 milliosmoles per kilogram Tween 80 concentrations up to 2%
Temperatures up to 40° C.

No delamination events were observed in these tests. The bi-layer coating also did not delaminate when subjected to a liquid nitrogen (−200° C.) freeze-thaw temperature cycle. The bi-layer coating further did not delaminate when scratched and then subjected to a liquid nitrogen (−200° C.) freeze-thaw temperature cycle.

TABLE 1

PLUNGER SLIDING FORCE MEASUREMENTS OF OMCTS-BASED PLASMA PASSIVATION LAYER OR PH PROTECTIVE COATING MADE WITH CARRIER GAS

| Example | Lubricity passivation layer or pH protective coating Type | Monomer | Coating Time (sec) | OMCTS Flow Rate (sccm) | O2 Flow Rate (sccm) | Carrier Gas (Ar) Flow Rate (sccm) | Power (Watts) | Initiation Force, $F_i$ (N, Kg.) | Maintenance Force, $F_m$ (N, Kg.) |
|---|---|---|---|---|---|---|---|---|---|
| A (Control) | Uncoated COC | n/a | n/a | n/a | n/a | n/a | n/a | >11 N >1.1 Kg. | >11 N >1.1 Kg. |
| B (Industry Standard) | Silicon oil on COC | n/a | n/a | n/a | n/a | n/a | n/a | 8.2 N 0.84 Kg. | 6.3 N 0.64 Kg. |
| C (without Oxygen) | L3 lubricity coating or layer over $SiO_x$ on COC | OMCTS | 10 sec | 3 | 0 | 65 | 6 | 4.6 N 0.47 Kg. | 4.6 N 0.47 Kg. |
| D (with Oxygen) | L2 lubricity and/or passivation layer or pH protective coating over $SiO_x$ on COC | OMCTS | 10 sec | 3 | 1 | 65 | 6 | 4.8 N 0.49 Kg. | 3.5 N 0.36 Kg. |

TABLE 2

OMCTS Lubricity and/or passivation layer or pH protective coating (E and F)

| Example | OMCTS (sccm) | $O_2$ (sccm) | Ar (sccm) | Initiation Force, $F_i$ (N) | Maintenance Force, $F_m$ (N) | ICPMS (μg./liter) | ICPMS Mode |
|---|---|---|---|---|---|---|---|
| E | 3.0 | 0.38 | 7.8 | 4.8 | 3.5 | <5 | static |
| F | 3.0 | 0.38 | 7.8 | 5.4 | 4.3 | 38 | dynamic |
| G ($SiO_x$ only) | n/a | n/a | n/a | 13 | 11 | <5 | static |
| H (silicon oil) | n/a | n/a | n/a | 8.2 | 6.3 | | |

TABLE 3

OMCTS Lubricity and/or passivation layer or pH protective coating

| Example | OMCTS (sccm) | O₂ (sccm) | Ar (sccm) | Initiation Force, $F_i$ (N) | Maintenance Force, $F_m$ (N) |
|---|---|---|---|---|---|
| I | 2.5 | 0.38 | 7.6 | 5.1 | 4.4 |
| J | 2.5 | 0.38 | — | 7.1 | 6.2 |
| K | 2.5 | — | — | 8.2 | 7.2 |

TABLE 4

HMDSO passivation layer or pH protective coating

| Example | HMDSO (sccm) | O₂ (sccm) | Ar (sccm) | Initiation Force, $F_i$ (N) | Maintenance Force, $F_m$ (N) |
|---|---|---|---|---|---|
| L | 2.5 | 0.38 | 7.6 | 9 | 8.4 |
| M | 2.5 | 0.38 | — | >11 | >11 |
| N | 2.5 | — | — | >11 | >11 |

TABLE 5

Figure 9:
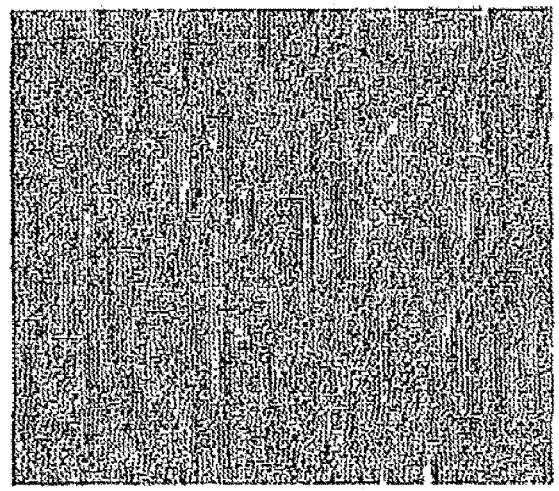
FIG. 9 shows a SEM image of Example P. The horizontal edge-to-edge scale is 5 μm.

| Example | | OMCTS (sccm) | Ar/O₂ (sccm) | Power (Watts) | Dep. Time (sec) | Plunger Force $F_i$ (lbs, Kg) | Plunger Force $F_m$ (lbs, Kg) | SEM Micrograph (5 micronAF Vertical) | AFM RMS (nanometers) |
|---|---|---|---|---|---|---|---|---|---|
| O | Baseline OMCTS | 2.0 | 10/0.38 | 3.5 | 10 | 4.66, 2.11 (ave) | 3.47, 1.57 (ave) | | |
| P | Lubricity | | | | | | | FIG. 9 | |
| Q | | | | | | | | | 19.6, 9.9, 9.4 (Average = 13.0) |
| R | High Power OMCTS | 2.0 | 10/0.38 | 4.5 | 10 | 4.9, 2.2 | 7.6, 3.4 | | |
| S | | | | | | | | FIG. 10 | |
| T | Lubricity | | | | | | | | 12.5, 8.4, 6.1 (Average = 6.3) |
| U | No O₂ OMCTS | 2.0 | 10/0 | 3.4 | 10 | 4.9, 2.2 | 9.7, 4.4 (stopped) | | |
| V | Lubricity | | | | | | | | 1.9, 2.6, 3.0 (Average = 2.3) |

TABLE 6

| | SiO$_x$/Lub | Coater | Mode | Siloxane Feed | Ar/O₂ | Power (W) | Dep. Time (Sec.) | $F_i$ (lb., Kg.) | $F_m$ (lb., Kg.) |
|---|---|---|---|---|---|---|---|---|---|
| Example W SiO$_x$/Baseline OMCTS Lub | SiO$_x$: | Auto-Tube | Auto | HMDSO 52.5 in, 133.4 cm. | 0 sccm Ar, 90 sccm O₂ | 37 | 7 | ~ | ~ |
| | Lubricity: | Auto-S | same | OMCTS, 2.0 sccm | 10 sccm Ar 0.38 sccm O₂ | 3.4 | 10 | 2.9, 1.3 | 3.3, 1.5 |
| Example X SiO$_x$/High Pwr OMCTS Lub | SiO$_x$: | same | same | same | same | 37 | 7 | ~ | ~ |
| | Lubricity: | same | same | same | same | 4.5 | 10 | 5, 2.3 | 9.5, 4.3 stopped |
| Example Y SiO$_x$/No O₂ OMCTS Lub | SiO$_x$: | Auto-Tube | same | same | 0 sccm Ar, 90 sccm O₂ | 37 | 7 | ~ | ~ |
| | Lubricity: | Auto-S | same | same | 10 sccm Ar 0 sccm O₂ | 3.4 | 10 | 5.6, | 9.5, 4.3 stopped |

TABLE 7

Silicon Extractables Comparison of Lubricity Coatings

| Package Type | Static (ug/L) | Dynamic (ug/L) |
|---|---|---|
| Cyclic Olefin Syringe with CV Holdings SiOCH Lubricity Coating | 70 | 81 |
| Borocilicate Glass Syringe with silicone oil | 825 | 835 |

TABLE 8

Summary Table of OMCTS passivation layer or pH protective coating from Tables 1, 2, 3 and 5

| Example | OMCTS (sccm) | O₂ (sccm) | Ar (sccm) | Power (Watt) | Dep Time (sec) | $F_i$ (lbs) | $F_m$ (lbs) |
|---|---|---|---|---|---|---|---|
| C | 3.0 | 0.00 | 65 | 6 | 10 | 1.0 | 1.0 |
| D | 3.0 | 1.00 | 65 | 6 | 10 | 1.1 | 0.8 |
| E | 3.0 | 0.38 | 7.8 | 6 | 10 | 0.8 | 1.1 |
| F | 3.0 | 0.38 | 7.8 | 6 | 10 | 1.2 | 1.0 |
| I | 2.5 | 0.38 | 7.6 | 6 | 10 | 1.1 | 1.0 |
| J | 2.5 | 0.38 | 0.0 | 6 | 10 | 1.6 | 1.4 |
| K | 2.5 | 0.00 | 0.0 | 6 | 10 | 1.8 | 1.6 |

TABLE 8-continued

Summary Table of OMCTS passivation layer or pH protective coating from Tables 1, 2, 3 and 5

| Example | OMCTS (sccm) | $O_2$ (sccm) | Ar (sccm) | Power (Watt) | Dep Time (sec) | $F_i$ (lbs) | $F_m$ (lbs) |
|---|---|---|---|---|---|---|---|
| O | 2.0 | 0.38 | 10 | 3.5 | 10 | 4.6 | 3.5 |
| R | 2.0 | 0.38 | 10 | 4.5 | 10 | 4.9 | 7.6 |
| U | 2.0 | 0.00 | 10 | 3.4 | 10 | 4.9 | 9.7 (stop) |
| W | 2.0 | 0.38 | 10 | 3.4 | 10 | 2.9 | 3.3 |
| X | 2.0 | 0.38 | 10 | 4.5 | 10 | 5.0 | 9.5 (stop) |
| Y | 2.0 | 0.00 | 10 | 3.4 | 10 | 5.6 | 9.5 (stop) |

TABLE 9

| | Process Parameters | | | | | Si Dissolution @ pH 8/40° C. | | | FTIR Absorbance | | | |
|---|---|---|---|---|---|---|---|---|---|---|---|---|
| Flow Rate Samples | OMCTS | Ar | $O_2$ Flow Rate | Power (W) | W/FM (kJ/kg) | Total Si (ppb) | Shelf life (days) | Rate of Dissolution (ppb/day) | Si—O—Si sym stretch (1000-1040 cm$^{-1}$) | Si—O—Si asym stretch (1060-1100 cm$^{-1}$) | Ratio Si—O—Si (sym/asym) | Oilyness |
| 1 | 3 | 10 | 0.5 | 14 | 21613 | 43464 | 385 | 293.18 | 0.153 | 0.219 | 0.700 | YES |
| 2 | 3 | 20 | 0.5 | 2 | 3088 | 7180 | 107 | 174.08 | 0.011 | 0.020 | 0.582 | NA |
| 3 | 1 | 20 | 0.5 | 14 | 62533 | 42252.17 | 1381 | 79.53 | 0.093 | 0.098 | 0.947 | NO |
| 4 | 2 | 15 | 0.5 | 8 | 18356 | 27398 | 380 | 187.63 | 0.106 | 0.141 | 0.748 | YES |
| 5 | 3 | 20 | 0.5 | 14 | 21613 | 24699 | 271 | 236.73 | 0.135 | 0.201 | 0.673 | YES |
| 6 | 1 | 10 | 0.5 | 14 | 62533 | 37094 | 1147 | 84.1 | 0.134 | 0.140 | 0.958 | NO |

TABLE 10

| Sample | OMCTS Flow Rate (sccm) | Argon Flow Rate (sccm) | $O_2$ Flow Rate (sccm) | Power (W) | Plasma Duration (sec) | W/FM (kJ/kg) | Total Si (ppb) (OMCTS) layer) | Calculated Shelf-life (days) | Average Rate of Dissolution (ppb/day) |
|---|---|---|---|---|---|---|---|---|---|
| | Process Parameters | | | | | | Si Dissolution @ pH 8/23° C./0.02% Tween ®-80 | | |
| PC194 018 | 0.5 | 20 | 0.5 | 150 | 20 | 1223335 | 73660 | 21045 | 3.5 |
| | 1.0 | 20 | 0.5 | 18 | 15 | 77157 | 42982 | 1330 | 32.3 |
| | Process Parameters | | | | | | Si Dissolution @ pH 8/23° C./0.2% Tween ®-80 | | |
| PC194 018 | 0.5 | 20 | 0.5 | 150 | 20 | 1223335 | 73660 | 38768 | 1.9 |
| | 1.0 | 20 | 0.5 | 18 | 15 | 77157 | 42982 | 665 | 64.6 |
| 048 | 4 | 80 | 2 | 35 | 20 | 37507 | 56520 | 1074 | 52.62 |
| | Process Parameters | | | | | | Si Dissolution @ pH 8/40° C./0.02% Tween ®-80 | | |
| PC194 018 | 0.5 | 20 | 0.5 | 150 | 20 | 1223335 | 73660 | 8184 | 9 |
| | 1.0 | 20 | 0.5 | 18 | 15 | 77157 | 42982 | 511 | 84 |
| | Process Parameters | | | | | | Si Dissolution @ pH 8/40° C./0.2% Tween ®-80 | | |
| PC194 018 | 0.5 | 20 | 0.5 | 150 | 20 | 1223335 | 73660 | 14732 | 5 |
| | 1.0 | 20 | 0.5 | 18 | 15 | 77157 | 42982 | 255 | 168 |

TABLE 11

| Samples ID | OMCTS Flow Rate (sccm) | Argon Flow Rate (sccm) | $O_2$ Flow Rate (sccm) | Power (W) | Plasma Duration (sec) | W/FM (kJ/kg) | Symmetric Stretch Peak at 1000-1040 cm$^{-1}$ | Assymetric Stretch Peak at 1060-1100 cm$^{-1}$ | Symmetric/ Assymetric Ratio |
|---|---|---|---|---|---|---|---|---|---|
| | Process Parameters | | | | | | FTIR Results | | |
| 1 | 1 | 20 | 0.5 | 20 | 20 | 85,730 | 0.0793 | 0.1007 | 0.79 |
| 2 | 1 | 20 | 0.5 | 40 | 20 | 171,460 | 0.0619 | 0.0507 | 1.22 |
| 3 | 1 | 20 | 0.5 | 60 | 20 | 257,190 | 0.1092 | 0.0904 | 1.21 |
| 4 | 1 | 20 | 0.5 | 80 | 20 | 342,919 | 0.1358 | 0.1116 | 1.22 |
| 5 | 1 | 20 | 0.5 | 100 | 20 | 428,649 | 0.209 | 0.1658 | 1.26 |
| 6 | 1 | 20 | 0.5 | 150 | 20 | 642,973 | 0.2312 | 0.1905 | 1.21 |
| 7 | 1 | 20 | 0.5 | 150 | 20 | 642,973 | 0.2324 | 0.1897 | 1.23 |

TABLE 11-continued

| Samples ID | OMCTS Flow Rate (sccm) | Argon Flow Rate (sccm) | $O_2$ Flow Rate (sccm) | Power (W) | Plasma Duration (sec) | W/FM (kJ/kg) | Symmetric Stretch Peak at 1000-1040 cm$^{-1}$ | Assymetric Stretch Peak at 1060-1100 cm$^{-1}$ | Symmetric/ Assymetric Ratio |
|---|---|---|---|---|---|---|---|---|---|
| 8 | 0.5 | 20 | 0.5 | 150 | 20 | 1,223,335 | 0.1713 | 0.1353 | 1.27 |
| 9 | 0.5 | 20 | 0.5 | 150 | 20 | 1,223,335 | 0.1475 | 0.1151 | 1.28 |

TABLE 12

| Samples ID | OMCTS Flow Rate (sccm) | Argon Flow Rate (sccm) | $O_2$ Flow Rate (sccm) | Power (W) | Plasma Duration (sec) | W/FM (kJ/kg) | O- Parameter | N- Parameter |
|---|---|---|---|---|---|---|---|---|
| | | | Process Parameters | | | | | |
| 1 | 1 | 20 | 0.5 | 20 | 20 | 85,730 | 0.343 | 0.436 |
| 2 | 1 | 20 | 0.5 | 40 | 20 | 171,460 | 0.267 | 0.408 |
| 3 | 1 | 20 | 0.5 | 60 | 20 | 257,190 | 0.311 | 0.457 |
| 4 | 1 | 20 | 0.5 | 80 | 20 | 342,919 | 0.270 | 0.421 |
| 5 | 1 | 20 | 0.5 | 100 | 20 | 428,649 | 0.177 | 0.406 |
| 6 | 1 | 20 | 0.5 | 150 | 20 | 642,973 | 0.151 | 0.453 |
| 7 | 1 | 20 | 0.5 | 150 | 20 | 642,973 | 0.151 | 0.448 |
| 8 | 0.5 | 20 | 0.5 | 150 | 20 | 1,223,335 | 0.134 | 0.623 |
| 9 | 0.5 | 20 | 0.5 | 150 | 20 | 1,223,335 | 0.167 | 0.609 |

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art and practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

The invention claimed is:

1. A filled package comprising: a vessel having a lumen defined at least in part by a wall, the wall having an interior surface facing the lumen and an outer surface; a barrier coating or layer of $SiO_x$, wherein x is from 1.5 to 2.9, from 2 to 1000 nm thick, the barrier coating or layer of $SiO_x$ having an interior surface facing the lumen and an outer surface facing the wall interior surface, the barrier coating or layer being effective to reduce the ingress of atmospheric gas into the lumen compared to an vessel without a barrier coating or layer; a passivation layer or pH protective coating of $SiO_xC_y$ or $SiN_xC_y$ wherein x is from about 0.5 to about 2.4 and y is from about 0.6 to about 3, the passivation layer or pH protective coating having an interior surface facing the lumen and an outer surface facing the interior surface of the barrier coating or layer, the passivation layer or pH protective coating being effective to increase the calculated shelf life of the package (total Si/Si dissolution rate); and a fluid composition contained in the lumen and having a pH between 4 and 10; wherein the calculated shelf life of the package is more than six months at a storage temperature of 4° C.; and wherein an FTIR absorbance spectrum of the passivation layer or pH protective coating has a ratio greater than 0.75 and at most 1.7, between the maximum amplitude of the Si—O—Si symmetrical stretch peak between about 1000 and 1040 cm$^{-1}$, and the maximum amplitude of the Si—O—Si asymetric stretch peak between about 1060 and about 1100 cm$^{-1}$.

2. The filled package of claim 1, in which at least a portion of the wall of the vessel comprises or consists essentially of a polyolefin, a cyclic olefin polymer, a cyclic olefin copolymer, a polyester, a polycarbonate, polylactic acid, glass, or a combination or copolymer of these.

3. The filled package of claim 1, in which the vessel comprises a syringe barrel, a cartridge, a vial, or a blister package.

4. The filled package of claim 1, in which the barrier coating or layer is from 10 nm to 300 nm thick.

5. The filled package of claim 1, in which the passivation layer or pH protective coating is applied by PECVD of a precursor feed comprising a linear siloxane, a linear silazane, a monocyclic siloxane, a polycyclic siloxane, a polysilsesquioxane, a monocyclic silazane, a polycyclic silazane, a polysilsesquiazane, a silatrane, a silquasilatrane, a silproatrane, an azasilatrane, an azasilquasiatrane, an azasilproatrane, or a combination of any two or more of these precursors.

6. The filled package of claim 1, in which the passivation layer or pH protective coating as applied is between 100 and 700 nm thick.

7. The filled package of claim 1, in which the rate of erosion of the passivation layer or pH protective coating, if directly contacted by a fluid composition having a pH of 8, is from 5% to 20%, of the rate of erosion of the barrier coating or layer, if directly contacted by the same fluid composition under the same conditions.

8. The filled package of claim 1, in which the passivation layer or pH protective coating is at least coextensive with the barrier coating or layer.

9. The filled package of claim 1, having a minimum shelf life, after the invention is assembled, of at least two years, wherein the shelf life is determined at 4° C.

10. The filled package of claim 1, in which the fluid composition removes the passivation layer or pH protective coating at a rate of 1 nm or less of passivation layer or pH protective coating thickness per 44 hours of contact.

11. The filled package of claim 1, in which the silicon dissolution rate by a 50 mM potassium phosphate buffer diluted in water for injection, adjusted to pH 8 with concentrated nitric acid, and containing 0.2 wt. % polysorbate-80 surfactant from the vessel is less than 170 ppb/day.

12. The filled package of claim 1, in which the total silicon content of the passivation layer or pH protective coating and barrier coating or layer, upon dissolution into 0.1 N potassium hydroxide aqueous solution at 40° C. from the vessel, is less than 66 ppm.

13. The filled package of claim 1, in which the calculated shelf life (total Si/Si dissolution rate) is more than 2 years and less than 5 years.

14. The filled package of claim 1, in which the passivation layer or pH protective coating is applied by PECVD at a power level of from 1 to 250 W.

15. The filled package of claim 1, in which the ratio of the electrode power to the plasma volume is from 6 W/ml to 60 W/ml.

16. The filled package of claim 1, in which the calculated shelf life (total Si/Si dissolution rate) is less than 5 years.

17. The filled package of claim 5, in which the precursor feed further comprises an oxidizing gas.

18. The filled package of claim 17, in which the precursor feed further comprises a noble gas.

19. The filled package of claim 18, in which the precursor feed comprises: from 0.5 to 10 standard volumes of an organosilicon precursor; from 0.1 to 10 standard volumes of an oxidizing gas; and from 1 to 100 sccm of a carrier gas.

20. The filled package of claim 1, in which the passivation layer or pH protective coating is effective to provide a lower frictional resistance than the uncoated interior surface.

21. The filled package of claim 20 wherein the frictional resistance is reduced by at least 45%, in comparison to the uncoated interior surface.

22. The filled package of claim 20, in which the passivation layer or pH protective coating is effective to reduce the frictional resistance between a portion of the wall contacted by the fluid composition and a relatively sliding part after the invention is assembled, wherein the filled package is a syringe comprising a syringe barrel and the relatively sliding part, wherein the wall defines at least a portion of the syringe barrel and the relatively sliding part comprises a plunger tip, piston, stopper, or seal.

* * * * *